(12) United States Patent
Sillers et al.

(10) Patent No.: US 9,605,269 B2
(45) Date of Patent: *Mar. 28, 2017

(54) DETOXIFICATION OF BIOMASS DERIVED ACETATE VIA METABOLIC CONVERSION TO ETHANOL, ACETONE, ISOPROPANOL, OR ETHYL ACETATE

(75) Inventors: William Ryan Sillers, Lebanon, NH (US); Hans Van Dijken, Schiedam HG (NL); Steve Licht, Utica, NY (US); Arthur J. Shaw, IV, Grantham, NH (US); Alan Benjamin Gilbert, Lebanon, NH (US); Aaron Argyros, White River Junction, VT (US); Allan C. Froehlich, Lebanon, NH (US); John E. McBride, Lyme, NH (US); Haowen Xu, Lebanon, NH (US); David A. Hogsett, Lebanon, NH (US); Vineet B. Rajgarhia, Lebanon, NH (US)

(73) Assignee: Lallemand Hungary Liquidity Management LLC, Budapest (HU)

( * ) Notice: Subject to any disclaimer, the term of this patent is extended or adjusted under 35 U.S.C. 154(b) by 0 days.

This patent is subject to a terminal disclaimer.

(21) Appl. No.: 13/696,207

(22) PCT Filed: May 5, 2011

(86) PCT No.: PCT/US2011/035416
§ 371 (c)(1),
(2), (4) Date: May 29, 2013

(87) PCT Pub. No.: WO2011/140386
PCT Pub. Date: Nov. 10, 2011

(65) Prior Publication Data
US 2013/0273555 A1 Oct. 17, 2013

Related U.S. Application Data

(60) Provisional application No. 61/351,133, filed on Jun. 3, 2010, provisional application No. 61/331,657, filed on May 5, 2010.

(51) Int. Cl.
| C12N 1/20 | (2006.01) |
| C12N 15/81 | (2006.01) |
| C12N 1/18 | (2006.01) |
| C12N 9/04 | (2006.01) |
| C12N 9/02 | (2006.01) |
| C12P 7/02 | (2006.01) |
| C12P 7/06 | (2006.01) |
| C12P 7/10 | (2006.01) |

(Continued)

(52) U.S. Cl.
CPC ............ *C12N 15/81* (2013.01); *C12N 1/16* (2013.01); *C12N 1/18* (2013.01); *C12N 9/0006* (2013.01); *C12N 9/0008* (2013.01); *C12N 9/0067* (2013.01); *C12N 15/74* (2013.01); *C12P 7/02* (2013.01); *C12P 7/04* (2013.01); *C12P 7/06* (2013.01); *C12P 7/10* (2013.01); *C12P 7/28* (2013.01); *C12P 7/62* (2013.01); *C12R 1/01* (2013.01); *C12R 1/645* (2013.01); *C12R 1/865* (2013.01); *C12Y 102/01012* (2013.01); *C12Y 112/99006* (2013.01); *Y02E 50/16* (2013.01); *Y02E 50/17* (2013.01); *Y02P 20/52* (2015.11)

(58) Field of Classification Search
CPC ... C12N 9/06; C12N 9/08; C12N 1/20; C12N 1/12; C12N 15/81
USPC .......................................... 435/471, 254.11
See application file for complete search history.

(56) References Cited

U.S. PATENT DOCUMENTS 7,018,829 B1 * 3/2006 Nielsen et al. ............ 435/254.2
7,846,712 B2 12/2010 Franden et al.
(Continued)

FOREIGN PATENT DOCUMENTS

| EP | 2 277 989 A1 | 1/2011 | |
| EP | 2277989 | * 1/2011 | .............. C12N 1/18 |

(Continued)

OTHER PUBLICATIONS

Bjorkqvist, S et al, Applied and Environmental Microbiology, vol. 63(1), 1997, pp. 128-132, Physiological Response to Anaerobicaity of Glycerol-3-Phosphate Dehydrogenase Mutants of *Saccharomyces cervisiae*.*

(Continued)

*Primary Examiner* — Albert Navarro
(74) *Attorney, Agent, or Firm* — Nutter McClennen & Fish LLP

(57) ABSTRACT

One aspect of the invention relates to a genetically modified thermophilic or mesophilic microorganism, wherein a first native gene is partially, substantially, or completely deleted, silenced, inactivated, or down-regulated, which first native gene encodes a first native enzyme involved in the metabolic production of an organic acid or a salt thereof, thereby increasing the native ability of said thermophilic or mesophilic microorganism to produce lactate or acetate as a fermentation product. In certain embodiments, the aforementioned microorganism further comprises a first non-native gene, which first non-native gene encodes a first non-native enzyme involved in the metabolic production of lactate or acetate. Another aspect of the invention relates to a process for converting lignocellulosic biomass to lactate or acetate, comprising contacting lignocellulosic biomass with a genetically modified thermophilic or mesophilic microorganism.

16 Claims, 30 Drawing Sheets

(51) Int. Cl.
*C12P 7/28* (2006.01)
*C12P 7/62* (2006.01)
*C12R 1/01* (2006.01)
*C12R 1/645* (2006.01)
*C12N 1/16* (2006.01)
*C12N 15/74* (2006.01)
*C12P 7/04* (2006.01)
*C12R 1/865* (2006.01)

(56) References Cited

U.S. PATENT DOCUMENTS

| | | | |
|---|---|---|---|
| 7,977,084 B2 | 7/2011 | Sun et al. | |
| 8,034,591 B2 | 10/2011 | Winkler et al. | |
| 8,071,358 B1* | 12/2011 | Dundon et al. | 435/254.2 |
| 8,663,970 B1* | 3/2014 | Huang et al. | 435/254.2 |
| 8,741,652 B2* | 6/2014 | Siddavattam et al. | 435/471 |
| 8,765,433 B2* | 7/2014 | Satagopan | C12N 9/0004 435/160 |
| 8,795,998 B2* | 8/2014 | Pronk | C12N 1/18 435/161 |
| 8,956,851 B2* | 2/2015 | Argyros et al. | 435/254.21 |
| 2006/0110810 A1* | 5/2006 | Rajgarhia et al. | 435/139 |
| 2007/0082386 A1* | 4/2007 | Gorwa-Grauslund | 435/161 |
| 2008/0261287 A1 | 10/2008 | Winkler et al. | |
| 2008/0293125 A1 | 11/2008 | Subbian et al. | |
| 2009/0155869 A1* | 6/2009 | Buelter | C12N 15/52 435/160 |
| 2009/0275097 A1* | 11/2009 | Sun | C12N 9/0006 435/160 |
| 2010/0028975 A1* | 2/2010 | Gorwa-Grauslund | 435/254.21 |
| 2010/0035320 A1* | 2/2010 | Blanchard et al. | 435/161 |
| 2010/0068776 A1* | 3/2010 | Woods et al. | 435/161 |
| 2010/0137655 A1* | 6/2010 | Soucaille | 568/852 |
| 2010/0205857 A1 | 8/2010 | Dijk et al. | |
| 2010/0248233 A1 | 9/2010 | Mueller et al. | |
| 2010/0297736 A1* | 11/2010 | Duhring | C12N 15/74 435/252.3 |
| 2011/0111473 A1 | 5/2011 | Peterson et al. | |
| 2011/0124074 A1 | 5/2011 | Den Haan et al. | |
| 2011/0152511 A1* | 6/2011 | Dayananda Siddavattam et al. | 536/23.2 |
| 2011/0189744 A1 | 8/2011 | McBride et al. | |
| 2011/0275130 A1* | 11/2011 | Pronk et al. | 435/165 |
| 2011/0312054 A1 | 12/2011 | Brevnova et al. | |
| 2012/0003701 A1 | 1/2012 | Brevnova et al. | |
| 2012/0040409 A1 | 2/2012 | Hau et al. | |
| 2012/0040426 A1 | 2/2012 | Sun et al. | |
| 2012/0045809 A1* | 2/2012 | Buelter et al. | 435/160 |
| 2012/0094343 A1 | 4/2012 | Hogsett et al. | |
| 2012/0129229 A1 | 5/2012 | McBride et al. | |
| 2012/0225451 A1 | 9/2012 | Winkler et al. | |
| 2012/0295319 A1* | 11/2012 | Nevoigt et al. | 435/161 |
| 2012/0322078 A1* | 12/2012 | Mcbride | C12P 7/04 435/6.18 |
| 2013/0071904 A1* | 3/2013 | Barak | 435/165 |
| 2013/0273555 A1* | 10/2013 | Sillers | C12N 1/18 435/6.18 |
| 2013/0323766 A1* | 12/2013 | Sillers et al. | 435/15 |
| 2013/0323822 A1* | 12/2013 | Brevnova et al. | 435/254.21 |
| 2014/0004597 A1* | 1/2014 | Chang et al. | 435/252.33 |
| 2014/0256011 A1* | 9/2014 | Zelle | C12N 15/81 435/161 |
| 2015/0079652 A1* | 3/2015 | Alcasabas | C12N 1/18 435/161 |
| 2015/0232863 A1* | 8/2015 | Argyros | C12N 15/81 435/254.21 |
| 2015/0275242 A1* | 10/2015 | Osterhout | C12P 7/6409 568/852 |

FOREIGN PATENT DOCUMENTS

| | | | | |
|---|---|---|---|---|
| GB | 2442116 | * | 3/2008 | C12Q 1/68 |
| WO | 2004/085627 | * | 10/2004 | C12N 1/18 |
| WO | WO 2006/009434 A1 | | 1/2006 | |
| WO | 2009/012210 | * | 1/2009 | C12N 1/16 |
| WO | 2009/013159 | * | 1/2009 | C12N 15/81 |
| WO | WO 2009/013159 A2 | | 1/2009 | |
| WO | 2009/043012 | * | 4/2009 | C12P 7/10 |
| WO | 2009/056984 | * | 5/2009 | C12N 15/82 |
| WO | 2009/078973 | * | 6/2009 | C12P 7/06 |
| WO | WO 2009/090050 A1 | | 7/2009 | |
| WO | 2009/098089 | * | 8/2009 | A01K 13/00 |
| WO | WO 2009/111672 A1 | | 9/2009 | |
| WO | WO 2009/137804 A1 | | 11/2009 | |
| WO | WO 2009/138877 A2 | | 11/2009 | |
| WO | WO 2009/139839 A1 | | 11/2009 | |
| WO | WO 2010/005551 A2 | | 1/2010 | |
| WO | WO 2010/005553 A1 | | 1/2010 | |
| WO | WO 2010/056805 A2 | | 5/2010 | |
| WO | WO 2010/060056 A2 | | 5/2010 | |
| WO | WO 2010/075529 A2 | | 7/2010 | |
| WO | WO 2011/153516 A2 | | 12/2011 | |
| WO | WO 2012/138942 A1 | | 10/2012 | |

OTHER PUBLICATIONS

Michnick, S et al, Yeast, vol. 13, pp. 783-793, 1997, Modulation of Glycerol and Ethanol yields during alcoholic fermentation in *Asccharomyces cervisiae* strains overexpressed or disrupted for GPD1 encoding Glycerol 3-phosphate dehydrogenase.*

Medina, V. G et al, Applied and Environmental Microbiology, vol. 76(1), 2010, published adhead of Print Nov. 13, 2009, pp. 190-195, Elimination of Glycerol production in Anaerobic cultures of a *Saccharomyces cerevisiae* strain Engineered to use Acetic Acid as an Electron Acceptor.*

Nissen, TL et al, Yeast, 2000, vol. 16, pp. 463-474, Anaerobic and aerobic batch cultivation of *Saccharomyces cerevisiae* mutants impaired in glycerol synthesis.*

U.S. Appl. No. 61/325,533, filed Apr. 2010, De Bont et al.*

Medina et al, published ahead of print, Nov. 13, 2009, Elimination of Glycerol Production in Anaerobic Cultures of a *Saccharomyes cerevisiae* Strain Engineered to use Acetic Acid as an Election Acceptor, Appl. Environ. Microbiology, vol. 76(1), pp. 190-195.*

Almeida João, R.M., et al., "Increased tolerance and conversion of inhibitors in lignocellulosic hydrolysates by *Saccharomyces cervisiae*," *J. Chem Tech. Biotech.* 82(4):340-349, Blackwell Scientific Publications, England (2007).

Ansell, R., et al., "The two isoenzymes for yeast $NAD^+$-dependent glycerol 3-phosphate dehydrogenase encoded by *GPD1* and *GPD2* have distinct roles in osmoadaptation and redox regulation,"*EMBO J* 16(9):2179-2187, Nature Publishing Group, England (1997).

Amarty, S. and Jeffries, T., "An improvement in *Pichia stipitis* fermentation of acid-hydrolysed hemicellulose achieved by overliming (calcium hydroxide treatment) and strain adaption,"*World J. Microbiol. Biotech.* 12(3):281-283, Oxford, England (1996).

Bermejo, L.L., et al., "Expression of *Clostridium acetobutylicum* ATCC 824 Genes in *Escherichia coli* for Acetone Production and Acetate Detoxification,"*Appl. Environ. Mircobiol.* 64(3):1079-1085, American Society for Microbiology, United States (1998).

Borneman, A.R., et al., "Comparative genome analysis of a *Saccharomyces cerevisiae* wine strain," *FEMS Yeast Res.* 8:1185-1195, Federation of European Microbiological Societies, Blackwell Publishing, England (2008).

Desai, S.G., et al., "Cloning of L-lactate dehydrogenase and elimination of lactic acid production via gene knockout in *Thermoanaerobacterium saccharolyticum* JW/SL-YS485," *Appl. Microbiol. Biotechnol* 65:600-605, Springer-Verlag, Germany (2004).

Guo, Z.-P., et al., "Minimization of glycerol synthesis in industrial ethanol yeast without influencing its fermentation performance," *Metabol. Eng.* 13(1):49-59, Elsevier, Inc., United States (2011).

Guo, Z.-P., et al., "Interruption of glycerol pathway in industrial alcoholic yeasts to improve the ethanol production," *Appl. Microbiol. Biotechnol.* 82:2):287-292, Springer-Verlag, Germany (2009).

(56) References Cited

OTHER PUBLICATIONS

Huang, C.F., et al., "Enhanced ethanol production by fermentation of rice straw hydrolysate without detoxification using a newly adapted strain of *Pichia stipitis*," *Biosource Tech.* 100(17):3914-3920, Elsevier B.V., England (2009).

Jeppsson, M., et al., "Reduced Oxidative Pentose Phosphate Pathway Flux in Recombinant Xylose-Utilizing *Saccharomyces cerevisiae* Strains Improves the Ethanol Yield from Xylose," *Appl. Environ. Microbiol.* 68(4):1604-1609, American Society for Microbiology, United States (2002).

Jeppsson, M., et al., "The level of glucose-6-phosphate dehydrogenase activity strongly influences xylose fermentation and inhibitor sensitivity in recombinant *Saccharomyces cerevisiae* strains," *Yeast* 20:1263-1272, John Wiley & Sons, Ltd., United States (2003).

Kacmar, J., et al., "The cytostat: A new way to study cell physiology in a precisely defined environment," *J. Biotechnol.* 126(2):163-172, Elsevier B.V., Netherlands (2006).

Karhumaa, K., et al., "Comparison of xylose reductase-xylitol dehydrogenase and the xylose isomerase pathways for xylose fermentation by recombinant *Saccharomyces cerevisiae*,"*Microbiol Cell Factories* 6(5):1-10, BioMed Central, England (2007).

Kong, Q.X., et al., "Overexpression GLT1 in gpd1Delta mutant to improve the production of ethanol of *Saccharomyces cerevisia*," *Appl. Microbiol. Biotechnol.* 73(6):1382-1386, Springer-Verlag, Germany (2007).

Kuyper, M., et al. "Minimal metabolic engineering of *Saccharomyces cerevisiae* for efficient anaerobic xylose fermentation: a proof of principle," *FEMS Yeast Res.* 4(6):655-664, Elsevier Science B.V., Netherlands (2004).

Kuyper, M., et al. "Metabolic engineering of a xylose-isomerase-expressing *Saccharomyces cerevisae* strain for rapid anaerobic xylose fermentation," *FEMS Yeast Res.* 5(4-5):399-409, Elsevier Science B V., Netherlands (2005).

Kuyper, M., et al. "Evolutionary engineering of mixed-sugar utilization by a xylose-fermenting *Saccharomyces cerevisiae* strain," *FEMS Yeast Res.* 5(10):925-934, Elsevier Science B.V., Netherlands (2005).

Leal, T.F. and Sá-Nogueira, "Purification, characterization and functional analysis of an endo-arabinanase (AbnA) from *Bacillus subtilis*," *FEMS Microbiol. Let.* 241:41-48, Elsevier, B.V., Netherlands (2004).

Lee, J.M. et al., "Detoxification of woody hydrolyzates with activated carbon for bioconversion to ethanol by the thermophilic anaerobic bacterium *Thermoanaerobacterium saccharolyticum*," *Biomass Bioenergy* 35(1):626-636, Pergamon Press, United States (2011).

Liden, G., et al., "A Glycerol-3-Phosphate Dehydrogenase-Deficient Mutant of *Saccharomyces cerevisiae* Expressing the Heterologous *XYL1* Gene," *Appl. Environ. Microbiol.* 62(10):3894-3896, American Society for Microbiology, United States (1996).

Lilly, M., et al., "Effect of Increased Yeast Alcohol Acetyltransferase Activity on Flavor Profiles of Wine and Distillates," *Appl. Environ. Microbiol.* 66(2):744-753, American Society for Microbiology, United States (2000).

Lynd, L.R., et al., "Microbial Cellulose Utilization: Fundamentals and Biotechnology," *Microbiol. Mol. Biol. Rev.* 66(3):506-577, American Society for Microbiology, United States (2002).

McLaughlin, S.B., et al., "High-Value Renewable Energy from Prairie Grasses," *Eviron. Sci. Technol.* 36(10):2122-2129, American Chemical Society, United States (2002).

Medina, V.G., et al., "Elimination of glycerol production in anaerobic cultures of *Saccharomyces cerevisiae* engineered for use of acetic acid as electron acceptor," *AEM Appl. Environ. Microbiol.* Manuscript for Publication, AEM Accepts, American Society for Microbiology, United States, Published online ahead of print on Nov. 13, 2009.

Mota, L.J., et al., "Control of the Arabinose Regulation in *Bacillus subtilis* AraR In Vivo: Crucial Roles of Operators, Cooperativity, and DNA Looping," *J. Bacteriol.* 183(14):4190-4201, American Society for Microbiology, United States (2001).

Mota, L.J., et al., "Mode of action of AraR, the key regulator of L-Arabinose metabolism in *Bacillus subtilis*," *Mol. Microbiol.* 33(3):476-489, Blackwell Science Ltd., England (1999).

Nakamura, Y., et al., "Codon usage tabulated from international DNA sequence databases: status for the year 2000." *Nucleic Acids Res.* 28(1):292, Oxford University Press, England (2000).

Páhlman, A-K., et al., "The Yeast Glycerol 3-Phosphatases Gpp1p and Gpp2p Are Required for Glycerol Biosyntheis and Differentially Involved in the Cellular Response to Osmotic, Anaerobic, and Oxidative Stress," *J. Biol. Chem.* 276(2):3553-3563, American Society for Biochemistry and Molecular Biology, United States (2001).

Pagliardini, J., et al., "Quantitative evaluation of yeast's requirement for glycerol formation in very high ethanol performance fed-batch process," *Microb. Cell Fact.* 9:36 (13 pages), BioMed Central, England (2010).

Sá-Nogueira, I., et al., "The *Bacillus subtilis* L-arabinose (*ara*) operon: nucleotide sequence, genetic organization and expression," *Microbiology* 143:957-969, Society for General Microbiology, Great Britain (1997).

Schleif, R., "Regulation of the L-arabinose operon of *Escherichia coli*," *Trends in Genet.* 16(12):559-565, Elsevier Science, Ltd., England (2000).

Schneider, H., "Selective removal of acetic acid from hardwoodspend sulfite liquor using a mutant yeast," *Enz. Micr. Technol.* 19:94-98, Elsevier Science, Inc., United States (1996).

Shanks, R.M.Q., et al., "*Saccharomyces cerevisiae*-Based Molecular Tool Kit for Manipulation of Genes from Gram-Negative Bacteria," *Appl. Environ. Microbiol.* 72(7):5027-5036, American Society for Microbiology, United States (2006).

Shaw, A.J., et al., "Identification of the [FeFe]-Hydrogenase Responsible for Hydrogen Generation in *Thermoanaerobacterium saccharolyticum* and Demonstration of Increased Ethanol Yield via Hydrogenase Knockout," *J. Bacteriol.* 191(20):6457-6464, American Society for Microbiology, United States (2009).

Shaw, A.J., et al., "Natural Competence in *Thermoanaerobacter* and *Thermoanaerobacterium* Species," *Appl. Environ. Microbiol.* 76(14):4713-4719, American Society for Microbiology, United States (2010).

Shaw, A.J., et al., "Marker Removal System for *Thermoanaerobacterium saccharolyticum* and Development of a Markerless Ethanologen," *Appl. Environ. Microbiol.* 77(7):2534-2536, American Society for Microbiology, United States (2011).

Valadi, H., et al., "Improved ethanol production by glycerol-3-phosphate dehydrogertase mutants of *Saccharomyces cerevisiae*," *Appl. Micribiol. Biotechnol.* 50:434-439, Springer-Verlag, Germany (1998).

Van Walsum, G.P., and Lynd, L.R., "Allocation of ATP to Synthesis of Cells and Hydrolytic Enzymes in Cellulolytic Fermentative Microorganisms: Bioenergetics, Kinetics, and Bioprocessing," *Biotechnol. Bioeng.* 58(2&3):316-320, John Wiley & Sons, Inc., United States (1998).

Van Den Berg, M.A., et al., "The Two Acetyl-coenzyme A Synthetases of *Saccharomyces cerevisiae* Differ with Respect to Kinetic Properties and Transcriptional Regulation," *J. Biol. Chem.* 271(46): 28953-28959, American Society for Biochemistry and Molecular Biology United States (1996).

Watanabe, S., et al., "Cloning, Expression, and Characterization of Bacterial L-Arabinose 1-Dehydrogenase Involved in an Alternative Pathway of L-Arabinose Metabolism," *J. Biol. Chem.* 281(5):2612-2623, American Society for Biochemistry and Molecular Biology, United States (2006).

Wolfe, A.J., "The Acetate Switch," *Microbiol. Mol. Biol. Rev.* 69(1):12-50, American Society for Microbiology, United States (2005).

Yoo, C.G., et al., "Optimization of two-stage fractionation process for lignocellulosic biomass using response surface methodology (RSM)," *Biomass and Bioenergy* 35:4901-4909, Elsevier, Ltd., England (2011).

GenBank Accession No. AAA45811, accessed at www.ncbi.nlm.nih.gov/protein/AAA45811, last updated Aug. 2, 1993.

(56) References Cited

OTHER PUBLICATIONS

GenBank Accession No. ACA51668, accessed at www.ncbi.nlm.nih.gov/protein/ACA51668, last updated Apr. 9, 2008.
GenBank Accession No. ACA51669, accessed at www.ncbi.nlm.nih.gov/protein/ACA1669, last updated Apr. 9, 2008.
GenBank Accession No. CAA93155, accessed at www.ncbi.nlm.nih.gov/nuccore/CAA93155, last updated Jan. 29, 1996.
GenBank Accession No. EU313774, accessed at www.ncbi.nlm.nih.gov/nuccore/EU313774, last updated Apr. 9, 2008.
GenBank Accession No. GQ354412, accessed at www.ncbi.nlm.nih.gov/nuccore/GQ354412, last updated Sep. 29, 2009.
GenBank Accession No. HQ157351, accessed at www.ncbi.nlm.nih.gov/nuccore/HQ157351, last updated Feb. 12, 2011.
GenBank Accession No. NP_149326, accessed at www.ncbi.nlm.nih.gov/protein/NP_149326, last updated Dec. 21, 2012.
GenBank Accession No. NP_149327 accessed at www.ncbi.nlm.nih.gov/protein/NP_149327, last updated Dec. 21, 2012.
GenBank Accession No. NP_149328, accessed at www.ncbi.nlm.nih.gov/protein/NP_149328, last updated Dec. 21, 2012.
GenBank Accession No. NP_349476 accessed at www.ncbi.nlm.nih.gov/protein/NP_349476, last updated Dec. 21, 2012.
GenBank Accession No. YP_872855 accessed at www.ncbi.nlm.nih.gov/protein/YP_872855, last updated Dec. 22, 2012.
GenBank Accession No. YP_001306374 accessed at www.ncbi.nlm.nih.gov/protein/YP_001306374, last updated Jan. 11, 2013.
GenBank Accession No. YP_001306375 accessed at www.ncbi.nlm.nih.gov/protein/YP_001306375, last updated Jan. 11, 2013.
GenBank Accession No. YP_001306376 accessed at www.ncbi.nlm.nih.gov/protein/YP_001306376, last updated Jan. 11, 2013.
GenBank Accession No. YP_001422565 accessed at www.ncbi.nlm.nih.gov/protein/YP_001422565, last updated Jan. 24, 2012.
GenBank Accession No. YP_002940318 accessed at www.ncbi.nlm.nih.gov/protein/YP_002940318, last updated Dec. 23, 2012.
GenBank Accession No. YP_002940319 accessed at www.ncbi.nlm.nih.gov/protein/YP_002940319, last updated Dec. 23, 2012.
GenBank Accession No. YP_002940320 accessed at www.ncbi.nlm.nih.gov/protein/YP_002940320, last updated Dec. 23, 2012.
GenBank Accession No. YP_003852249 accessed at www.ncbi.nlm.nih.gov/protein/YP_003852249, last updated Dec. 31, 2012.
"Backtranseq" accessed at emboss.bioinformatics.nl/cgi/bin/emboss/backtranseq, accessed on Mar. 28, 2013.
International Search Report in International Application No. PCT/US2011/035416, European Patent Office, Netherlands, mailed Nov. 17, 2011.
"The SEED: an Annotation/Analysis Tool Provided by FIG" accessed at www.nmpdr.org/FIG/subsys.cgi?user=&ssa_name=L-Arabinose_utilization&request=show_ssa, accessed on May 16, 2013.

* cited by examiner

DETOXIFICATION OF BIOMASS DERIVED ACETATE VIA METABOLIC CONVERSION TO ETHANOL, ACETONE, ISOPROPANOL, OR ETHYL ACETATE

CROSS-REFERENCE TO RELATED APPLICATIONS

This application is the National Stage of International Application Number PCT/US2011/035416, filed May 5, 2011, which claims the benefit of U.S. Provisional Application No. 61/351,133, filed Jun. 3, 2010, and U.S. Provisional Application No. 61/331,657, filed May 5, 2010, which are incorporated by reference herein.

U.S. GOVERNMENT SUPPORT

This invention was partially made with government support under Department of Energy Grants GO18103 and GO17057. The government has certain rights in the invention.

REFERENCE TO A SEQUENCE LISTING SUBMITTED ELECTRONICALLY VIA EFS-WEB

The content of the electronically submitted sequence listing (Name: SequenceListing.ascii.txt; Size: 295,780 bytes; and Date of Creation: Nov. 5, 2012) is herein incorporated by reference in its entirety.

BACKGROUND OF THE INVENTION

Energy conversion, utilization and access underlie many of the great challenges of our time, including those associated with sustainability, environmental quality, security, and poverty. New applications of emerging technologies are required to respond to these challenges. Biotechnology, one of the most powerful of the emerging technologies, can give rise to important new energy conversion processes. Plant biomass and derivatives thereof are a resource for the biological conversion of energy to forms useful to humanity.

Among forms of plant biomass, lignocellulosic biomass ("biomass") is particularly well-suited for energy applications because of its large-scale availability, low cost, and environmentally benign production. In particular, many energy production and utilization cycles based on cellulosic biomass have near-zero greenhouse gas emissions on a life-cycle basis. The primary obstacle impeding the more widespread production of energy from biomass feedstocks is the general absence of low-cost technology for overcoming the recalcitrance of these materials to conversion into useful products. Lignocellulosic biomass contains carbohydrate fractions (e.g., cellulose and hemicellulose) that can be converted into ethanol or other products such as lactic acid and acetic acid. In order to convert these fractions, the cellulose and hemicellulose must ultimately be converted or hydrolyzed into monosaccharides; it is the hydrolysis that has historically proven to be problematic.

Biologically mediated processes are promising for energy conversion. Biomass processing schemes involving enzymatic or microbial hydrolysis commonly involve four biologically mediated transformations: (1) the production of saccharolytic enzymes (cellulases and hemicellulases); (2) the hydrolysis of carbohydrate components present in pre-treated biomass to sugars; (3) the fermentation of hexose sugars (e.g., glucose, mannose, and galactose); and (4) the fermentation of pentose sugars (e.g., xylose and arabinose). These four transformations occur in a single step in a process configuration called consolidated bioprocessing (CBP), which is distinguished from other less highly integrated configurations in that it does not involve a dedicated process step for cellulase and/or hemicellulase production.

CBP offers the potential for lower cost and higher efficiency than processes featuring dedicated cellulase production. The benefits result in part from avoided capital costs, substrate and other raw materials, and utilities associated with cellulase production. In addition, several factors support the realization of higher rates of hydrolysis, and hence reduced reactor volume and capital investment using CBP, including enzyme-microbe synergy and the use of thermophilic organisms and/or complexed cellulase systems. Moreover, cellulose-adherent cellulolytic microorganisms are likely to compete successfully for products of cellulose hydrolysis with non-adhered microbes, e.g., contaminants, which could increase the stability of industrial processes based on microbial cellulose utilization. Progress in developing CBP-enabling microorganisms is being made through two strategies: engineering naturally occurring cellulolytic microorganisms to improve product-related properties, such as yield and titer; and engineering non-cellulolytic organisms that exhibit high product yields and titers to express a heterologous cellulase and hemicellulase system enabling cellulose and hemicellulose utilization.

Biological conversion of lignocellulosic biomass to ethanol or other chemicals requires a microbial catalyst to be metabolically active during the extent of the conversion. For CBP, a further requirement is placed on the microbial catalyst—it must also grow and produce sufficient cellulolytic and other hydrolytic enzymes in addition to metabolic products. A significant challenge for a CBP process occurs when the lignocellulosic biomass contains compounds inhibitory to microbial growth, which is common in natural lignocellulosic feedstocks. Arguably the most important inhibitory compound is acetic acid (acetate), which is released during deacetylation of polymeric substrates. Acetate is particularly inhibitory for CBP processes, as cells must constantly expend energy to export acetate anions, which then freely diffuse back into the cell as acetic acid. This phenomena, combined with the typically low sugar release and energy availability during the fermentation, limits the cellular energy that can be directed towards cell mass generation and enzyme production, which further lowers sugar release.

Removal of acetate prior to fermentation would significantly improve CBP dynamics; however, chemical and physical removal systems are typically too expensive or impractical for industrial application. Thus, there is a need for an alternate acetate removal system for CBP that does not suffer from the same problems associated with these chemical and physical removal systems. As a novel alternative, this invention describes the metabolic conversion of acetate to a less inhibitory compound, such as a non-charged solvent, including but not limited to, acetone, isopropanol, ethyl acetate, or ethanol. Such conversion would negate the most inhibitory effects of acetate while also resulting in several process benefits described below. This invention also describes the adaptation of CBP organisms to growth in the presence of inhibitory compounds encountered in biomass processing, such as acetate.

BRIEF SUMMARY OF THE INVENTION

The invention is generally directed to the reduction or removal of acetate from biomass processing such as the CBP processing of lignocellulosic biomass. The invention is also generally directed to the adaptation of CBP organisms to growth in the presence of inhibitory compounds, including, but not limited to, acetate.

One aspect of the invention relates to a recombinant microorganism comprising one or more native and/or heterologous enzymes that function in one or more engineered metabolic pathways to convert acetate to ethanol, wherein said one or more native and/or heterologous enzymes is activated, upregulated or downregulated. In certain embodiments, the acetate is produced as a by-product of biomass processing. In certain embodiments, the recombinant microorganism produces ethanol. In some embodiments, the recombinant microorganism produces an ethanol yield selected from: (a) at least about 1% more ethanol than is produced by a microorganism without activation, upregulation, or downregulation of one or more native and/or heterologous enzymes; (b) at least about 2% more ethanol than is produced by a microorganism without activation, upregulation, or downregulation of one or more native and/or heterologous enzymes; (c) at least about 3% more ethanol than is produced by a microorganism without activation, upregulation, or downregulation of one or more native and/or heterologous enzymes; (d) at least about 4% more ethanol than is produced by a microorganism without activation, upregulation, or downregulation of one or more native and/or heterologous enzymes; (e) at least about 5% more ethanol than is produced by a microorganism without activation, upregulation, or downregulation of one or more native and/or heterologous enzymes; (f) at least about 6% more ethanol than is produced by a microorganism without activation, upregulation, or downregulation of one or more native and/or heterologous enzymes; (g) at least about 7% more ethanol than is produced by a microorganism without activation, upregulation, or downregulation of one or more native and/or heterologous enzymes; (h) at least about 8% more ethanol than is produced by a microorganism without activation, upregulation, or downregulation of one or more native and/or heterologous enzymes; (i) at least about 9% more ethanol than is produced by a microorganism without activation, upregulation, or downregulation of one or more native and/or heterologous enzymes; (j) at least about 10% more ethanol than is produced by a microorganism without activation, upregulation, or downregulation of one or more native and/or heterologous enzymes; (k) at least about 11% more ethanol than is produced by a microorganism without activation, upregulation, or downregulation of one or more native and/or heterologous enzymes; (l) at least about 12% more ethanol than is produced by a microorganism without activation, upregulation, or downregulation of one or more native and/or heterologous enzymes; (m) at least about 15% more ethanol than is produced by a microorganism without activation, upregulation, or downregulation of one or more native and/or heterologous enzymes; (n) at least about 20% more ethanol than is produced by a microorganism without activation, upregulation, or downregulation of one or more native and/or heterologous enzymes; (o) at least about 30% more ethanol than is produced by a microorganism without activation, upregulation, or downregulation of one or more native and/or heterologous enzymes; (p) at least about 40% more ethanol than is produced by a microorganism without activation, upregulation, or downregulation of one or more native and/or heterologous enzymes; or (q) at least about 50% more ethanol than is produced by a microorganism without activation, upregulation, or downregulation of one or more native and/or heterologous enzymes.

In particular aspects, the engineered metabolic pathways comprise the steps of: (a) conversion of acetate to acetyl-CoA and (b) conversion of acetyl-CoA to ethanol. In certain embodiments, acetate is converted to acetyl-CoA by an acetyl-CoA transferase (ACS). In further embodiments, the acetyl-CoA transferase (ACS) is encoded by an ACS1 polynucleotide. In some embodiments, acetate is converted to acetyl-P by an acetate kinase, and acetyl-P is converted to acetyl-CoA by a phosphotransacetylase. In further embodiments, the acetate kinase and the phosphotransacetylase are from one or more of an *Escherichia*, a *Thermoanaerobacter*, a *Clostridia*, or a *Bacillus* species.

In some embodiments, acetyl-CoA is converted to acetaldehyde by an acetaldehyde dehydrogenase, and acetaldehyde is converted to ethanol by an alcohol dehydrogenase. In further embodiments, the acetaldehyde dehydrogenase is from *C. phytofermentans*. In some embodiments, the acetyl-CoA is converted to ethanol by a bifunctional acetaldehyde/alcohol dehydrogenase. In further embodiments, the bifunctional acetaldehyde/alcohol dehydrogenase is from *E. coli, C. acetobutylicum, T. saccharolyticum, C. thermocellum,* or *C. phytofermentans*. In some embodiments, the bifunctional acetaldehyde/alcohol dehydrogenase is from *E. coli, T. saccharolyticum, C. phytofermentans, Chlamydomonas reinhardtii, Piromyces* SP E2, or *Bifidobacterium adolescentis*. In certain embodiments, the bifunctional acetaldehyde/alcohol dehydrogenase is selected from SEQ ID NO:50, SEQ ID NO:52, SEQ ID NO:54, SEQ ID NO:56, SEQ ID NO:58, SEQ ID NO:62, SEQ ID NO:64, or SEQ ID NO:66.

In particular aspects, one or more downregulated native enzymes are encoded by a gpd1 polynucleotide, a gpd2 polynucleotide, or both a gpd1 polynucleotide and a gpd2 polynucleotide.

In certain embodiments, the recombinant microorganism that converts acetate to ethanol is selected from the group consisting of *Saccharomyces cerevisiae, Kluyveromyces lactis, Kluyveromyces marxianus, Pichia pastoris, Yarrowia lipolytica, Hansenula polymorpha, Phaffia rhodozyma, Candida utilis, Arxula adeninivorans, Pichia stipitis, Debaryomyces hansenii, Debaryomyces polymorphus, Schizosaccharomyces pombe, Candida albicans,* and *Schwanniomyces occidentalis*. In a further embodiment, the recombinant microorganism is *Saccharomyces cerevisiae*.

Another aspect of the invention relates to a recombinant microorganism comprising one or more native and/or heterologous enzymes that function in one or more engineered metabolic pathways to convert acetate to acetone, wherein said one or more native and/or heterologous enzymes is activated, upregulated or downregulated. In certain embodiments, the acetate is produced as a by-product of biomass processing. In certain embodiments, the recombinant microorganism produces acetone.

In further embodiments, the recombinant microorganism produces an acetone yield selected from (a) at least about 0.05-fold more acetone than is produced by a microorganism without activation, upregulation, or downregulation of one or more native and/or heterologous enzymes; (b) at least about 0.1-fold more acetone than is produced by a microorganism without activation, upregulation, or downregulation of one or more native and/or heterologous enzymes; (c) at least about 0.5-fold more acetone than is produced by a microorganism without activation, upregulation, or downregulation of one or more native and/or heterologous enzymes; (d) at least about 1.0-fold more acetone than is produced by a microorganism without activation, upregulation, or downregulation of one or more native and/or heterologous enzymes; (e) at least about 2.0-fold more acetone than is produced by a microorganism without activation, upregulation, or downregulation of one or more native and/or heterologous enzymes; or (f) at least about 5.0-fold more acetone than is produced by a microorganism without activation, upregulation, or downregulation of one or more native and/or heterologous enzymes.

In particular aspects, the engineered metabolic pathways comprise the steps of: (a) conversion of acetate to acetyl-CoA; (b) conversion of acetyl-CoA to acetoacetyl-CoA; (c) conversion of acetoacetyl-CoA to acetoacetate; and (d) conversion of acetoacetate to acetone. In some embodiments, the acetate is converted to acetyl-CoA by an acetyl-CoA synthetase. In further embodiments, the acetyl-CoA synthetase is encoded by a polynucleotide selected from the group consisting of a yeast ACS1 polynucleotide and a yeast ACS2 polynucleotide. In certain embodiments, the yeast ACS1 polynucleotide is from *Saccharomyces cerevisiae* or *Saccharomyces kluyveri*. In certain embodiments, the yeast ACS2 polynucleotide is from *Saccharomyces cerevisiae* or *Saccharomyces kluyveri*. In some embodiments, the acetate is converted to acetyl-CoA by a CoA transferase.

In some embodiments, the acetate is converted to acetyl-P by an acetate kinase, and acetyl-P is converted to acetyl-CoA by a phosphotransacetylase. In further embodiments, the acetate kinase and the phosphotransacetylase are from *T. saccharolyticum*. In some embodiments, the acetate kinase is from *T. saccharolyticum* DSM 8691 (GenBank Accession No. ACA51668) and the phosphotransacetylase is from *T. saccharolyticum* DSM 8691 (GenBank Accession No. ACA51669).

In some embodiments, the acetyl-CoA is converted to acetoacetyl-CoA by a thiolase. In some embodiments, the acetoacetyl-CoA is converted to acetoacetate by a CoA transferase. In some embodiments, the acetoacetate is converted to acetone by an acetoacetate decarboxylase. In further embodiments, the thiolase, the CoA transferase, and the acetoacetate decarboxylase are from *C. acetobutylicum*. In certain embodiments, the thiolase is from *C. acetobutylicum* or *T. thermosaccharolyticum*. In certain embodiments, the thiolase is selected from *Thermosipho melanesiensis* DSM 12029 (GenBank Accession No. YP_001306374), *Kosmotoga olearia* DSM 21960 (GenBank Accession No. YP_002940320), or *Thermoanaerobacterium thermosaccharolyticum* DSM 571 (GenBank Accession No. YP_003852249). In certain embodiments, the CoA transferase is from a bacterial source. In further embodiments, the bacterial source is selected from the group consisting of *Thermoanaerobacter tengcongensis, Thermoanaerobacterium thermosaccharolyticum, Thermosipho africanus*, and *Paenibacillus macerans*. In certain embodiments, the CoA transferase is selected from *Thermosipho melanesiensis* DSM 12029 (GenBank Accession No. YP_001306376), *Kosmotoga olearia* DSM 21960 (GenBank Accession No. YP_002940319), *Thermosipho melanesiensis* DSM 12029 (GenBank Accession No. YP_001306375), *Kosmotoga olearia* DSM 21960 (GenBank Accession No. YP_002940318), or combinations thereof. In certain embodiments, the acetoacetate decarboxylase is from a bacterial source. In further embodiments, the bacterial source is selected from the group consisting of *C. acetobutylicum, Paenibacillus macerans, Acidothermus cellulolyticus, Bacillus amyloliquefaciens*, and *Rubrobacter xylanophilus*. In certain embodiments, the *Bacillus amyloliquefaciens* is *Bacillus amyloliquefaciens* FZB42 BGSC 10A6 (GenBank Accession No. YP_001422565).

In certain embodiments, the recombinant microorganism that converts acetate to acetone is *Escherichia coli*. In certain embodiments, the recombinant microorganism is a thermophilic or mesophilic bacterium. In further embodiments, the thermophilic or mesophilic bacterium is a species of the genera *Thermoanaerobacterium, Thermoanaerobacter, Clostridium, Geobacillus, Saccharococcus, Paenibacillus, Bacillus, Caldicellulosiruptor, Anaerocellum*, or *Anoxybacillus*. In further embodiments, the recombinant microorganism is a bacterium selected from the group consisting of: *Thermoanaerobacterium thermosulfurigenes, Thermoanaerobacterium aotearoense, Thermoanaerobacterium polysaccharolyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter thermohydrosulfuricus, Thermoanaerobacter ethanolicus, Thermoanaerobacter brocki, Clostridium thermocellum, Clostridium cellulolyticum, Clostridium phytofermentans, Clostridium straminosolvens, Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchalkensis, Anoxybacillus gonensis, Caldicellulosiruptor acetigenus, Caldicellulosiruptor saccharolyticus, Caldicellulosiruptor kristjanssonii, Caldicellulosiruptor owensensis, Caldicellulosiruptor lactoaceticus*, and *Anaerocellum thermophilum*. In other embodiments, the microorganism is selected from the group consisting of *Clostridium thermocellum*, and *Thermoanaerobacterium saccharolyticum*.

In other embodiments, the recombinant microorganism is eukaryotic. In certain embodiments, the recombinant microorganism is a yeast selected from the group consisting of *Saccharomyces cerevisiae, Kluyveromyces lactis, Kluyveromyces marxianus, Pichia pastoris, Yarrowia lipolytica, Hansenula polymorpha, Phaffia rhodozyma, Candida utliis, Arxula adeninivorans, Pichia stipitis, Debaryomyces hansenii, Debaryomyces polymorphus, Schizosaccharomyces pombe, Candida albicans*, and *Schwanniomyces occidentalis*. In further embodiments, the recombinant microorganism is *Saccharomyces cerevisiae*.

Another aspect of the invention relates to a recombinant microorganism comprising one or more native and/or heterologous enzymes that function in one or more engineered metabolic pathways to convert acetate to isopropanol, wherein said one or more native and/or heterologous enzymes is activated, upregulated or downregulated. In certain embodiments, the acetate is produced as a by-product of biomass processing. In certain embodiments, the recombinant microorganism produces isopropanol.

In certain aspects, the engineered metabolic pathways comprise the steps of: (a) conversion of acetate to acetyl-CoA; (b) conversion of acetyl-CoA to acetoacetyl-CoA; (c) conversion of acetoacetyl-CoA to acetoacetate; (d) conversion of acetoacetate to acetone; and (e) conversion of acetone to isopropanol.

In some embodiments, the acetate is converted to acetyl-CoA by an acetyl-CoA synthetase. In further embodiments, the acetyl-CoA synthetase is encoded by a polynucleotide selected from the group consisting of a yeast ACS1 polynucleotide and a yeast ACS2 polynucleotide.

In some embodiments, the acetyl-CoA is converted to acetoacetyl-CoA by a thiolase.

In some embodiments, the acetoacetyl-CoA is converted to acetoacetate by a CoA transferase. In further embodiments, the CoA transferase is from a bacterial source. In certain embodiments, the bacterial source is selected from the group consisting of *Thermoanaerobacter tengcongensis*,

*Thermoanaerbacterium thermosaccharolyticum, Thermosipho africanus,* and *Paenibacillus macerans.*

In some embodiments, the acetoacetate is converted to acetone by an acetoacetate decarboxylase. In further embodiments, the acetoacetate decarboxylase is from a bacterial source. In certain embodiments, the bacterial source is selected from the group consisting of *C. acetobutylicum, Paenibacillus macerans, Acidothermus cellulolyticus, Bacillus amyloliquefaciens,* and *Rubrobacter xylanophilus.*

In some embodiments, the acetone is converted to isopropanol by an alcohol dehydrogenase.

In certain embodiments, the recombinant microorganism that converts acetate to isopropanol is selected from the group consisting of *Saccharomyces cerevisiae, Kluyveromyces lactis, Kluyveromyces marxianus, Pichia pastoris, Yarrowia lipolytica, Hansenula polymorpha, Phaffia rhodozyma, Candida utliis, Arxula adeninivorans, Pichia stipitis, Debaryomyces hansenii, Debaryomyces polymorphus, Schizosaccharomyces pombe, Candida albicans,* and *Schwanniomyces occidentalis.* In further embodiments, the recombinant microorganism is *Saccharomyces cerevisiae.*

In certain embodiments, the recombinant microorganism that converts acetate to isopropanol is selected a thermophilic or mesophilic bacterium. In some embodiments, the thermophilic or mesophilic bacterium is a species of the genera *Thermoanaerobacterium, Thermoanaerobacter, Clostridium, Geobacillus, Saccharococcus, Paenibacillus, Bacillus, Caldicellulosiruptor, Anaerocellum,* or *Anoxybacillus.* In some embodiments, the recombinant microorganism is a bacterium selected from the group consisting of: *Thermoanaerobacterium thermosulfurigenes, Thermoanaerobacterium aotearoense, Thermoanaerobacterium polysaccharolyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter thermohydrosulfuricus, Thermoanaerobacter ethanolicus, Thermoanaerobacter brocki, Clostridium thermocellum, Clostridium cellulolyticum, Clostridium phytofermentans, Clostridium straminosolvens, Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchalkensis, Anoxybacillus gonensis, Caldicellulosiruptor acetigenus, Caldicellulosiruptor saccharolyticus, Caldicellulosiruptor kristjanssonii, Caldicellulosiruptor owensensis, Caldicellulosiruptor lactoaceticus,* and *Anaerocellum thermophilum.* In certain embodiments, the recombinant microorganism is *Thermoanaerobacterium saccharolyticum.*

In other aspects, the engineered metabolic pathways for the conversion of acetate to isopropanol comprise the steps of: (a) conversion of acetate to acetyl-P and acetyl-P to acetyl-CoA; (b) conversion of acetyl-CoA to acetoacetyl-CoA; (c) conversion of acetoacetyl-CoA to acetoacetate; (d) conversion of acetoacetate to acetone; and (e) conversion of acetone to isopropanol. In some aspects, the one or more down-regulated native enzymes in the recombinant microorganism that produces isopropanol are selected from phosphotransacetylase, acetate kinase, or both.

In some embodiments, the acetate is converted to acetyl-P by an acetate kinase; and the acetyl-P is converted to acetyl-CoA by a phosphotransacetylase. In certain embodiments, the acetate kinase and the phosphotransacetylase are from *T. saccharolyticum*. In certain embodiments, the acetate kinase is from *T. saccharolyticum* DSM 8691 (GenBank Accession No. ACA51668) and the phosphotransacetylase is from *T. saccharolyticum* DSM 8691 (GenBank Accession No. ACA51669).

In some embodiments, the acetyl-CoA is converted to acetoacetyl-CoA by a thiolase. In certain embodiments, the thiolase is selected from *Thermosipho melanesiensis* DSM 12029 (GenBank Accession No. YP_001306374), *Kosmotoga olearia* DSM 21960 (GenBank Accession No. YP_002940320), or *Thermoanaerobacterium thermosaccharolyticum* DSM 571 (GenBank Accession No. YP_003852249).

In some embodiments, the acetoacetyl-CoA is converted to acetoacetate by a CoA transferase. In certain embodiments, the CoA transferase is from a bacterial source. In some embodiments, the CoA transferase is selected from *Thermosipho melanesiensis* DSM 12029 (GenBank Accession No. YP_001306376), *Kosmotoga olearia* DSM 21960 (GenBank Accession No. YP_002940319), *Thermosipho melanesiensis* DSM 12029 (GenBank Accession No. YP_001306375), *Kosmotoga olearia* DSM 21960 (GenBank Accession No. YP_002940318), or combinations thereof.

In some embodiments, the acetoacetate is converted to acetone by an acetoacetate decarboxylase. In certain embodiments, the acetoacetate decarboxylase is from a bacterial source. In some embodiments, the acetoacetate decarboxylase is *Bacillus amyloliquefaciens* FZB42 BGSC 10A6 (GenBank Accession No. YP_001422565).

In some embodiments, the acetone is converted to isopropanol by an alcohol dehydrogenase. In certain embodiments, the alcohol dehydrogenase is a secondary alcohol dehydrogenase (adhB) from *T. ethanolicus*.

Another aspect of the invention relates to a recombinant microorganism comprising one or more native and/or heterologous enzymes that function in one or more engineered metabolic pathways to convert acetate to ethyl acetate, wherein said one or more native and/or heterologous enzymes is activated, upregulated or downregulated. In certain embodiments, the acetate is produced as a by-product of biomass processing. In certain embodiments, the recombinant microorganism produces ethyl acetate.

In certain aspects, the engineered metabolic pathways comprise the steps of: (a) conversion of acetate to acetyl-CoA and (b) conversion of acetyl-CoA and ethanol to ethyl acetate. In some embodiments, the acetate is converted to acetyl-CoA by an acetyl-CoA synthetase. In further embodiments, the acetyl-CoA synthetase is encoded by a polynucleotide selected from the group consisting of a yeast ACS1 polynucleotide and a yeast ACS2 polynucleotide.

In some embodiments, the acetate is converted to acetyl-P by an acetate kinase, and the acetyl-P is converted to acetyl-CoA by a phosphotransacetylase.

In some embodiments, the acetyl-CoA and ethanol are converted to ethyl acetate by an alcohol acetyltransferase. In further embodiments, the alcohol acetyltransferase is encoded by a yeast ATF1 polynucleotide.

In some embodiments, the recombinant microorganism that converts acetate to ethyl acetate is a thermophilic or mesophilic bacterium. In further embodiments, the thermophilic or mesophilic bacterium is a species of the genera *Thermoanaerobacterium, Thermoanaerobacter, Clostridium, Geobacillus, Saccharococcus, Paenibacillus, Bacillus, Caldicellulosiruptor, Anaerocellum,* or *Anoxybacillus.* In certain embodiments, the microorganism is a bacterium selected from the group consisting of: *Thermoanaerobacterium thermosulfurigenes, Thermoanaerobacterium aotearoense, Thermoanaerobacterium polysaccharo-*

*lyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter thermohydrosulfuricus, Thermoanaerobacter ethanolicus, Thermoanaerobacter brocki, Clostridium thermocellum, Clostridium cellulolyticum, Clostridium phytofermentans, Clostridium straminosolvens, Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchatkensis, Anoxybacillus gonensis, Caldicellulosiruptor acetigenus, Caldicellulosiruptor saccharolyticus, Caldicellulosiruptor kristjanssonii, Caldicellulosiruptor owensensis, Caldicellulosiruptor lactoaceticus*, and *Anaerocellum thermophilum*. In particular aspects, the recombinant microorganism is selected from the group consisting of *Clostridium thermocellum*, and *Thermoanaerobacterium saccharolyticum*.

In other embodiments, the recombinant microorganism is eukaryotic. In certain embodiments, the recombinant microorganism is a yeast selected from the group consisting of *Saccharomyces cerevisiae, Kluyveromyces lactis, Kluyveromyces marxianus, Pichia pastoris, Yarrowia lipolytica, Hansenula polymorpha, Phaffia rhodozyma, Candida utliis, Arxula adeninivorans, Pichia stipitis, Debaryomyces hansenii, Debaryomyces polymorphus, Schizosaccharomyces pombe, Candida albicans*, and *Schwanniomyces occidentalis*. In further embodiments, the recombinant microorganism is *Saccharomyces cerevisiae*.

In other aspects of the invention, the one or more downregulated native enzymes of the recombinant microorganisms of the invention is encoded by a gpd1 polynucleotide, a gpd2 polynucleotide, or both a gpd1 polynucleotide and a gpd2 polynucleotide. In certain aspects, the recombinant microorganisms of the invention further comprise a native and/or heterologous gpd1 polynucleotide operably linked to a native gpd2 promoter polynucleotide or a native and/or heterologous gpd2 polynucleotide operably linked to a native gpd1 promoter polynucleotide.

In additional aspects of the invention, the recombinant microorganisms of the invention further comprise a mutation in a hydrogenase. In some embodiments, the hydrogenase is an hfs hydrogenase from *T. saccharolyticum*. In certain embodiments, the mutation in an hfs hydrogenase from *T. saccharolyticum* is selected from: (a) a deletion of an adenine at position 2219 in hfsA (or 1545) of GenBank Accession No. GQ354412; (b) a deletion of an adenine at position 2954 in hfsB (or 1546) of GenBank Accession No. GQ354412; (c) a deletion of an adenine at position 2736 in hfsB (or 1546) of GenBank Accession No. GQ354412; (d) a deletion of an adenine at position 4272 in hfsC (or 1547) of GenBank Accession No. GQ354412; (e) a deletion of a guanine at position 5386 in hfsD (or 1548) of GenBank Accession No. GQ354412; (f) a deletion of a guanine at position 5980 in hfsD (or 1548) of GenBank Accession No. GQ354412; (g) a deletion of an adenine at position 5514 in hfsD (or 1548) of GenBank Accession No. GQ354412; (h) or combinations of one or more of (a)-(g).

Another aspect of the invention relates to a recombinant microorganism comprising one or more native and/or heterologous enzymes that function in one or more engineered metabolic pathways to convert acetate to ethanol, wherein said one or more native and/or heterologous enzymes is a bifunctional acetaldehyde/alcohol dehydrogenase. In some embodiments, the bifunctional acetaldehyde/alcohol dehydrogenase is from *E. coli, C. acetobutylicum, T. saccharolyticum, C. thermocellum*, or *C. phytofermentans*. In other embodiments, the bifunctional acetaldehyde/alcohol dehydrogenase is from *E. coli, T. saccharolyticum, C. phytofermentans, Chlamydomonas reinhardtii, Piromyces* SP E2, or *Bifidobacterium adolescentis*. In further embodiments, bifunctional acetaldehyde/alcohol dehydrogenase is selected from SEQ ID NO:50, SEQ ID NO:52, SEQ ID NO:54, SEQ ID NO:56, SEQ ID NO:58, SEQ ID NO:62, SEQ ID NO:64, or SEQ ID NO:66.

The invention also relates to a process for converting biomass to ethanol, acetone, isopropanol, or ethyl acetate comprising contacting biomass with a recombinant microorganism of the invention. In certain aspects, the biomass comprises lignocellulosic biomass. In some embodiments, the lignocellulosic biomass is selected from the group consisting of grass, switch grass, cord grass, rye grass, reed canary grass, mixed prairie grass, miscanthus, sugar-processing residues, sugarcane bagasse, sugarcane straw, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, agave, and combinations thereof. In certain embodiments, the biomass is corn mash or corn starch.

In certain aspects, the process reduces or removes acetate from the consolidated bioprocessing (CBP) media. In some embodiments, the reduction or removal of acetate occurs during fermentation. In certain aspects, the process requires less neutralizing base to maintain the pH during fermentation than for a microorganism without activation, upregulation, or downregulation of one or more native and/or heterologous enzymes as described herein.

The invention further relates to a fermentation medium comprising one or more recombinant microorganisms of the invention.

The invention also relates to an engineered metabolic pathway for reducing or removing acetate from consolidated bioprocessing (CBP) media utilizing the recombinant microorganisms of the invention.

In certain aspects, the recombinant microorganism comprising one or more native and/or heterologous enzymes that function in one or more of the engineered metabolic pathways described herein is a yeast strain that has improved tolerance and robustness to growth in the presence of a biomass inhibitor, including but not limited to, acetate and other CBP by-products.

In some embodiments, the recombinant microorganism is a yeast strain having a specific growth rate ($h^{-1}$) in the presence of acetate selected from: a) at least about 0.02, b) at least about 0.04, c) at least about 0.06, d) at least about 0.08, e) at least about 0.1, f) at least about 0.12, or g) at least about 0.14. In particular aspects, the recombinant microorganism is a yeast strain selected from M1360, M1361, or M1362. In some aspects, the recombinant microorganism is yeast strain M1927. In some aspects, the specific growth rate ($h^{-1}$) is obtained using a medium comprising xylose.

In some embodiments, the recombinant microorganism is a yeast strain having an optical density in the presence of acetate selected from: (a) at least about 0.2, (b) at least about 0.3, (c) at least about 0.4, (d) at least about 0.5, or (e) at least about 0.6. In particular aspects, the recombinant microorganism is yeast strain M1339. In some aspects, the optical density is obtained using a medium comprising xylose.

In some embodiments, the recombinant microorganism is a yeast strain having a theoretical anaerobic biomass yield (%), at 5%, 7%, or 9% solids equivalent pressate, selected from: a) at least about 10%; b) at least about 20%; c) at least about 30%; d) at least about 40%; e) at least about 50%; f) at least about 60%; g) at least about 70%; h) at least about 80%; i) at least about 90%; or j) at least about 100%. In particular aspects, the recombinant microorganism is selected from yeast strain M1360, M1443, or M1577.

In some embodiments, the recombinant microorganism is a yeast strain having a specific growth rate ($h^{-1}$) in the presence of 5-hydroxymethylfurfural and furfural selected from: a) at least about 0.05, b) at least about 0.1, c) at least about 0.15, or d) at least about 0.2. In particular aspects, the recombinant microorganism is yeast strain M1715 or M1577. In some aspects, the specific growth rate ($h^{-1}$) is obtained using a medium comprising xylose.

In some embodiments, the recombinant microorganism is a yeast strain having a biomass yield (g/g), at 13%, 15%, or 17% solids equivalent pressate, selected from: a) at least about 0.02; b) at least about 0.04; c) at least about 0.06; or d) at least about 0.08. In particular aspects, the recombinant microorganism is selected from yeast strain M1760, M1818, or M1819.

The invention also relates to yeast strains that have improved tolerance and robustness to growth in the presence of a biomass inhibitor. In some embodiments, the yeast strain adapted for growing in the presence of acetate has a specific growth rate ($h^{-1}$) in the presence of a biomass inhibitor selected from: a) at least about 0.005, b) at least about 0.01, c) at least about 0.02, d) at least about 0.04, e) at least about 0.06, f) at least about 0.08, g) at least about 0.1, h) at least about 0.12, or i) at least about 0.14. In some embodiments, the biomass inhibitor comprises acetate. In further embodiments, the yeast strain is selected from M1339, M1360, M1361, or M1362. In some embodiments, the specific growth rate ($h^{-1}$) is obtained using a medium comprising xylose.

In some embodiments, the yeast strain adapted for growing in the presence of a biomass inhibitor has a theoretical biomass yield (%), at 5%, 7%, or 9% solids equivalent pressate, selected from: a) at least about 10%; b) at least about 20%; c) at least about 30%; d) at least about 40%; e) at least about 50%; f) at least about 60%; g) at least about 70%; h) at least about 80%; i) at least about 90%; or j) at least about 100%. In some embodiments, the biomass inhibitor comprises acetate. In further embodiments, the yeast strain is selected from M1360, M1443, or M1577.

In some embodiments, the yeast strain adapted for growing in the presence of a biomass inhibitor has a specific growth rate ($h^{-1}$) selected from: a) at least about 0.05, b) at least about 0.1, c) at least about 0.15, or d) at least about 0.2. In some embodiments, the biomass inhibitor comprises acetate. In further embodiments, the yeast strain is selected from M1715 or M1577. In some embodiments, the specific growth rate ($h^{-1}$) is obtained using a medium comprising xylose.

In some embodiments, the yeast strain adapted for growing in the presence of a biomass inhibitor has a biomass yield (g/g), at 13%, 15%, or 17% solids equivalent pressate, selected from: a) at least about 0.02; b) at least about 0.04; c) at least about 0.06; or d) at least about 0.08. In some embodiments, the biomass inhibitor comprises acetate. In further embodiments, the yeast strain of claim 93, wherein said yeast strain is selected from M1760, M1818, or M1819.

In some embodiments, the yeast strain adapted for growing in the presence of a biomass inhibitor produces an ethanol yield selected from: (a) at least about 1% more ethanol than is produced by a microorganism that has not been adapted for growing in the presence of the biomass inhibitor; (b) at least about 5% more ethanol than is produced by a microorganism that has not been adapted for growing in the presence of the biomass inhibitor; (c) at least about 10% more ethanol than is produced by a microorganism that has not been adapted for growing in the presence of the biomass inhibitor; (d) at least about 20% more ethanol than is produced by a microorganism that has not been adapted for growing in the presence of the biomass inhibitor; (e) at least about 30% more ethanol than is produced by a microorganism that has not been adapted for growing in the presence of the biomass inhibitor; (f) at least about 40% more ethanol than is produced by a microorganism that has not been adapted for growing in the presence of the biomass inhibitor; (g) at least about 50% more ethanol than is produced by a microorganism that has not been adapted for growing in the presence of the biomass inhibitor; (h) at least about 60% more ethanol than is produced by a microorganism that has not been adapted for growing in the presence of the biomass inhibitor, (i) at least about 70% more ethanol than is produced by a microorganism that has not been adapted for growing in the presence of the biomass inhibitor; (j) at least about 80% more ethanol than is produced by a microorganism that has not been adapted for growing in the presence of the biomass inhibitor; (k) at least about 90% more ethanol than is produced by a microorganism that has not been adapted for growing in the presence of the biomass inhibitor; (l) at least about 95% more ethanol than is produced by a microorganism that has not been adapted for growing in the presence of the biomass inhibitor. In some embodiments, the yeast strain is selected from M1927 or M2108. In further embodiments, the yeast strain is M2108.

In some embodiments, the yeast strain adapted for growing in the presence of a biomass inhibitor, in a simultaneous saccharification and fermentation (SSF) performed at 38° C., produces an increased ethanol yield compared to an ethanol yield produced by a microorganism that has not been adapted for growing in the presence of the biomass inhibitor. In certain embodiments, the increased ethanol yield is selected from: (a) at least about 1%; (b) at least about 5%; (c) at least about 10%; (d) at least about 20%; (e) at least about 30%; (f) at least about 40%; (g) at least about 50%; (h) at least about 60%; (i) at least about 70%; (j) at least about 80%; (k) at least about 90%; (l) at least about 95%.

In certain aspects, the acetate present in the biomass inhibitor is an amount selected from a) at least about 0.1 g/L; b) at least about 1 g/L; c) at least about 2 g/L; d) at least about 3 g/L; e) at least about 4 g/L; f) at least about 5 g/L; g) at least about 6 g/L; h) at least about 7 g/L; or i) at least about 8 g/L. In other aspects, the acetate present in the biomass inhibitor is an amount selected from a) at least about 0.01% (w/v); b) at least about 0.1% (w/v); c) at least about 0.2% (w/v); d) at least about 0.3% (w/v); e) at least about 0.4% (w/v); f) at least about 0.5% (w/v); g) at least about 0.6% (w/v); h) at least about 0.7% (w/v); or i) at least about 0.8% (w/v).

The invention also relates to methods for producing yeast strains adapted for growing in the presence of a biomass inhibitor. In some embodiments, the method for producing a yeast strain of the invention adapted for growing in the presence of a biomass inhibitor, comprises continuously incubating a yeast strain in the presence of the biomass inhibitor. In further embodiments, the biomass inhibitor comprises acetate.

The invention also relates to a yeast strain adapted for growing in the presence of a biomass inhibitor produced by a process. In some embodiments, a yeast strain of the invention adapted for growing in the presence of a biomass inhibitor is produced by a process comprising continuously incubating a yeast strain in the presence of the biomass inhibitor. In further embodiments, the biomass inhibitor comprises acetate.

Another aspect of the invention relates to a method for generating a recombinant yeast host cell comprising at least one gene of interest, wherein said method comprises: a) generating a nucleotide sequence that is capable of homologous recombination with a yeast host cell and that comprises said at least one gene of interest, at least one positive selection marker, and at least one negative selection marker; b) transforming a yeast host cell with said nucleotide sequence to obtain a first population of transformants of said yeast host cell; c) selecting for resistance to said at least one positive selection marker to obtain yeast host cells transformed with said nucleotide sequence; d) transforming the yeast host cells of c) with a second nucleotide sequence capable of removing said at least one positive selection marker and said at least one negative selection marker from the yeast host cell; and e) selecting for resistance to 5-fluorodeoxyuridine (FUDR) to obtain recombinant yeast host cells transformed with said at least one gene of interest, wherein said negative selection marker comprises the thymidine kinase gene from Herpes Simplex Virus, which creates sensitivity to 5-fluorodeoxyuridine (FUDR). In some aspects the method further comprises transforming the yeast host cell of c) with a nucleotide sequence that is capable of homologous recombination with said yeast host cell and that comprises said at least one gene of interest, a second positive selection marker, and at least one negative selection marker. In some aspects, the yeast host cell is *S. cerevisiae*.

BRIEF DESCRIPTION OF THE DRAWINGS/FIGURES

Figure 7:
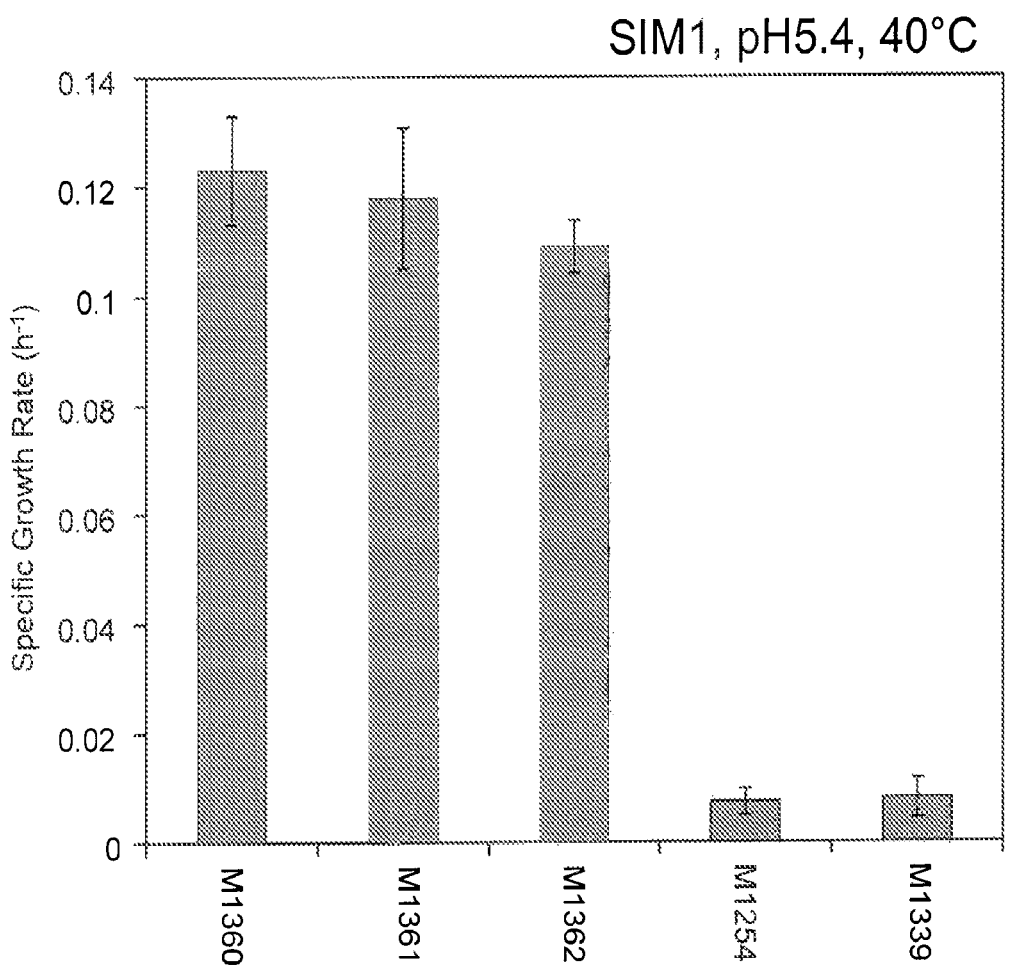

FIG. 7 is a graph depicting the specific growth rate of strains M1360, M1361, M1362, M1254, and M1339 on xylose in the presence of acetate, nine other acids, and five aldehydes. The acids include lactic, 2-furoic, ferulic, 3,4-dihydroxybenzoic, 3,5-dihydroxybenzoic, gallic, homovanillic, syringic, and vanillic acid; the aldehydes include furfural, 5-hydroxymethylfurfural (HMF), 3,4-dihydroxybenzaldehyde, syringaldehyde, and vanillin.

Figure 8:
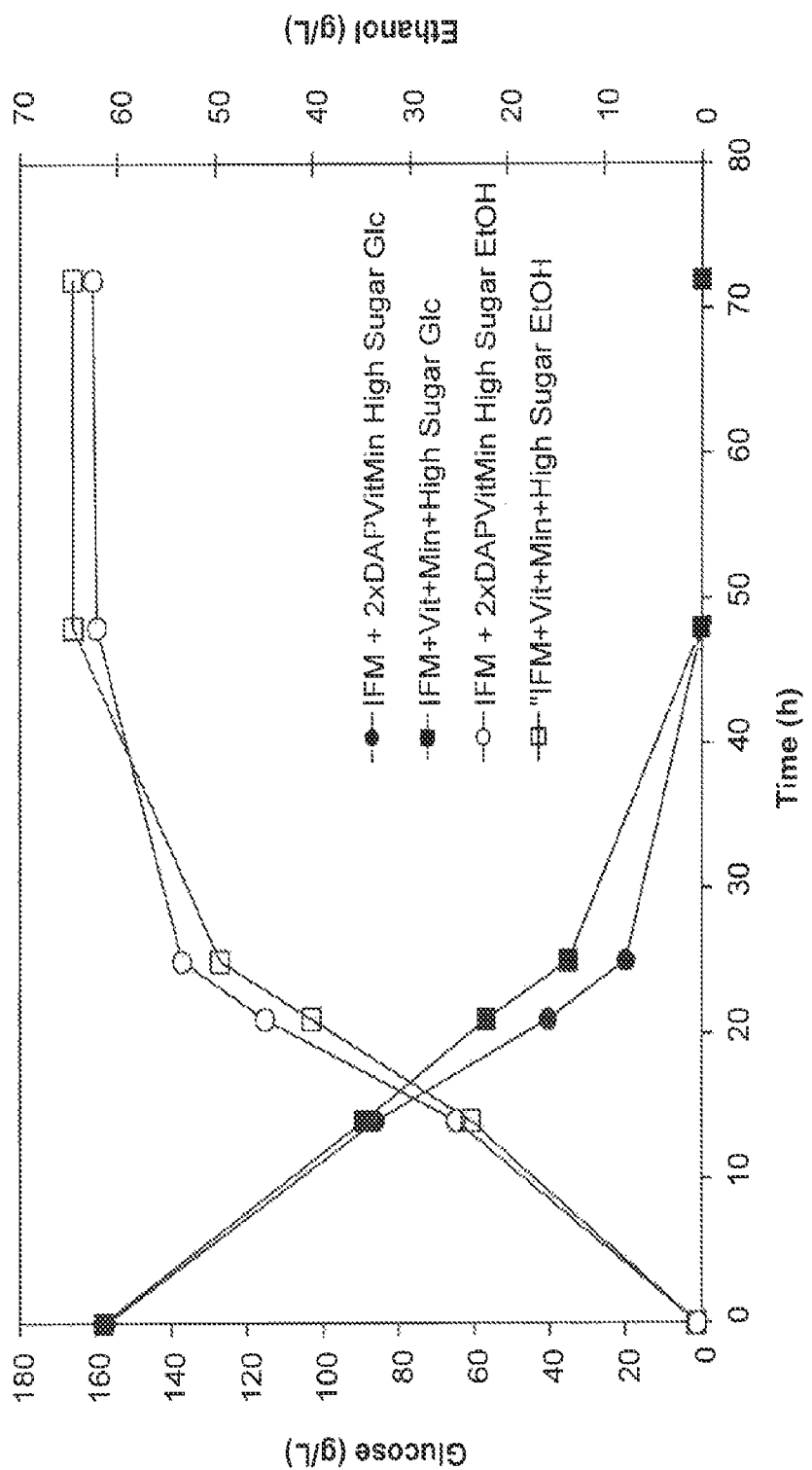

FIG. 8 is a graph depicting performance of strain M1360 grown at 40° C. on Industrial Fermentation Medium (IFM), as measured by glucose utilization (g/L) and ethanol production (g/L).

Figure 9:
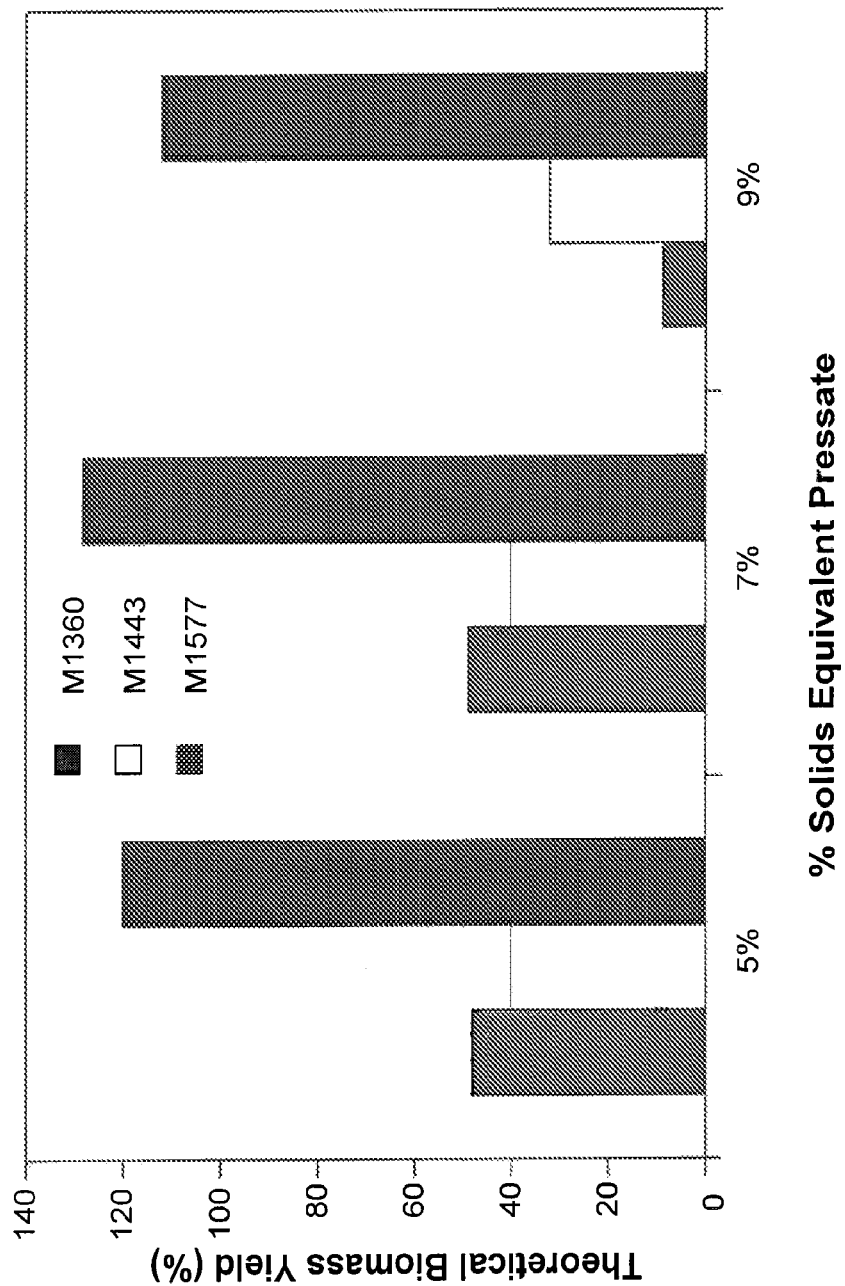

FIG. 9 is a graph depicting theoretical biomass yield (%) of strains M1360, M1443, and M1577 in process conditions at 5%, 7%, and 9% solids equivalent pressate.

Figure 10:
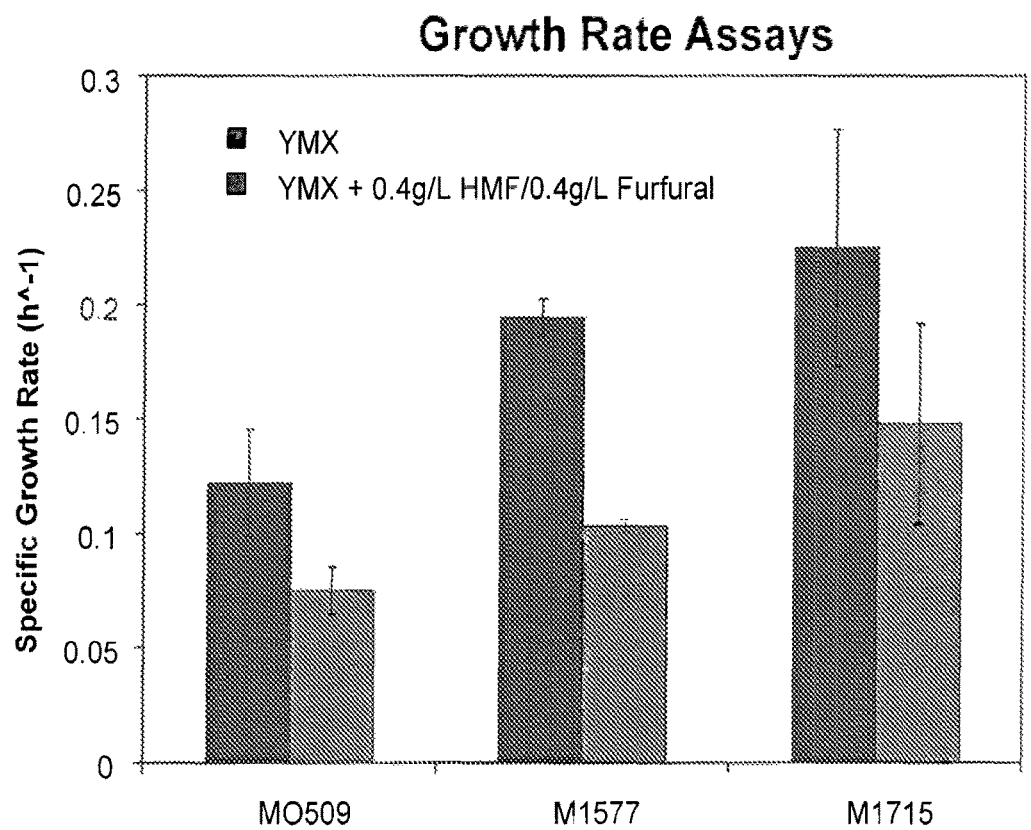

FIG. 10 is a graph depicting the specific growth rate of strains M0509, M1577, and M1715 on xylose and on xylose in the presence of inhibitors HMF and furfural.

Figure 11:
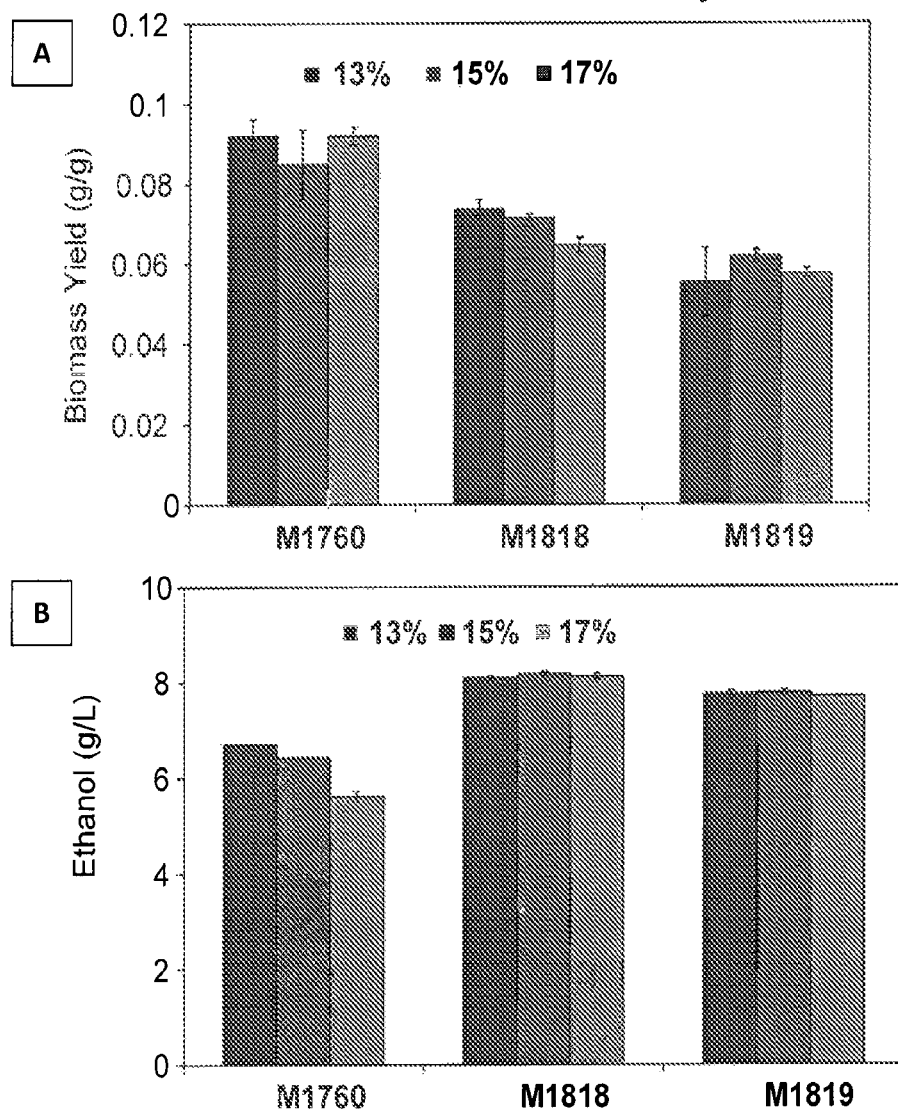

FIG. 11A is a graph depicting biomass yield (g/g) of strains M1760, M1818, and M1819 in a pressate assay.

FIG. 11B is a graph depicting ethanol yield (g/L) of strains M1760, M1818, and M1819 in a pressate assay.

Figure 12:
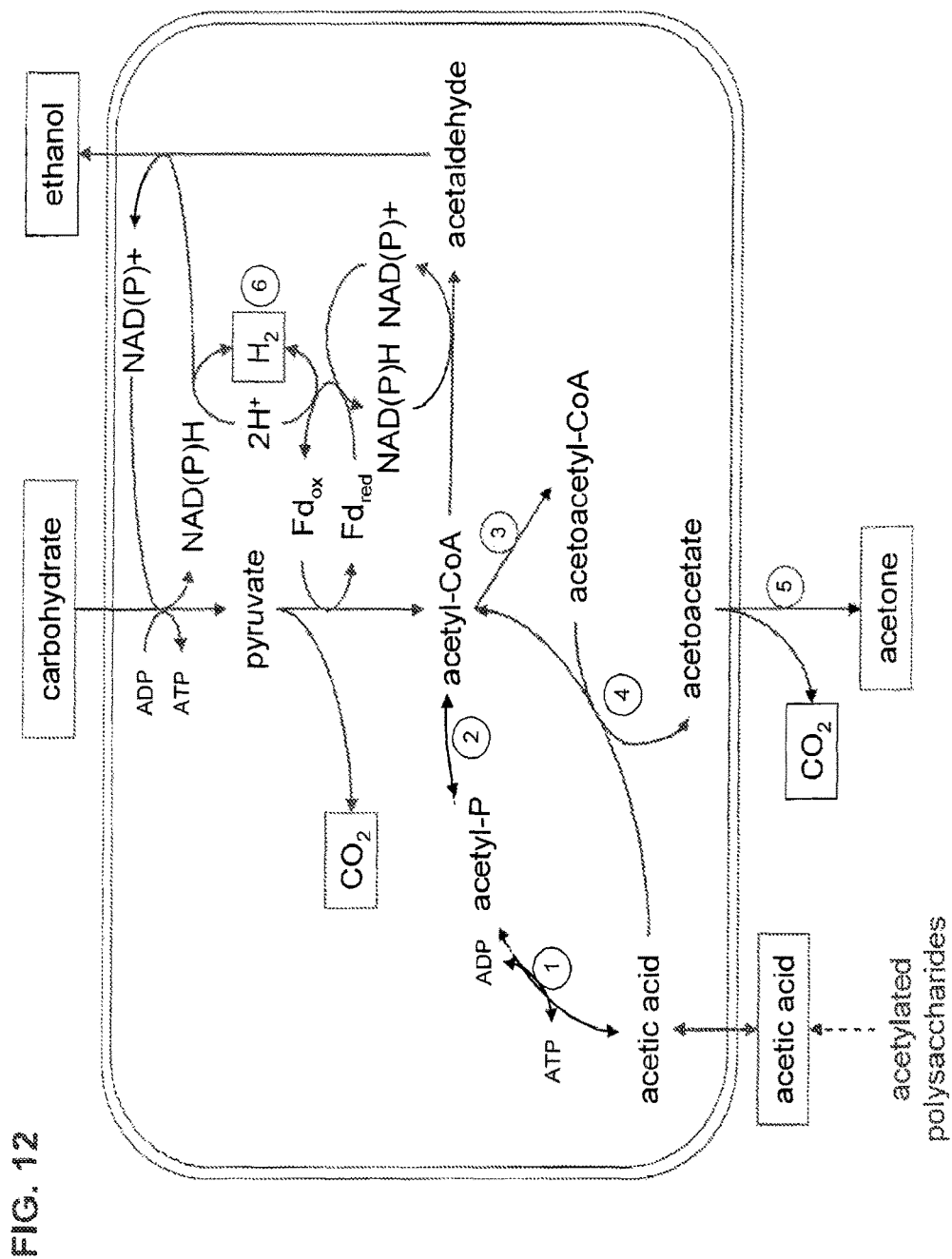

FIG. 12 shows a schematic of a proposed engineered pathway to convert acetate to acetone.

Figure 13:
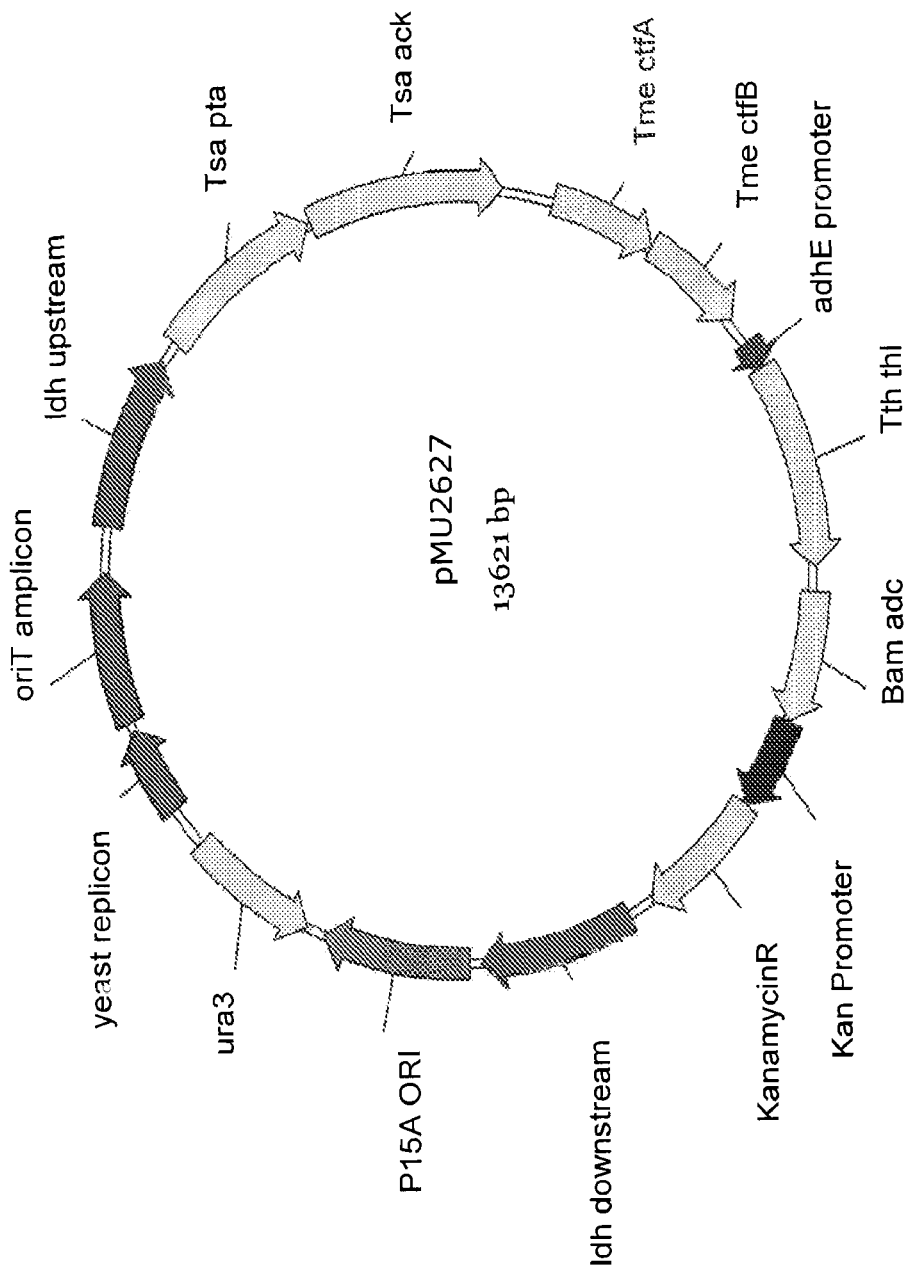

FIG. 13 depicts the vector pMU22627 for the conversion of acetate to acetone in *T. saccharolyticum*.

Figure 14:
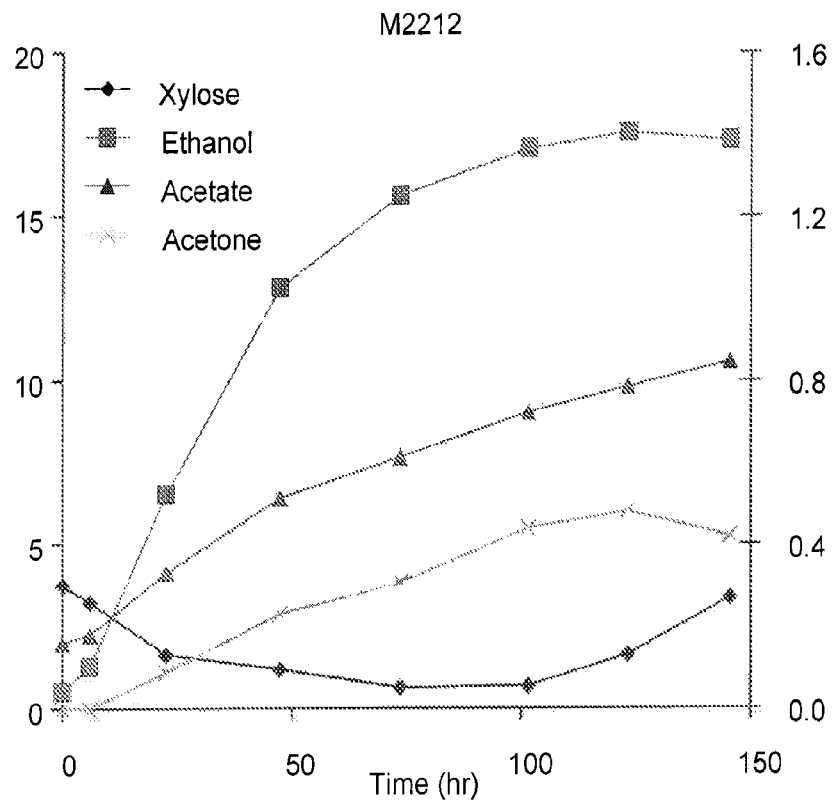

FIG. 14 is a graph depicting the metabolic results of a fermentation of lignocellulosic derived hemicellulose washate with *T. saccharolyticum* strain M2212.

Figure 15:
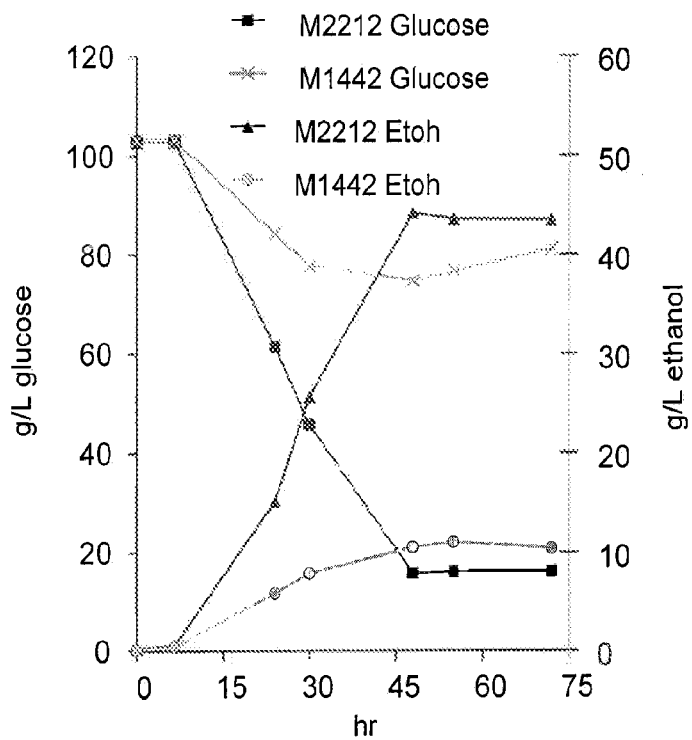

FIG. 15 is a graph depicting glucose consumption and ethanol production of a fermentation with *T. saccharolyticum* strains M1442 and M2212.

Figure 16:
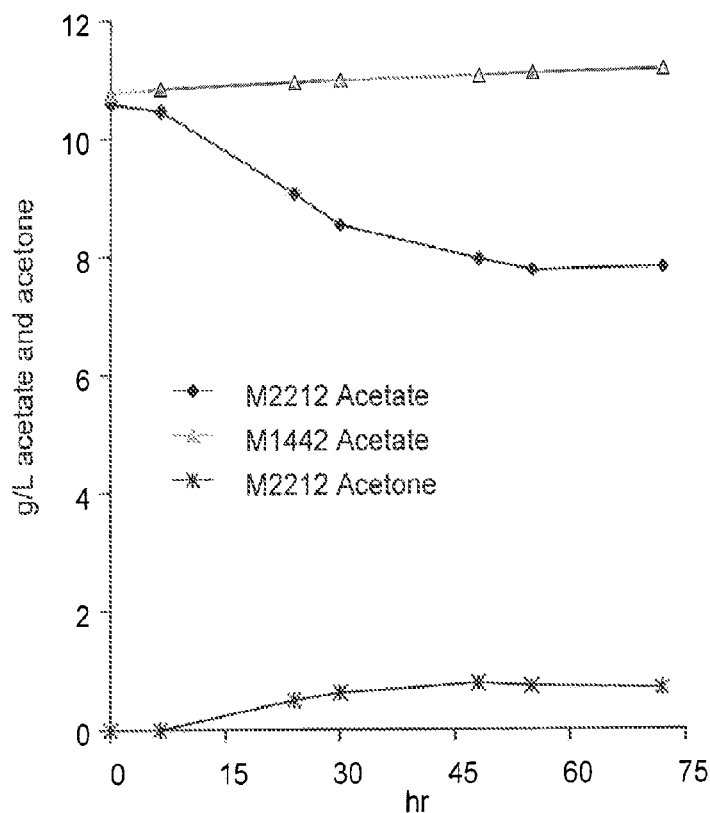

FIG. 16 is a graph depicting acetate consumption and acetone production of a fermentation with *T. saccharolyticum* strains M1442 and M2212.

Figure 17:
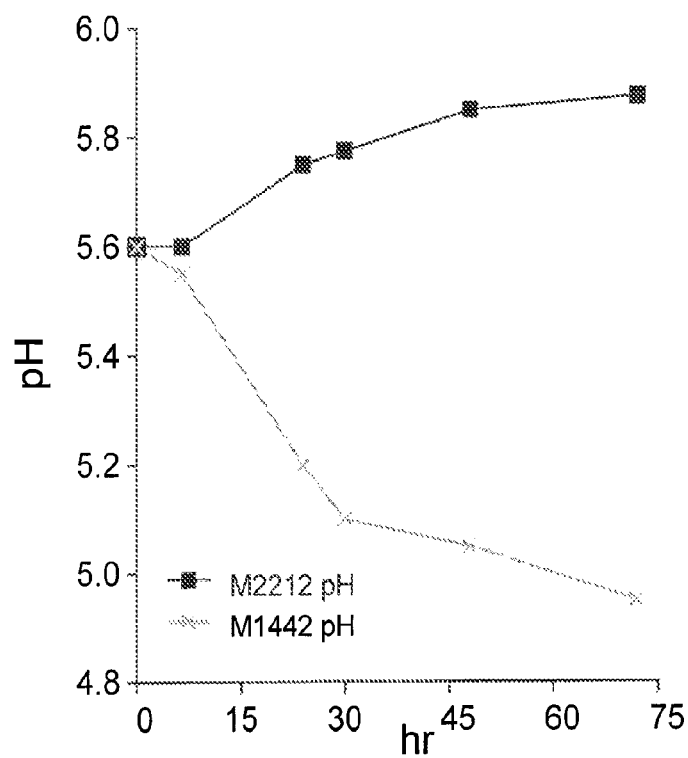

FIG. 17 is a graph depicting pH of a fermentation with *T. saccharolyticum* strains M1442 and M2212.

Figure 18:
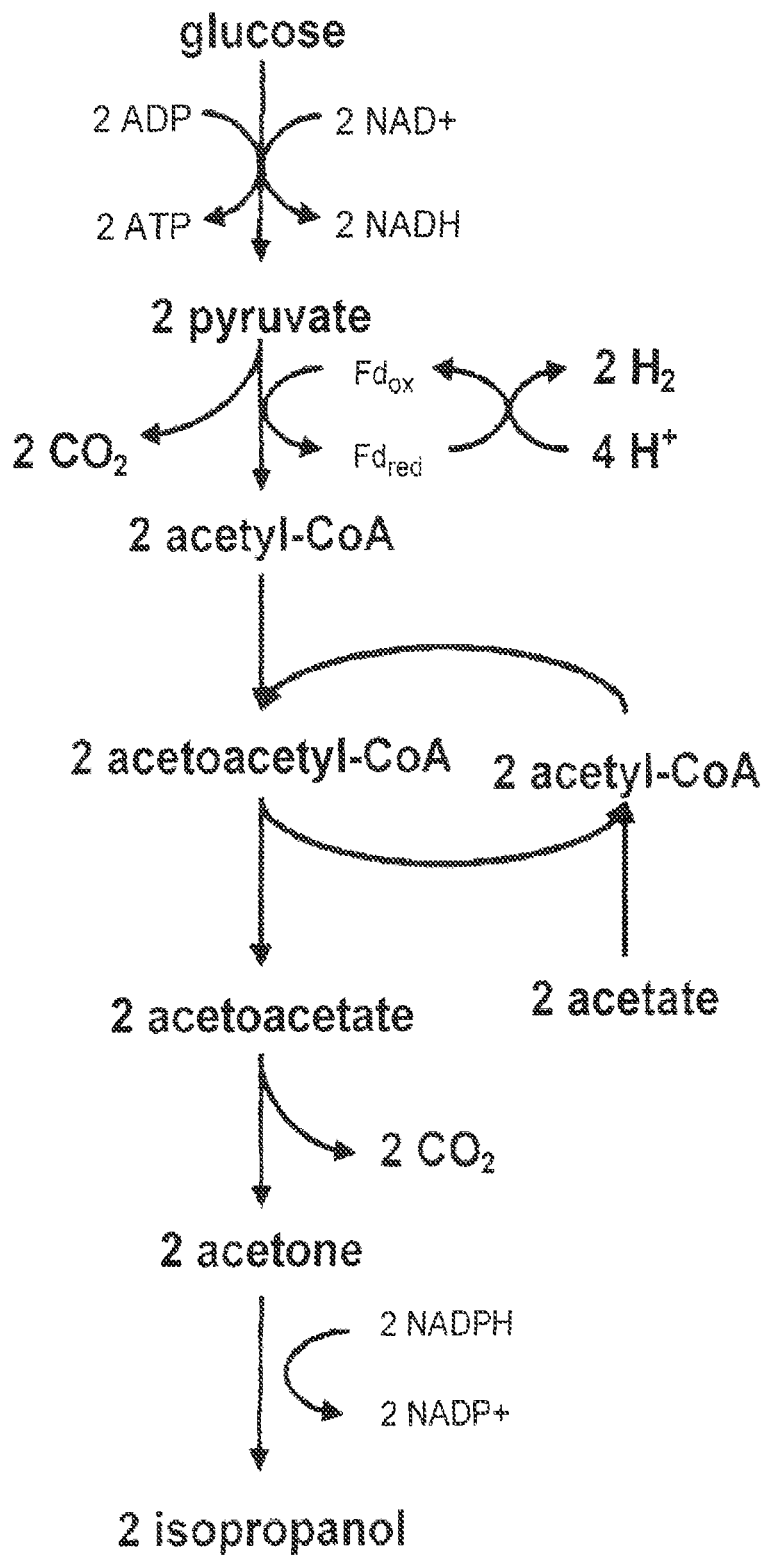

FIG. 18 shows a schematic of a proposed engineered pathway to convert acetate to isopropanol.

Figure 19:
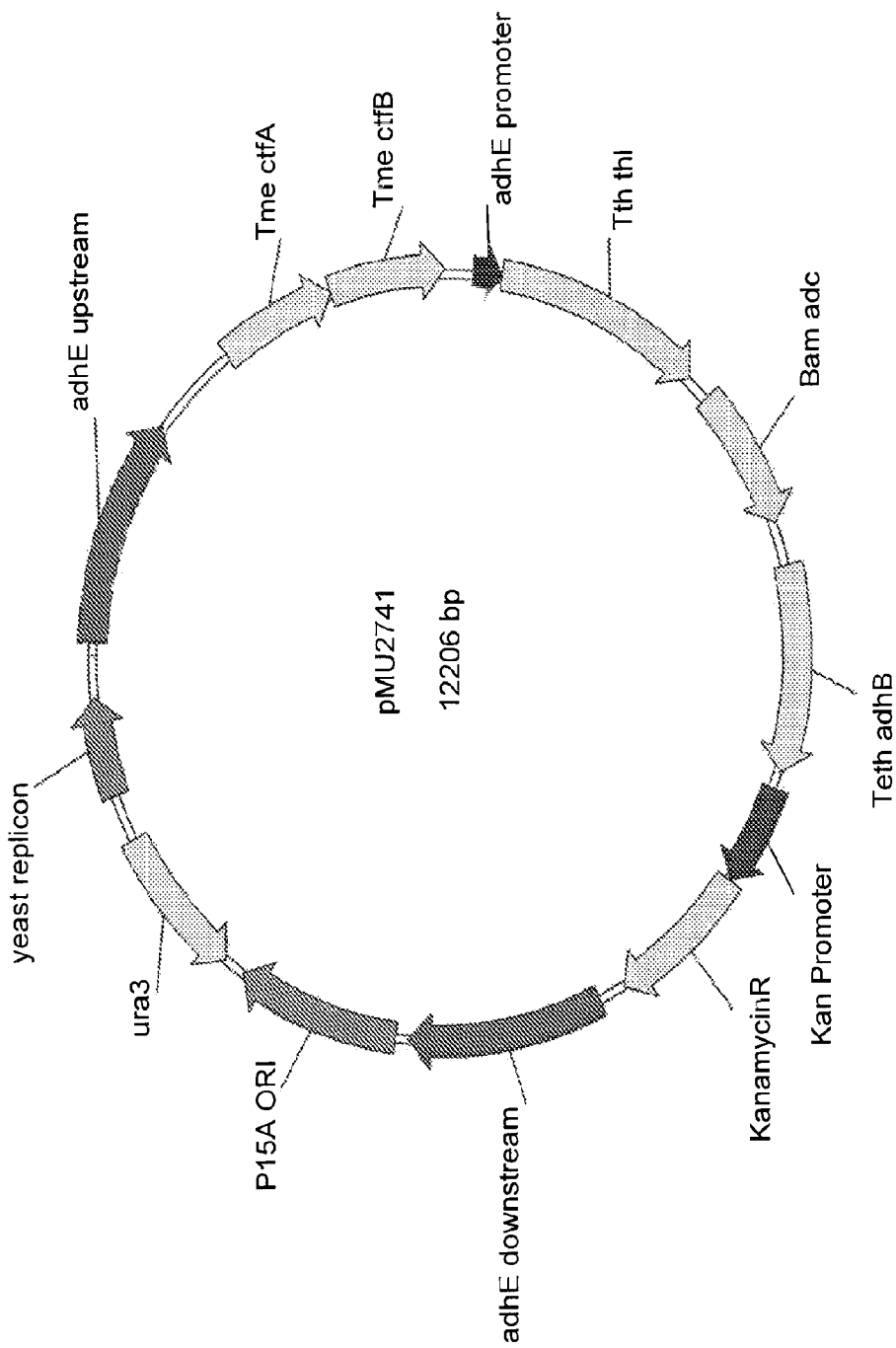

FIG. 19 depicts the vector pMU2741 for the conversion of acetate to isopropanol.

Figure 20:
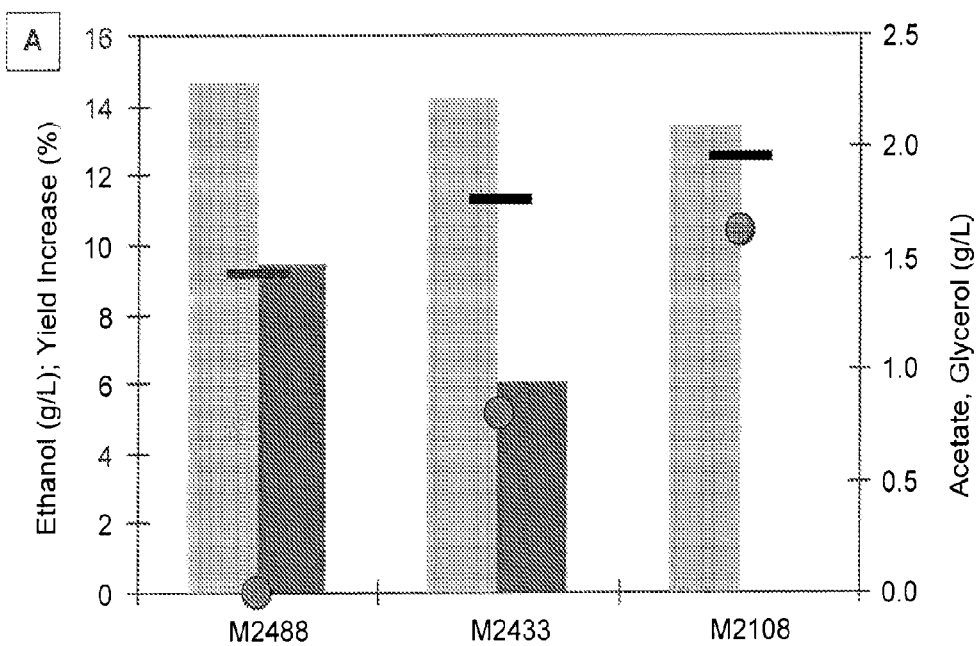
Figure 20:
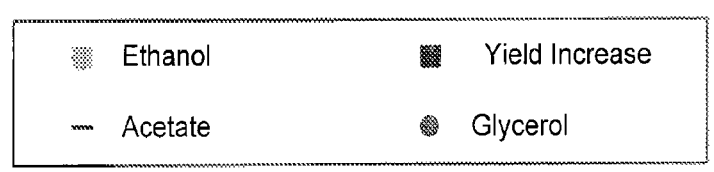
Figure 20:
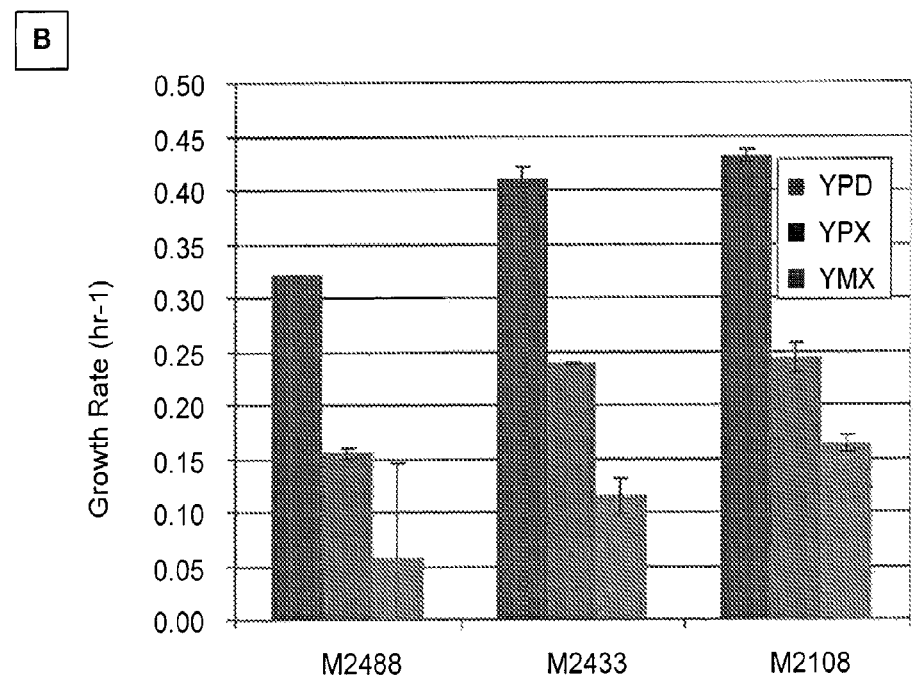

FIG. 20A is a graph depicting the metabolic results of a fermentation of minimal media comprising glucose and acetate with *S. cerevisiae* strains M2108, M2433, and M2488.

FIG. 20B is a graph depicting the growth rate ($hr^{-1}$) of a fermentation of minimal media comprising glucose and acetate with *S. cerevisiae* strains M2108, M2433, and M2488.

Figure 21:
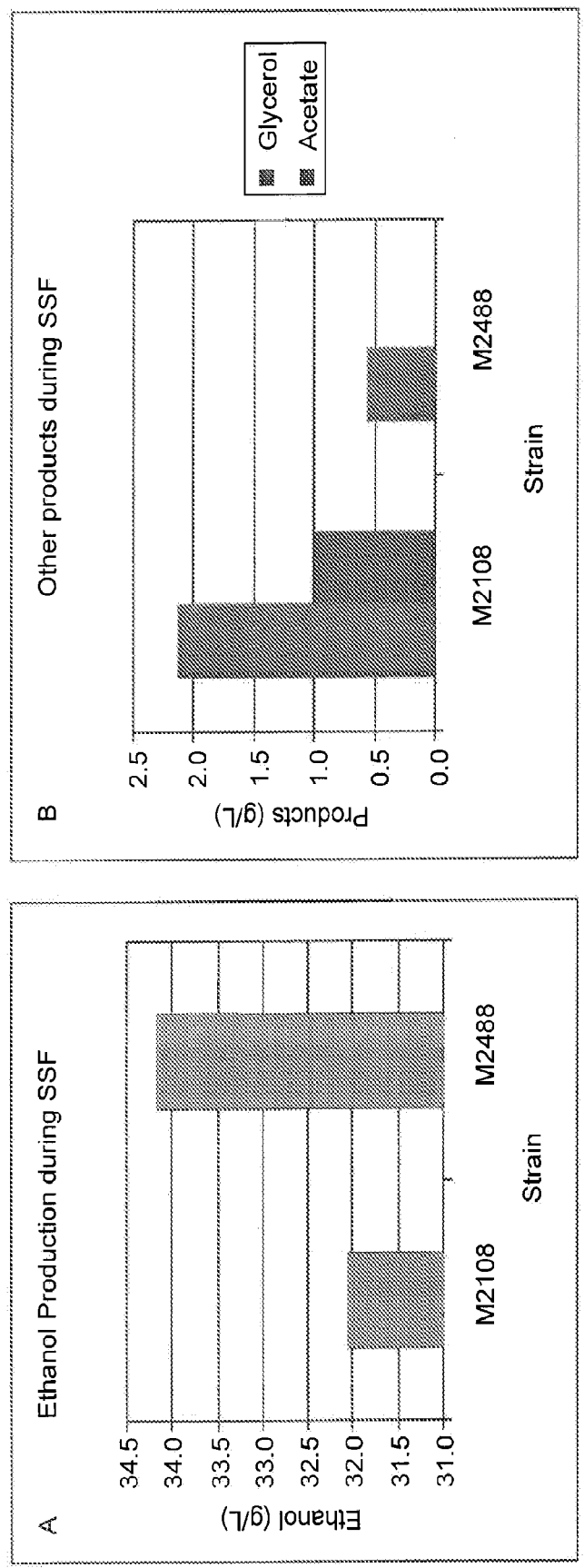

FIG. 21A is a graph depicting the ethanol production (g/L) of a fermentation using simultaneous saccharification and fermentation (SSF) with *S. cerevisiae* strains M2108 and M2488.

FIG. 21B is a graph depicting the glycerol production (g/L) and acetate production (g/L) of a fermentation using SSF with *S. cerevisiae* strains M2108 and M2488.

Figure 22:
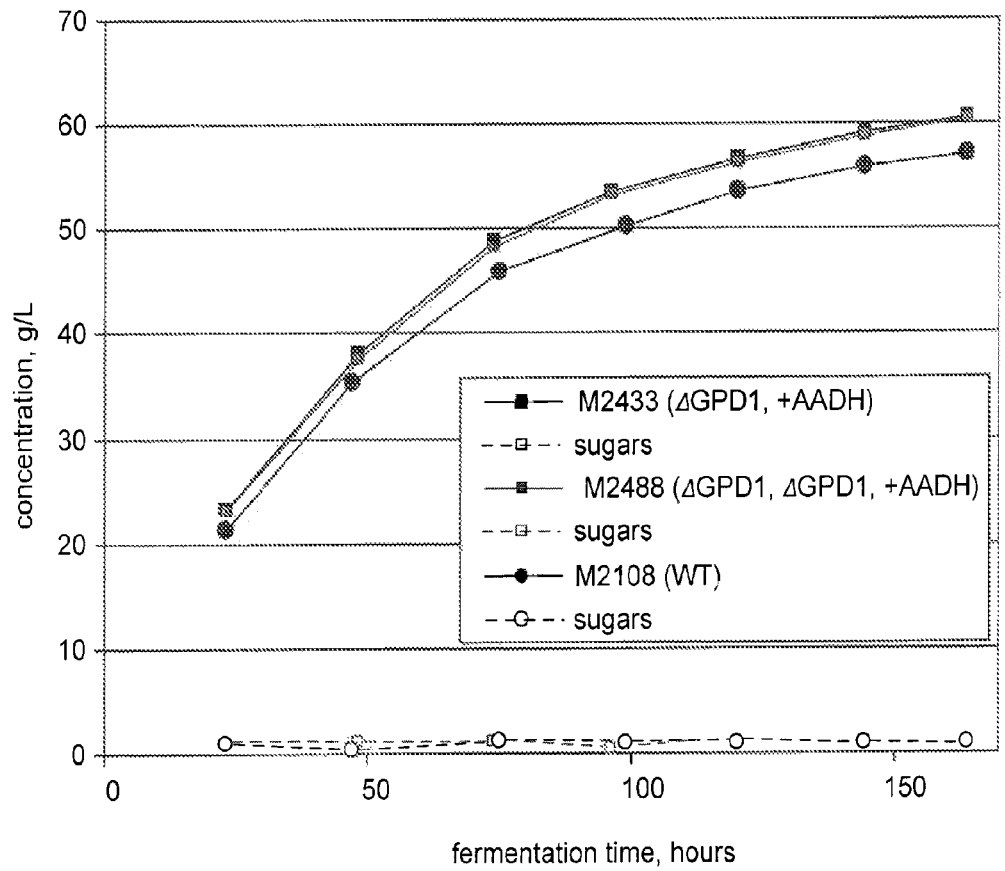

FIG. 22 is a graph depicting the ethanol production (g/L) of a fermentation using SSF with *S. cerevisiae* strains M2108, M2433, and M2488.

Figure 23:
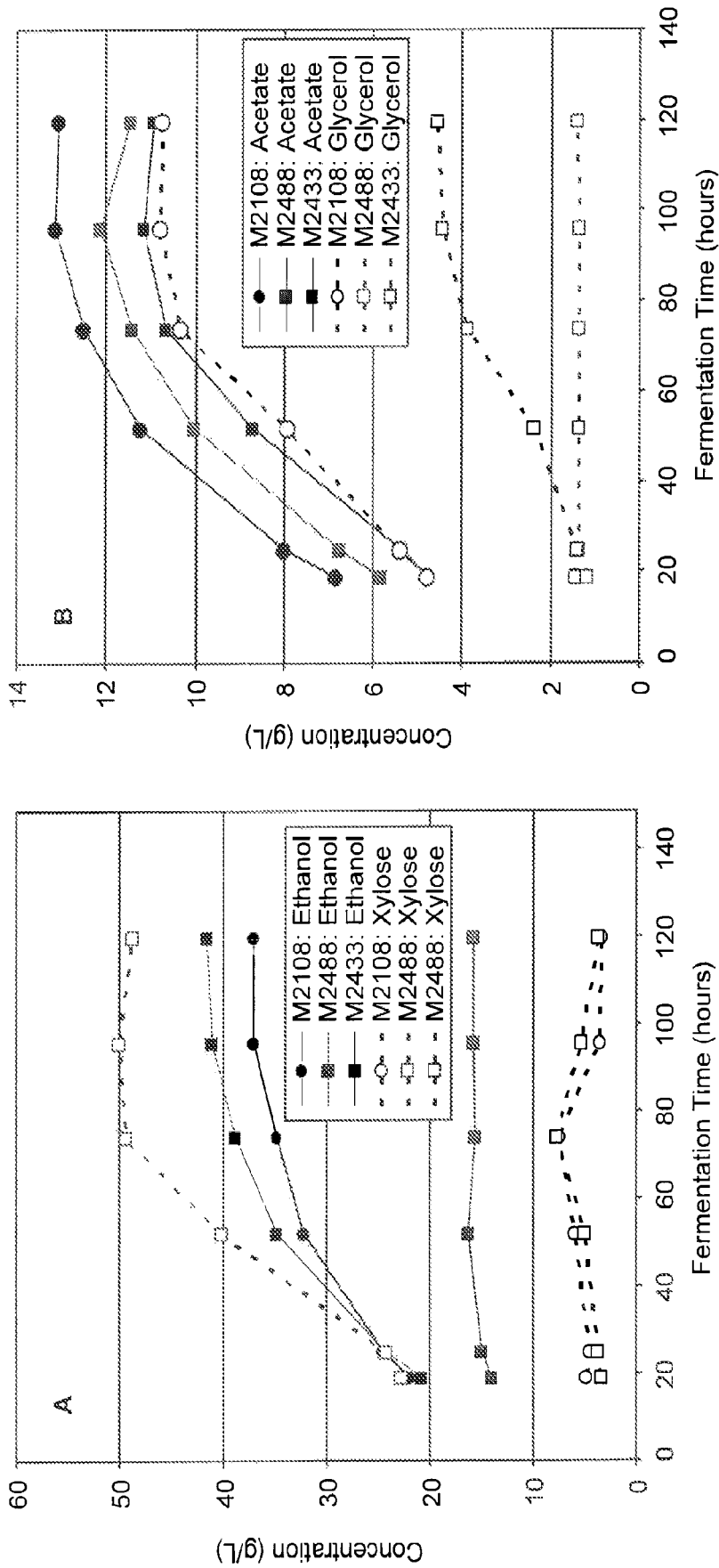

FIG. 23A is a graph depicting ethanol production (g/L) and xylose utilization (g/L) of a washate fermentation with *S. cerevisiae* strains M2108, M2433, and M2488.

FIG. 23B is a graph depicting acetate production (g/L) and glycerol production (g/L) of a washate fermentation with *S. cerevisiae* strains M2108, M2433, and M2488.

Figure 24:
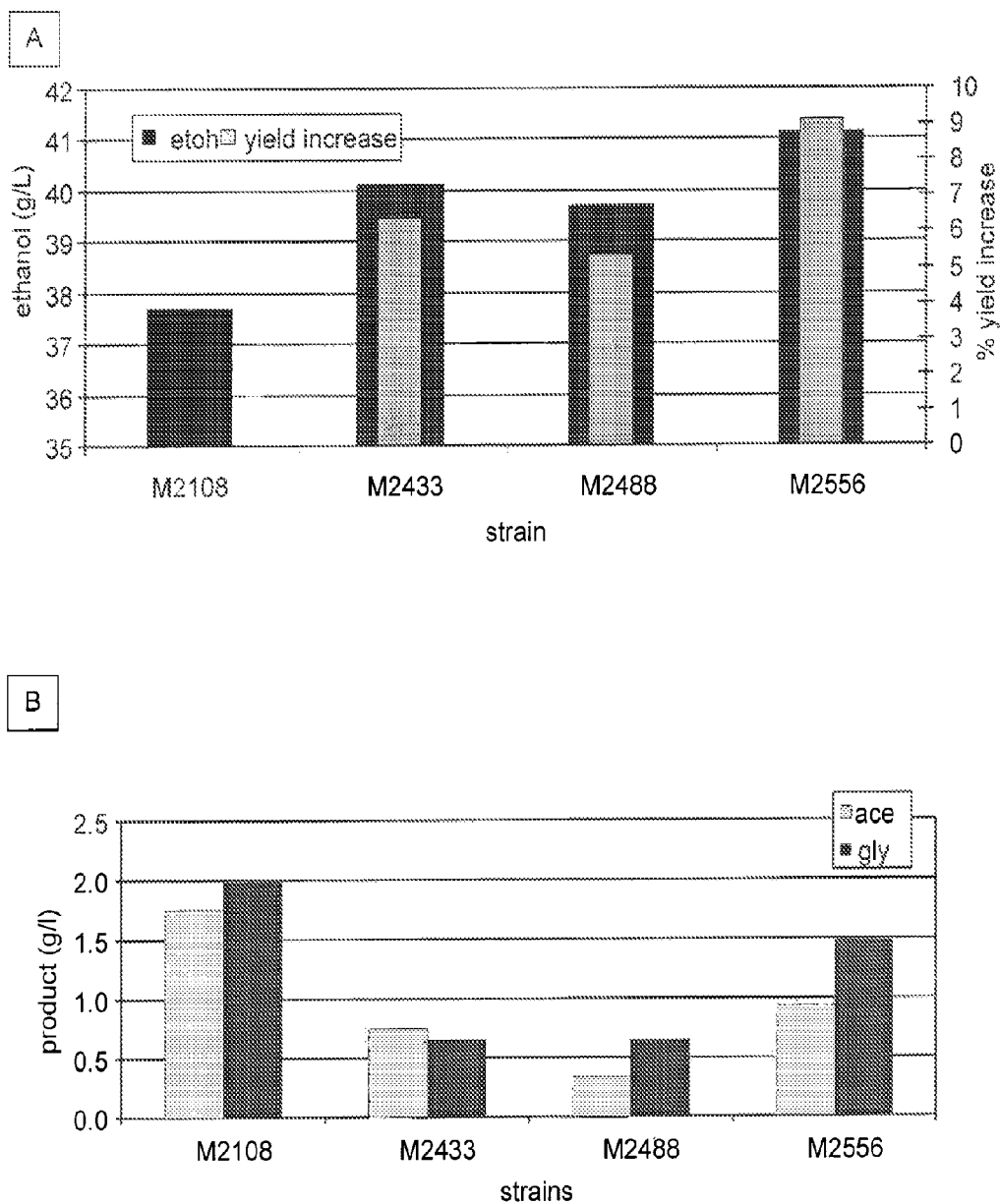

FIG. 24A is a graph depicting ethanol production (g/L) and yield increase (%) of a fermentation using SSF with *S. cerevisiae* strains M2108, M2433, M2488, and M2556.

FIG. 24B is a graph depicting acetate production (g/L) and glycerol production (g/L) of a fermentation using SSF with *S. cerevisiae* strains M2108, M2433, M2488, and M2556.

Figure 25:
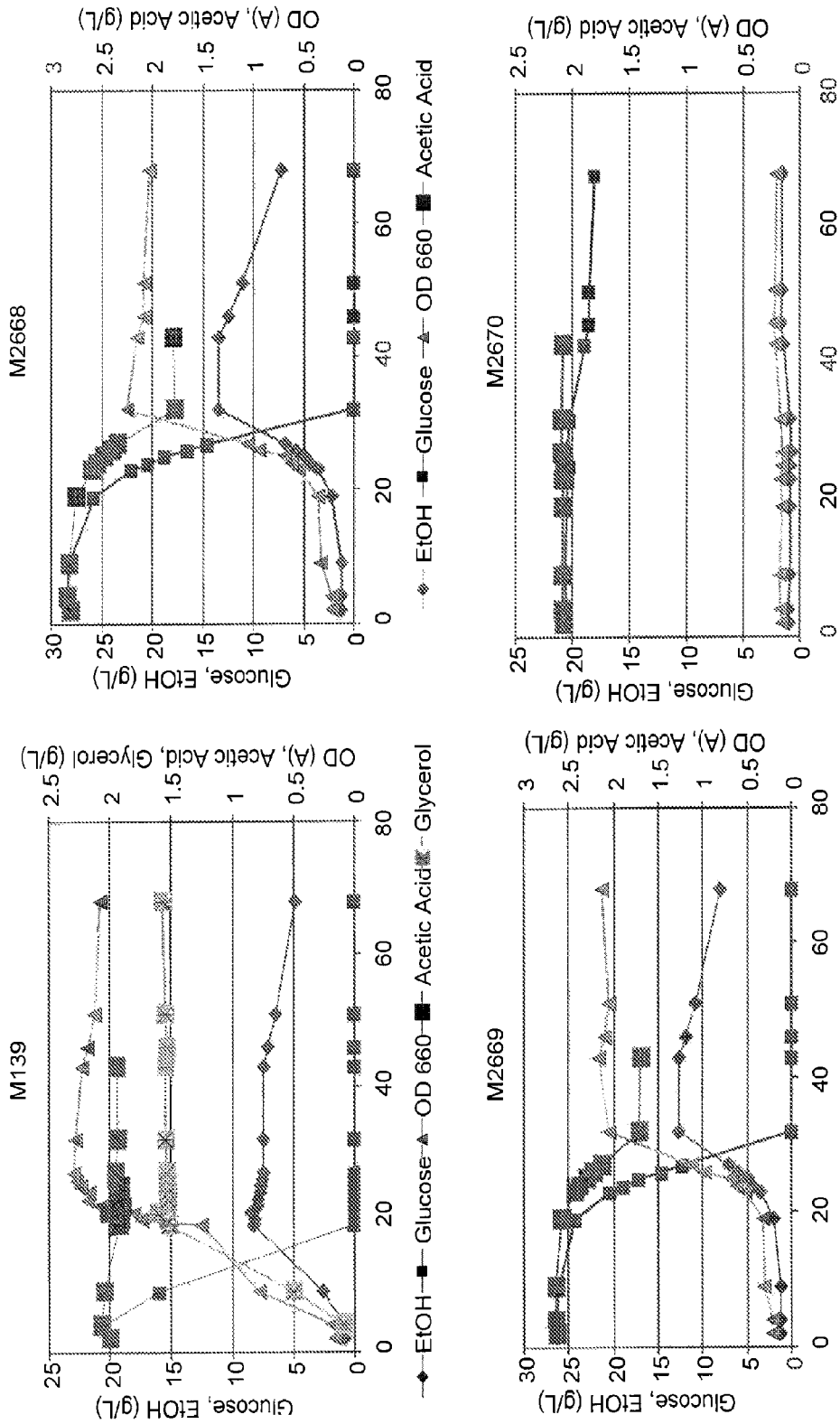

FIG. 25 shows graphs depicting the metabolic results of a fermentation using Verduyn media with *S. cerevisiae* strains M139, M2668, M2669, and M2670.

Figure 26:
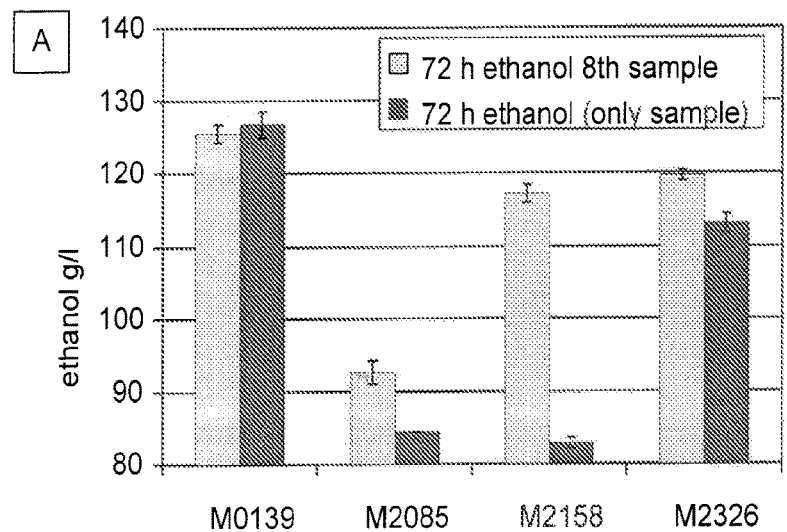
Figure 26:
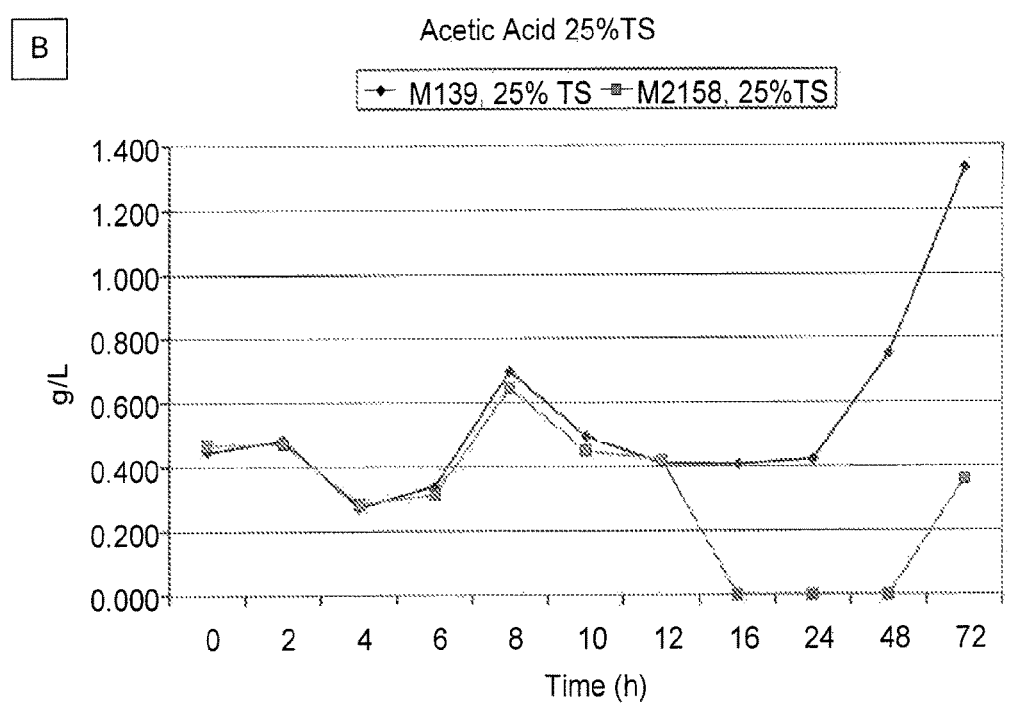

FIG. 26A is a graph depicting the ethanol production (g/L) of a fermentation using 25% solids corn mash with *S. cerevisiae* strains M139, M2085, M2158, and M2326.

FIG. 26B is a graph depicting acetate utilization (g/L) of a fermentation using 25% solids corn mash with *S. cerevisiae* strains M139 and M2158.

Figure 27:
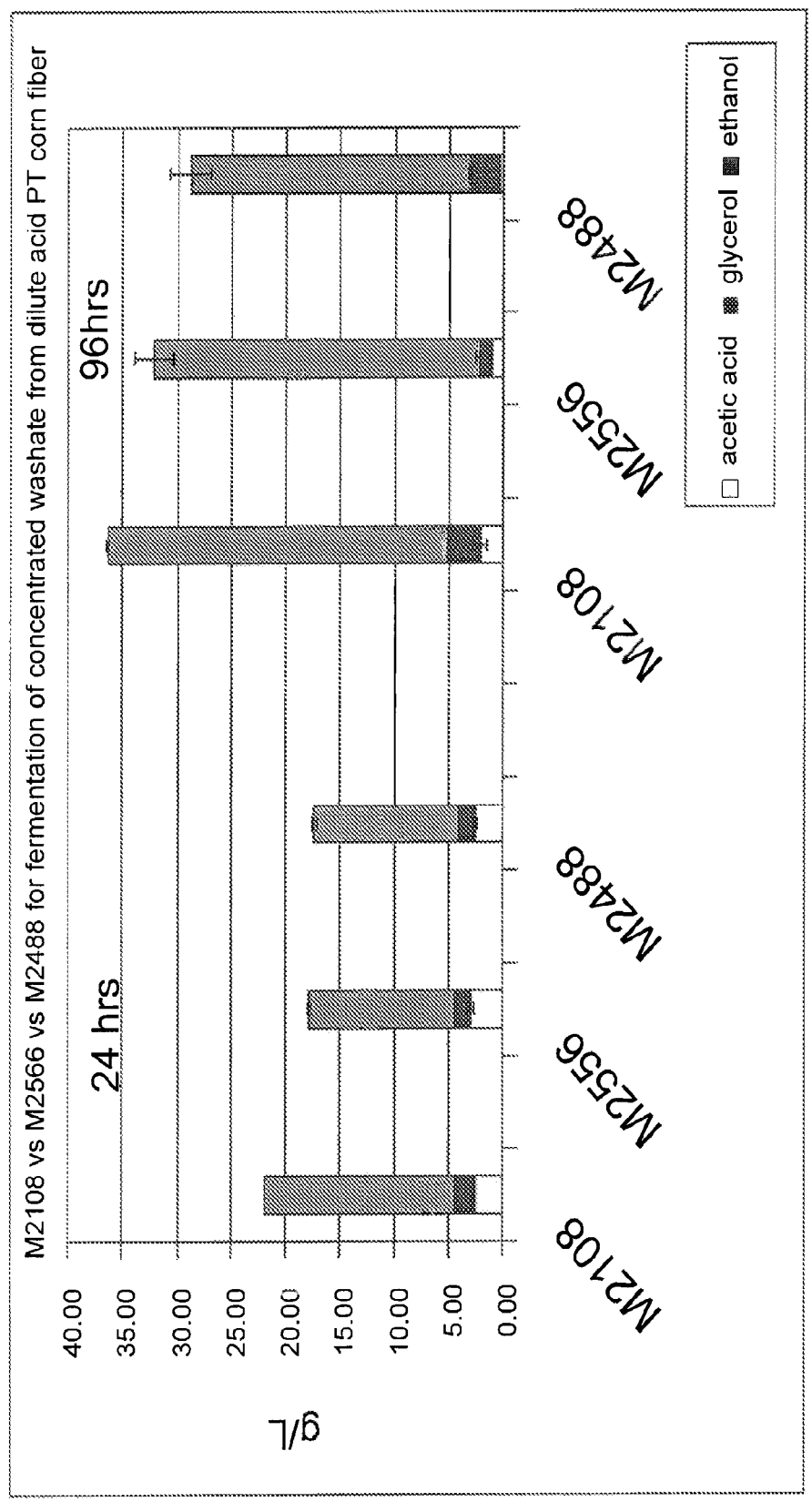

FIG. 27 is a graph depicting the metabolic results of a fermentation using corn fiber washate with *S. cerevisiae* strains M2108, M2488, and M2556.

Figure 28:
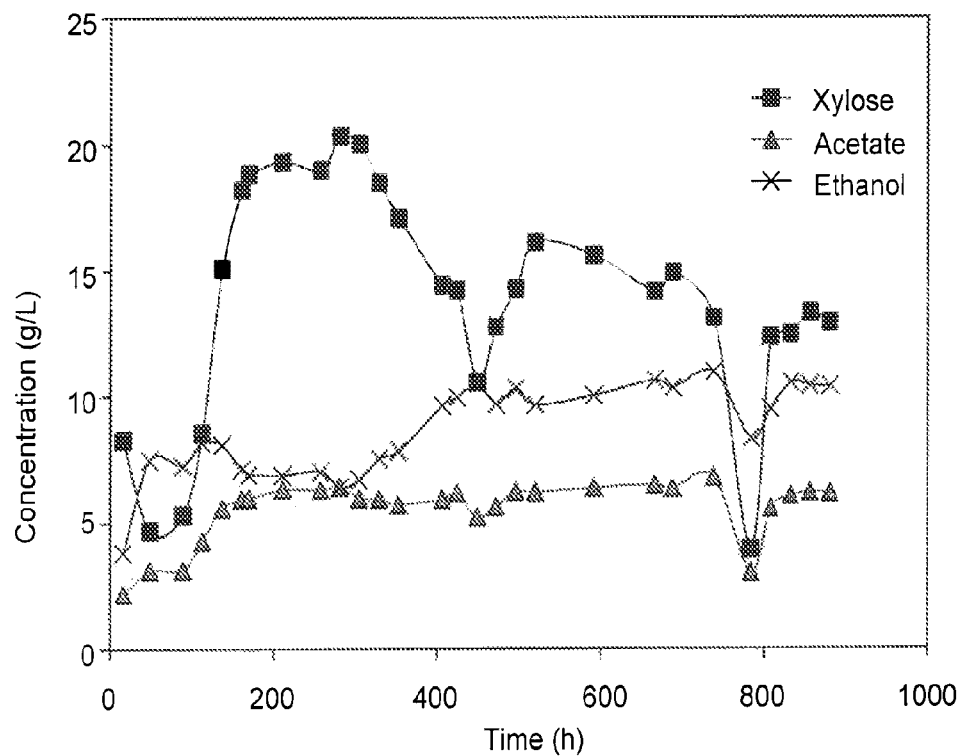

FIG. 28 is a graph depicting xylose, acetate, and ethanol concentrations (g/L) from chemostat adaptation of M1927 in wash liquor from hardwood.

Figure 29:
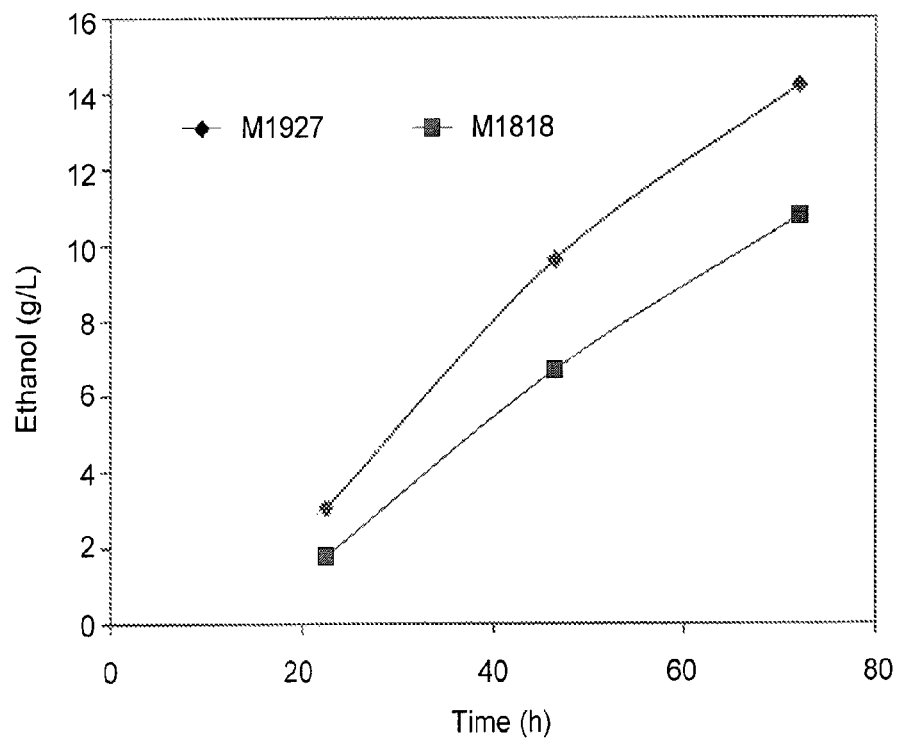

FIG. 29 is a graph depicting ethanol production (g/L) of a wash liquor fermentation with *S. cerevisiae* strains M1818 and M1927.

Figure 30:
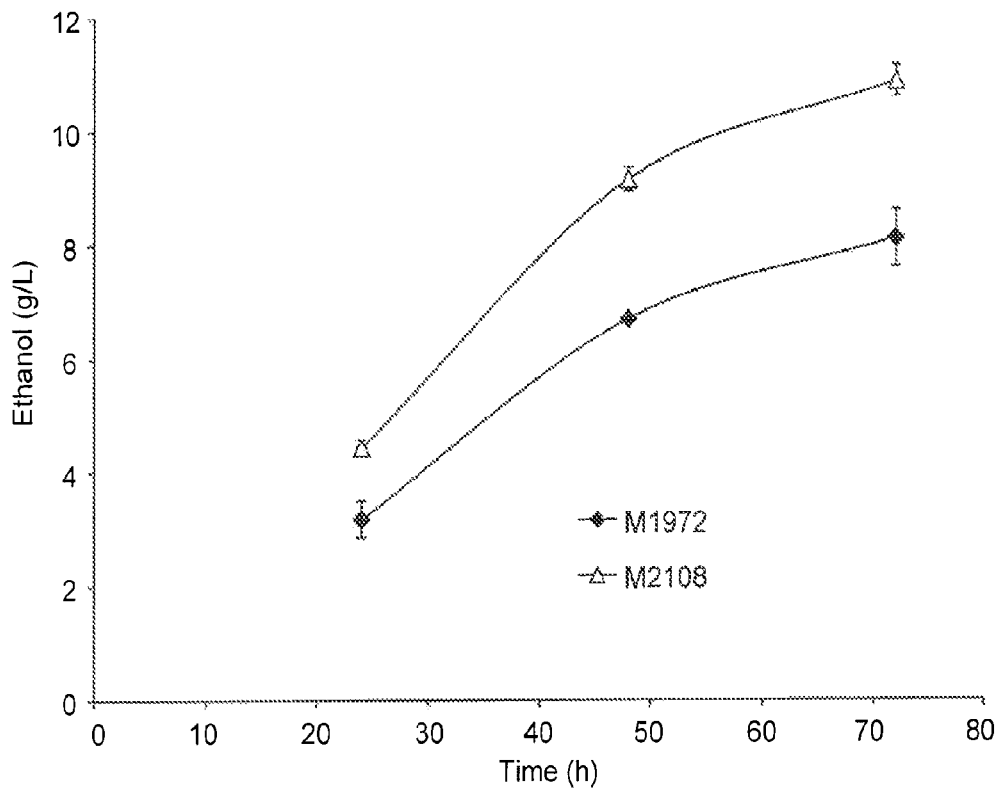

FIG. 30 is a graph depicting ethanol production (g/L) of a wash liquor fermentation with *S. cerevisiae* strains M1927 and M2108.

Figure 31:
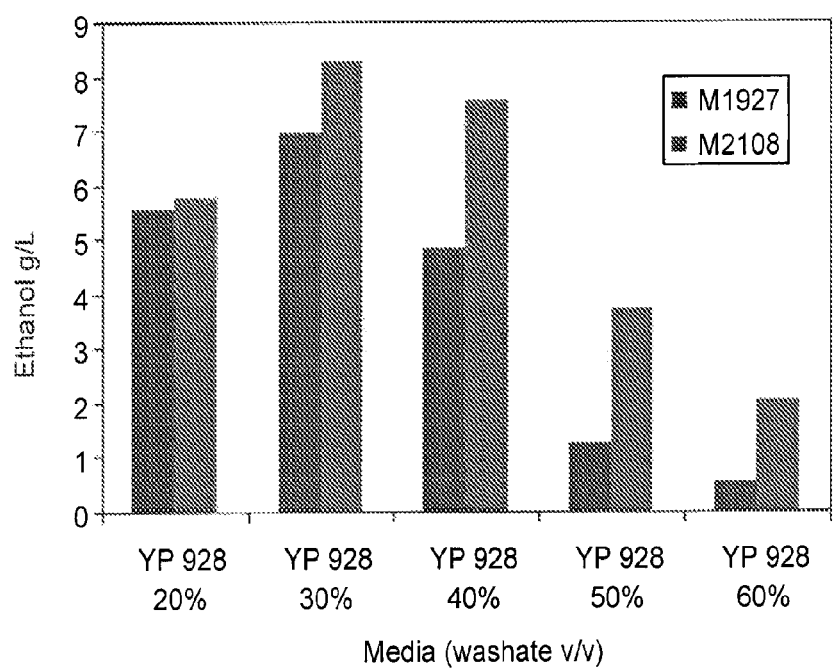

FIG. 31 is a graph depicting ethanol production (g/L) of a wash liquor fermentation with *S. cerevisiae* strains M1927 and M2108.

Figure 32:
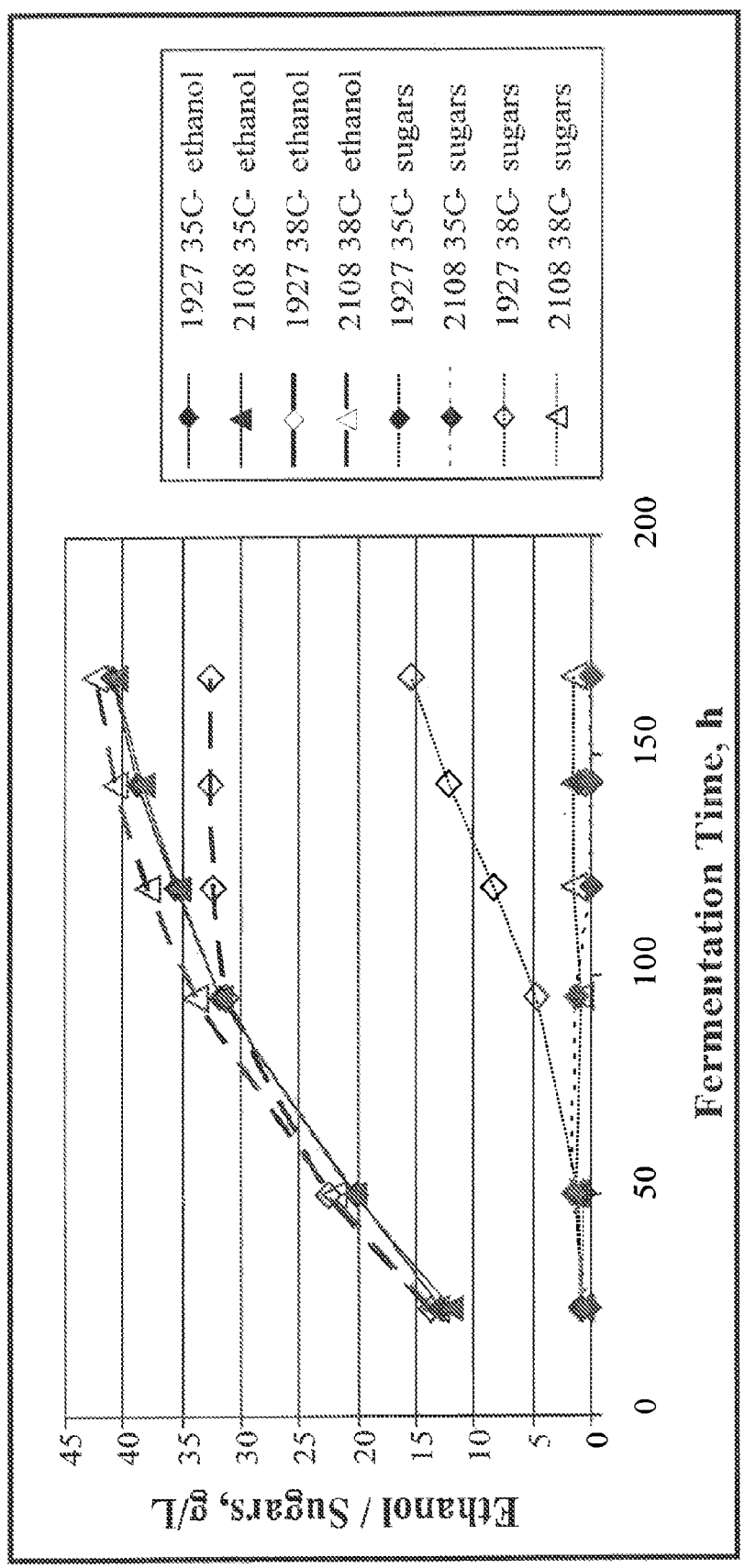

FIG. 32 is a graph depicting ethanol production (g/L) and sugar consumption (g/L) of a fermentation using SSF with *S. cerevisiae* strains M1927 and M2108.

Figure 33:
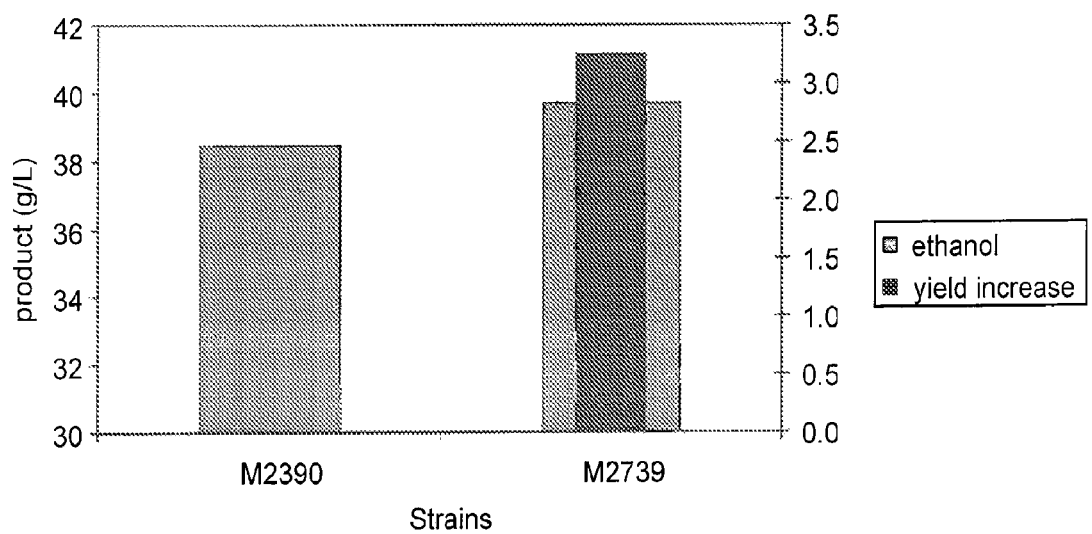

FIG. 33 is a graph depicting ethanol production (g/L) and yield increase (%) of a fermentation using SSF with *S. cerevisiae* strains M2390 and M2739.

Figure 34:
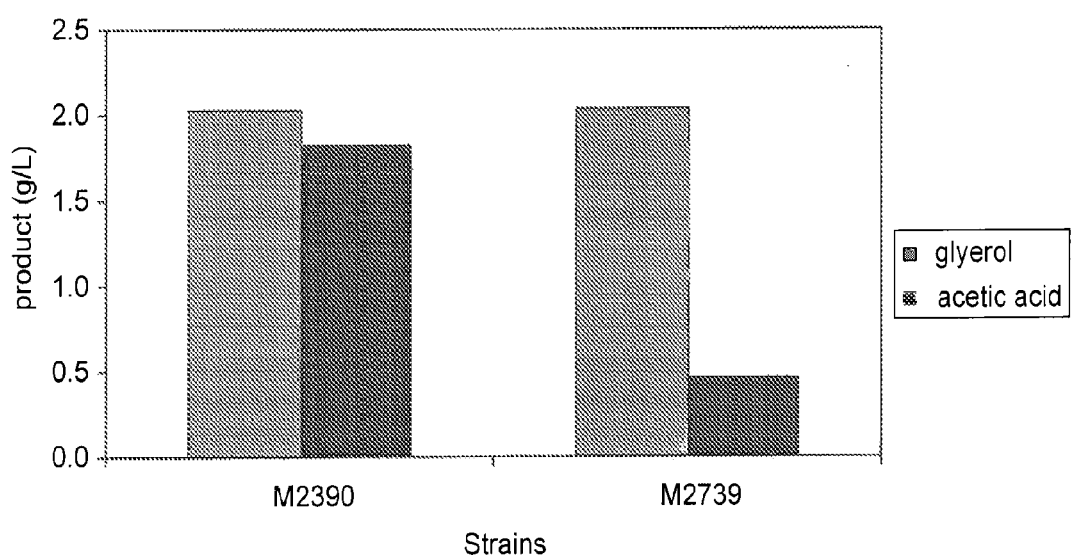

FIG. 34 is a graph depicting glycerol production (g/L) and acetic acid utilization (g/L) of a fermentation using SSF with *S. cerevisiae* strains M2390 and M2739.

Figure 35:
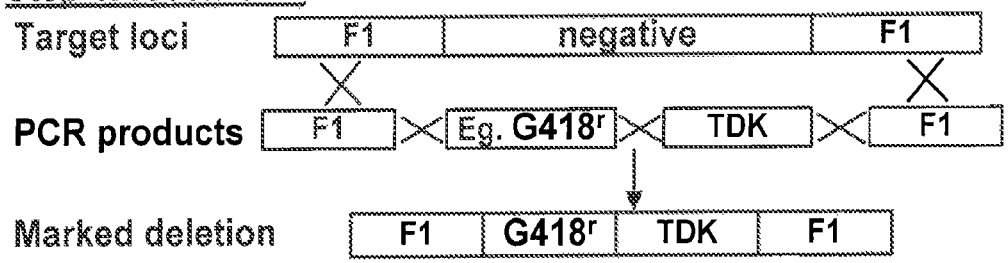
Figure 35:
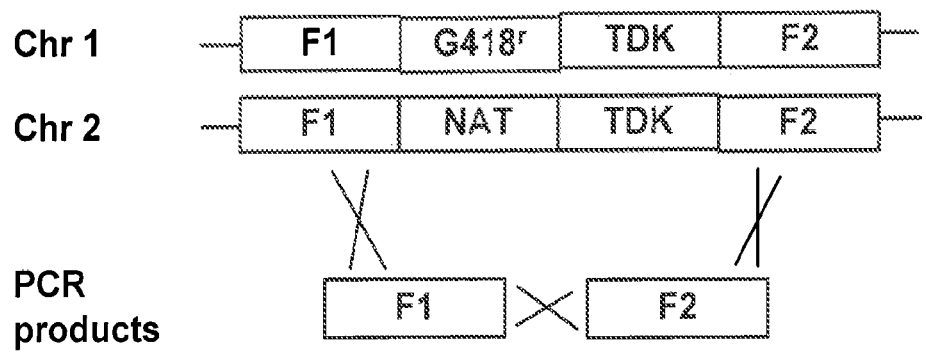

FIG. 35 is a schematic illustrating homologous recombination using a thymidine kinase (TDK) counter-selection method.

DETAILED DESCRIPTION OF THE INVENTION

Aspects of the present invention relate to the engineering of a microorganism to detoxify biomass-derived acetate via metabolic conversion to ethanol, acetone, isopropanol, or ethyl acetate. To overcome the inhibitory effects of acetate, the acetate can be converted to a less inhibitory compound that is a product of bacterial or yeast fermentation, as described herein. Less inhibitory compounds such as ethanol, acetone, isopropanol, or ethyl acetate can be readily recovered from the fermentation media. Additional advantages of the present invention over existing means for reducing acetate include:

Reduced cost compared to chemical or physical acetate removal systems;

Reduced loss of sugar yield (washing) compared to chemical or physical acetate removal systems;

Reduced demand for base addition during fermentation;

Reduced overall fermentation cost;

Improved pH control; and

Reduced costs, including capital, operating, and environmental, for wastewater treatment and water recycling.

Definitions

The term "heterologous" when used in reference to a polynucleotide, a gene, a polypeptide, or an enzyme refers to a polynucleotide, gene, polypeptide, or an enzyme not normally found in the host organism. "Heterologous" also includes a native coding region, or portion thereof, that is reintroduced into the source organism in a form that is different from the corresponding native gene, e.g., not in its natural location in the organism's genome. The heterologous polynucleotide or gene may be introduced into the host organism by, e.g., gene transfer. A heterologous gene may include a native coding region that is a portion of a chimeric gene including non-native regulatory regions that is reintroduced into the native host. Foreign genes can comprise native genes inserted into a non-native organism, or chimeric genes.

The term "heterologous polynucleotide" is intended to include a polynucleotide that encodes one or more polypeptides or portions or fragments of polypeptides. A heterologous polynucleotide may be derived from any source, e.g., eukaryotes, prokaryotes, viruses, or synthetic polynucleotide fragments.

The terms "promoter" or "surrogate promoter" is intended to include a polynucleotide that can transcriptionally control a gene-of-interest that it does not transcriptionally control in nature. In certain embodiments, the transcriptional control of a surrogate promoter results in an increase in expression of the gene-of-interest. In certain embodiments, a surrogate promoter is placed 5' to the gene-of-interest. A surrogate promoter may be used to replace the natural promoter, or may be used in addition to the natural promoter. A surrogate promoter may be endogenous with regard to the host cell in which it is used, or it may be a heterologous polynucleotide sequence introduced into the host cell, e.g., exogenous with regard to the host cell in which it is used.

The terms "gene(s)" or "polynucleotide" or "polynucleotide sequence(s)" are intended to include nucleic acid molecules, e.g., polynucleotides which include an open reading frame encoding a polypeptide, and can further include non-coding regulatory sequences, and introns. In addition, the terms are intended to include one or more genes that map to a functional locus. In addition, the terms are intended to include a specific gene for a selected purpose. The gene may be endogenous to the host cell or may be recombinantly introduced into the host cell, e.g., as a plasmid maintained episomally or a plasmid (or fragment thereof) that is stably integrated into the genome. In addition to the plasmid form, a gene may, for example, be in the form of linear DNA. In certain embodiments, the gene or polynucleotide is involved in at least one step in the bioconversion of a acetate to a non-charged solvent, including but not limited to, acetone, isopropanol, ethyl acetate, or ethanol. Accordingly, the term is intended to include any gene encoding a polypeptide, such as the enzymes acetate kinase (ACK), phosphotransacetylase (PTA), lactate dehydrogenase (LDH), pyruvate formate lyase (PFL), aldehyde dehydrogenase (ADH) and/or alcohol dehydrogenase (ADH), acetyl-CoA transferase (ACS), acetaldehyde dehydrogenase, acetaldehyde/alcohol dehydrogenase, glycerol-3-phosphate dehydrogenase (GPD), acetyl-CoA synthetase, thiolase, CoA transferase, acetoacetate decarboxylase, alcohol acetyltransferase enzymes in the D-xylose pathway, such as xylose isomerase and xylulokinase, enzymes in the L-arabinose pathway, such as L-arabinose isomerase and L-ribulose-5-phosphate 4-epimerase. The term gene is also intended to cover all copies of a particular gene, e.g., all of the DNA sequences in a cell encoding a particular gene product.

The term "transcriptional control" is intended to include the ability to modulate gene expression at the level of transcription. In certain embodiments, transcription, and thus gene expression, is modulated by replacing or adding a surrogate promoter near the 5' end of the coding region of a gene-of-interest, thereby resulting in altered gene expression. In certain embodiments, the transcriptional control of one or more genes is engineered to result in the optimal expression of such genes, e.g., in a desired ratio. The term also includes inducible transcriptional control as recognized in the art.

The term "expression" is intended to include the expression of a gene at least at the level of mRNA production.

The term "expression product" is intended to include the resultant product, e.g., a polypeptide, of an expressed gene.

The term "increased expression" is intended to include an alteration in gene expression at least at the level of increased mRNA production and, preferably, at the level of polypeptide expression. The term "increased production" is intended to include an increase in the amount of a polypeptide expressed, in the level of the enzymatic activity of the polypeptide, or a combination thereof, as compared to the native production of, or the enzymatic activity, of the polypeptide.

The terms "activity," "activities," "enzymatic activity," and "enzymatic activities" are used interchangeably and are intended to include any functional activity normally attributed to a selected polypeptide when produced under favorable conditions. Typically, the activity of a selected polypeptide encompasses the total enzymatic activity associated with the produced polypeptide. The polypeptide produced by a host cell and having enzymatic activity may be located in the intracellular space of the cell, cell-associated, secreted into the extracellular milieu, or a combination thereof. Techniques for determining total activity as compared to secreted activity are described herein and are known in the art.

The term "xylanolytic activity" is intended to include the ability to hydrolyze glycosidic linkages in oligopentoses and polypentoses.

The term "cellulolytic activity" is intended to include the ability to hydrolyze glycosidic linkages in oligohexoses and polyhexoses. Cellulolytic activity may also include the ability to depolymerize or debranch cellulose and hemicellulose.

As used herein, the term "lactate dehydrogenase" or "LDH" is intended to include the enzymes capable of converting pyruvate into lactate. It is understood that LDH can also catalyze the oxidation of hydroxybutyrate. LDH includes those enzymes that correspond to Enzyme Commission Number 1.1.1.27.

As used herein the term "alcohol dehydrogenase" or "ADH" is intended to include the enzymes capable of converting acetaldehyde into an alcohol, such as ethanol. ADH also includes the enzymes capable of converting acetone to isopropanol. ADH includes those enzymes that correspond to Enzyme Commission Number 1.1.1.1.

As used herein, the term "phosphotransacetylase" or "PTA" is intended to include the enzymes capable of converting acetyl-phosphate into acetyl-CoA. PTA includes those enzymes that correspond to Enzyme Commission Number 2.3.1.8.

As used herein, the term "acetate kinase" or "ACK" is intended to include the enzymes capable of converting acetate into acetyl-phosphate. ACK includes those enzymes that correspond to Enzyme Commission Number 2.7.2.1.

As used herein, the term "pyruvate formate lyase" or "PFL" is intended to include the enzymes capable of converting pyruvate into acetyl-CoA and formate. PFL includes those enzymes that correspond to Enzyme Commission Number 2.3.1.54.

As used herein, the term "acetaldehyde dehydrogenase" or "ACDH" is intended to include the enzymes capable of converting acetyl-CoA to acetaldehyde. ACDH includes those enzymes that correspond to Enzyme Commission Number 1.2.1.3.

As used herein, the term "acetaldehyde/alcohol dehydrogenase" is intended to include the enzymes capable of converting acetyl-CoA to ethanol. Acetaldehyde/alcohol dehydrogenase includes those enzymes that correspond to Enzyme Commission Numbers 1.2.1.10 and 1.1.1.1.

As used herein, the term "glycerol-3-phosphate dehydrogenase" or "GPD" is intended to include the enzymes capable of converting dihydroxyacetone phosphate to glycerol-3-phosphate. GPD includes those enzymes that correspond to Enzyme Commission Number 1.1.1.8.

As used herein, the term "acetyl-CoA synthetase" or "ACS" is intended to include the enzymes capable of converting acetate to acetyl-CoA. Acetyl-CoA synthetase includes those enzymes that correspond to Enzyme Commission Number 6.2.1.1.

As used herein, the term "thiolase" is intended to include the enzymes capable of converting acetyl-CoA to acetoacetyl-CoA. Thiolase includes those enzymes that correspond to Enzyme Commission Number 2.3.1.9.

As used herein, the term "CoA transferase" is intended to include the enzymes capable of converting acetate and acetoacetyl-CoA to acetoacetate and acetyl-CoA. CoA transferase includes those enzymes that correspond to Enzyme Commission Number 2.8.3.8.

As used herein, the term "acetoacetate decarboxylase" is intended to include the enzymes capable of converting acetoacetate to acetone and carbon dioxide. Acetoacetate decarboxylase includes those enzymes that correspond to Enzyme Commission Number 4.1.1.4.

As used herein, the term "alcohol acetyltransferase" is intended to include the enzymes capable of converting acetyl-CoA and ethanol to ethyl acetate. Alcohol acetyltransferase includes those enzymes that correspond to Enzyme Commission Number 2.3.1.84.

The term "pyruvate decarboxylase activity" is intended to include the ability of a polypeptide to enzymatically convert pyruvate into acetaldehyde and carbon dioxide (e.g., "pyruvate decarboxylase" or "PDC"). Typically, the activity of a selected polypeptide encompasses the total enzymatic activity associated with the produced polypeptide, comprising, e.g., the superior substrate affinity of the enzyme, thermostability, stability at different pHs, or a combination of these attributes. PDC includes those enzymes that correspond to Enzyme Commission Number 4.1.1.1.

The term "ethanologenic" is intended to include the ability of a microorganism to produce ethanol from a carbohydrate as a fermentation product. The term is intended to include, but is not limited to, naturally occurring ethanologenic organisms, ethanologenic organisms with naturally occurring or induced mutations, and ethanologenic organisms which have been genetically modified.

The terms "fermenting" and "fermentation" are intended to include the enzymatic process (e.g., cellular or acellular, e.g., a lysate or purified polypeptide mixture) by which ethanol is produced from a carbohydrate, in particular, as a product of fermentation.

The term "secreted" is intended to include the movement of polypeptides to the periplasmic space or extracellular milieu. The term "increased secretion" is intended to include situations in which a given polypeptide is secreted at an increased level (i.e., in excess of the naturally-occurring amount of secretion). In certain embodiments, the term "increased secretion" refers to an increase in secretion of a given polypeptide that is at least about 10% or at least about 100%, 200%, 300%, 400%, 500%, 600%, 700%, 800%, 900%, 1000%, or more, as compared to the naturally-occurring level of secretion.

The term "secretory polypeptide" is intended to include any polypeptide(s), alone or in combination with other polypeptides, that facilitate the transport of another polypeptide from the intracellular space of a cell to the extracellular milieu. In certain embodiments, the secretory polypeptide(s) encompass all the necessary secretory polypeptides sufficient to impart secretory activity to a Gram-negative or Gram-positive host cell or to a yeast host cell. Typically, secretory proteins are encoded in a single region or locus that may be isolated from one host cell and transferred to another host cell using genetic engineering. In certain embodiments, the secretory polypeptide(s) are derived from any bacterial cell having secretory activity or any yeast cell having secretory activity. In certain embodiments, the secretory polypeptide(s) are derived from a host cell having Type II secretory activity. In certain embodiments, the host cell is a thermophilic bacterial cell. In certain embodiments, the host cell is a yeast cell.

The term "derived from" is intended to include the isolation (in whole or in part) of a polynucleotide segment from an indicated source or the purification of a polypeptide from an indicated source. The term is intended to include, for example, direct cloning, PCR amplification, or artificial synthesis from or based on a sequence associated with the indicated polynucleotide source.

By "thermophilic" is meant an organism that thrives at a temperature of about 45° C. or higher.

By "mesophilic" is meant an organism that thrives at a temperature of about 20-45° C.

The term "organic acid" is art-recognized. "Organic acid," as used herein, also includes certain organic solvents such as ethanol. The term "lactic acid" refers to the organic acid 2-hydroxypropionic acid in either the free acid or salt form. The salt form of lactic acid is referred to as "lactate" regardless of the neutralizing agent, i.e., calcium carbonate or ammonium hydroxide. The term "acetic acid" refers to the organic acid methanecarboxylic acid, also known as ethanoic acid, in either free acid or salt form. The salt form of acetic acid is referred to as "acetate."

Certain embodiments of the present invention provide for the "insertion," (e.g., the addition, integration, incorporation, or introduction) of certain genes or particular polynucleotide sequences within thermophilic or mesophilic microorganisms, which insertion of genes or particular polynucleotide sequences may be understood to encompass "genetic modification(s)" or "transformation(s)" such that the resulting strains of said thermophilic or mesophilic microorganisms may be understood to be "genetically modified" or "transformed." In certain embodiments, strains may be of bacterial, fungal, or yeast origin.

Certain embodiments of the present invention provide for the "inactivation" or "deletion" of certain genes or particular polynucleotide sequences within thermophilic or mesophilic microorganisms, which "inactivation" or "deletion" of genes or particular polynucleotide sequences may be understood to encompass "genetic modification(s)" or "transformation(s)" such that the resulting strains of said thermophilic or mesophilic microorganisms may be understood to be "genetically modified" or "transformed." In certain embodiments, strains may be of bacterial, fungal, or yeast origin.

The term "CBP organism" is intended to include microorganisms of the invention, e.g., microorganisms that have properties suitable for CBP.

In one aspect of the invention, the genes or particular polynucleotide sequences are inserted to activate the activity for which they encode, such as the expression of an enzyme. In certain embodiments, genes encoding enzymes in the metabolic production of ethanol, e.g., enzymes that metabolize pentose and/or hexose sugars, may be added to a mesophilic or thermophilic organism. In certain embodiments of the invention, the enzyme may confer the ability to metabolize a pentose sugar and be involved, for example, in the D-xylose pathway and/or L-arabinose pathway. In certain embodiments of the invention, genes encoding enzymes in the conversion of acetate to a non-charged solvent, including but not limited to, acetone, isopropanol, ethyl acetate, or ethanol, may be added to a mesophilic or thermophilic organism.

In one aspect of the invention, the genes or particular polynucleotide sequences are partially, substantially, or completely deleted, silenced, inactivated, or down-regulated in order to inactivate the activity for which they encode, such as the expression of an enzyme. Deletions provide maximum stability because there is no opportunity for a reverse mutation to restore function. Alternatively, genes can be partially, substantially, or completely deleted, silenced, inactivated, or down-regulated by insertion of nucleic acid sequences that disrupt the function and/or expression of the gene (e.g., P1 transduction or other methods known in the art). The terms "eliminate," "elimination," and "knockout" are used interchangeably with the terms "deletion," "partial deletion," "substantial deletion," or "complete deletion." In certain embodiments, strains of thermophilic or mesophilic microorganisms of interest may be engineered by site directed homologous recombination to knockout the production of organic acids. In still other embodiments, RNAi or antisense DNA (asDNA) may be used to partially, substantially, or completely silence, inactivate, or down-regulate a particular gene of interest.

In certain embodiments, the genes targeted for deletion or inactivation as described herein may be endogenous to the native strain of the microorganism, and may thus be understood to be referred to as "native gene(s)" or "endogenous gene(s)." An organism is in "a native state" if it has not been genetically engineered or otherwise manipulated by the hand of man in a manner that intentionally alters the genetic and/or phenotypic constitution of the organism. For example, wild-type organisms may be considered to be in a native state. In other embodiments, the gene(s) targeted for deletion or inactivation may be non-native to the organism.

Similarly, the enzymes of the invention as described herein can be endogenous to the native strain of the microorganism, and can thus be understood to be referred to as "native" or "endogenous."

The term "upregulated" means increased in activity, e.g., increase in enzymatic activity of the enzyme as compared to activity in a native host organism.

The term "downregulated" means decreased in activity, e.g., decrease in enzymatic activity of the enzyme as compared to activity in a native host organism.

The term "activated" means expressed or metabolically functional.

The term "adapted for growing" means selection of an organism for growth under conditions in which the organism does not otherwise grow or in which the organism grows slowly or minimally. Thus, an organism that is said to be adapted for growing under the selected condition, grows better than an organism that has not been adapted for growing under the selected conditions. Growth can be measured by any methods known in the art, including, but not limited to, measurement of optical density or specific growth rate.

The term "biomass inhibitors" means the inhibitors present in biomass that inhibit processing of the biomass by organisms, including but not limited to, CBP organisms. Biomass inhibitors include, but are not limited to, acids, including without limitation, acetic, lactic, 2-furoic, 3,4-dihydroxybenzoic, 3,5-dihydroxybenzoic, vanillic, homovanillic, syringic, gallic, and ferulic acids; aldehydes, including without limitation, 5-hydroxymethylfurfural, furfural, 3,4-hydroxybenzaldehyde, vanillin, and syringaldehyde. Biomass inhibitors include products removed from pretreated cellulosic material or produced as a result of treating or processing cellulosic material, including but not limited to, inhibitors removed from pretreated mixed hardwood or any other pretreated biomass.

Biomass

Biomass can include any type of biomass known in the art or described herein. The terms "lignocellulosic material," "lignocellulosic substrate," and "cellulosic biomass" mean any type of biomass comprising cellulose, hemicellulose, lignin, or combinations thereof, such as but not limited to woody biomass, forage grasses, herbaceous energy crops, non-woody-plant biomass, agricultural wastes and/or agricultural residues, forestry residues and/or forestry wastes, paper-production sludge and/or waste paper sludge, wastewater-treatment sludge, municipal solid waste, corn fiber from wet and dry mill corn ethanol plants, and sugar-processing residues. The terms "hemicellulosics," "hemicellulosic portions," and "hemicellulosic fractions" mean the non-lignin, non-cellulose elements of lignocellulosic material, such as but not limited to hemicellulose (i.e., comprising xyloglucan, xylan, glucuronoxylan, arabinoxylan, mannan, glucomannan, and galactoglucomannan, inter alia), pectins (e.g., homogalacturonans, rhamnogalacturonan I and II, and xylogalacturonan), and proteoglycans (e.g., arabinogalactan-protein, extensin, and proline-rich proteins).

In a non-limiting example, the lignocellulosic material can include, but is not limited to, woody biomass, such as recycled wood pulp fiber, sawdust, hardwood, softwood, and combinations thereof; grasses, such as switch grass, cord grass, rye grass, reed canary grass, miscanthus, or a combination thereof; sugar-processing residues, such as but not limited to sugar cane bagasse; agricultural wastes, such as but not limited to rice straw, rice hulls, barley straw, corn cobs, cereal straw, wheat straw, canola straw, oat straw, oat hulls, and corn fiber; stover, such as but not limited to soybean stover, corn stover; succulents, such as but not limited to, Agave; and forestry wastes, such as but not limited to, recycled wood pulp fiber, sawdust, hardwood (e.g., poplar, oak, maple, birch, willow), softwood, or any combination thereof. Lignocellulosic material may comprise one species of fiber, alternatively, lignocellulosic material may comprise a mixture of fibers that originate from different lignocellulosic materials. Other lignocellulosic materials are agricultural wastes, such as cereal straws, including wheat straw, barley straw, canola straw and oat straw; corn fiber, stovers, such as corn stover and soybean stover, grasses, such as switch grass, reed canary grass, cord grass, and miscanthus; or combinations thereof.

Paper sludge is also a viable feedstock for lactate or acetate production. Paper sludge is solid residue arising from pulping and paper-making, and is typically removed from process wastewater in a primary clarifier. At a disposal cost of $30/wet ton, the cost of sludge disposal equates to $5/ton of paper that is produced for sale. The cost of disposing of wet sludge is a significant incentive to convert the material for other uses, such as conversion to ethanol. Processes provided by the present invention are widely applicable. Moreover, the saccharification and/or fermentation products may be used to produce ethanol or higher value added chemicals, such as organic acids, aromatics, esters, acetone and polymer intermediates.

Acetate

Acetate is produced from acetyl-CoA in two reaction steps catalyzed by phosphotransacetylyase (PTA) and acetate kinase (ACK). The reactions mediated by these enzymes are shown below:

PTA reaction: acetyl-CoA+phosphate=CoA+acetyl phosphate (EC 2.3.1.8)

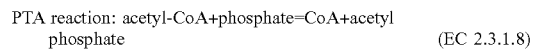

ACK reaction: ADP+acetyl phosphate=ATP+acetate (EC 2.7.2.1)

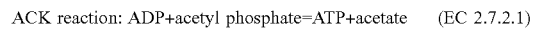

Both C. thermocellum and C. cellulolyticum make acetate under standard fermentation conditions and have well annotated genes encoding PTA and ACK (see Table 7 of International Appl. No. PCT/US2009/064128, which is incorporated by reference herein).

Consolidated Bioprocessing

Consolidated bioprocessing (CBP) is a processing strategy for cellulosic biomass that involves consolidating into a single process step four biologically-mediated events: enzyme production, hydrolysis, hexose fermentation, and pentose fermentation. Implementing this strategy requires development of microorganisms that both utilize cellulose, hemicellulosics, and other biomass components while also producing a product of interest at sufficiently high yield and concentrations. The feasibility of CBP is supported by kinetic and bioenergetic analysis. See van Walsum and Lynd (1998) *Biotech. Bioeng.* 58:316.

Xylose Metabolism

Xylose is a five-carbon monosaccharide that can be metabolized into useful products by a variety of organisms. There are two main pathways of xylose metabolism, each unique in the characteristic enzymes they utilize. One pathway is called the "Xylose Reductase-Xylitol Dehydrogenase" or XR-XDH pathway. Xylose reductase (XR) and xylitol dehydrogenase (XDH) are the two main enzymes used in this method of xylose degradation. XR, encoded by the XYL1 gene, is responsible for the reduction of xylose to xylitol and is aided by cofactors NADH or NADPH. Xylitol is then oxidized to xylulose by XDH, which is expressed through the XYL2 gene, and accomplished exclusively with the cofactor NAD+. Because of the varying cofactors needed in this pathway and the degree to which they are available for usage, an imbalance can result in an overproduction of xylitol byproduct and an inefficient production of desirable ethanol. Varying expression of the XR and XDH enzyme levels have been tested in the laboratory in the attempt to optimize the efficiency of the xylose metabolism pathway.

The other pathway for xylose metabolism is called the "Xylose Isomerase" (XI) pathway. Enzyme XI is responsible for direct conversion of xylose into xylulose, and does not proceed via a xylitol intermediate. Both pathways create xylulose, although the enzymes utilized are different. After production of xylulose both the XR-XDH and XI pathways proceed through enzyme xylulokinase (XK), encoded on gene XKS1, to further modify xylulose into xylulose-5-P where it then enters the pentose phosphate pathway for further catabolism.

Studies on flux through the pentose phosphate pathway during xylose metabolism have revealed that limiting the speed of this step may be beneficial to the efficiency of fermentation to ethanol. Modifications to this flux that may improve ethanol production include a) lowering phosphoglucose isomerase activity, b) deleting the GND1 gene, and c) deleting the ZWF1 gene (Jeppsson et al., 2002). Since the pentose phosphate pathway produces additional NADPH during metabolism, limiting this step will help to correct the already evident imbalance between NAD(P)H and NAD+ cofactors and reduce xylitol byproduct. Another experiment comparing the two xylose metabolizing pathways revealed that the XI pathway was best able to metabolize xylose to produce the greatest ethanol yield, while the XR-XDH pathway reached a much faster rate of ethanol production (Karhumaa et al., *Microb Cell Fact.* 2007 Feb. 5; 6:5). See also International Publication No. WO2006/009434, incorporated herein by reference in its entirety.

Arabinose Metabolism

Arabinose is a five-carbon monosaccharide that can be metabolized into useful products by a variety of organisms. L-Arabinose residues are found widely distributed among many heteropolysaccharides of different plant tissues, such as arabinans, arabinogalactans, xylans and arabinoxylans. *Bacillus* species in the soil participate in the early stages of plant material decomposition, and *B. subtilis* secretes three enzymes, an endo-arabanase and two arabinosidases, capable of releasing arabinosyl oligomers and L-arabinose from plant cell.

Three pathways for L-arabinose metabolism in microorganisms have been described. Many bacteria, including *Escherichia coli*, use arabinose isomerase (AraA; E.C. 5.3.1.4), ribulokinase (AraB; E.C. 2.7.1.16), and ribulose phosphate epimerase (AraD; E.C. 5.1.3.4) to sequentially convert L-arabinose to D-xylulose-5-phosphate through L-ribulose and L-ribulose 5-phosphate. See, e.g., Sa-Nogueira I, et al., *Microbiology* 143:957-69 (1997). The D-xylulose-5-phosphate then enters the pentose phosphate pathway for further catabolism. In the second pathway, L-arabinose is converted to L-2-keto-3-deoxyarabonate (L-KDA) by the consecutive action of enzymes arabinose dehydrogenase (ADH), arabinolactone (AL), and arabinonate dehydratase (AraC). See, e.g., Watanabe, S, et al., *J. Biol. Chem.* 281: 2612-2623 (2006). L-KDA can be further metabolized in two alternative pathways: 1) L-KDA conversion to 2-ketoglutarate via 2-ketoglutaric semialdehyde (KGSA) by L-KDA dehydratase and KGSA dehydrogenase or 2) L-KDA conversion to pyruvate and glycolaldehyde by L-KDA aldolase. In the third, fungal pathway, L-arabinose is converted to D-xylulose-5-phosphate through L-arabinitol, L-xylulose, and xylitol, by enzymes such as NAD (P)H-dependent aldose reductase (AR), L-arabinitol 4-dehydrogenase (ALDH), L-xylulose reductase (LXR), xylitol dehydrogenase (XylD), and xylulokinase (XylB). These, and additional proteins involved in arabinose metabolism and regulation may be found at nmpdr.org/FIG/wiki/rest.cgi/ NmpdrPlugin/SeedViewer?page=Subsystems; subsystem=L-Arabinose_utilization, visited Mar. 21, 2011, which is incorporated by reference herein in its entirety.

AraC protein regulates expression of its own synthesis and the other genes of the Ara system. See Schleif, R., *Trends Genet.* 16(12):559-65 (2000). In *E. coli*, the AraC protein positively and negatively regulates expression of the proteins required for the uptake and catabolism of the sugar L-arabinose. Homologs of AraC, such as regulatory proteins RhaR and RhaS of the rhamnose operon, have been identified that contain regions homologous to the DNA-binding domain of AraC (Leal, T. F. and de Sa-Nogueira, I., *FEMS Microbiol Lett.* 241(1):41-48 (2004)). Such arabinose regulatory proteins are referred to as the AraC/XylS family. See also, Mota, L. J., et al., *Mol. Microbiol.* 33(3):476-89 (1999); Mota, L. J., et al., *J. Bacteriol.* 183(14):4190-201 (2001).

In *E. coli*, the transport of L-arabinose across the *E. coli* cytoplasmic membrane requires the expression of either the high-affinity transport operon, araFGH, a binding protein-dependent system on the low-affinity transport operon, araE, or a proton symporter. Additional arabinose transporters include those identified from *K. marxianus* and *P. guilliermondii*, disclosed in U.S. Pat. No. 7,846,712, which is incorporated by reference herein.

In some embodiments, the recombinant microorganisms of the invention have the ability to metabolize arabinose using one or more of the above enzymes.

Glycerol Reduction

Anaerobic growth conditions require the production of endogenouse electron acceptors, such as the coenzyme nicotinamide adenine dinucleotide ($NAD^+$). In cellular redox reactions, the $NAD^+$/NADH couple plays a vital role as a reservoir and carrier of reducing equivalents. Ansell, R., et al., *EMBO J.* 16:2179-87 (1997). Cellular glycerol production, which generates an $NAD^+$, serves as a redox valve to remove excess reducing power during anaerobic fermentation in yeast. Glycerol production is, however, an energetically wasteful process that expends ATP and results in the loss of a reduced three-carbon compound. Ansell, R., et al., *EMBO J.* 16:2179-87 (1997). To generate glycerol from a starting glucose molecule, glycerol 3-phosphate dehydrogenase (GPD) reduces dihydroxyacetone phosphate to glycerol 3-phosphate and glycerol 3-phosphatase (GPP) dephosphorylates glycerol 3-phosphate to glycerol. Despite being energetically wasteful, glycerol production is a necessary metabolic process for anaerobic growth as deleting GPD activity completely inhibits growth under anaeroblic conditions. See Ansell, R., et al., *EMBO J.* 16:2179-87 (1997).

GPD is encoded by two isogenes, gpd1 and gpd2. GPD1 encodes the major isoform in anaerobically growing cells, while GPD2 is required for glycerol production in the absence of oxygen, which stimulates its expression. Pahlman, A-K., et al., *J. Biol. Chem.* 276:3555-63 (2001). The first step in the conversion of dihydroxyacetone phosphate to glycerol by GPD is rate controlling. Guo, Z. P., et al., *Metab. Eng.* 13:49-59 (2011). GPP is also encoded by two isogenes, gpp1 and gpp2. The deletion of GPP genes arrests growth when shifted to anaerobic conditions, demonstrating that GPP is important for cellular tolerance to osmotic and anaerobic stress. See Pahlman, A-K., et al., *J. Biol. Chem.* 276:3555-63 (2001).

Because glycerol is a major by-product of anaerobic production of ethanol, many efforts have been made to delete cellular production of glycerol. However, because of the reducing equivalents produced by glycerol synthesis, deletion of the glycerol synthesis pathway cannot be done without compensating for this valuable metabolic function. Attempts to delete glycerol production and engineer alternate electron acceptors have been made. Lidén, G., et al., *Appl. Env. Microbiol.* 62:3894-96 (1996); Medina, V. G., et al., *Appl. Env. Microbiol.* 76:190-195 (2010). Lidén and Medina both deleted the gpd1 and gpd2 genes and attempted to bypass glycerol formation using additional carbon sources. Lidén engineered a xylose reductase from *Pichia stipitis* into an *S. cerevisiae* gpd1/2 deletion strain. The xylose reductase activity facilitated the anaerobic growth of the glycerol-deleted strain in the presence of xylose. See Lidén, G., et al., *Appl. Env. Microbiol.* 62:3894-96 (1996). Medina engineered an acetylaldehyde dehydrogenase, mhpF, from *E. coli* into an *S. cerevisiae* gpd1/2 deletion strain to convert acetyl-CoA to acetaldehyde. The acetylaldehyde dehydrogenase activity facilitated the anaerobic growth of the glycerol-deletion strain in the presence of acetic acid but not in the presence of glucose as the sole source of carbon. Medina, V. G., et al., *Appl. Env. Microbiol.* 76:190-195 (2010); see also EP 2277989. Medina noted several issues with the mhpF-containing strain that needed to be addressed before implementing industrially, including significantly reduced growth and product formation rates than yeast comprising GPD1 and GPD2.

Thus, in some embodiments of the invention, the recombinant host cells comprise a deletion or alteration of one or more glycerol producing enzymes. Additional deletions or alterations to modulate glycerol production include, but are not limited to, engineering a pyruvate formate lyase in a recombinant host cell, and are described in U.S. Appl. No. 61/472,085, incorporated by reference herein in its entirety.

Microorganisms

The present invention includes multiple strategies for the development of microorganisms with the combination of substrate-utilization and product-formation properties required for CBP. The "native cellulolytic strategy" involves engineering naturally occurring cellulolytic microorganisms to improve product-related properties, such as yield and titer. The "recombinant cellulolytic strategy" involves engineering natively non-cellulolytic organisms that exhibit high product yields and titers to express a heterologous cellulase system that enables cellulose utilization or hemicellulose utilization or both.

Many bacteria have the ability to ferment simple hexose sugars into a mixture of acidic and pH-neutral products via the process of glycolysis. The glycolytic pathway is abundant and comprises a series of enzymatic steps whereby a six carbon glucose molecule is broken down, via multiple intermediates, into two molecules of the three carbon compound pyruvate. This process results in the net generation of ATP (biological energy supply) and the reduced cofactor NADH.

Pyruvate is an important intermediary compound of metabolism. For example, under aerobic conditions pyruvate may be oxidized to acetyl coenzyme A (acetyl-CoA), which then enters the tricarboxylic acid cycle (TCA), which in turn generates synthetic precursors, $CO_2$, and reduced cofactors. The cofactors are then oxidized by donating hydrogen equivalents, via a series of enzymatic steps, to oxygen resulting in the formation of water and ATP. This process of energy formation is known as oxidative phosphorylation.

Under anaerobic conditions (no available oxygen), fermentation occurs in which the degradation products of organic compounds serve as hydrogen donors and acceptors. Excess NADH from glycolysis is oxidized in reactions involving the reduction of organic substrates to products, such as lactate and ethanol. In addition, ATP is regenerated from the production of organic acids, such as acetate, in a process known as substrate level phosphorylation. Therefore, the fermentation products of glycolysis and pyruvate metabolism include a variety of organic acids, alcohols and $CO_2$.

Most facultative anaerobes metabolize pyruvate aerobically via pyruvate dehydrogenase (PDH) and the tricarboxylic acid cycle (TCA). Under anaerobic conditions, the main energy pathway for the metabolism of pyruvate is via pyruvate-formate-lyase (PFL) pathway to give formate and acetyl-CoA. Acetyl-CoA is then converted to acetate, via phosphotransacetylase (PTA) and acetate kinase (ACK) with the co-production of ATP, or reduced to ethanol via acetaldehyde dehydrogenase (AcDH) and alcohol dehydrogenase (ADH). In order to maintain a balance of reducing equivalents, excess NADH produced from glycolysis is re-oxidized to NAD+ by lactate dehydrogenase (LDH) during the reduction of pyruvate to lactate. NADH can also be re-oxidized by AcDH and ADH during the reduction of acetyl-CoA to ethanol, but this is a minor reaction in cells with a functional LDH.

Host Cells

Host cells useful in the present invention include any prokaryotic or eukaryotic cells; for example, microorganisms selected from bacterial, algal, and yeast cells. Among host cells thus suitable for the present invention are microorganisms, for example, of the genera *Aeromonas, Aspergillus, Bacillus, Escherichia, Kluyveromyces, Pichia, Rhodococcus, Saccharomyces* and *Streptomyces*.

In some embodiments, the host cells are microorganisms. In one embodiment the microorganism is a yeast. According to the present invention the yeast host cell can be, for example, from the genera *Saccharomyces, Kluyveromyces, Candida, Pichia, Schizosaccharomyces, Hansenula, Kloeckera, Schwanniomyces*, and *Yarrowia*. Yeast species as host cells may include, for example, *S. cerevisiae, S. bulderi, S. barnetti, S. exiguus, S. uvarum, S. diastaticus, K. lactis, K. marxianus*, or *K. fragilis*. In some embodiments, the yeast is selected from the group consisting of *Saccharomyces cerevisiae, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe* and *Schwanniomyces occidentalis*. In one particular embodiment, the yeast is *Saccharomyces cerevisiae*. In another embodiment, the yeast is a thermotolerant *Saccharomyces cerevisiae*. The selection of an appropriate host is deemed to be within the scope of those skilled in the art from the teachings herein.

In some embodiments, the host cell is an oleaginous cell. The oleaginous host cell can be an oleaginous yeast cell. For example, the oleaginous yeast host cell can be from the genera *Blakeslea, Candida, Cryptococcus, Cunninghamella, Lipomyces, Mortierella, Mucor, Phycomyces, Pythium, Rhodosporidum, Rhodotorula, Trichosporon* or *Yarrowia*. According to the present invention, the oleaginous host cell can be an oleaginous microalgae host cell. For example, the oleaginous microalgea host cell can be from the genera *Thraustochytrium* or *Schizochytrium*. Biodiesel could then be produced from the triglyceride produced by the oleaginous organisms using conventional lipid transesterification processes. In some particular embodiments, the oleaginous host cells can be induced to secrete synthesized lipids. Embodiments using oleaginous host cells are advantageous because they can produce biodiesel from lignocellulosic feedstocks which, relative to oilseed substrates, are cheaper, can be grown more densely, show lower life cycle carbon dioxide emissions, and can be cultivated on marginal lands.

In some embodiments, the host cell is a thermotolerant host cell. Thermotolerant host cells can be particularly useful in simultaneous saccharification and fermentation processes by allowing externally produced cellulases and ethanol-producing host cells to perform optimally in similar temperature ranges.

Thermotolerant host cells can include, for example, *Issatchenkia orientalis, Pichia mississippiensis, Pichia mexicana, Pichia farinosa, Clavispora opuntiae, Clavispora lusitaniae, Candida mexicana, Hansenula polymorpha* and *Kluyveromyces* host cells. In some embodiments, the thermotolerant cell is an *S. cerevisiae* strain, or other yeast strain, that has been adapted to grow in high temperatures, for example, by selection for growth at high temperatures in a cytostat.

In some particular embodiments, the host cell is a *Kluyveromyces* host cell. For example, the *Kluyveromyces* host cell can be a *K. lactis, K. marxianus, K. blattae, K. phaffii, K. yarrowii, K. aestuarii, K. dobzhanskii, K. wick-* erhamii *K. thermotolerans*, or *K. waltii* host cell. In one embodiment, the host cell is a *K. lactis*, or *K. marxianus* host cell. In another embodiment, the host cell is a *K. marxianus* host cell.

In some embodiments, the thermotolerant host cell can grow at temperatures above about 30° C., about 31° C., about 32° C., about 33° C., about 34° C., about 35° C., about 36° C., about 37° C., about 38° C., about 39° C., about 40° C., about 41° C. or about 42° C. In some embodiments of the present invention the thermotolerant host cell can produce ethanol from cellulose at temperatures above about 30° C., about 31° C., about 32° C., about 33° C., about 34° C., about 35° C., about 36° C., about 37° C., about 38° C., about 39° C., about 40° C., about 41° C., about 42° C., or about 43° C., or about 44° C., or about 45° C., or about 50° C.

In some embodiments of the present invention, the thermotolerant host cell can grow at temperatures from about 30° C. to 60° C., about 30° C. to 55° C., about 30° C. to 50° C., about 40° C. to 60° C., about 40° C. to 55° C. or about 40° C. to 50° C. In some embodiments of the present invention, the thermotolterant host cell can produce ethanol from cellulose at temperatures from about 30° C. to 60° C., about 30° C. to 55° C., about 30° C. to 50° C., about 40° C. to 60° C., about 40° C. to 55° C. or about 40° C. to 50° C.

In some embodiments, the host cell has the ability to metabolize xylose. Detailed information regarding the development of the xylose-utilizing technology can be found in the following publications: Kuyper M et al. *FEMS Yeast Res.* 4: 655-64 (2004), Kuyper M et al. *FEMS Yeast Res.* 5:399-409 (2005), and Kuyper M et al. *FEMS Yeast Res.* 5:925-34 (2005), which are herein incorporated by reference in their entirety. For example, xylose-utilization can be accomplished in *S. cerevisiae* by heterologously expressing the xylose isomerase gene, XylA, e.g. from the anaerobic fungus *Piromyces* sp. E2, overexpressing five *S. cerevisiae* enzymes involved in the conversion of xylulose to glycolytic intermediates (xylulokinase, ribulose 5-phosphate isomerase, ribulose 5-phosphate epimerase, transketolase and transaldolase) and deleting the GRE3 gene encoding aldose reductase to minimise xylitol production.

The host cells can contain antibiotic markers or can contain no antibiotic markers.

In certain embodiments, the host cell is a microorganism that is a species of the genera *Thermoanaerobacterium, Thermoanaerobacter, Clostridium, Geobacillus, Saccharococcus, Paenibacillus, Bacillus, Caldicellulosiruptor, Anaerocellum*, or *Anoxybacillus*. In certain embodiments, the host cell is a bacterium selected from the group consisting of: *Thermoanaerobacterium thermosulfurigenes, Thermoanaerobacterium aotearoense, Thermoanaerobacterium polysaccharolyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter thermohydrosulfuricus, Thermoanaerobacter ethanolicus, Thermoanaerobacter brocki, Clostridium thermocellum, Clostridium cellulolyticum, Clostridium phytofermentans, Clostridium straminosolvens, Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchalkensis, Anoxybacillus gonensis, Caldicellulosiruptor acetigenus, Caldicellulosiruptor saccharolyticus, Caldicellulosiruptor kristjansonii, Caldicellulosiruptor owensensis, Caldicellulosiruptor lactoaceticus*, and *Anaerocellum thermophilum*. In certain embodiments, the host cell is *Clostridium thermocellum, Clostridium cellulolyticum*, or *Thermoanaerobacterium saccharolyticum*.

Codon Optimized Polynucleotides

The polynucleotides encoding heterologous enzymes described herein can be codon-optimized. As used herein the term "codon-optimized coding region" means a nucleic acid coding region that has been adapted for expression in the cells of a given organism by replacing at least one, or more than one, or a significant number, of codons with one or more codons that are more frequently used in the genes of that organism.

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism.

The CAI of codon optimized sequences of the present invention corresponds to between about 0.8 and 1.0, between about 0.8 and 0.9, or about 1.0. A codon optimized sequence may be further modified for expression in a particular organism, depending on that organism's biological constraints. For example, large runs of "As" or "Ts" (e.g., runs greater than 3, 4, 5, 6, 7, 8, 9, or 10 consecutive bases) can be removed from the sequences if these are known to effect transcription negatively. Furthermore, specific restriction enzyme sites may be removed for molecular cloning purposes. Examples of such restriction enzyme sites include PacI, AscI, BamHI, BglII, EcoRI and XhoI. Additionally, the DNA sequence can be checked for direct repeats, inverted repeats and mirror repeats with lengths of ten bases or longer, which can be modified manually by replacing codons with "second best" codons, i.e., codons that occur at the second highest frequency within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

The Standard Genetic Code

| | T | C | A | G |
|---|---|---|---|---|
| T | TTT Phe (F) | TCT Ser(S) | TAT Tyr(Y) | TGT Cys(C) |
| | TTC " | TCC " | TAC " | TGC |
| | TTA Leu(L) | TCA " | TAA Ter | TGA Ter |
| | TTG " | TCG " | TAG Ter | TGG Trp(W) |

TABLE 1-continued

The Standard Genetic Code

|   | T | C | A | G |
|---|---|---|---|---|
| C | CTT Leu(L) | CCT Pro(P) | CAT His(H) | CGT Arg(R) |
|   | CTC" | CCC" | CAC" | CGC" |
|   | CTA" | CCA" | CAA Gln(Q) | CGA" |
|   | CTG" | CCG" | CAG" | CGG" |
| A | ATT Ile(I) | ACT Thr(T) | AAT Asn(N) | AGT Ser(S) |
|   | ATC" | ACC" | AAC" | AGC" |
|   | ATA" | ACA" | AAA Lys(K) | AGA Arg(R) |
|   | ATG Met (M) | ACG" | AAG" | AGG" |
| G | GTT Val(V) | GCT Ala(A) | GAT Asp(D) | GGT Gly(G) |
|   | GTC" | GCC" | GAC" | GGC" |
|   | GTA" | GCA" | GAA Glu(E) | GGA" |
|   | GTG" | GCG" | GAG" | GGG" |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at kazusa.or.jp/codon/ (visited Dec. 18, 2009), and these tables can be adapted in a number of ways. See Nakamura, Y., et al. "Codon usage tabulated from the international DNA sequence databases: status for the year 2000," *Nucl. Acids Res.* 28:292 (2000). Codon usage tables for yeast, calculated from GenBank Release 128.0 [15 Feb. 2002], are reproduced below as Table 2. This table uses mRNA nomenclature, and so instead of thymine (T) which is found in DNA, the tables use uracil (U) which is found in RNA. The table has been adapted so that frequencies are calculated for each amino acid, rather than for all 64 codons.

TABLE 2

Codon Usage Table for *Saccharomyces cerevisiae* Genes

| Amino Acid | Codon | Number | Frequency per hundred |
|---|---|---|---|
| Phe | UUU | 170666 | 26.1 |
| Phe | UUC | 120510 | 18.4 |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Ile | AUU | 196893 | 30.1 |
| Ile | AUC | 112176 | 17.2 |
| Ile | AUA | 116254 | 17.8 |
| Met | AUG | 136805 | 20.9 |
| Val | GUU | 144243 | 22.1 |
| Val | GUC | 76947 | 11.8 |

TABLE 2-continued

Codon Usage Table for *Saccharomyces cerevisiae* Genes

| Amino Acid | Codon | Number | Frequency per hundred |
|---|---|---|---|
| Val | GUA | 76927 | 11.8 |
| Val | GUG | 70337 | 10.8 |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Pro | CCU | 88263 | 13.5 |
| Pro | CCC | 44309 | 6.8 |
| Pro | CCA | 119641 | 18.3 |
| Pro | CCG | 34597 | 5.3 |
| Thr | ACU | 132522 | 20.3 |
| Thr | ACC | 83207 | 12.7 |
| Thr | ACA | 116084 | 17.8 |
| Thr | ACG | 52045 | 8.0 |
| Ala | GCU | 138358 | 21.2 |
| Ala | GCC | 82357 | 12.6 |
| Ala | GCA | 105910 | 16.2 |
| Ala | GCG | 40358 | 6.2 |
| Tyr | UAU | 122728 | 18.8 |
| Tyr | UAC | 96596 | 14.8 |
| His | CAU | 89007 | 13.6 |
| His | CAC | 50785 | 7.8 |
| Gln | CAA | 178251 | 27.3 |
| Gln | CAG | 79121 | 12.1 |
| Asn | AAU | 233124 | 35.7 |
| Asn | AAC | 162199 | 24.8 |
| Lys | AAA | 273618 | 41.9 |
| Lys | AAG | 201361 | 30.8 |
| Asp | GAU | 245641 | 37.6 |
| Asp | GAC | 132048 | 20.2 |
| Glu | GAA | 297944 | 45.6 |
| Glu | GAG | 125717 | 19.2 |
| Cys | UGU | 52903 | 8.1 |
| Cys | UGC | 31095 | 4.8 |
| Trp | UGG | 67789 | 10.4 |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Gly | GGU | 156109 | 23.9 |
| Gly | GGC | 63903 | 9.8 |
| Gly | GGA | 71216 | 10.9 |
| Gly | GGG | 39359 | 6.0 |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions can be designed by various different methods.

In one method, a codon usage table is used to find the single most frequent codon used for any given amino acid, and that codon is used each time that particular amino acid appears in the polypeptide sequence. For example, referring to Table 2 above, for leucine, the most frequent codon is UUG, which is used 27.2% of the time. Thus all the leucine residues in a given amino acid sequence would be assigned the codon UUG.

In another method, the actual frequencies of the codons are distributed randomly throughout the coding sequence. Thus, using this method for optimization, if a hypothetical polypeptide sequence had 100 leucine residues, referring to Table 2 for frequency of usage in the *S. cerevisiae*, about 5, or 5% of the leucine codons would be CUC, about 11, or 11% of the leucine codons would be CUG, about 12, or 12% of the leucine codons would be CUU, about 13, or 13% of the leucine codons would be CUA, about 26, or 26% of the leucine codons would be UUA, and about 27, or 27% of the leucine codons would be UUG.

These frequencies would be distributed randomly throughout the leucine codons in the coding region encoding the hypothetical polypeptide. As will be understood by those of ordinary skill in the art, the distribution of codons in the sequence can vary significantly using this method; however, the sequence always encodes the same polypeptide.

When using the methods above, the term "about" is used precisely to account for fractional percentages of codon frequencies for a given amino acid. As used herein, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes for a hypothetical polypeptide having 62 leucine residues, the fractional frequency of codon usage would be calculated by multiplying 62 by the frequencies for the various codons. Thus, 7.28 percent of 62 equals 4.51 UUA codons, or "about 5," i.e., 4, 5, or 6 UUA codons, 12.66 percent of 62 equals 7.85 UUG codons or "about 8," i.e., 7, 8, or 9 UUG codons, 12.87 percent of 62 equals 7.98 CUU codons, or "about 8," i.e., 7, 8, or 9 CUU codons, 19.56 percent of 62 equals 12.13 CUC codons or "about 12," i.e., 11, 12, or 13 CUC codons, 7.00 percent of 62 equals 4.34 CUA codons or "about 4," i.e., 3, 4, or 5 CUA codons, and 40.62 percent of 62 equals 25.19 CUG codons, or "about 25," i.e., 24, 25, or 26 CUG codons.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the VectorNTI Suite, available from InforMax, Inc., Bethesda, Md., and the "backtranslate" function in the GCG—Wisconsin Package, available from Accelrys, Inc., San Diego, Calif. In addition, various resources are publicly available to codon-optimize coding region sequences, e.g., the "backtranslation" function atentelechon.com/bioinformatics/backtranslation.php?lang=eng (visited Dec. 18, 2009) and the "backtranseq" function available at emboss.bioinformatics.nl/cgi-bin/emboss/backtranseq (visited Dec. 18, 2009). Constructing a rudimentary algorithm to assign codons based on a given frequency can also easily be accomplished with basic mathematical functions by one of ordinary skill in the art.

A number of options are available for synthesizing codon optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence is synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In additional embodiments, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon optimized for the given species. However, such sequences are still much closer to the codon usage of the desired species than the native codon usage. The advantage of this approach is that synthesizing codon-optimized nucleic acid fragments encoding each fragment, variant, and derivative of a given polypeptide, although routine, would be time consuming and would result in significant expense.

Transposons

To select for foreign DNA that has entered a host it is preferable that the DNA be stably maintained in the organism of interest. With regard to plasmids, there are two processes by which this can occur. One is through the use of replicative plasmids. These plasmids have origins of replication that are recognized by the host and allow the plasmids to replicate as stable, autonomous, extrachromosomal elements that are partitioned during cell division into daughter cells. The second process occurs through the integration of a plasmid onto the chromosome. This predominately happens by homologous recombination and results in the insertion of the entire plasmid, or parts of the plasmid, into the host chromosome. Thus, the plasmid and selectable marker(s) are replicated as an integral piece of the chromosome and segregated into daughter cells. Therefore, to ascertain if plasmid DNA is entering a cell during a transformation event through the use of selectable markers requires the use of a replicative plasmid or the ability to recombine the plasmid onto the chromosome. These qualifiers cannot always be met, especially when handling organisms that do not have a suite of genetic tools.

One way to avoid issues regarding plasmid-associated markers is through the use of transposons. A transposon is a mobile DNA element, defined by mosaic DNA sequences that are recognized by enzymatic machinery referred to as a transposase. The function of the transposase is to randomly insert the transposon DNA into host or target DNA. A selectable marker can be cloned onto a transposon by standard genetic engineering. The resulting DNA fragment can be coupled to the transposase machinery in an in vitro reaction and the complex can be introduced into target cells by electroporation. Stable insertion of the marker onto the chromosome requires only the function of the transposase machinery and alleviates the need for homologous recombination or replicative plasmids.

The random nature associated with the integration of transposons has the added advantage of acting as a form of mutagenesis. Libraries can be created that comprise amalgamations of transposon mutants. These libraries can be used in screens or selections to produce mutants with desired phenotypes. For instance, a transposon library of a CBP organism could be screened for the ability to produce more ethanol, or less lactic acid and/or more acetate.

Native Cellulolytic Strategy

Naturally occurring cellulolytic microorganisms are starting points for CBP organism development via the native strategy. Anaerobes and facultative anaerobes are of particular interest. The primary objective is to engineer the detoxification of biomass derived acetate to a non-charged solvent, including but not limited to, acetone, isopropanol, ethyl acetate, or ethanol. Metabolic engineering of mixed-acid fermentations in relation to, for example, ethanol production, has been successful in the case of mesophilic, non-cellulolytic, enteric bacteria. Recent developments in suitable gene-transfer techniques allow for this type of work to be undertaken with cellulolytic bacteria.

Recombinant Cellulolytic Strategy

Non-cellulolytic microorganisms with desired product-formation properties are starting points for CBP organism development by the recombinant cellulolytic strategy. The primary objective of such developments is to engineer a heterologous cellulase system that enables growth and fermentation on pretreated lignocellulose. The heterologous production of cellulases has been pursued primarily with bacterial hosts producing ethanol at high yield (engineered strains of *E. coli*, *Klebsiella oxytoca*, and *Zymomonas mobilis*) and the yeast *Saccharomyces cerevisiae*. Cellulase expression in strains of *K. oxytoca* resulted in increased hydrolysis yields—but not growth without added cellulase—for microcrystalline cellulose, and anaerobic growth on amorphous cellulose. Although dozens of saccharolytic enzymes have been functionally expressed in *S. cerevisiae*, anaerobic growth on cellulose as the result of such expression has not been definitively demonstrated.

Aspects of the present invention relate to the use of thermophilic or mesophilic microorganisms as hosts for modification via the native cellulolytic strategy. Their potential in process applications in biotechnology stems from their ability to grow at relatively high temperatures with attendant high metabolic rates, production of physically and chemically stable enzymes, and elevated yields of end products. Major groups of thermophilic bacteria include eubacteria and archaebacteria. Thermophilic eubacteria include: phototropic bacteria, such as cyanobacteria, purple bacteria, and green bacteria; Gram-positive bacteria, such as *Bacillus*, *Clostridium*, Lactic acid bacteria, and Actinomyces; and other eubacteria, such as *Thiobacillus*, Spirochete, *Desulfotomaculum*, Gram-negative aerobes, Gram-negative anaerobes, and *Thermotoga*. Within archaebacteria are considered Methanogens, extreme thermophiles (an art-recognized term), and *Thermoplasma*. In certain embodiments, the present invention relates to Gram-negative organotrophic thermophiles of the genera *Thermus*, Gram-positive eubacteria, such as genera *Clostridium*, and also which comprise both rods and cocci, genera in group of eubacteria, such as *Thermosipho* and *Thermotoga*, genera of Archaebacteria, such as *Thermococcus*, *Thermoproteus* (rod-shaped), *Thermofilum* (rod-shaped), *Pyrodictium*, *Acidianus*, *Sulfolobus*, *Pyrobaculum*, *Pyrococcus*, *Thermodiscus*, *Staphylothermus*, *Desulfurococcus*, *Archaeoglobus*, and *Methanopyrus*. Some examples of thermophilic or mesophilic (including bacteria, procaryotic microorganism, and fungi), which may be suitable for the present invention include, but are not limited to: *Clostridium thermosulfurogenes*, *Clostridium cellulolyticum*, *Clostridium thermocellum*, *Clostridium thermohydrosulfuricum*, *Clostridium thermoaceticum*, *Clostridium thermosaccharolyticum*, *Clostridium tartarivorum*, *Clostridium thermocellulaseum*, *Clostridium phytofermentans*, *Clostridium straminosolvens*, *Thermoanaerobacterium thermosaccarolyticum*, *Thermoanaerobacterium saccharolyticum*, *Thermobacteroides acetoethylicus*, *Thermoanaerobium brockii*, *Methanobacterium thermoautotrophicum*, *Anaerocellum thermophilium*, *Pyrodictium occultum*, *Thermoproteus neutrophilus*, *Thermofilum librum*, *Thermothrix thioparus*, *Desulfovibrio thermophilus*, *Thermoplasma acidophilum*, *Hydrogenomonas thermophilus*, *Thermomicrobium roseum*, *Thermus flavas*, *Thermus ruber*, *Pyrococcus furiosus*, *Thermus aquaticus*, *Thermus thermophilus*, *Chloroflexus aurantiacus*, *Thermococcus litoralis*, *Pyrodictium abyssi*, *Bacillus stearothermophilus*, *Cyanidium caldarium*, *Mastigocladus laminosus*, *Chlamydothrix calidissima*, *Chlamydothrix penicillata*, *Thiothrix carnea*, *Phormidium tenuissimum*, *Phormidium geysericola*, *Phormidium subterraneum*, *Phormidium bijahensis*, *Oscillatoria filiformis*, *Synechococcus lividus*, *Chloroflexus aurantiacus*, *Pyrodictium brockii*, *Thiobacillus thiooxidans*, *Sulfolobus acidocaldarius*, *Thiobacillus thermophilica*, *Bacillus stearothermophilus*, *Cercosulcifer hamathensis*, *Vahlkampfia reichi*, *Cyclidium citrullus*, *Dactylaria gallopava*, *Synechococcus lividus*, *Synechococcus elongatus*, *Synechococcus minervae*, *Synechocystis aquatilus*, *Aphanocapsa thermalis*, *Oscillatoria terebriformis*, *Oscillatoria amphibia*, *Oscillatoria germinata*, *Oscillatoria okenii*, *Phormidium laminosum*, *Phormidium parparasiens*, *Symploca thermalis*, *Bacillus acidocaldarias*, *Bacillus coagulans*, *Bacillus thermocatenalatus*, *Bacillus licheniformis*, *Bacillus pamilas*, *Bacillus macerans*, *Bacillus circulans*, *Bacillus laterosporus*, *Bacillus brevis*, *Bacillus subtilis*, *Bacillus sphaericus*, *Desulfotomaculum nigrificans*, *Streptococcus thermophilus*, *Lactobacillus thermophilus*, *Lactobacillus bulgaricus*, *Bifidobacterium thermophilum*, *Streptomyces fragmentosporus*, *Streptomyces thermonitrificans*, *Streptomyces thermovulgaris*, *Pseudonocardia thermophila*, *Thermoactinomyces vulgaris*, *Thermoactinomyces sacchari*, *Thermoactinomyces candidas*, *Thermomonospora curvata*, *Thermomonospora viridis*, *Thermomonospora citrina*, *Microbispora thermodiastatica*, *Microbispora aerata*, *Microbispora bispora*, *Actinobifida dichotomica*, *Actinobifida chromogena*, *Micropolyspora caesia*, *Micropolyspora faeni*, *Micropolyspora cectivugida*, *Micropolyspora cabrobrunea*, *Micropolyspora thermovirida*, *Micropolyspora viridinigra*, *Methanobacterium thermoautothropicum*, *Caldicellulosiruptor acetigenus*, *Caldicellulosiruptor saccharolyticus*, *Caldicellulosiruptor kristjanssonii*, *Caldicellulosiruptor owensensis*, *Caldicellulosiruptor lactoaceticus*, variants thereof, and/or progeny thereof.

In particular embodiments, the present invention relates to thermophilic bacteria selected from the group consisting of

*Clostridium cellulolyticum, Clostridium thermocellum*, and *Thermoanaerobacterium saccharolyticum*.

In certain embodiments, the present invention relates to thermophilic bacteria selected from the group consisting of *Fervidobacterium gondwanense, Clostridium thermolacticum, Moorella* sp., and *Rhodothermus marinus*.

In certain embodiments, the present invention relates to thermophilic bacteria of the genera *Thermoanaerobacterium* or *Thermoanaerobacter*, including, but not limited to, species selected from the group consisting of: *Thermoanaerobacterium thermosulfurigenes, Thermoanaerobacterium aotearoense, Thermoanaerobacterium polysaccharolyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter thermohydrosulfuricus, Thermoanaerobacter ethanolicus, Thermoanaerobacter brockii*, variants thereof, and progeny thereof.

In certain embodiments, the present invention relates to microorganisms of the genera *Geobacillus, Saccharococcus, Paenibacillus, Bacillus*, and *Anoxybacillus*, including, but not limited to, species selected from the group consisting of: *Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchalkensis, Anoxybacillus gonensis*, variants thereof, and progeny thereof.

In certain embodiments, the present invention relates to mesophilic bacteria selected from the group consisting of *Saccharophagus degradans; Flavobacterium johnsoniae; Fibrobacter succinogenes; Clostridium hungatei; Clostridium phytofermentans; Clostridium cellulolyticum; Clostridium aldrichii; Clostridium termitididis; Acetivibrio cellulolyticus; Acetivibrio ethanolgignens; Acetivibrio multivorans; Bacteroides cellulosolvens*; and *Alkalibacter saccharofomentans*, variants thereof and progeny thereof.

Organism Development Via the Native Cellulolytic Strategy

One approach to organism development for CBP begins with organisms that naturally utilize cellulose, hemicellulose and/or other biomass components, which are then genetically engineering to enhance product yield and tolerance. For example, *Clostridium thermocellum* is a thermophilic bacterium that has among the highest rates of cellulose utilization reported. Other organisms of interest are xylose-utilizing thermophiles such as *Thermoanaerobacterium saccharolyticum* and *Thermoanaerobacterium thermosaccharolyticum*. Organic acid production may be responsible for the low concentrations of produced ethanol generally associated with these organisms. Thus, one objective is to eliminate production of acetic and lactic acid in these organisms via metabolic engineering. Substantial efforts have been devoted to developing gene transfer systems for the above-described target organisms and multiple *C. thermocellum* isolates from nature have been characterized. See McLaughlin et al. (2002) *Environ. Sci. Technol.* 36:2122. Metabolic engineering of thermophilic, saccharolytic bacteria is an active area of interest, and knockout of lactate dehydrogenase in *T. saccharolyticum* has recently been reported. See Desai et al. (2004) *Appl. Microbiol. Biotechnol.* 65:600. Knockout of acetate kinase and phosphotransacetylase in this organism is also possible.

Organism Development Via the Recombinant Cellulolytic Strategy

An alternative approach to organism development for CBP involves conferring the ability to grow on lignocellulosic materials to microorganisms that naturally have high product yield and tolerance via expression of a heterologous cellulasic system and perhaps other features. For example, *Saccharomyces cerevisiae* has been engineered to express over two dozen different saccharolytic enzymes. See Lynd et al. (2002) *Microbiol. Mol. Biol. Rev.* 66:506.

Whereas cellulosic hydrolysis has been approached in the literature primarily in the context of an enzymatically-oriented intellectual paradigm, the CBP processing strategy requires that cellulosic hydrolysis be viewed in terms of a microbial paradigm. This microbial paradigm naturally leads to an emphasis on different fundamental issues, organisms, cellulasic systems, and applied milestones compared to those of the enzymatic paradigm. In this context, *C. thermocellum* has been a model organism because of its high growth rate on cellulose together with its potential utility for CBP.

In certain embodiments, organisms useful in the present invention may be applicable to the process known as simultaneous saccharification and fermentation (SSF), which is intended to include the use of said microorganisms and/or one or more recombinant hosts (or extracts thereof, including purified or unpurified extracts) for the contemporaneous degradation or depolymerization of a complex sugar (i.e., cellulosic biomass) and bioconversion of that sugar residue into ethanol by fermentation.

Ethanol Production

According to the present invention, a recombinant microorganism can be used to produce ethanol from biomass, which is referred to herein as lignocellulosic material, lignocellulosic substrate, or cellulosic biomass. Methods of producing ethanol can be accomplished, for example, by contacting the biomass with a recombinant microorganism as described herein, and as described in commonly owned International Appl. No. PCT/US2009/002902, International Appl. No. PCT/US2009/003972, International Appl. No. PCT/US2009/003970, International Appl. No. PCT/US2009/065571, International Appl. No. PCT/US2009/069443, International Appl. No. PCT/US2009/064128, International Appl. No. PCT/IB2009/005881, U.S. Appl. No. 61/116,981, U.S. Appl. No. 61/351,165, and U.S. Appl. No. 61/420,142, the contents of each are incorporated by reference herein.

In addition, to produce ethanol, the recombinant microorganisms as described herein can be combined, either as recombinant host cells or as engineered metabolic pathways in recombinant host cells, with the recombinant microorganisms described in commonly owned International Appl. No. PCT/US2009/002902, International Appl. No. PCT/US2009/003972, International Appl. No. PCT/US2009/003970, International Appl. No. PCT/US2009/065571, International Appl. No. PCT/US2009/069443, International Appl. No. PCT/US2009/064128, International Appl. No. PCT/IB2009/005881, U.S. Appl. No. 61/351,165, and U.S. Appl. No. 61/420,142, the contents of each are incorporated by reference herein. The recombinant microorganism as described herein can also be engineered with the enzymes and/or metabolic pathways described in commonly owned International Appl. No. PCT/US2009/002902, International Appl. No. PCT/US2009/003972, International Appl. No. PCT/US2009/003970, International Appl. No. PCT/US2009/065571, International Appl. No. PCT/US2009/069443, International Appl. No. PCT/US2009/064128, International Appl. No. PCT/IB2009/005881, U.S. Appl. No. 61/351,165, and U.S. Appl. No. 61/420,142, the contents of each are incorporated by reference herein.

Numerous cellulosic substrates can be used in accordance with the present invention. Substrates for cellulose activity assays can be divided into two categories, soluble and insoluble, based on their solubility in water. Soluble substrates include cellodextrins or derivatives, carboxymethyl cellulose (CMC), or hydroxyethyl cellulose (HEC). Insoluble substrates include crystalline cellulose, microcrystalline cellulose (Avicel), amorphous cellulose, such as phosphoric acid swollen cellulose (PASC), dyed or fluorescent cellulose, and pretreated lignocellulosic biomass. These substrates are generally highly ordered cellulosic material and thus only sparingly soluble.

It will be appreciated that suitable lignocellulosic material may be any feedstock that contains soluble and/or insoluble cellulose, where the insoluble cellulose may be in a crystalline or non-crystalline form. In various embodiments, the lignocellulosic biomass comprises, for example, wood, corn, corn stover, sawdust, bark, leaves, agricultural and forestry residues, grasses such as switchgrass, ruminant digestion products, municipal wastes, paper mill effluent, newspaper, cardboard or combinations thereof.

In some embodiments, the invention is directed to a method for hydrolyzing a cellulosic substrate, for example a cellulosic substrate as described above, by contacting the cellulosic substrate with a recombinant microorganism of the invention. In some embodiments, the invention is directed to a method for hydrolyzing a cellulosic substrate, for example a cellulosic substrate as described above, by contacting the cellulosic substrate with a co-culture comprising yeast cells expressing heterologous cellulases.

In some embodiments, the invention is directed to a method for fermenting cellulose. Such methods can be accomplished, for example, by culturing a host cell or co-culture in a medium that contains insoluble cellulose to allow saccharification and fermentation of the cellulose.

The production of ethanol can, according to the present invention, be performed at temperatures of at least about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C. In some embodiments of the present invention the thermotolerant host cell can produce ethanol from cellulose at temperatures above about 30° C., about 31° C., about 32° C., about 33° C., about 34° C., about 35° C., about 36° C., about 37° C., about 38° C., about 39° C., about 40° C., about 41° C., about 42° C., or about 43° C., or about 44° C., or about 45° C., or about 50° C. In some embodiments of the present invention, the thermotolterant host cell can produce ethanol from cellulose at temperatures from about 30° C. to 60° C., about 30° C. to 55° C., about 30° C. to 50° C., about 40° C. to 60° C., about 40° C. to 55° C. or about 40° C. to 50° C.

In some embodiments, methods of producing ethanol can comprise contacting a cellulosic substrate with a recombinant microorganism or co-culture of the invention and additionally contacting the cellulosic substrate with externally produced cellulase enzymes. Exemplary externally produced cellulase enzymes are commercially available and are known to those of skill in the art.

In some embodiments, the methods comprise producing ethanol at a particular rate. For example, in some embodiments, ethanol is produced at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, at least about 300 mg per hour per liter, at least about 400 mg per hour per liter, or at least about 500 mg per hour per liter.

In some embodiments, the host cells of the present invention can produce ethanol at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, at least about 300 mg per hour per liter, at least about 400 mg per hour per liter, or at least about 500 mg per hour per liter more than a control strain (lacking heterologous cellulases) and grown under the same conditions. In some embodiments, the ethanol can be produced in the absence of any externally added cellulases.

Ethanol production can be measured using any method known in the art. For example, the quantity of ethanol in fermentation samples can be assessed using HPLC analysis. Many ethanol assay kits are commercially available that use, for example, alcohol oxidase enzyme based assays. Methods of determining ethanol production are within the scope of those skilled in the art from the teachings herein. The U.S. Department of Energy (DOE) provides a method for calculating theoretical ethanol yield. Accordingly, if the weight percentages are known of C6 sugars (i.e., glucan, galactan, mannan), the theoretical yield of ethanol in gallons per dry ton of total C6 polymers can be determined by applying a conversion factor as follows:

> (1.11 pounds of C6 sugar/pound of polymeric sugar)×(0.51 pounds of ethanol/pound of sugar)×(2000 pounds of ethanol/ton of C6 polymeric sugar)×(1 gallon of ethanol/6.55 pounds of ethanol)×(1/100%), wherein the factor (1 gallon of ethanol/6.55 pounds of ethanol) is taken as the specific gravity of ethanol at 20° C.

And if the weight percentages are known of C5 sugars (i.e., xylan, arabinan), the theoretical yield of ethanol in gallons per dry ton of total C5 polymers can be determined by applying a conversion factor as follows:

> (1.136 pounds of C5 sugar/pound of C5 polymeric sugar)×(0.51 pounds of ethanol/pound of sugar)×(2000 pounds of ethanol/ton of C5 polymeric sugar)×(1 gallon of ethanol/6.55 pounds of ethanol)×(1/100%), wherein the factor (1 gallon of ethanol/6.55 pounds of ethanol) is taken as the specific gravity of ethanol at 20° C.

It follows that by adding the theoretical yield of ethanol in gallons per dry ton of the total C6 polymers to the theoretical yield of ethanol in gallons per dry ton of the total C5 polymers gives the total theoretical yield of ethanol in gallons per dry ton of feedstock.

Applying this analysis, the DOE provides the following examples of theoretical yield of ethanol in gallons per dry ton of feedstock: corn grain, 124.4; corn stover, 113.0; rice straw, 109.9; cotton gin trash, 56.8; forest thinnings, 81.5; hardwood sawdust, 100.8; bagasse, 111.5; and mixed paper, 116.2. It is important to note that these are theoretical yields. The DOE warns that depending on the nature of the feedstock and the process employed, actual yield could be anywhere from 60% to 90% of theoretical, and further states that "achieving high yield may be costly, however, so lower yield processes may often be more cost effective." (Ibid.)

TDK Counterselection

In the field of genetic engineering, cells containing an engineering event are often identified through use of positive selections. This is done by creating genetic linkage between the positive selection encoded by a dominant marker such as an antibiotic resistance gene, the desired genetic modification, and the target loci. Once the modifications are identified, it is often desirable to remove the dominant marker so that it can be reused during subsequent genetic engineering events.

However, if a dominant marker does not also have a counter selection, a gene expressing a protein that confers a counter-selection, must be genetically linked to the dominant marker, the desired genetic modification, and the target loci. To avoid such limitations, the methods of the invention include linking and/or designing a transformation associated with recombination between the thymidine kinase gene (TDK) from the Herpes Simplex Virus Type 1 (GenBank Accession No. AAA45811; SEQ ID NO:84) and one or more antibiotic resistance genes. See, e.g., FIG. 35. Examples of such antibiotic resistant genes, include but are not limited to aminoglycoside phosphotransferase (Kan; resistant to G418), nourseothricin acetyltransferease (Nat; resistant to nourseothricin), hygromycin B phosphotransferase (hph; resistant to hygromycin B), or a product of the Sh ble gene 1 (ble; resistant to Zeocin). Using such counter-selection methods with linked positive/negative selectable markers, as described below in Example 4, transformants comprising the desired genetic modification have been obtained in several different yeast strains, including *S. cerevisiae* strains M139, M2390, and various hardwood strains described herein.

EXEMPLIFICATION

The invention now being generally described, it will be more readily understood by reference to the following examples, which are included merely for purposes of illustration of certain aspects and embodiments of the present invention, and are not intended to limit the invention.

Example 1

Detoxification of Lignocellulosic Material Through In Vivo Uptake of Acetate and Formation of Ethanol Acetate is a major inhibitor of cellular growth and is present in large quantities in biomass derived substrates. During the conversion of lignocellulosic materials into ethanol, a large portion of cellular energy must be spent to avoid the harmful effects of acetic acid. Because of these effects, cellular growth and other important phenotypes are decreased resulting in a sub-optimal process.

In order to overcome the inhibitory effects of acetate, it is desired to convert the acetate from an inhibitory compound into a less inhibitory compound, e.g., ethanol, that is also the primary product produced during yeast fermentation. Attempts to overcome the inhibitory effects of acetate have relied upon endogenous gene activity for the conversion of acetate to acetyl-CoA, a metabolic intermediate prior to ethanol formation, without success. It has recently been shown that a glycerol deletion mutant can be engineered in yeast for the conversion of acetate to a less inhibitory compound. See Medina, V. G., et al., *Appl. Environ. Microbiol.*, published online ahead of print on Nov. 13, 2009. The glycerol deletion mutant cannot regenerate NAD+, and therefore is incapable of growing anaerobically. By the introduction of an enzyme from *E. coli*, an acetaldehyde dehydrogenase (MhpF), the yeast strain was able to grow anaerobically, although far slower than the non-engineered strain. Because the growth of this deletion mutant is significantly inhibited, it requires more optimization before such a strain could even be used in an industrial process.

Figure 1:
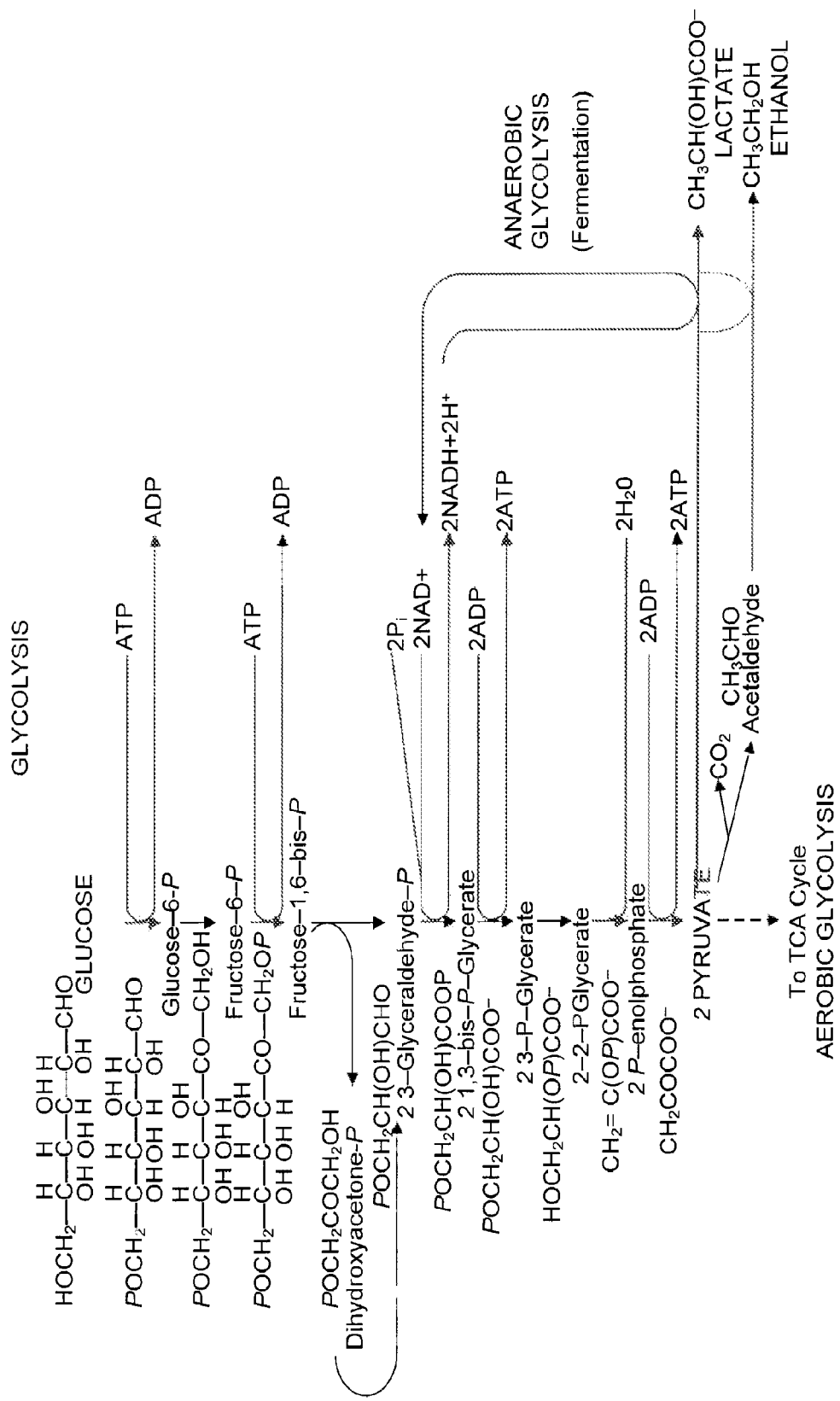
FIG. 1 depicts the glycolysis pathway.
Figure 2:
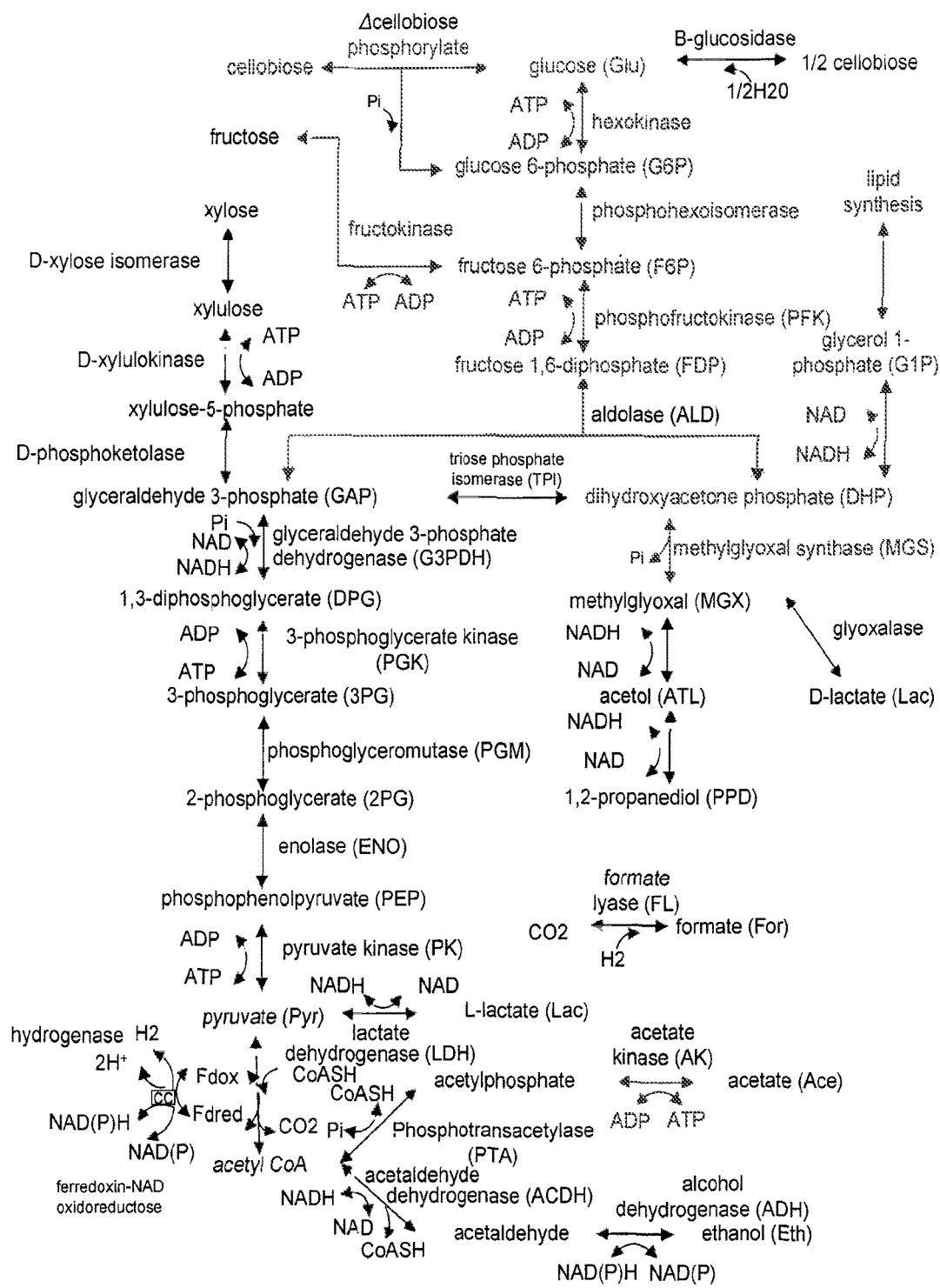
FIG. 2 shows a schematic of the glycolysis/fermentation pathway.
Figure 3:
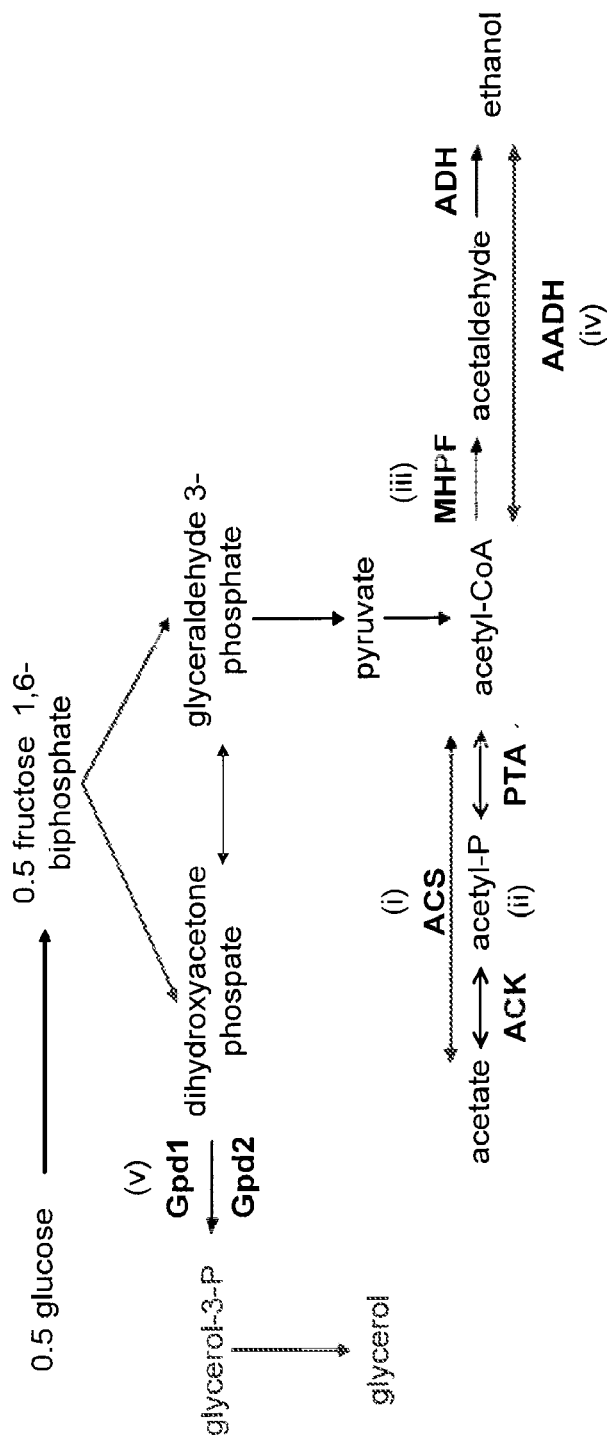
FIG. 3 shows a schematic of the proposed routes and genetic changes during acetate uptake to ethanol.

The present Example overcomes the likely bottlenecks for acetate uptake and ethanol formation during anaerobic growth, by providing novel routes (see FIG. 3) for the conversion of acetate to ethanol that have not been previously described. These routes significantly improve this process by the introduction of additional enzyme activities converting the acetate to acetyl-CoA, as well as the introduction of heterologous enzymes from other microbial sources to improve on this first conversion. Additionally, the heterologous introduction of a bifunctional acetaldehyde/alcohol dehydrogenase allows for the direct conversion of ethanol from acetyl-CoA with a single enzyme, with the promise of significantly increasing in vivo formation kinetics.

The conversion of acetate to ethanol according to this Example is as follows:

1) Conversion of Acetate to Acetyl-CoA

Acetate is converted in yeast to acetyl-CoA by an acetyl-CoA transferase (ACS). The endogenous activity during anaerobic fermentation is likely by the ACS2 enzyme. By transforming the yeast host cell with and expressing the higher affinity ACS1 enzyme during fermentation or by increasing expression of the ACS2 enzyme, higher acetate uptake and activity can be achieved. See FIG. 3, (i). Heterologous activity can also be achieved by the introduction of acetate to acetyl-CoA converting genes from other organisms, such as *E. coli*.

Alternate pathways from acetate to acetyl-CoA can be achieved by the expression of the typical bacterial system of phosphotransacetylase (PTA) and acetate kinase (ACK). See FIG. 3, (ii). Theses two enzymes can act sequentially to produce acetyl-CoA from acetate. Due to the difference in co-factors between PTA/ACK and ACS, this pathway could have higher activity in vivo when heterologously expressed. Sources for PTA and ACK can come from a large variety of bacterial sources including but not limited to *Escherichia, Thermoanaerobacter, Clostridia*, and *Bacillus* species.

2) Conversion of Acetyl-CoA to Ethanol

The conversion of acetyl-CoA to acetaldehyde by the MhpF enzyme has recently been used with the attendant problems discussed above. See FIG. 3, (iii). By replacing this activity with either an improved acetaldehyde dehydrogenase (e.g., from *C. phytofermentans* or other source) or a bifunctional acetaldehyde/alcohol dehydrogenase (AADH) the in vivo kinetics of the reaction can be increased, providing for improved growth of the host strain. See FIG. 3, (iv). The sources for the bi-functional alcohol/aldehyde dehydrogenase can come from a variety of microbial sources, including but not limited to *E. coli, C. acetobutylicum, T. saccharolyticum, C. thermocellum*, or *C. phytofermentans*.

3) Deletion or Alteration of Glycerol Formation Genes

The deletion or alteration of the glycerol formation genes may enhance the acetate uptake through the above-mentioned enzymatic routes. Deletion of gpd1, gpd2, or both genes and/or deletion of gpp1, gpp2, or both genes may be used to eliminate glycerol formation and enhance ethanol yield. See FIG. 3, (v). However, the complete elimination of glycerol may not be practical for an industrial process. See Guo, Z P., et al., *Metab. Eng.* 13:49-59 (2011). Thus, rather than the complete removal of any one, all, or some combination of these glycerol formation genes, one or more of these genes can be altered or downregulated to reduce glycerol formation and enhance ethanol yield.

Example 2

Detoxification of Biomass Derived Acetate Via Metabolic Conversion to Acetone, Isopropanol, or Ethyl Acetate As described herein, acetic acid is an unavoidable product of pretreatment and hydrolysis, and very harmful to fermenting organisms, especially at the industrially relevant pH range of 4-5. Removal of acetic acid prior to fermentation by chemical or physical methods is either prohibitively expensive or results in lost sugar yield (washing). By engineering a pathway to convert acetic acid to acetone, isopropanol, or ethyl acetate in ethanol producing organisms, acetic acid toxicity can be lowered and an easily recovered co-product can be produced. In addition, conversion of acetate to a solvent will lower the demand for base addition, lowering the overall fermentation cost and making pH control more manageable and robust. Such considerations become especially important at industrial scale. Further, removal of acetate will lower the amount of organic compounds sent for wastewater treatment, which will also result in lower capital and operating expenses for water recycling.

However, very little is known regarding the use of metabolic conversion to detoxify acetate from lignocellulosic biomass. In one example, acetic acid was aerobically removed from hardwood-spent sulphite liquor using a mutant yeast. Schneider, H., *Enz. Micr. Technol.* 19:94-98 (1996). The mutant yeast, however, was not able to grow on sugars, and required another strain to anaerobically convert the hydrolysate sugars to ethanol. The pathways that can be used include those that have served different purposes in different host organisms, as described in the art. For example, the metabolic conversion of acetate to acetone has been demonstrated in *C. acetobutylicum* and related organisms (native converters) and in *E. coli* (engineered to include the acetone pathway). See, e.g., Bermejo, L. L., et al., *Appl. Environ. Microbiol.* 64(3):1079-85 (1998). Production of isopropanol from carbohydrates also occurs natively in organisms related to *C. acetobutylicum*, and the carbohydrate-isopropanol pathway has been engineered in *E. coli* and yeast. See, e.g., U.S. Patent Appl. Pub. No. 2008/0293125. Ethyl acetate is a product of some yeast and bacterial fermentations and is an important flavor enhancing compound. However, ethyl acetate is considered undesirable at high levels during alcoholic beverage fermentations and as such, attempts have been made to modify its production. These metabolic pathways have not been used to detoxify acetate from lignocellulosic biomass.

This Example describes the novel use of these metabolic pathways to detoxify lignocellulosic biomass and derived hydrolysates and the incorporation of these pathways into an ethanol producing organism. The ethanol producing organism can be bacterial or fungal, or it can be a consolidated bioprocessing (CBP) organism also producing cellulases and other hydrolytic enzymes.

2.1 Engineering Acetate to Acetone Pathways in Bacterial and Yeast Platforms

Figure 4:
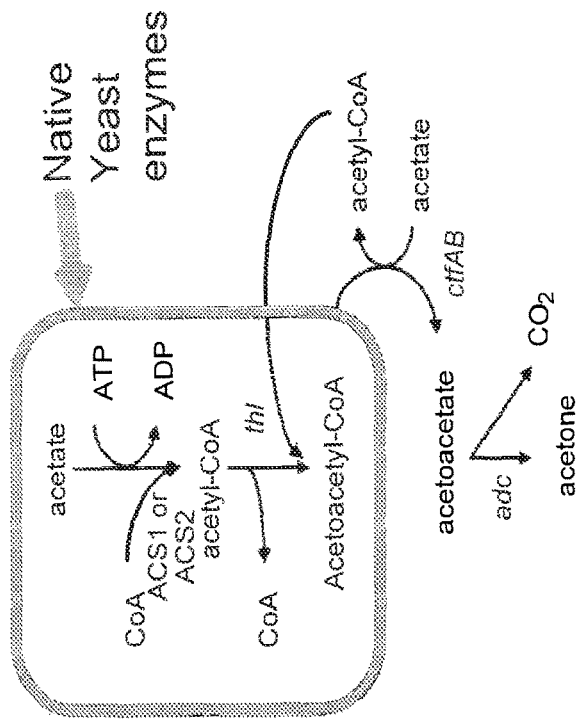
FIG. 4A shows a schematic of the proposed bacterial route from acetate to acetone.
FIG. 4B shows a schematic of the proposed yeast route from acetate to acetone.
Figure 4:
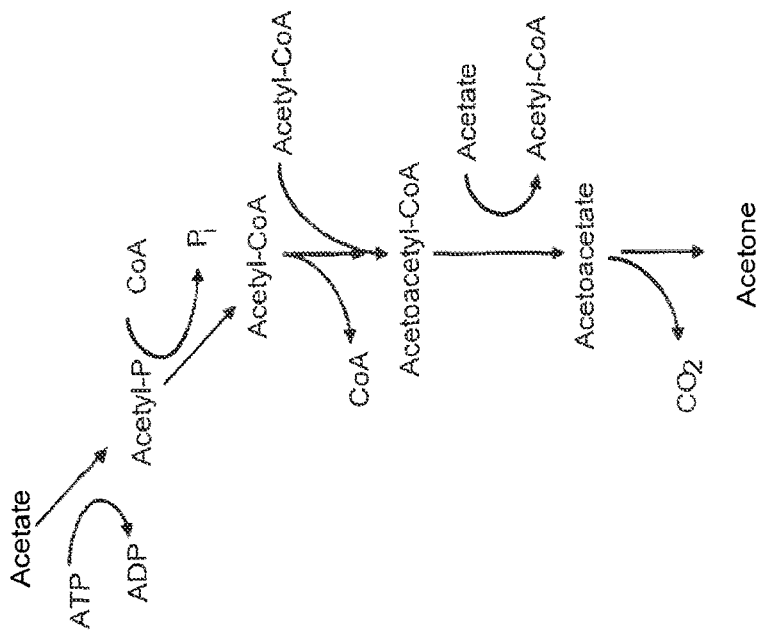

Acetic acid diffuses freely into the cell during hydrolysis of acetylated polysaccharides, where its conversion to acetone involves four major steps: (i) activation of extracellular acetate to acetyl-CoA, (ii) condensation of acetyl-CoA to acetoacetyl-CoA, (iii) CoA transfer resulting in acetyl-CoA and acetoacetate, and (iv) decarboxylation of acetoacetate to acetone. See FIGS. 4A and 4B. In yeast four enzymatic steps are involved (two enzymes are native and two are engineered from a bacterial source). See FIG. 4B.

In bacteria, the conversion involves five enzymatic steps, in which acetic acid is activated to acetyl-CoA by acetate kinase (ack) (FIG. 12 (1)), phosphotransacetylase (pta) (FIG. 12 (2)), and a half-reaction of CoA transferase (ctfA ctfB) (FIG. 12 (4)). Two acetyl-CoA molecules are then converted to acetoacetyl-CoA by thiolase (thl) (FIG. 12 (3)), acetoacetate by the other half reaction of CoA transferase (ctfA ctfB) (FIG. 12 (4)), and finally to acetone and $CO_2$ by acetoacetate decarboxylase (adc) (FIG. 12 (5)). Although the synthetic pathway shares a common intermediate with the ethanol production pathway, carbohydrate to ethanol production remains highly coupled due to the requirement to balance NAD(P)+/NAD(P)H generation. Hydrogenases (FIG. 12 (6)) act to uncouple electron acceptor regeneration and ethanol formation, resulting in production of acetic acid through the reversible acetate kinase and phosphotransacetylase pathway.

(i) Activation of Extracellular Acetate to Acetyl-CoA

The first step in the acetate metabolism is the conversion of acetate to acetyl-CoA. See FIGS. 4A and 4B. In both *E. coli* and yeast this can be accomplished via acetyl-CoA synthetase (acetate+ATP+CoA→ acetyl-CoA+AMP+PPi). Constitutive expression of this enzyme may be tricky as both in *E. coli* and *S. cerevisiae*, the functioning of this enzyme is subject to complex regulatory circuits. See Wolfe, A. J., *Micr. Mol. Biol. Rev.* 69:12-50 (2005); van den Berg, M. A., et al., *J. Biol. Chem.* 271:28953-28959 (1996), respectively. In *E. coli*, activation of acetate can also be accomplished via acetate kinase and phosphotransacetylase, as both reactions are reversible. In one aspect, acetyl-CoA synthetase is used.

(ii) Condensation of Acetyl-CoA to Acetoacetyl-CoA

This step can occur either by native enzymes in yeast, e.g., Erg10, or in bacteria, e.g., thiolase in bacteria, or by genes isolated from *C. acetobutylicum* or *T. thermosaccharolyticum*.

(iii) CoA Transfer

This step is specific to the reaction of acetoacetyl-CoA+acetate ↔ acetoacetate+acetyl-CoA and has only been characterized in organisms similar to *C. acetobutylicum*. Other CoA transferases perform similar reactions and can be engineered to perform this reaction. Such other CoA transferases include, but are not limited to, those from bacterial sources of *Thermoanaerobacter tengcongensis, Thermoanaerbacterium thermosaccharolyticum, Thermosipho africanus,* and *Paenibacillus macerans*.

(iv) Decarboxylation of Acetoacetate to Acetone

This step can be performed by the acetoacetate decarboxylase found in *C. acetobutylicum, Paenibacillus macerans, Acidothermus cellulolyticus, Bacillus amyloliquefaciens,* and *Rubrobacter xylanophilus* or other bacteria. Eukaryotic acetoacetate decarboxylases may also be used to engineer this pathway.

Figure 5:
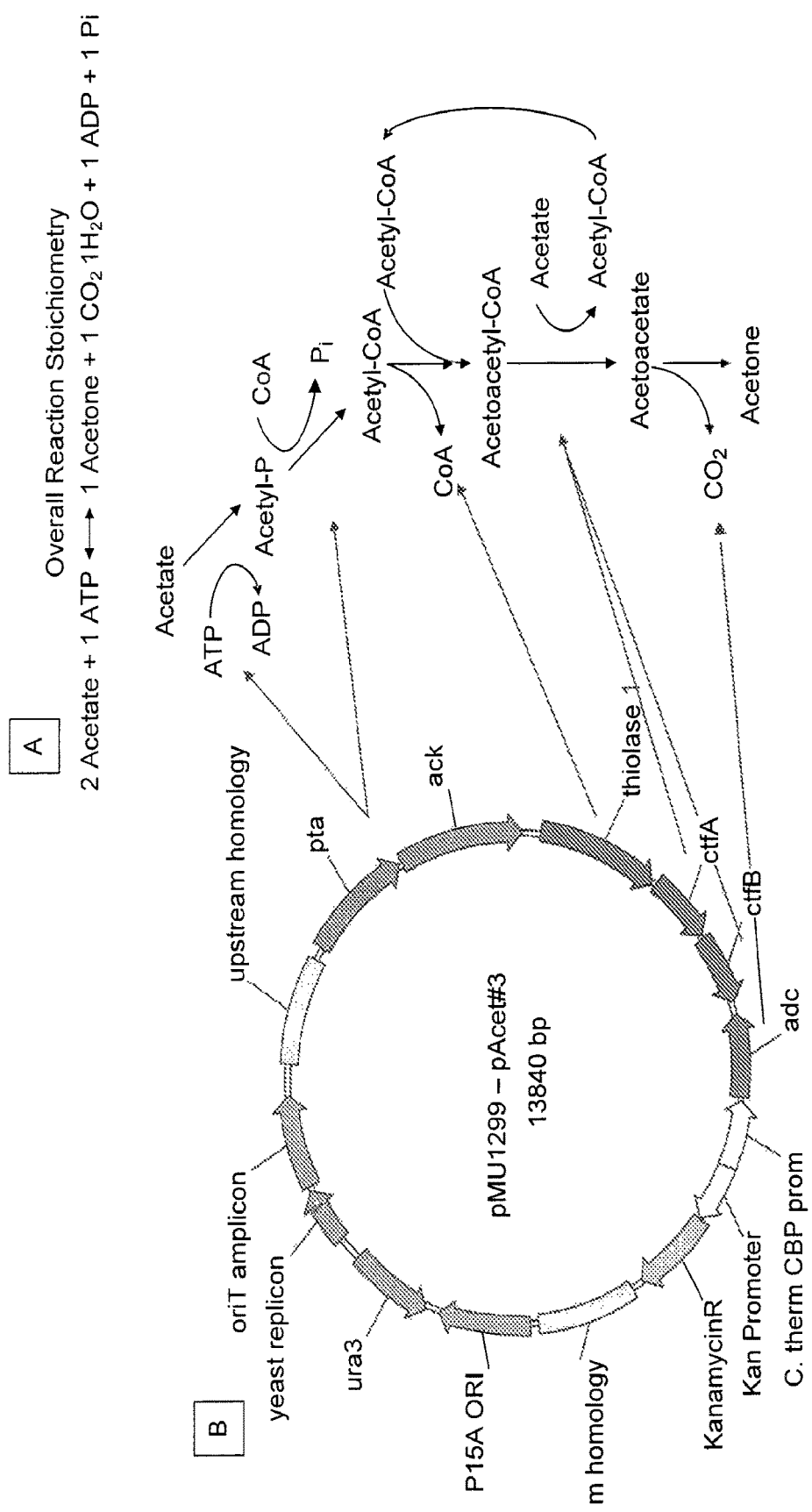
FIG. 5A depicts the overall reaction stoichiometry of the proposed bacterial route from acetate to acetone.
FIG. 5B depicts the vector pMU1299-pAcet#3 for the conversion of acetate to acetone in *T. saccharolyticum* and *E. coli*.

To use the above pathway, enzymes to metabolize the conversion of acetate to acetone in *T. saccharolyticum* and *E. coli* have been engineered in pMU1299. See FIG. 5B. Plasmid pMU1299 replicates in yeast and *E. coli* and integrates into *T. saccharolyticum*'s genome in the L-ldh locus. pMU1299 comprises native *T. saccharolyticum* pta and ack genes driven by the native pta promoter and C. acetobutylicum thiolase1, CoA transferase (ctfAB), and acetoacetate decarboxylase (adc) genes driven by the C. thermocellum cbp promoter. The plasmid or genomic integration is selected for by kanamycin resistance in bacteria, and the plasmid is maintained in yeast by ura3 complementation.

pMU1299 was transformed into E. coli and the production of acetone was determined. Cultures were grown at 37° C. in LB medium supplemented with 25 g/L glucose and 4 g/L sodium acetate for 170 hours. The results from pMU1299 in E. coli were compared to a control strain carrying plasmid pMU433, which has only the pta, ack, and kan$^R$ genes. The overall reaction stoichiometry is shown in FIG. 5A. The fermentation results are shown in Table 3. Compared to the media only sample, acetate levels decrease, acetone is produced, and an additional 3 g/L of glucose is consumed by the strains carrying pMU1299.

TABLE 3

E. coli Fermentation of Acetic Acid to Acetone

| | Glucose (g/L) | Lactic Acid (g/L) | Acetic Acid (g/L) | Ethanol | Acetone |
|---|---|---|---|---|---|
| Media only | 24.482 | 0 | 4.218 | 0 | 0 |
| pAcet#3 | 16.138 | 5.903 | 3.062 | 0.5 | 1.849 |
| pAcet#7 | 15.865 | 6.229 | 2.837 | 0.5 | 1.937 |
| pAcet#12 | 15.998 | 6.226 | 2.880 | 0.5 | 1.911 |
| pAcet#13 | 16.075 | 6.170 | 2.926 | 0.5 | 1.885 |
| pMU433 control | 19.490 | 3.649 | 5.136 | 0.385 | 0 |

2.1.1 Decreasing Acetic Acid Production Via PTA and ACK Through Spontaneous Mutations in Hydrogenase As discussed above, the acetic acid to acetone synthetic pathway shares a common intermediate (acetyl-CoA) with the ethanol production pathway. In the latter, carbohydrate to ethanol production remains highly coupled due to the requirement to balance NAD(P)+/NAD(P)H generation. Hydrogenases (FIG. 12 (6)) act to uncouple electron acceptor regeneration and ethanol formation, resulting in production of acetic acid through the reversible acetate kinase and phosphotransacetylase pathway. Thus, to increase the conversion of exogenous acetic acid to acetone and reduce the intracellular production of acetic acid, hydrogenases can be manipulated using, e.g., mutagenesis.

During growth adaptation of the Δldh, Δpta, and Δack ethanologen strain M0863, spontaneous hfs hydrogenase mutations were introduced. Strain M0863 was derived from strain M0355, a T. saccharolyticum strain engineered to have markerless deletions of the L-lactate dehydrogenase ldh, phosphotransacetylase pta, and acetate kinase ack genes, the construction of which is described in Shaw et al., AEM 77: 2534-2536 (2011). Subsequently, strain M0355 was treated with nitrosoguanidine and screened for improved growth on steam pretreated hardwood hydrolysate through several rounds of mutagenesis and selection (Panlabs Biologics, Taipei, Taiwan). A population enriched for growth in hardwood hydrolysate was then inoculated into a cytostat (Kacmar et al., J. of Biotechnology 126:163-172 (2006)) and selected for increased growth rate at a fixed cell culture population. One strain isolated from the cytostat selection via plating on agar-containing solid medium was designated M0863.

The hfs hydrogenase mutations were characterized and are described in Shaw et al., J. Bact. 191:6457-64 (2009), incorporated by reference herein in its entirety, examples of which are shown in Table 4 below.

TABLE 4

Spontaneous hfs hydrogenase mutations in T. saccharolyticum

| Gene Name | GenBank GQ354412 nucleotide | Ref | SNP | Codon Change | Present in strains |
|---|---|---|---|---|---|
| orl545 (hfsA) | 2219 | A | — | V:GTA @ 53 -> V:GTx | M700 |
| orl546 (hfsB) | 2954 | A | — | K:AAA @ 218 -> X:AAx | M731 |
| orl546 (hfsB) | 2736 | A | — | E:GAA @ 145 -> X:GAx | M734, M863, M1442 |
| orl547 (hfsC) | 4272 | A | — | R:AGA @ 85 -> X:AGx | M699 |
| orl548 (hfsD) | 5386 | G | A | A:GCA @ 65 -> T:aCA | M699 |
| orl548 (hfsD) | 5980 | G | A | E:GAA @ 263 -> K:aAA | M734 |
| orl548 (hfsD) | 5514 | A | T | R:AGA @ 107 -> S:AGt | M863, M1442 |

These mutations were then re-introduced into wild-type T. saccharolyticum via a non-replicating plasmid with two regions of homology to the T. saccharolyticum chromosome flanking a kanamycin resistance marker (kanR). The upstream homology region, containing mutations in both hfsB and hfsD, was generated by PCR from T. saccharolyticum strain M0863 chromosomal DNA. The downstream region was also generated by PCR from M0863 chromosomal DNA, but did not contain deviations from the wild-type sequence. The plasmid was constructed via yeast-homology cloning and transformed into T. saccharolyticum following a natural competence protocol (Shaw et al., AEM 76:4713-4719 (2010)). Transformants were screened for the presence of the kanR marker by colony PCR and then for the presence of hfsB and hfsD mutations by DNA sequencing. Since incorporation of hfs mutations is dependent upon the location of homologous recombination cross-over, it was expected that a certain percentage of the kanR transformants would contain M0863 hfsB and hfsD loci, while others would contain wildtype hfsB and hfsD loci. One strain with M0863 loci was identified and designated M2204, and one strain with wildtype loci was identified and designated M2205.

M2204, M2205, and the wildtype strains were incubated in 10 mL of TSC7 medium initially containing 30.4 mM cellobiose at 55° C. under a 95% nitrogen and 5% carbon dioxide atmosphere in anaerobic butyl stoppered tubes. The inoculum was 5% v/v from an overnight culture, and the bottles were incubated for 48 hours without agitation. The metabolites lactic acid, acetic acid, and ethanol were measured via high performance liquid chromatography (HPLC) with an Aminex HPX-87H column (Bio-Rad Laboratories, Hercules Calif.) and a refractive index detector. As shown in Table 5 below, strain M2204, containing the M0863 hfs sequence, had dramatically reduced acetic acid compared to the WT and M2205 strains. The results are the average of four individual bottle fermentations.

TABLE 5

Mutations in hfs hydrogenase decrease acetic acid production.

| | Units in mM | | | | |
|---|---|---|---|---|---|
| Strain | Cellobiose | Lactic Acid | Acetic Acid | Ethanol | (E + L)/A ratio |
| WT | 2.2 | 13.8 | 34.7 | 63.5 | 2.2 |
| M2204 | 0.5 | 20.3 | 4.2 | 91.7 | 26.7 |
| M2205 | 2.3 | 9.9 | 29.8 | 67.9 | 2.6 |

2.1.2 Acetone Production in *T. saccharolyticum*

To use the above pathway to produce acetone in *T. saccharolyticum*, various genes were screened in a *T. saccharolyticum* strain engineered to metabolize the conversion of acetate to acetone.

Plasmids were generated via yeast-homology cloning, as described by Shanks et al., *AEM* 72:5027-5036 (2006). Genes of interest for the acetone production pathway were introduced downstream of a recombinant copy of the *T. saccharolyticum* pta and ack genes and their native promoter, which created a synthetic gene operon for transcription of the acetone pathway genes. In addition to transcription occurring from the pta promoter, genes of interest were cloned with either their native promoter and Shine-Delgarno upstream sequences, or the cbp promoter and Shine-Delgarno sequence from *C. thermocellum* (Genbank HQ157351) or the adhE promoter and Shine-Delgarno sequence from *T. saccharolyticum* (Genbank EU313774). In some cases, transcription was confirmed in engineered strains via reverse-transcriptase real time PCR. Plasmids were designed either to replicate, using a gram positive origin of replication, see WO/2010/075529, incorporated by reference herein in its entirety, or to integrate into the *T. saccharolyticum* chromosome at the ldh locus using the same ldh flanking homology regions as described in Shaw et al., *AEM* 77: 2534-2536 (2011), incorporated by reference herein in its entirety.

Plasmids were transformed into *T. saccharolyticum* following a natural competence protocol (Shaw et al., *AEM* 76:4713-4719 (2010)) and selected for either kanamycin or erythromycin antibiotic resistance (Shaw et al., *J. Bact.* 191:6457-64 (2009)). Antibiotic resistant transformants were screened via colony PCR or plasmid miniprep for proper chromosomal integration or replicating plasmid maintenance, respectively.

Acetone was detected by high performance liquid chromatography (HPLC) with an Aminex HPX-87H column (Bio-Rad Laboratories, Hercules Calif.) and a refractive index and $UV_{260\ nm}$ detector operating in series to distinguish acetone from the closely eluting ethanol. Alternatively, acetone was detected directly in fermentation cultures via the Rothera test, in which 5 mL of fermentation medium was saturated with ammonium sulfate $(NH_4)_2SO_4$ followed by addition 50 mg of sodium nitroprusside and thorough mixing. 1 mL of 18 M $NH_4OH$ was then added as a top layer, and acetone was detected via the generation of a red to purple band forming within 2 min to 1 hour at the interface of the fermentation medium and 18 M $NH_4OH$. The results of the screen are shown in Table 6 below.

TABLE 6

Screen for genes involved in acetone production

| Source Strain | $T_{opt}°$ C. | Gene | Genbank Protein | Acetone detected* |
|---|---|---|---|---|
| *Thermoanaerobacterium saccharolyticum* DSM 8691 | 60 | pta | ACA51668 | yes |
| *Thermoanaerobacterium saccharolyticum* DSM 8691 | 60 | ack | ACA51669 | yes |
| *Clostridium acetobutylicum* ATCC 824 | 35 | thl | NP_349476 | no |
| *Thermosipho melanesiensis* DSM 12029 | 70 | thl | YP_001306374 | yes |
| *Kosmotoga olearia* DSM 21960 | 65 | thl | YP_002940320 | yes |
| *Thermoanaerobacterium thermosaccharolyticum* DSM 571 | 60 | thl | YP_003852249 | yes |
| *Thermoanaerobacterium thermosaccharolyticum* DSM 571 | 60 | actA | CAA93155 | no |
| *Clostridium acetobutylicum* ATCC 824 | 35 | ctfA | NP_149326 | no |
| *Thermosipho melanesiensis* DSM 12029 | 70 | ctfA | YP_001306376 | yes |
| *Kosmotoga olearia* DSM 21960 | 65 | ctfA | YP_002940319 | yes |
| *Clostridium acetobutylicum* ATCC 824 | 35 | ctfB | NP_149327 | no |
| *Thermosipho melanesiensis* DSM 12029 | 70 | ctfB | YP_001306375 | yes |
| *Kosmotoga olearia* DSM 21960 | 65 | ctfB | YP_002940318 | yes |
| *Clostridium acetobutylicum* ATCC 824 | 35 | adc | NP_149328 | no |
| *Acidothermus cellulolyticus* B11 ATCC 43068 | 55 | adc | YP_872855 | no |
| *Bacillus amyloliquefaciens* FZB42 BGSC 10A6 | 50 | adc | YP_001422565 | yes |

Plasmid pMU2627 (FIG. 13; SEQ ID NO:1), containing the *T. saccharolyticum* pta and ack encoding phosphotransferase and acetate kinase, the *T. melanesiensis* ctfA and ctfB encoding acetate CoA transferase, the *T. thermosaccharolyticum* thl encoding thiolase, and the *B. amyloliquefaciens* adc encoding acetoacetate decarboxylase, was integrated into the chromosome of *T. saccharolyticum* strain M1442, (an ethanologen strain containing the M0863-derived spontaneous mutations in hydrogenase). Lee et al., *Biomass and Bioenergy* 35:626-636 (2011). pMU2627 was generated via yeast-homology cloning, as described by Shanks et al. *AEM* 72:5027-5036 (2006) from plasmid pMU433, which contained the ldh targeting homology regions, the *T. saccharolyticum* pta and ack, the kanR antibiotic resistance gene, the p15A *E. coli* origin of replication, the *S. cerevisiae* CEN/ARS origin of replication, and the *S. cerevisiae* ura3 gene. Primers X12406, X12407, X12408, X12409, X13293, and X13294 were used to amplify the specified gene targets and create homology 5' tails for yeast ligation into SnaB1 restriction digested pMU433. See Table 7 below.

TABLE 7

Primers used in the construction of pMU2726 and pMU2741

| Primer Name | Sequence (5'-3') | Amplification Target | SEQ ID NO: |
|---|---|---|---|
| X12406 | AAGATACTGAAAAGATTGTAAAGAGTATAA AATAGTGCTGCACCAGTTGCTTTGTATGC | Tme ctfAB | 3 |
| X12407 | GTGCAGACAGATGGAATTGCTGCATTAGAT ATTTTCAATAACAACAGCTG | | 4 |
| X12408 | CAGCTGTTGTTATTGAAAATATCTAATGCAG CAATTCCATCTGTCTGCAC | Bam adc | 5 |
| X12409 | ACCTATCACCTCAAATGGTTCGCTGGGTTTT TATTTTTCCTCTAAGTAGTTATAAACCG | | 6 |
| X13293 | AATTAATAATCGCTGATGATCTTAAAATCTT TTAACATTTGTCAAGGTTTATCCCTCCC | Tth thl | 7 |
| X13294 | AAATGAGGGGGTGCAGACAGATGGAATTGC TGCAGTGCTATCTTTCGACAACCATTGCT | | 8 |
| X12411 | CGGTTTATAACTACTTAGAGGAAAAATAACC CTTTCTGTGATCTTGTTT | Tet adhB | 9 |
| X12412 | TCTTACCTATCACCTCAAATGGTTCGCTGGG TTTACCAAGAGTTTACTGGCCGATGTG | | 10 |

M2212 was inoculated (at $OD_{600}=0.36$) in TSC7 medium (Table 8) and fermented at 51° C. in a fed-batch of 34% v/v untreated, hemicellulose enriched washate containing acetylated xylan at a concentration of 147 g/L carbohydrates. The pH was maintained at 5.8 using 5 M potassium hydroxide. Total carbohydrates fed were 50 g/L. The batch fermentation was fed at 20% v/v batch for the first 26 hours and then increased 3% v/v per day to a final concentration of 34% at 140 hours. The results of the fermentation, measuring xylose, ethanol, acetate, and acetone, are shown in FIG. 14.

TABLE 8

TSC7 Medium

| Component | g/L final |
|---|---|
| Yeast Extract | 8.5 |
| Trisodium citrate * 2 $H_2O$ | 1 |
| $KH_2PO_4$ | 1 |
| $MgSO_4$ *7H2O | 2 |
| $(NH_4)_2SO_4$ | 4 |
| $CaCl_2$*2$H_2O$ | 0.2 |
| $FeSO_4$*7$H_2O$ | 0.2 |
| Methionine | 0.12 |
| L-Cysteine HCl | 0.5 |

A comparison of the acetone production of the engineered M2212 strain and the parent ethanologen strain M1442 was performed on 100 g/L maltodextrin and 10 g/L acetic acid. The strains were grown in pressure bottles containing TSC7 medium with 4 g/L $(NH_4)_2SO_4$ and without a pH control. As shown in FIG. 15, M2212 had greater maltodextrin consumption (reported as glucose units) and ethanol production compared to the parental strain. M2212 converted the acetic acid in the media to acetone, as shown in FIG. 16, and also maintained a pH in the range of 5.6-5.9 (FIG. 17). The parent ethanologen strain, however, produced no detectable acetone (FIG. 16) and the excess acetic acid in the media caused the pH to drop over the course of the fermentation (FIG. 17). Thus, this Example shows that a *T. saccharolyticum* strain engineered to convert acetate to acetone, also produces an increased ethanol yield and avoids a decrease in pH caused by excess acetic acid in the fermentation medium. The data shown in FIGS. 15-17 are from replicate fermentations, with standard deviations of <1 g/L.

2.2 Engineering Yeast to Metabolize Acetic Acid to Isopropanol Anaerobically

This metabolic pathway builds off the acetate to acetone pathway using an additional final step to convert acetone to isopropanol, as follows:

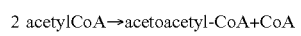

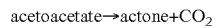

Introduction of these reactions into yeast will not only eliminate the necessity of pH control (when urea is used as nitrogen source) but will likely also enhance alcohol yield. The reducing equivalents that are formed in excess during biomass formation can be used to reduce acetone, and glycerol formation (from sugar) is no longer necessary. The requirement for ATP poses no problem as the amount is relatively small in comparison to the total amount formed. Even this small amount of ATP for isopropanol synthesis will be beneficial as it requires extra alcohol production at the expense of biomass formation. Acetone additions to anaerobic yeast cultures have shown that acetone decreases with the appearance of isopropanol. To date 200 mg/L of isopropanol has been produced in this manner. This illustrates the endogenous activity of the acetone to isopropanol activity in vivo in yeast. A concomitant decrease in glycerol formation is observed suggesting the NADH required in this step can reduce the reducing equivalents typically produced during glycerol formation.

2.3 Engineering *T. saccharolyticum* to Metabolize Acetic Acid to Isopropanol This metabolic pathway builds off the acetate to acetone pathway to produce isopropanol. See FIG. 18. The synthetic acetone pathway described above was modified in the following ways: addition of a secondary alcohol dehydrogenase (adhB) from *T. ethanolicus*, deletion of pta and ack, and targeted integration of the synthetic pathway in the *T. saccharolyticum* native adhE locus, which eliminates ethanol formation. With these modifications, the following stoichiometry was predicted, with a $\Delta G_0 = -188$ kJ/rxn at pH 7:

Glucose+2 Acetate→2 Isopropanol+4CO$_2$+2H2.

Plasmid pMU2741 (FIG. 19; SEQ ID NO:2) was constructed via yeast-homology cloning, as described by Shanks et al., *AEM* 72:5027-5036 (2006) with primers X12406, X12407, X12408, X12409, X13293, X13294, X12411, and X12412. See Table 7. It contains the *T. melanesiensis* ctfA and ctfB genes encoding acetate CoA transferase, the *T. thermosaccharolyticum* thl gene encoding thiolase, the *B. amyloliquefaciens* adc gene encoding acetoacetate decarboxylase, and the *T. ethanolicus* adhB gene encoding secondary alcohol dehydrogenase (GenBank Accession No. TEU49975). It was transformed into strain M0355, an Δldh Δpta Δack strain described in Shaw et al., *AEM* 77: 2534-2536 (2011), with a wildtype hydrogenase gene that does not have spontaneous mutations. Transformants were screened for their fermentation profile by anaerobic growth in TSC7 medium at 55° C. for 72 hours without agitation. Several transformants followed the predicted stoichiometry, an example of which (strain 4A) is shown below in Table 9.

TABLE 9

Isopropanol production in an engineered *T. saccharolyticum* strain

| | Units in mM | | | |
|---|---|---|---|---|
| | Glucose | Glycerol | Acetic Acid | Isopropanol |
| Medium | 50.8 | 1.2 | 61.9 | 0 |
| Strain 4A | 45.8 | 2.5 | 54.3 | 11 |
| Δ Predicted | −5 | 0 | −10 | 10 |

2.4 Engineering Yeast and Bacteria to Convert Acetate and Ethanol to Ethyl Acetate Each step of this metabolic pathway can proceed as follows:

acetate+CoA+ATP=acetyl-CoA+AMP+H$_2$O acetyl-CoA+ethanol=ethyl acetate+CoA

With the overall reaction proceeding: acetate+ethanol+ATP↔ ethyl acetate+H$_2$O+AMP.

Acetate and ethanol will both be formed during hydrolysis and fermentation, and the necessary enzymes for this pathway include acetate activation to acetyl-CoA (see acetone section 1 above), and an alcohol acetyltransferase to convert acetyl-CoA and ethanol to ethyl acetate. Yeast contain native acetyl-CoA synthetases and a native alcohol acetyltransferase (ATF1), which when overexpressed has been shown to reduce acetate levels from 0.5 g/L to 0.2 g/L during an alcoholic fermentation. Lilly, et al., *Appl. Environ. Microbiol.* 66:744-53 (2000).

Example 3

Engineering of Yeast Strains with Improved Tolerance to Acetate and Other CBP By-Products As described herein, a large portion of cellular energy must be spent to avoid the harmful effects of acetic acid during the conversion of lignocellulosic materials into ethanol. Because of these effects, cellular growth and other important phenotypes are decreased resulting in a sub-optimal process. Additional acidic and other organic by-products, including aldehydes, can also add to sub-optimal processing of lignocellulosic materials.

The present invention describes various engineered pathways for overcoming the inhibitory effects of biomass inhibitors, including but not limited to, acetate and other CBP by-products, by converting the acetate into a less inhibitory compound, such as those described herein. To improve the ability of yeast strains to grow in the presence of a biomass inhibitor, yeast strains were engineered that have increased growth tolerance to biomass inhibitors.

1) Adaptation of Yeast Strains to Acetate and Other By-Products in Pretreated Cellulosic Raw Material M1254 is a yeast strain previously isolated based on high tolerance to hydrolysate. See commonly owned International Appl. No. PCT/US2009/065571, the contents of which are incorporated by reference herein. Increased xylose utilization in the presence of inhibitors is critical to performance for the yeast platform. M1254 was therefore evolved in the cytostat using a feed medium containing 2 g/L yeast extract, 2 g/L peptone, 2 g/L xylose, and 8 g/L acetate at pH 5.4 and at 39.8° C. After approximately 10 days of continuous cultivation in the cytostat, a sample was taken and M1339 was isolated as a single colony from the heterogeneous population. M1339 was selected based on growth assays described below.

M1339 then was further adapted in the cytostat in medium containing 5 g/L xylose, 10 hydrolysate based acids (1 g/L lactic, 8 g/L acetic, 30 mg/L 2-furoic, 2.5 mg/L 3,4-dihydroxybenzoic, 2.5 mg/L 3,5-dihydroxybenzoic, 5 mg/L vanillic, 2.5 mg/L homovanillic, 15 mg/L syringic, 17.5 mg/L gallic, and 15 mg/L ferulic) and five aldehydes (175 mg/L 5-hydroxymethylfurfural, 150 mg/L furfural, 6 mg/L 3,4-hydroxybenzaldehyde, 12 mg/L vanillin, and 27 mg/L syringaldehyde) at pH 5.4 and 40° C. This adaptation led to the isolation of M1360, M1361, and M1362.

M1360 then was further adapted in a chemostat containing 0.1 g/L glucose, 5 g/L xylose, 0.4 g/L furfural, and 0.4 g/L 5-hydroxymethylfurfural. After selection, M1499 was isolated. M1499 was then adapted in separate streams as follows.

One adaptation stream started with a chemostat selection based on medium containing 10 g/L yeast extract, 20 g/L peptone, 20 g/L xylose, supplemented with soluble inhibitors removed from pretreated mixed hardwood at 35° C. This chemostat selection resulted in the identification of strain M1646. M1646 was subsequently adapted in a chemostat again to soluble inhibitors obtaining by rinsing water through pretreated mixed hardwood, including acetate, and supplemented solely with 6.7 g/L yeast nitrogen base without amino acids at 35° C. After selection, M1715 was isolated. M1715 was then adapted on 5 g/L xylose and 6.7 g/L yeast nitrogen base at 40° C. in the cytostat, in order to ensure strong thermotolerance, and the resulting strain was M1760. Starting from M1646, an additional selection strategy was implemented involving beginning with 10 g/L M1646 and performing repeated batch fermentations of wash liquor from pretreated hardwood, which includes acetate, with the transfer of all cells from one batch fermentation to the next. After a series of transfers, M1819 was isolated from these fermentations.

Starting from M1499 again, M1499 was adapted in a chemostat with 5 g/L yeast extract, 5 g/L peptone, 5 g/L xylose, and 8 g/L acetate at a feed pH of 5.4 and 35° C. Therefore acetate was the only inhibitor in this selection and becomes more inhibitory as the pH in the chemostat was lower than in the feed medium. After weeks of selection, M1577 was isolated. M1577 was then adapted in a chemostat containing 6.7 g/L yeast nitrogen base without amino acids and 20 g/L xylose with supplemented soluble inhibitors from pretreated hardwood, which includes acetate. The resulting strain from this selection is M1818.

Strain M1818 was further adapted in serial batch culture using wash liquor from pretreated hardwood, which includes acetate and other biomass derived inhibitors. The adaptations were carried out at 39° C., pH 6.5, with 6.7 g/L yeast nitrogen base without amino acids as the media. After adaptation, colonies derived from plating the growth media were screened for their performance in wash liquor containing media, and the strain M1927 was identified as the top performer. M1927 was adapted to washate generated from pretreated mixed hardwood at 38° C. The washate was supplemented with 5 g/L xylose, 6.7 g/L yeast nitrogen base without amino acids, and ergosterol/Tween 80 at standard concentrations and adjusted to pH 5.5 using calcium hydroxide. Over the first 100 h, the chemostat feed medium was slowly increased in washate concentration. Ultimately, the feed medium reached 33% washate and the growth rate was 0.076 h$^{-1}$. See FIG. 28. Samples were regularly taken from the chemostat and performance tracked by HPLC and offline pH measurement. No pH control was implemented and the effluent pH was approximately 5.2 throughout adaptation. In total, the adaptation lasted nearly 900 hours and 97 generations. A sample was taken at roughly 450 h and plated for single colonies. From the single colonies, nearly all colonies were improved with respect to M1927. Six colonies were screened in total in duplicate, and 11 of the 12 screens resulted in higher ethanol titers and lower residual xylose than the fermentations with M1927. All fermentations are inoculated with approximately 0.03 g/L DCW and thus significant fermentation will only occur in conjunction with substantial growth in washate. The colonies screened from adaptation showed higher fermentation rates and titers than M1927. M2108 emerged as the top performing colony.

2) Analysis of Yeast Strains with Improved Growth and Performance Profiles

To evaluate the adaptation of yeast strains to inhibitors in pretreated cellulosic raw material, growth assays were performed. The yeast strains were grown on xylose in the presence of acetate or in the presence of acetate, nine other hydrolysate-based acids, and five aldehydes (see above). Growth assays involved inoculating 96-well plates and cultivation at specified temperatures with shaking in a BioTek Synergy 2 plate reader. The initial optical density (OD) for all strains tested was standardized to the same OD, typically at OD=0.03, with a minimum of 3 replicate measurements per strain. The OD was measured every 15 minutes at an absorbance of 600 nm. The specific growth rate was calculated using the standard technique of determining the slope of a line with best fit to a semilog plot of optical density over time. All growth assays which follow used this method for determining specific growth rate and were used for identifying more tolerant strains.

Figure 6:
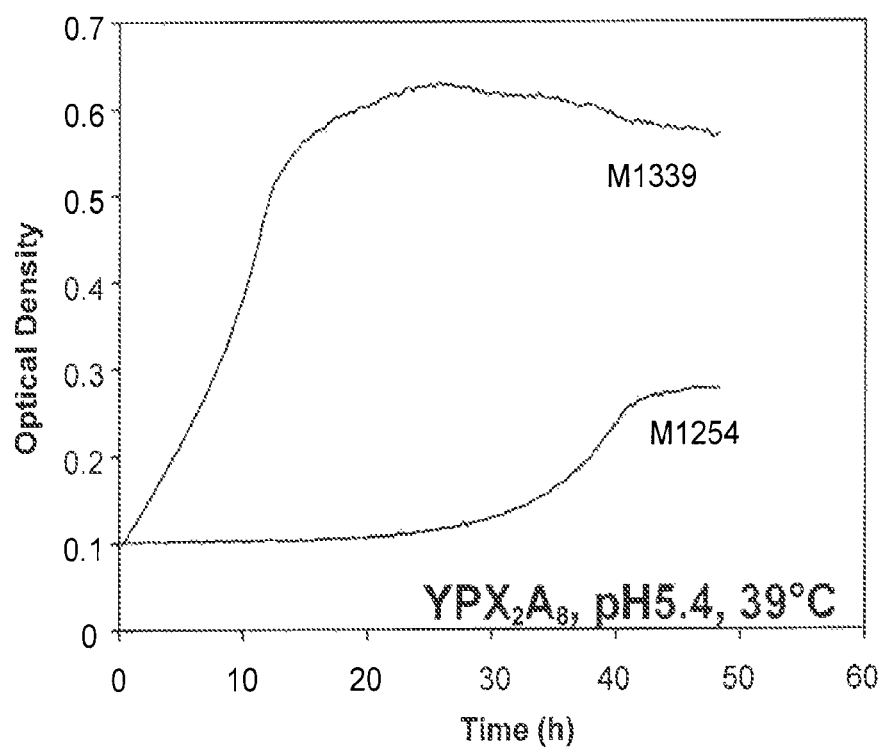
FIG. 6 is a graph depicting the growth of strains M1254 and M1339 on xylose in the presence of acetate.

Yeast strains M1339 and M1254 were grown on xylose at pH 5.4 and 39° C. for 48 hours in the presence of acetate (8 g/L). Growth rate, as measured at an absorbance of 600 nm, was monitored every 15 minutes over the incubation period. As shown in FIG. 6, yeast strain M1339 had improved tolerance and grew more quickly in the presence of acetate as compared to yeast strain M1254. The growth rate of M1339 in this condition is increased 3-fold over the growth rate of M1254 in this complex medium containing 2 g/L yeast extract, 2 g/L peptone, 2 g/L xylose and 8 g/L acetate at pH 5.4.

Yeast strains M1360, M1361, M1362, M1254, and M1339 were grown on xylose at pH 5.4 and 40° C. for 48 hours in the presence of acetate, nine other hydrolysate-based acids, and five aldehydes (see above). Specific growth rate, as measured at an optical density of 600 nm using a BioTek Synergy 2 plate reader, was calculated from the slope of a line fit to a semilog plot of optical density over time. As shown in FIG. 7, yeast strains M1360, M1361, and M1362 had an improved tolerance to growth in the presence of acetate and other inhibitors as compared to yeast strains M1254 and M1339. The specific growth rate increased dramatically in this toxic medium for M1360, M1361, and M1362, representing a 16-fold increase in growth rate for M1360 as compared to M1254, which grows slowly in this medium. The specific growth rate of yeast strains M0509, M1577, and M1715 on xylose or xylose and inhibitors 5-hydroxymethylfurfural (0.4 g/L) and furfural (0.4 g/L) was also measured. As shown in FIG. 10, strains M1577 and M1715 had increased growth rates as compared to previous strain M0509.

To evaluate the performance of improved yeast strains in process conditions, glucose utilization, ethanol production, and biomass yield were measured. Yeast strain M1360 was inoculated (60 mg/L) in a medium containing 150 g/L glucose, 3 g/L corn steep liquor, 1.23 g/L magnesium sulfate heptahydrate, either 1.1 or 2.2 g/L diammonium phosphate (DAP), supplemented with trace metals (0.1 mg/L potassium iodide, 1 mg/L boric acid, 3 mg/L iron sulfate heptahydrate, 4.5 mg/L calcium chloride dehydrate, 0.4 mg/L disodium molybdenum dihydrate, 0.3 mg/L copper (II) sulfate pentahydrate, 0.3 mg/L cobalt(II) chloride hexahydrate, 0.84 mg/L manganese chloride dihyrate, 4.5 mg/L zinc sulfate hepatahydrate, 15 mg/L ethyldiaminetetraacetate) and vitamins (0.05 mg/L biotin, 1 mg/L calcium pantothenate, 1 mg/L nicotinic acid, 25 mg/L myo-inositol, 1 mg/L thiamine hydrochloride, 1 mg/L pyridoxol hydrochloride, and 0.2 mg/L para-aminobenzoic acid) and grown at 40° C. at pH 5.0. Glucose utilization (g/L) and ethanol production (g/L) were measured over a time period of 72 hours. As shown in FIG. 8, glucose utilization was rapid in the presence or absence of 2×DAP and ethanol production was high.

The improved performance of yeast strains M1360, M1443, and M1577 in process conditions was also measured using a pressate assay. Briefly, the pressate assay first requires the removal of liquid from pretreated substrate by applying pressure to a batch of solid substrate in a hydraulic press. The liquid squeezed from the solids is defined as pressate, and the pressate contains the concentration of soluble inhibitors present in the substrate. For example, if the substrate was 50% moisture content and 50% solid content prior to pressing, the pressate created is defined as 50% solids equivalent. Therefore a 25% solids equivalent pressate would be a medium wherein half of the liquid was pressate. Typically, a strain is inoculated at 0.1 g/L dry cell weight with 6.7 g/L yeast nitrogen base without amino acids and 20 g/L sugar (either glucose or xylose) at pH 5.0 in a sealed anaerobic bottle. The strains are then incubated for 24 hours before the terminal dry cell weight, sugar, and ethanol concentrations are measured. Thus, the anaerobic biomass yield can be determined based on consumed sugar; the theoretical anaerobic biomass yield is 0.1 g biomass/g consumed sugar.

The anaerobic biomass yield on 20 g/L glucose of strains M1360, M1443, and M1577 at 5%, 7%, and 9% solids equivalent pressate was measured. M1443 is a CBP derivative of M1360, that has been engineered to express *Saccharomycopsis fibuligera* beta-glucosidase, *T. emersonii* cellobiohydrolase I and *Chrysosporium lucknowense* cellobiohydrolase II. FIG. 9 shows the results of each strain at the various solids equivalent pressate. Strains M1360 and M1443 gave similar theoretical biomass yields at 5% and 7% solids equivalent pressate; however, at 9% solids equivalent pressate, strain M1360 had an about 3-fold lower theoretical biomass yield as compared to M1443. See FIG. 9. By comparison, strain M1577 gave at least about a 3-fold higher theoretical biomass yield than either strains M1360 or M1443 at 5%, 7%, or 9% solids equivalent pressate. See FIG. 9. Strains M1760, M1818, and M1819 were also evaluated using a pressate assay at 13%, 15%, and 17% solids equivalent pressate using 20 g/L xylose as the carbon source. See FIG. 11A (biomass yield (g/g)) and 11B (ethanol production (g/L)). Thus, the adapted strains demonstrate high anaerobic biomass yields and improved performance in process conditions, when the inhibitor mix is pressed out of solids used in process.

Strain M1818 was compared directly against M1927 during batch fermentation of wash liquor from pretreated hardwood. In addition, M1927 was compared directly against M2108 in a similar experimental setup after this new strain was derived. FIGS. 29 and 30 show the comparison of strain performance in these conditions. When a concentrated wash liquor (via evaporation of washate) was fermented at 20% of the final fermentation volume at pH 6, 35° C. with yeast nitrogen base media (6.7 g/L), M1927 clearly outperformed the parental strain M1818, making ≥30% more ethanol in 72 hours. FIG. 29. When M2108 was compared to M1927 in a similar manner, except with more stringent conditions (25% v/v washate fermentation, pH 5.5, 38° C.) another ≥30% increase in ethanol titer was observed. FIG. 30.

In addition to these tests, M2108 was compared to M1927 for its ability to tolerate higher concentrations of washate. See FIG. 31. In these tests, a toxic liquor MS928 was used at different v/v concentrations from 20% to 60% with yeast extract (10 g/L) and peptone media (20 g/L) present. Fermentation were carried out at 35° C. At washate concentrations greater than 30%, M2108 performed significantly better than M1927, yielding a 40% increase in ethanol titer at 40% v/v washate, and a 4.5 fold increase in titer at 60% v/v washate where M1927 grew only minimally. FIG. 31.

Finally, FIG. 32 demonstrates the positive impact that adaptation against the wash liquor had on the SSF process of converting the insoluble cellulosic solids from the pretreatment process. Here M1927 and M2108 were compared for their performance at both 35° C. and 38° C. during a fed-batch, 22% solids (final) SSF of MS887 pretreated substrate (solids, glucan containing material) in pH and temperature controlled, stirred bioreactors (1 L reactions). The fermentations were run at 35° C. and 38° C., pH 5.0, using 12 g/L corn steep liquor and 0.5 g/L DAP (diammonium phosphate) as media components and loading 2 mg TS cellulase enzyme per g solids in the reactor. The MS887 pretreated substrate was fed over 48 h, and ammonium hydroxide was used for pH control. Both strains performed well at the lower temperature fermenting all the sugar that was released into ethanol. FIG. 32. At 38° C., M2108 was able to ferment all the sugar to ethanol and demonstrated an increased yield due to higher hydrolysis temperature. M1927 was not able to ferment at the higher temperature and sugar began to accumulate between 48 and 96 hours. FIG. 32. These data sets indicate that the process of adaptation has significantly improved the performance of this strain background for converting lignocellulosic derived materials to ethanol.

Example 4

Engineered Yeast Strains for Production of Ethanol

The present example describes the construction of recombinant yeast strains that convert acetic acid to ethanol and the analysis of such strains in industrial process conditions.

4.1 Construction of Δura3 Strain, M1901

The starting background strain for the recombinant yeast strains was an auxotrophic Δura3 strain, M1901, derived from M139, which is a high performance ethanologen from the distillery industry (Anchor Yeast, Cape Town, South Africa). See, e.g., Borneman, et al., *FEMS Yeast Res.* 8(7) 1185-95 (2008). The URA3 gene was deleted by transforming a PCR fragment (using primers X11276 and X11279, see Table 10 below) containing only the upstream and downstream regulatory sequences without the coding sequences (SEQ ID NO:81). The resulting transformants were plated on 5-FOA, a commonly used drug in yeast genetics to select against the URA3 gene. Colonies were picked from 5-FOA plates and the deletion was confirmed by colony PCR.

TABLE 10

Primers used for construction of the recombinant yeast strains of this Example.

| Primer Name | Sequence (5'-3') | Description | SEQ ID NO |
|---|---|---|---|
| X11276 | GGAGAATCCATACAAGAAATCG | URA3 deletion 5' | 11 |
| X11279 | AGGTCTGTTGAGTGCAATCG | URA3 deletion 3' | 12 |
| X11824 | AAGCCTACAGGCGCAAGATAACACATCAC | GPD1 5' Fwd | 13 |
| X11825 | CGGCGGGGACGAGGCAAGCTAAACAGATCTCTAGACCTACTATCAGCAGCAGCAGACAT | GPD1 5' Rev | 14 |
| X11828 | TCTTCTTGTCGCTTTTTCTCCTCGATAGAACCTCTACATGAAGATTAGATTTATTGGAG | GPD1 3' Fwd | 15 |

TABLE 10-continued

Primers used for construction of the recombinant yeast strains of this Example.

| Primer Name | Sequence (5'-3') | Description | SEQ ID NO |
|---|---|---|---|
| X11829 | CTCAGCATTGATCTTAGCAGATTCAGGATCTAGGT | GPD1 3' Rev | 16 |
| X11816 | GCAGTCATCAGGATCGTAGGAGATAAGCA | GPD2 5' Fwd | 17 |
| X11817 | GGGGACGAGGCAAGCTAAACAGATCTCTAGACCT AGACAGCAAGCATTGATAAGGAAGG | GPD2 5' Rev | 18 |
| X11819 | TATCTCTTCTTGTCGCTTTTTCTCCTCGATAGAAC CTCTGATCTTTCCTGTTGCCTCTT | GPD2 3' Fwd | 19 |
| X11821 | TCACAAGAGTGTGCAGAAATAGGAGGTGGA | GPD2 3' Rev | 20 |
| X11826 | ACAAATATTGATAATATAAAGATGTCTGCTGCTG CTGATAGTAGGTCTAGAGATCTGTT | Antibiotic Fwd | 21 |
| X11656 | AACTTCATCTTACAAAAGATCACGTGATCTGTTGT ATTAAGGGTTCTCGAGAGCTCGTT | Antibiotic Rev | 22 |
| X11657 | CCATCCAGTGTCGAAAACGAGCTCTCGAGAACCC TTAATACAACAGATCACGTGATCTT | K. Lactis URA3 Fwd | 23 |
| X11827 | TTATCTTTCTCCAATAAATCTAATCTTCATGTAGA GGTTCTATCGAGGAGAAAAAGCGA | K. Lactis URA3 Rev | 24 |
| X10876 | GCCTCACGAAAAGGACTGTTCGTAG | URA3 5' | 25 |
| X10877 | GCGATTGGCAGTGGAACAGTGGTAA | URA3 3' | 26 |
| X14177 | TAGATTGAACCAGGCATGCCAAAGTTAGTTAGAT CAGGGTATATTTGTGTTTGTGGAGGG | GPD1 5' Rev2 | 27 |
| X14170 | GTATATTGTACACCCCCCCCCTCCACAAACACAA ATATACCCTGATCTAACTAACTTTGG | PFK1p-PiroADH-HXT2t Fwd | 28 |
| X14176 | ATGTCGCTGGCCGGGTGACCCGGCGGGGACAAG GCAAGCTCCATTATTATGTTGGTCTTG | PFK1p-PiroADH-HXT2t Rev | 29 |
| X14171 | ACGCCGATCGGCCATACTAAACAAGACCAACATA ATAATGGAGCTTGCCTTGTCCCCGC | Antibiotic Fwd 2 | 30 |
| X13734 | TTCGTCCCCCCGTTTCTTTTCTTTGGACTATCATGT AGTCTCTCGACACTGGATGGCGG | Antibiotic Rev 2 | 31 |
| X13728 | ACTGCTGTCGATTCGATACTAACGCCGCCATCCA GTGTCGAGAGACTACATGATAGTCC | TDK Fwd | 32 |
| X14175 | TTTCTACGCCACTTGGTGCGGTCCATGTAAAATG ATTGCTCCGATTTGGTTCCCAGAAAC | TDK Rev | 33 |
| X14172 | ATCTTCTATGCTCATACCCTTTGTTTCTGGGAACC AAATCGGAGCAATCATTTTACATGG | PDCt-PiroADH-ADH1p Fwd | 34 |
| X14174 | CGAAAAAAGTGGGGGAAAGTATGATATGTTATCT TTCTCCCGATTTTTTTCTAAACCGTG | PDCt-PiroADH-ADH1p Rev | 35 |
| X14173 | AGGATATCCGAAATATTCCACGGTTTAGAAAAAA ATCGGGAGAAAGATAACATATCATAC | GPD1 3' Fwd2 | 36 |
| X14180 | GATTGTGCAAAGAATTGGTTAC | PiroADH Fwd | 37 |
| X14179 | TCTACGCCACTTGGTGCGGTCCATGTAAAATGAT TGCTCCCATTATTATGTTGGTCTTG | Hxt2 t Rev | 38 |
| X14178 | CGCCGATCGGCCATACTAAACAAGACCAACATAA TAATGGGAGCAATCATTTTACATGG | PDCt Rev | 39 |
| X14186 | AGATTGAACCAGGCATGCCAAAGTTAGTTAGATC AGGGTTGATAAGGAAGGGGAGCGAAG | GPD2 5' Rev 2 | 40 |
| X14183 | CTTTCCCTTTCCTTTTCCTTCGCTCCCCTTCCTTAT CAACCCTGATCTAACTAACTTTGG | PFK1p-PiroADH-HXT2t Fwd 2 | 41 |
| X14185 | AATTGGTTGGGGGAAAAAGAGGCAACAGGAAAG ATCAGACGATTTTTTTCTAAACCGTGG | PDCt-PiroADH-ADH1p Rev 2 | 42 |

TABLE 10-continued

Primers used for construction of the recombinant yeast strains of this Example.

| Primer Name | Sequence (5'-3') | Description | SEQ ID NO |
|---|---|---|---|
| X14184 | AAAAGGATATCCGAAATATTCCACGGTTTAGAAA AAAATCGTCTGATCTTTCCTGTTGCC | GPD2 3' Fwd 2 | 43 |
| X11631 | TTGCCAAAGTGGATTCTCCTACTCAAGCTTTGCAA ACAT | FCY1 5' Fwd | 44 |
| X12233 | GTTAGTTAGATCAGGGTAAAAATTATAGATGAGG TTAGCTATGAAATTTTTAACTCTTT | FCY1 5' Rev | 45 |
| X12232 | GAGAGCCAGCTTAAAGAGTTAAAAATTTCATAGC TAACCTCATCTATAATTTTTACCCT | PFK1p-PiroADH-HXT2t Fwd 3 | 46 |
| X11750 | ATAAAATTAAATACGTAAATACAGCGTGCTGCGT GCTCGATTTTTTCTAAACCGTGGA | PDCt-PiroADH-ADH1p Rev 3 | 47 |
| X11633 | AGCACGCAGCACGCTGTATTTACGTAT | FCY1 3' Fwd | 48 |
| X11634 | TAGCCCTTGGTTGAGCTTGAGCGACGTTGAGGT | FCY1 3' Rev | 49 |

TABLE 11

Strains and Plasmids used in this Example.

| Strain or Plasmid | Relevant Characteristics | SEQ ID NO |
|---|---|---|
| Yeast Strains | | |
| M139 | *S. cerevisiae* | |
| M1901 | Δura3 | |
| M1991 | Δura3 Δgpd1 Δgpd2 | |
| M2032 | Δgpd1 Δgpd2 | |
| M2108 | Acetic acid tolerance, xylose utilization | |
| M2433 | M2108 Δgpd1 *Piromyces* SP E2 AADH | |
| M2488 | M2108 Δgpd1 Δgpd2 *Piromyces* SP E2 AADH | |
| M2556 | M2108 Δfcy1 *Piromyces* SP E2 AADH | |
| M2390 | *S. cerevisiae* (Ethanol Red ®) | |
| M2739 | M2390 Δfcy1 *Piromyces* SP E2 AADH | |
| Plasmids | | |
| pMU2484 | *E. coli* AADH (SEQ ID NOs: 50 and 51) | 68 |
| pMU2570 | *C. phytofermentans* AADH (SEQ ID NOs: 52 and 53) | 69 |
| pMU2745 | *B. adolescentis* AADH (SEQ ID NOs: 54 and 55) | 70 |
| pMU2690 | *Piromyces* SP E2 AADH (SEQ ID NOs: 56 and 57), ADH1 promoter, PDC terminator | 71 |
| pMU2691 | *Piromyces* SP E2 AADH (SEQ ID NOs: 56 and 57), PFK1 promoter, HXT2 terminator | 72 |
| pMU2687 | *Chlamydomonas reinhardtii* AADH (SEQ ID NOs: 58 and 59) | 73 |
| pAU31 | *E. coli* MhpF (SEQ ID NOs: 60 and 61) | 74 |
| pAU34 | *C. phytofermentans* ADH (1428) (SEQ ID NOs: 62 and 63) | 75 |
| pAU37 | *C. phytofermentans* ADH (2642) (SEQ ID NOs: 64 and 65) | 76 |
| pAU67 | *T. saccharolyticum* AADH (SEQ ID NOs: 66 and 67) | 77 |
| pMU2623 | HSV, Thymidine Kinase (TDK) expression cassette, HXT2 promoter, ACT1 terminator | 78 |
| pMU2660 | CloNat marker cassette, AgTEF promoter, AgTEF terminator | 79 |
| pMU187/pUG6 | KanMX marker cassette, AgTEF promoter, AgTEF terminator | 80 |

4.2 Construction of a Δura3Δgpd1Δgpd2 Strain, M1991.

The gpd1 and gpd2 genes were deleted by transformation of M1901 with PCR fragments corresponding to the 5' upstream region, G418 resistance cassette, Clonat resistance cassette (two antibiotic markers are used to delete both gene copies from diploid strains), K. lactis URA3 cassette (for negative selection), and 3' downstream regions of each locus. The gpd1 5' region was generated using primers X11824 and X11825, gpd1 3' region using primers X11828 and X11829, antibiotic markers were amplified using X11826 and X11656, K. lactis ura3 gene using X11657 and X11827, gpd2 5'region using X11816 and X11817, and gpd2 3' region using X11819 and X11821. See Table 10 above. Transformants were selected on double antibiotic plates. Markers were removed by transformation with PCR flanks to the upstream and downstream regions and then selected on FOA for removal of the ura3 K. lactis gene. Colonies were PCR screened for proper deletions at each locus. The sequences of the deleted gpd1 and gpd2 loci are shown below.

GPD1 deletion sequence (SEQ ID NO:82; a small part of the coding sequence was not deleted, represented in boldface below; deletion represented by Δ between $g^{542}$ and $t^{543}$):

```
tacaaacgcaacacgaaagaacaaaaaaagaagaaaacagaaggccaagacagggtcaatgagactgttgtcctc ctactgtccctatgtctctggccgatcacgcgccattgtccctcagaaacaaatcaaacacccacaccccgggcacccaaagtcc ccacccacaccaccaatacgtaaacgggcgccccctgcaggccctcctgcgcgcggcctcccgccttgcttctctcccttcc ttttcttttccagttttccctatttgtccttttccgcacaacaagtatcagaatgggttcatcaaatctatccaacctaattcgcacgt agactggcttggtattggcagtttcgtagttatatatatactaccatgagtgaaactgttacgttaccttaaattctttctcccttttaattttc ttttatcttactctcctacataagacatcaagaaacaattgtatattgtacaccccccccctccacaaacacaaatattgataatataaa gatgtctgctgctgctgatagΔtctacatgaagattagatttattggagaaagataacatatcatactttccccacttttttcgag gctcttctatatcatattcataaattagcattatgtcatttctcataactactttatcacgttagaaattacttattattaaattaatacaaa atttagtaaccaaataaatataaataaatatgtatatttaaattttaaaaaaaaaatcctatagagcaaaaggattttccattataatatta gctgtacacctcttccgcatttttttgagggtggttacaacaccactcattcagaggctgtcggcacagttgcttctagcatctggcgt ccgtatgtatgggtgtattttaaataataaacaaagtgccacaccttcaccaattatgtctttaagaaatggacaagttccaaagagct tgcccaaggctcgacaaggatgtactttggaatatctatattcaagtacgtggcgcgcatatgtttgagtgtgcacacaataaaggtt
```

GPD2 deletion sequence (SEQ ID NO:83; entire coding sequence was deleted; deletion represented by Δ between $c^{485}$ and $c^{486}$):

```
atagccatcatgcaagcgtgtatcttctaagattcagtcatcatcattaccgagtttgttttccttcacatgatgaagaaggt ttgagtatgctcgaaacaataagacgacgatggctctgccattgttatattacgcttttgcggcgaggtgccgatgggttgctgagg ggaagagtgtttagcttacggacctattgccattgttattccgattaatctattgttcagcagctcttctctaccctgtcattctagtattt ttttttttttttttggttttacttttttttctttttttttcttcttgccttttttttcttgttactttttttctagttttttttccttccactaagc tttttccttgatttatccttgggttcttctttctactcctttagattttttttttatatattaattttaagtttatgtattttggtagattcaa ttctctttcccttttcttttccttcgctccccttccttatcΔctctgatctttcctgttgcctcttttttccccccaaccaatttatcattatac acaagttctacaactactactagtaacattactacagttattataattttctattctcttttctttaagaatctatcattaacgttaatttctata tatacataactaccattatacacgctattatcgtttacatatcacatcaccgttaatgaaagatacgacaccctgtacactaacacaattaaataat cgccataaccttttctgttatctatagcccttaaagctgtttcttcgagcttttttcactgcagtaattctccacatgggcccagccactgagataag agcgctatgttagtcactactgacggctctccagtcatttatgtgatttttttagtgactcatgtcgcatttggcccgtttttttccgctgtcgcaa cctatttccattaacggtgccgtatggaagagtcatttaaaggcaggagagagagattactcatcttcattggatcagattgatgactgcgtacgg cagat
```

4.3 Construction of a Δgpd1Δgpd2 Strain, M2032.

The M1991 strain was transformed with a PCR product amplifying the wildtype ura3 gene (primers X10876 and X10877; see Table 10 above). Strains were selected on uracil minus media and screened by PCR to confirm the reintroduction of the wildtype ura3 gene.

4.4 Analysis of Acetaldehyde Dehydrogenases and Bifunctional Acetaldehyde/Alcohol Dehydrogenases.

Testing of various acetaldehyde dehydrogenases (ADHs) and bifunctional acetaldehyde/alcohol dehydrogenases (AADHs) were performed using a ura3 selection plasmid overexpressing the target genes. Genes were either amplified from genomic DNA (*E. coli, C. phytofermentans, T. saccharolyticum, Bifidobacterium adolescentis*) or from codon optimized synthesized genes (*Piromyces* SP E2 and *Chlamydomonas reinhardtii*). Plasmids were transformed into M1991 using standard techniques and selected on uracil minus media. An in vivo screening assay was developed using minimal YNB media buffered with acetate at about pH 5.0. This pH is near the pKa of acetic acid and allows for sufficient transport of acetic acid into the cell for conversion to ethanol. When grown anaerobically in this media, Δgpd1Δgpd2 strains (e.g., M2032) cannot ferment glucose due to the inability of the cell to recycle NAD+ during glycolysis. The introduction of a functional ADH or AADH allows for regeneration of NAD+ through the conversion of acetic acid into ethanol. Strains that show anaerobic growth and increased yields of ethanol through the elimination of glycerol formation and acetic acid uptake are demonstrated as functionally expressing ADHs or AADHs. See Table 12 below.

TABLE 12

Product formation, acetate utilization, and growth rates of ADHs and AADHs in a glycerol deletion strain.

| Strain | Glycerol (g/L) | Acetate Uptake (g/L) | Ethanol (g/L) | Ethanol Yield (g ethanol produced/g sugar consumed) | Growth Rate (hr$^{-1}$) |
|---|---|---|---|---|---|
| Parent strain M139 | 1.37 | 0.14 | 10.41 | 0.42 | 0.27 |
| M2032 (Δgpd1Δgpd2) | 0.00 | 0.00 | 0.00 | 0.00 | 0.01 |

TABLE 12-continued

Product formation, acetate utilization, and growth rates of ADHs and AADHs in a glycerol deletion strain.

| Strain | Glycerol (g/L) | Acetate Uptake (g/L) | Ethanol (g/L) | Ethanol Yield (g ethanol produced/g sugar consumed) | Growth Rate (hr$^{-1}$) |
|---|---|---|---|---|---|
| Eco AADH | 0.00 | 0.62 | 11.39 | 0.46 | 0.17 |
| Cph AADH | 0.00 | 0.66 | 11.21 | 0.45 | 0.18 |
| Chl AADH | 0.00 | 0.32 | 9.04 | 0.47 | 0.04 |
| Pir AADH | 0.00 | 0.68 | 11.17 | 0.45 | 0.17 |
| Bad AADH | 0.00 | 0.67 | 10.95 | 0.44 | 0.18 |
| Eco MhpF | 0.00 | 0.03 | 0.50 | 0.02 | 0.06 |
| Cph ADH (1428) | 0.00 | 0.60 | 11.29 | 0.45 | 0.19 |
| Cph ADH (2642) | 0.00 | 0.74 | 11.22 | 0.45 | 0.20 |
| Tsac AADH | 0.00 | 0.59 | 11.89 | 0.48 | 0.16 |

The positive growth rates and enhanced ethanol yields of the ADH/AADH expressing strains demonstrates the functionality of the ADH/AADHs. The lower growth rate and ethanol titer of the *Chlamydomonas reinhardtii* AADH (Table 12) is potentially due to a predicted mitochondrial targeting sequence in the upstream portion of this gene. Removal of this sequence could enhance the growth rate and ethanol titer of this strain.

A second comparison of various ADH/AADHs was performed under fermentation conditions using Verduyn media in pH controlled, nitrogen sparged biostat fermentors run at 35° C. As shown in Table 13 below and FIG. 25, strains expressing *Piromyces* SP E2 AADH and *B. adolescentis* AADH outperformed the *E. coli* ADH mhpF, which did not show robust growth.

TABLE 13

Summary of strain performance in batch reactors.

| Relevant Genotype | Yeast strain | | | |
|---|---|---|---|---|
| | M139 Positive Control | M2688 Δgpd1Δgpd2Δura3 plus pMU2691 (*Piromyces* AdhE)-PFK promoter | M2669 Δgpd1Δgpd2Δura3 plus pMU2745 (*B. adolescentis* AdhE)-PFK promoter | M2670 Δgpd1Δgpd2Δura3 plus pMU2937 (*E. coli* mphF)-PFK promoter |
| Specific Growth Rate (h$^{-1}$) | 0.30 | 0.16 | 0.14 | 0.02 |
| Biomass yield on glucose (g g$^{-1}$) | 0.06 | 0.04 | 0.04 | 0 |
| Glyerol yield on glucose (g g$^{-1}$) | 0.078 | 0 | 0 | 0.003 |
| Ethanol yield on glucose (g g$^{-1}$), not corrected for evaporation | 0.42 | 0.48 | 0.49 | 0.08 |

4.5 Production of Ethanol Using Industrial Yeast Strains.

Following the identification of suitable ADH and AADHs for the conversion of acetate to ethanol, industrial acetic acid tolerant yeast were engineered to replace glycerol formation with the conversion of lignocellulose derived acetate to ethanol. The parent strain M2108 (a robust, adapted xylose-utilizing strain, created as described in Example 3) was used to create two derivatives, M2433, a Δgpd1 strain expressing four copies of *Piromyces* SP E2 AADH, and M2488, a Δgpd1Δgpd2 strain expressing eight copies of *Piromyces* SP E2 AADH. M2433 was created by transforming PCR products that were assembled by yeast via homologous recombination to create a cassette that replaces GPD1 with two copies of the *Piromyces* SP E2 AADH, a positive selection marker (the KanMX and CloNat markers—one for each copy of the chromosome), and a negative selection marker, the thymidine kinase gene (TDK) from the Herpes Simplex Virus (GenBank Accession No. AAA45811; SEQ ID NO:84), which creates sensitivity to the drug 5-fluorode-oxyuridine (FUDR) at each chromosomal GPD1 locus. This results in a total of four copies of the AADH being overexpressed. PCR products that were generated for this cassette are shown below in Table 14. These products were transformed by electroporation into M2108, first selecting for resistance to the CloNat drug, and confirming correct integration via PCR, and subsequently transforming with the same products, except using the KanMX marker instead of the CloNat marker and selecting on both G418 and the CloNat drug. Again, these strains were verified by PCR for the correct genotype. Following this step, the double resistant strain was transformed with two PCR products that are able to remove the markers via homologous recombination. These products were created with the primer pairs X14180/X14179 and X14180/X14178. See Table 10. After transformation with these fragments, colonies were selected for resistance to FUDR and confirmed for sensitivity to G418 and CloNat, as well as verified via PCR for correct integration. The resulting strain was called M2433.

TABLE 14

PCR products generated to created GPD1 knockout and Piromyces AADH overexpression in M2108.

| Piece ID No. | Description | Primers | Template |
|---|---|---|---|
| 1 | gpd1 f1 | X11824/X14177 | M2108 gDNA |
| 2 | PFK1p-PiroADH-HXT2t | X14170/X14176 | pMU2691 |
| 3 | AgTEFp-antibiotic-AgTEFt | X14171/X13734 | pMU2660/pMU187 |
| 4 | HXT2p-TDK-ACT1t | X13728/X14175 | pMU2623 |
| 5 | PDCt-PiroADH-ADH1p | X14172/X14174 | pMU2690 |
| 6 | gpd1 f2 | X14173/X11829 | M2018 gDNA |

After GPD1 had been cleanly replaced in M2108, further modifications were made to cleanly replace GPD2 with two copies (at each chromosome, so four copies total) of the Piromyces SP E2 AADH, in a manner exactly analogous to that described above. Table 15 below contains the PCR fragments that were generated for this step. The same steps were taken as described above with two transformation steps to create the double GPD2 replacement followed by a transformation to clean out the antibiotic and negative selection markers using the same two clean up fragments from above. The strain with both GPD1 and GPD2 deleted and eight copies of the Piromyces SP E2 AADH overexpressed was called M2488.

TABLE 15

PCR products generated to create GPD2 knockout and Piromyces AADH overexpression in M2433.

| Piece ID No. | Description | Primers | Template |
|---|---|---|---|
| 1 | gpd2 f1 | X11816/X14186 | M2108 gDNA |
| 2 | PFK1p-PiroADH-HXT2t | X14183/X14176 | pMU2691 |
| 3 | AgTEFp-antibiotic-AgTEFt | X14171/X13734 | pAG187/pUG6 |
| 4 | HXT2p-TDK-ACT1t | X13728/X14175 | pMU2623 |
| 5 | PDCt-PiroADH-ADH1p | X14172/X14185 | pMU2690 |
| 6 | gpd2 f2 | X 14184/X11821 | M2018 gDNA |

M2108, M2433, and M2488 were examined for ethanol yield, glycerol production, and acetate utilization. Strains were grown in nitrogen purged sealed bottles to establish anaerobic conditions, and several different media were used. Minimal glucose media (FIG. 20A) consisted of 6.7 g/L of yeast nitrogen base, 25 g/L of glucose, 2 g/L of acetic acid, 20 mg/L egosterol, and 420 mg/L tween 80. Minimal xylose media was the same as above, except that xylose was substituted for glucose. YPD and YPX media contained yeast extract (10 g/L), peptone (20 g/L), acetate (2 g/L), 20 mg/L egosterol, 420 mg/L tween 80, and either 20 g/L glucose (YPD), or 20 g/L xylose (YPX). The media pH was adjusted to 5.0 for minimal media (no pH adjustment was carried out for YP based media), and the growth experiments were carried out at 35° C.

FIG. 20A shows the product titers and yield increases for these strains when grown in this minimal media with glucose and acetate. M2433 has a partial glycerol deletion pathway and produced about half the glycerol of the parental strain, while M2488 produced no glycerol. FIG. 20A. The M2488 strain utilized more acetate than M2433 and had a higher ethanol yield increase. FIG. 20A. Nonetheless, a partial deletion of the glycerol pathway still showed an increase in ethanol yield, a decrease in glycerol formation, and an increase in acetate utilization, when compared to the parent M2108. See FIG. 20A. However, the deletion strains showed reduced growth compared to the parent M2108 in various media (YPD, YPX, YMX). See FIG. 20B.

The M2488 and M2433 strains were then compared to M2108 using simultaneous saccharification and fermentation (SSF) at small scale (20 mL total volume) to determine if increased ethanol yields and acetate utilization could be achieved with lignocellulosic material. SSF conditions were as follows: final solids loading was 20% (w/w) of substrate MS737 (an insoluble substrate derived from pretreating hardwood with water), 5 mg AB Enzyme Cellulase preparation/g TS, 1% v/v inoculum, 35° C., pH 5.5 controlled with 5 g/L CaCO$_3$. The medium used was yeast extract (10 g/L) and peptone (20 g/L), and reactions were carried out in sealed nitrogen purged 150 mL pressure bottles by combining all the above ingredients in a batch culture, gently mixing at 125 rpm on a shaker, and sampling over 144 hours. FIGS. 21A and 21B shows the final ethanol, glycerol, and acetate levels of a SSF comparing M2488 and M2108. The ethanol titer was increased (FIG. 21A) and glycerol production was decreased (FIG. 21B) for M2488, when compared to the parent strain M2108. Despite having a Δgpd1Δgpd2 background, some glycerol was detected in M2488, which was likely released from the lignocellulosic material and introduced by the enzymes used for hydrolysis. Significantly, final acetate levels were lower in the M2488 strain demonstrating the conversion of lignocellulose-derived acetate to ethanol under industrial processing conditions.

4.6 Production of Ethanol Using Hardwood Processing Media

A larger scale SSF, comprising glucose/cellulose, was performed to compare the production of ethanol between the gpd deletion strains M2433 and M2488 and the parent strain M2108 under industrially relevant conditions for hardwood processing. SSF conditions were as follows: final solids loading was 22% (w/w) of substrate MS0944 (an insoluble substrate derived from pretreating hardwood with water), 6 mg AB Enzyme Cellulase preparation/g TS, 0.5 g/L dry cell weight inoculum, 35° C., pH 5.0 controlled with 5M NH$_4$OH. Fed batch was carried out over 50 hours with five equal feedings at time 0, 18, 26, 42, and 50 hours. The medium used was 12 g/L corn steep liquor (CSL) and 0.5 g/L diammonium phosphate (DAP). The reaction was carried out at a 1 kg reaction size (about 1 L volume) in a pH and temperature controlled bioreactor from Sartorius for 168 hours. As shown in FIG. 22, M2433 and M2488 worked equally well, giving a 6% yield increase over M2108, representing an improvement of about 3 gallons ethanol produced per ton of biomass. That both gpd deletion strains showed a similar yield increase over the parent strain was unexpected given the differences observed between M2433 and M2488 grown on minimal media with glucose. The gpd deletion strains also required less neutralizing base (12.1 g 5 M NH$_4$OH for M2433 and 9.4 g 5 M NH$_4$OH for M2488) to maintain pH in the fermentation process as compared to M2108 (15.6 g 5 M NH$_4$OH).

The gpd deletion strains were also examined in a washate fermentation, which comprises xylose/hemicellulose. Washate fedbatch conditions were as follows: washate CS 0944 from a water pretreatment of hardwood was concentrated by evaporation to bring the sugar concentration (glucose+xylose) to 164 g/L. 2 g/L dry cell weight was used as inoculum to start the fed-batch fermentation, temperature was controlled at 35° C., and pH was adjusted and controlled at 6.5 with 15 M NH$_4$OH. The starting batch volume at time 0 was 575 mL, and washate made up 17.4% (v/v). Feeding of washate started 3 hours into the fermentation, and continued at 0.14 mL/min for the first 15 h and then the feed rate was adjusted to 0.1 mL/min for the rest of the feed until 72 h. The final washate concentration after feed was 53% (v/v) and final volume was 1000 mL. The medium used was 12 g/L CSL and 0.5 g/L DAP. As shown in FIG. 23A, during washate fermentation, M2433 produced about a 12% yield increase in ethanol as compared to M2108, which represents an improvement of about 1.4 gallons ethanol produced per ton of biomass. M2488, the Δgpd1Δgpd2 background, produced significantly less ethanol than M2108 (FIG. 23A), despite maintaining lower concentrations of glycerol and acetate compared to M2108 and M2433 (FIG. 23B), demonstrating that a double gpd deletion strain is not robust enough under washate processing conditions. Thus, given the differences in robustness between the M2433 and M2488 deletion strains on different biomass processing media, one can select a strain that provides the optimal production profile for the biomass processing media.

Another set of strains was created to examine the yield benefits in a GPD1/2 wild-type background during fermentation of carbohydrates by S. cerevisiae. Strains were built that overexpress four copies of the Piromyces SP E2 AADH at the FCY1 loci. This was done in a manner very similar to that described above. PCR products were generated and transformed that allowed for the yeast strain to create an insertion via homologous recombination. The fragments used for this transformation are given in Table 16 below. After transformation, strains were selected for resistant to 5-fluorocytosine, which is toxic to cells that have an intact FCY1 locus. Strains with replacement of both copies of FCY1 by the Piromyces SP E2 AADH gene cassettes were confirmed by PCR. This procedure was carried out in both M2108 (generating M2556) as well as in M2390 (generating M2739).

TABLE 16

PCR products used to replace the FCY1 loci with 2 copies (each) of the Piromyces SP E2 AADH.

| Piece ID No. | Description | Primers | Template |
|---|---|---|---|
| 1 | FCY f1 | X11631/X12233 | gDNA |
| 2 | PFK1p-PiroADH-HXT2t | X12232/X14179 | pMU2691 |
| 3 | PCDt-PiroADH-ADH1p | X14178/X11750 | pMU2690 |
| 4 | FCY1 f2 | X11633/X11634 | gDNA |

An SSF was performed to compare the production of ethanol in these newly created non-gpd deletion strains against that produced by the wild-type strain, M2108, as well as the GPD1 (M2433) and GPD1 and GPD2 (M2488) deletion strains. SSF at small scale (20 mL total volume) was used to determine if increased ethanol yields and acetate utilization could be achieved with lignocellulosic material. Small scale SSF conditions were as described above: final solids loading was 20% (w/w) of substrate MS737 (an insoluble substrate derived from pretreating hardwood with water), 5 mg AB Enzyme Cellulase preparation/g TS, 1% v/v inoculum, 35° C., pH 5.5 controlled with 5 g/L CaCO$_3$. The medium used was yeast extract (10 g/L) and peptone (20 g/L), and reactions were carried out in sealed nitrogen purged 150 mL pressure bottles by combining all the above ingredients in a batch culture, gently mixing at 125 rpm on a shaker, and sampling over 144 hours. As shown in FIG. 24A, M2556 produced more ethanol as compared to either gpd deletion strain, although all three produced more ethanol than the parent strain M2108. M2556 demonstrated an about 9% increase in ethanol yield, while M2433 and M2488 showed an about 6.5% and about 5.5% increase in ethanol yield, respectively. M2556 also produced more glycerol and used less acetate than either gpd deletion strain, but M2556 had lower glycerol and acetate levels than M2108. FIG. 24B. FIGS. 33 and 34 show results for a derivative of M2390 expressing the AADH. This strain, M2739, showed the same ability to increase ethanol yield, and take up acetate, in SSF with 20% solids using pretreated hardwood in small 20 mL sealed bottles, relative to the parental strain M2390. FIGS. 33 and 34. These results show that overexpressing AADH is applicable to multiple industrial background strains. Overall, these results demonstrate that ethanol yield improvements can be obtained by engineering an improved AADH in a host cell, in the presence or absence of gpd deletions. Overexpressing AADH can also lead to concomitant decreases in acetate and glycerol in SSF, without having to delete gpd.

4.7 Production of Ethanol Using Corn Processing Media 4.7.1 Corn Mash

The amount of fermentable substrate available for industrial production of ethanol by S. cerevisiae is limited to the glucose released during the mashing process and/or enzymatic hydrolysis by addition of amylase enzymes. In this process, a small amount of acetate, between 0.2-0.5 g/L, is produced. Addition of a bifunctional ADH can enable uptake of this acetate and conversion to ethanol resulting in a higher ethanol yield. Additionally, acetate can act as an electron sink during anaerobic or microaerobic growth allowing for reduction of glycerol and increased ethanol yield. See U.S. Appl. No. 61/472,085, incorporated by reference herein in its entirety.

A shake flask fermentation analysis was done using 25% solids corn mash to compare the glycerol deletion mutant M2085 (gpd1Δgpd2Δfdh1Δfdh2Δ) with M2158 (fcyΔ:: ADHE gpd1Δ::ADHE gpd2Δfdh1Δfdh2Δ), a glycerol deletion mutant containing 8 copies of a the *E. coli* bifunctional ADH (SEQ ID NO:51). The flasks were either sampled multiple times or sampled only at the end point ("only sample"). Analysis of ethanol levels indicates that AADH expression allowed for increased ethanol yield when fermentations were sampled multiple times. See FIG. 26A. Because sampling involves removal of the air lock, a temporary aerobic or microaerobic environment may be created. When the airlock was left on during the course of the fermentation, no benefit of AADH expression was observed. FIG. 26B shows acetate uptake by M2158 but not by the wild type strain. The slight increase in acetate at the end of the fermentation was likely a result of cell lysis and is usually observed with all strains.

4.7.2 Corn Fiber

Acetate present in corn fiber is not accessible following mashing and enzymatic hydrolysis by amylases used in the industry. However, this acetate can be released if the fiber that remains after distillation is hydrolyzed. To determine if the acetate generated by hydrolysis of corn fiber can be converted to ethanol, strains M2556 (contains the *Piromyces* SP E2 bifunctional ADH) and M2488 (contains deletions of both gpd1 and gpd2 in addition to expression of the *Piromyces* SP E2 bifunctional ADH) were inoculated into fermentations containing 30% solids corn fiber washate. The experiments were done in shake flasks stoppered with airlocks and sampled at 24 and 96 hours in order to measure metabolites by HPLC. As shown in FIG. 27, strains containing AADH are shown to remove acetate from hydrolyzed fiber resulting in a reduction in glycerol levels.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

---

What is claimed is:

1. A recombinant yeast comprising one or more native and one or more heterologous enzymes that function in one or more engineered metabolic pathways to convert acetate to ethanol, wherein said one or more native and/or heterologous enzymes is activated, upregulated or downregulated, wherein at least one of said one or more native enzymes is a glycerol-3-phosphate dehydrogenase (GPD) that is downregulated and encoded by a gpd1 polynucleotide, a gpd2 polynucleotide, or both a gpd1 and a gpd2 polynucleotide, and wherein at least one of said one or more heterologous enzymes is a bifunctional acetaldehyde/alcohol dehydrogenase.

2. The recombinant yeast of claim 1, wherein one of said engineered metabolic pathways comprises the following steps: (a) conversion of acetate to acetyl-CoA and (b) conversion of acetyl-CoA to ethanol.

3. The recombinant yeast of claim 1, wherein said microorganism is selected from the group consisting of *Saccharomyces cerevisiae, Kluyveromyces lactis, Kluyveromyces marxianus, Pichia pastoris, Yarrowia lipolytica, Hansenula polymorpha, Phaffia rhodozyma, Candida utliis, Arxula adeninivorans, Pichia stipitis, Debaryomyces hansenii, Debaryomyces polymorphus, Schizosaccharomyces pombe, Candida albicans,* and *Schwanniomyces occidentalis.*

4. The recombinant yeast of claim 2, wherein said acetate is converted to acetyl-CoA by an acetyl-CoA transferase.

5. The recombinant yeast of claim 2, wherein said acetate is converted to acetyl-P by an acetate kinase; and wherein said acetyl-P is converted to acetyl-CoA by a phosphotransacetylase.

6. The recombinant yeast of claim 4, wherein said acetyl-CoA is converted to acetaldehyde by an acetaldehyde dehydrogenase; and wherein said acetaldehyde is converted to ethanol by an alcohol dehydrogenase.

7. The recombinant yeast of claim 4, wherein said acetyl-CoA is converted to ethanol by the bifunctional acetaldehyde/alcohol dehydrogenase.

8. A process for converting biomass to ethanol comprising contacting biomass with a recombinant yeast according to claim 1.

9. The recombinant yeast of claim 1, wherein the gpd1 polynucleotide is operably linked to a native gpd2 promoter polynucleotide or the gpd2 polynucleotide is operably linked to a native gpd1 promoter polynucleotide.

10. The recombinant yeast of claim 7, wherein said bifunctional acetaldehyde/alcohol dehydrogenase is from *E. coli, C. acetobutylicum, T saccharolyticum, C. thermocellum, C. phytofermentans, Chlamydomonas reinhardtii, Piromyces* SP E2, or *Bifidobacterium adolescentis*.

11. The recombinant yeast of claim 10, wherein said bifunctional acetaldehyde/alcohol dehydrogenase is selected from SEQ ID NO: 50, SEQ ID NO:52, SEQ ID NO: 54, SEQ ID NO: 56, SEQ ID NO: 58, SEQ ID NO: 62, SEQ ID NO: 64, SEQ ID NO: 66.

12. The recombinant yeast of claim 1, further comprising a mutation in a hydrogenase.

13. A fermentation medium comprising one or more recombinant yeasts according to claim 1.

14. The recombinant yeast of claim 4, wherein said acetyl-CoA transferase is encoded by an acetylCoA synthetase 1 (ACS1) polynucleotide.

15. The recombinant yeast of claim 4, wherein said acetyl-CoA transferase is encoded by a polynucleotide increasing expression of acetylCoA synthetase 2 (ACS2) enzymes.

16. The recombinant yeast of claim 7, wherein said bifunctional acetaldehyde/alcohol dehydrogenase is *Piromyces* SP E2.

* * * * *

SEQUENCE LISTING

```
<160> NUMBER OF SEQ ID NOS: 84

<210> SEQ ID NO 1
<211> LENGTH: 13621
<212> TYPE: DNA
<213> ORGANISM: Artificial sequence
<220> FEATURE:
<223> OTHER INFORMATION: pMU2627 plasmid

<400> SEQUENCE: 1
gcatcaggcg catatttgaa tgtatttaga aaaataaaca aaaagagttt gtagaaacgc       60
aaaaaggcca tccgtcagga tggccttctg cttaatttga tgcctggcag tttatggcgg      120
gcgtcctgcc cgccaccctc cgggccgttg cttcgcaacg ttcaaatccg ctcccggcgg      180
atttgtccta ctcaggagag cgttcaccga caaacaacag ataaaacgaa aggcccagtc      240
tttcgactga gcctttcgtt ttatttgatg cctggctcat cgaggtatcc aagcgattca      300
atagtaacag tccttgtatg ccctctttct ttatcacgat atccatctgc aatagatagg      360
tatattcttc cggaactgcg tctacttttc tttaaataca cattaaactc ccccaataaa      420
attcaatata actatattat accacaatcc ataataatcc gcaaccaaaa tatgacaaaa      480
atttaaaaaa attttaccca aaatcgttag taaaattgct ggttccgggt tacgctacat      540
aaaattttgc tgcaaaacta gggtaaaaaa aatacaaacc atgcgtcaat agaaattgac      600
ggcagtatat taaagcagta taatgaatat atggaaaaac aaaagggcaa tataatatta      660
aaagggaaat ataaacctga atataaggaa aagttgctta atttagccaa attttttact      720
gataatggct ttgttcctac tgaacatgca ttgaatgaaa tacttgggaa aacagcttct      780
ggaagattgc cagatgacaa acagatgtta ttggatgtat tacaaaatgg tgaaaattat      840
attgaaccta atggcaatat agtcaggtat aaaaatggca tatcaataca tatcgataaa      900
gaacatggct ggataattac tataactcca aggaaacgaa tagtaaagga atggaggcga      960
attaatgagt aatgtcgcaa tgcaattaat agaaatttgt cggaaatatg taaataataa     1020
tttaaacata aatgaattta tcgaagactt tcaagtgctt tatgaacaaa agcaagattt     1080
```

```
attgacagat gaagaaatga gcttgtttga tgatatttat atggcttgtg aatactatga    1140
acaggatgaa aatataagaa atgaatatca cttgtatatt ggagaaaatg aattaagaca    1200
aaaagtgcaa aaacttgtaa aaaagttagc agcataataa accgctaagg catgatagct    1260
aaagcgtgcc cattgtgaag tggattgtat tctacaatta aacctaatac gctcataata    1320
tgcgcctttc taaaaaatta ttaattgtac ttattatttt ataaaaaata tgttaaaatg    1380
taaaatgtgt atacaatata tttcttctta gtaagaggaa tgtataaaaa taaatatttt    1440
aaaggaaggg acgatcttat gagcattatt caaaacatca ttgaaaaagc taaaagcgat    1500
aaaaagaaaa ttgttctgcc agaaggtgca gaacccagga cattaaaagc tgctgaaata    1560
gttttaaaag aagggattgc agatttagtg cttcttggaa atgaagatga gataagaaat    1620
gctgcaaaag acttggacat atccaaagct gaaatcattg accctgtaaa gtctgaaatg    1680
tttgataggt atgctaatga tttctatgag ttaaggaaga acaaaggaat cacgttggaa    1740
aaagccagag aaacaatcaa ggataatatc tattttggat gtatgatggt taagaaggt     1800 tatgctgatg gattggtatc tggcgctatt catgctactg cagatttatt aagacctgca    1860
tttcagataa ttaaaacggc tccaggagca aagatagtat caagcttttt tataatggaa    1920
gtgcctaatt gtgaatatgg tgaaaatggt gtattcttgt ttgctgattg tgcggtcaac    1980
ccatcgccta atgcagaaga acttgcttct attgccgtac aatctgctaa tactgcaaag    2040
aatttgttgg gctttgaacc aaaagttgcc atgctatcat tttctacaaa aggtagtgca    2100
tcacatgaat tagtagataa agtaagaaaa gcgacagaga tagcaaaaga attgatgcca    2160
gatgttgcta tcgacggtga attgcaattg gatgctgctc ttgttaaaga agttgcagag    2220
ctaaaagcgc cgggaagcaa agttgcggga tgtgcaaatg tgcttatatt ccctgattta    2280
caagctggta atataggata taagcttgta cagaggttag ctaaggcaaa tgcaattgga    2340
cctataacac aaggaatggg tgcaccggtt aatgatttat caagaggatg cagctataga    2400
gatattgttg acgtaatagc aacaacagct gtgcaggctc aataaaatgt aaagtatgga    2460
ggatgaaaat tatgaaaata ctggttatta attgcggaag ttcttcgcta aaatatcaac    2520
tgattgaatc aactgatgga aatgtgttgg caaaaggcct tgctgaaaga atcggcataa    2580
atgattccat gttgacacat aatgctaacg gagaaaaaat caagataaaa aaagacatga    2640
aagatcacaa agacgcaata aaattggttt tagatgcttt ggtaaacagt gactacggcg    2700
ttataaaaga tatgtctgag atagatgctg taggacatag agttgttcac ggaggagaat    2760
cttttacatc atcagttctc ataaatgatg aagtgttaaa agcgataaca gattgcatag    2820
aattagctcc actgcacaat cctgctaata tagaaggaat taaagcttgc cagcaaatca    2880
tgccaaacgt tccaatggtg gcggtatttg atacagcctt tcatcagaca atgcctgatt    2940
atgcatatct ttatccaata ccttatgaat actacacaaa gtacaggatt agaagatatg    3000
gatttcatgg cacatcgcat aaatatgttt caaataggge tgcagagatt ttgaataaac    3060
ctattgaaga tttgaaaatc ataacttgtc atcttggaaa tggctccagc attgctgctg    3120
tcaaatatgg taaatcaatt gacacaagca tgggatttac accattagaa ggtttggcta    3180
tgggtacacg atctggaagc atagacccat ccatcatttc gtatcttatg gaaaagaaa     3240 atataagcgc tgaagaagta gtaaatatat taaataaaaa atctggtgtt tacggtatt     3300 caggaataag cagcgatttt agagacttag aagatgccgc cttaaaaat ggagatgaaa      3360 gagctcagtt ggctttaaat gtgtttgcat atcgagtaaa aagacgatt ggcgcttatg      3420
```

```
cagcagctat gggaggcgtc gatgtcattg tatttacagc aggtgttggt gaaaatggtc    3480
ctgagatacg agaatttata cttgatggat tagagttttt agggttcagc ttggataaag    3540
aaaaaaataa agtcagagga aaagaaacta ttatatctac gccgaattca aaagttagcg    3600
tgatggttgt gcctactaat gaagaataca tgattgctaa agatactgaa aagattgtaa    3660
agagtataaa atagtgctgc accagttgct ttgtatgcat ttgggaaagg tgcagaaaac    3720
tttaatggtt tctacgacaa cactgaaatt ccaaggatta ttggaagaat agctggatat    3780
gagattacat tccctattta cgaacttcca atttcaggag acattaaca gtaaaagtgc     3840 cttattaatc ttaaactcca ggaattcctg gagtttttt ttaatgcact ttatatgctt     3900
aaaattaaaa aattcacaca tttatcattt ttgattatcg ttaagaaaaa agttataatt    3960
tctttgataa aactttacaa aaaggggtgg tttatttgaa agttgtagat atatcaaaaa    4020
taaacgagtt ggtaaaagaa ggtgcaacgt taatgatagg tggattttg ggtgttggaa     4080 ctccagaaaa tataattgat gaaatcataa gacacaacat atcaaacctt acggtaattg    4140
caaatgatac agcatttgaa gatagggga ttggaaaatt agtaaaaaat aaattatgta     4200
aaaaggtaat tgtttctcac attggaacaa atccagaaac gcaaaggcaa atgattgaag    4260
gaacattgga agttgaattg gttcctcaag gaacacttgc agaaagaata cgtgccgcag    4320
gggttggatt aggtggaatt ttaactccaa caggtgtagg taccgtggtt gaaaaagata    4380
aaaaagtaat tgaagtggaa ggaaaaaaat atttacttga acttcccatt cacgctgatg    4440
ttgctttaat aaaggcaaaa aaagctgatt atttaggtaa tttggtctat aacctaactg    4500
ctgaaaattt taaccctatt atggcacttg ccgctaaaac ggtaattgct gaagttgaag    4560
aaatagttcc aacaggtacc ttaagtccaa atgaaattaa aactcccggt ataattgttg    4620
attatatagt tacgggggtg acaagatgaa cccaaaagaa aaaatagcca taagagttgc    4680
acaggaactt aaaaaaggac aattagtaaa tcttggcatt ggtcttccta cactagttgc    4740
aaattacatt ccaaaagata tacatgtctt ctttcaaagt gaaaatggaa taattggaat    4800
gggccctgct ccaaaagaag ggtatgaaaa tagcgatcta acaaatgccg gagcaagtta    4860
tataactgct ttacctggtg ctatgacatt tgatagtgct ttctcatttg gaataattag    4920
aggtggccat ttagatgtaa ccgtattagg aggtttacag gtagatgaag aaggacatct    4980
tgcaaattgg atgattccgg gaaaaatgat tccaggatg ggtggagcaa tggacctcgt     5040
aacaggtgca aaaaaggtta tagtagctat gacacacacc gcaaaggaa caccaaaaat     5100 agttaaaaaa tgtactctgc cattaacttc cattagaaaa gttgatctta tagtaacaga    5160
acttgccgta attgaaccta ccgatgaagg tttattgtta aaagaaatat ctaaagagac    5220
tactctagat gaagttctta aacttacaga agcaaaatta ataatcgctg atgatcttaa    5280
aatcttttaa catttgtcaa ggtttatccc tccccttgta cctttgtgtc cattataccaa   5340 tacccaaaaa tcacaagcaa taaataatt tcagtaaaat tttttagtta atcgtttata     5400
aaaaattttc tatattgaca aaataatagt gataatatat catataagtg taaggtgatt    5460
gttaaatgaa taacaaaaat tatttacatc acacagtcca aaattcaatt cattcaagcg    5520
aatttcctgt tgaaatgctt gaaaaactga tacaatcacc tgaaatgtag agatttattg    5580
ttaataaatt aacacggagg tgtttattat gaaagaagta gttattgcaa gtggtgtaag    5640
gactgctgtc gggaaatttg gtggcacgct tctaaatgta cctgcagtag atttaggtgc    5700
tgtgaataat aaaagaagca taaaagagc caatgtgaaa cctgagatg ttagtgaagt      5760 gataatggga aatgtattgc aggcaggtct tgggcagaac cccgcaagac aagctgaaat    5820
```

```
aaaagcgggc ataccagtag aagttccggc tatgactgta acatggtat gtggatcagg    5880 tcttagagct gtgacacttg ctgctcaggc agttatgctt ggtgatgctg acattgttgt    5940
agccggtgga atggaaaata tgtcaagagc accatatata ttaaatgatg ctcgctttgg    6000
gtacaggatg aacaatggcc agcttgtaga tgaaatggta tatgatggtt aacagatgt    6060 ttttaaccaa tatcacatgg gaatcactgc cgaaaatctt gctgaaaaat acggcatatc    6120
aagagaagag caggatgaat ttgcatatag aagccaaaaa ttagcgtcag aagcgatatc    6180
atcaggaaga tttgaggatg atagagttcc tgtgattgtg ccgcagaaaa aaggtgaacc    6240
gatagaattt aaagttgatg aacatgtgag acctaatacg acaattgaag cacttgcaaa    6300
attaaaacca gcattccaaa aagatggaac tgtaactgct ggaaatgcat caggaattaa    6360
cgatgcagct gcagcagtag ttgtgatgtc aaaagaaaag gcatgtgaac ttggaataaa    6420
gaccattgca acgattaaat catttggtta tgcaggtgtt gaccccagca tcacgggaat    6480
tggtccagta tatgctacga gaaaggcatt agaaaaagct aatctaactg tagatgattt    6540
agatttaatt gaagcaaatg aagcatttgc agcacaatca ctggctgttg caaaagaatt    6600
aaaatttaat atggacagag tgaatgtaaa tggtggcgca attgcgatag gtcatccaat    6660
cggcgccagc ggatgtagaa ttctagtgac gcttttatat gagatgcaga agaggaattc    6720
gcatactgga cttgcaacat tgtgcatcgg cggaggaatg ggaatagcaa tggttgtcga    6780
aagatagcac tgcagcaatt ccatctgtct gcacccctc atttatttca ataaatatat    6840 atataccta ttatgtattg gattaaatgt aaatgcgaat gtaagataat agcatagtta    6900
aagaaaagga aagggtgtca ttcaatgaaa attgatgtga agatatagc aaaaaattta    6960 aatacgccac taacagccc tgcttatcct atccccaatt ataaatttgt taaccgtgaa    7020 tattaaata ttatttaccg aacgatgaa aaagctttac gtgcagcagt gccggaacct    7080
cttgaaatta ctgaaccttt agtgaaattc gaagtgatgt ggatgcccga tgtttccgga    7140
cttggtgcct atacagaggc aggacaagtc atccctgtca gctttaatgg tgaagaagga    7200
gattatgtac attctatgta tgtagacaat ttcccggcta ttgcaagcgg acggaactt    7260 actgcatatc caaagaaatt gggtgcccct aagctgtata tagactctga tactcttgtt    7320
ggcacattag attatggcag tcttcgtgtg gcaactgcga ctatggggta taaacatttc    7380
gaaatggaca aggaaaaagc gaaagggaa atttgccgac ctaattttat ggttaagatt    7440
gctactgatt acaatggtga tttaagggtt tgtgatttgg tgcggacgca aataacaaat    7500
atagaagtta aaggtgcctg gactggaccg gcgcggcttc aattatttga acatgctctg    7560
gcacctcttg cagatttgcc tgtattagaa gttgtttcag catctcatat ccttacagat    7620
ttaaccttaa atgcagcaca gccggtttat aactacttag aggaaaaata aaaacccagc    7680
gaaccatttg aggtgatagg taagattata ccgaggtatg aaaacgagaa ttggaccttt    7740
acagaattac tctatgaagc gccatatta aaaagctacc aagacgaaga ggatgaagag    7800
gatgaggagg cagattgcct tgaatatatt gacaatactg ataagataat atatctttta    7860
tatagaagat atcgccgtat gtaaggattt caggggcaa ggcataggca gcgcgcttat    7920
caatatatct atagaatggg caaagcataa aaacttgcat ggactaatgc ttgaaaccca    7980
ggacaataac cttatagctt gtaaattcta tcataattgt ggtttcaaaa tcggctccgt    8040
cgatactatg ttatacgcca actttcaaaa caactttgaa aaagctgttt tctggtattt    8100
aaggttttag aatgcaagga acagtgaatt ggagttcgtc ttgttataat tagcttcttg    8160
```

```
gggtatcttt aaatactgta gaaaagagga aggaaataat aaatggctaa aatgagaata    8220
tcaccggaat tgaaaaaact gatcgaaaaa taccgctgcg taaaagatac ggaaggaatg    8280
tctcctgcta aggtatataa gctggtggga gaaaatgaaa acctatattt aaaaatgacg    8340
gacagccggt ataaagggac cacctatgat gtggaacggg aaaaggacat gatgctatgg    8400
ctggaaggaa agctgcctgt tccaaaggtc ctgcactttg aacggcatga tggctggagc    8460
aatctgctca tgagtgaggc cgatggcgtc ctttgctcgg aagagtatga agatgaacaa    8520
agccctgaaa agattatcga gctgtatgcg gagtgcatca ggctctttca ctccatcgac    8580
atatcggatt gtccctatac gaatagctta gacagccgct tagccgaatt ggattactta    8640
ctgaataacg atctggccga tgtggattgc gaaaactggg aagaagacac tccatttaaa    8700
gatccgcgcg agctgtatga tttttttaaag acggaaaagc ccgaagagga acttgtcttt    8760
tcccacggcg acctgggaga cagcaacatc tttgtgaaag atggcaaagt aagtggcttt    8820
attgatcttg ggagaagcgg cagggcggac aagtggtatg acattgcctt ctgcgtccgg    8880
tcgatcaggg aggatatcgg ggaagaacag tatgtcgagc tatttttga cttactgggg    8940
atcaagcctg attgggagaa aataaaatat tatattttac tggatgaatt gttttagtac    9000
ctagatttag atgtctaaaa agcttttag acatctaatc ttttctgaag tacatccgca    9060
actgtccata ctctgatgtt ttatatcttt tctaaaagtt cgctagatag gggtcccgag    9120
cgcctacgag gaatttgtat cggatccgca agagattata tcgagtgcct ttaagaaggc    9180
taaaaattac gaagatgtga tacacaaaaa ggcaaaagat tacggcaaaa acataccgga    9240
tagtcaagtt aaaggagtat tgaaacagat agagattact gccttaaacc atgtagacaa    9300
gattgtcgct gctgaaaaga cgatgcagat agattccctc gtgaagaaaa atatgtctta    9360
tgatatgatg gatgcattgc aggatataga aaaggatttg ataaatcagc agatgttcta    9420
caacgaaaat ctaataaaca taaccaatcc gtatgtgagg cagatattca ctcagatgag    9480
ggatgatgag atgcgattta tcactatcat acagcagaac atagaatcgt taaagtcaaa    9540
gccgactgag cccaacagca tagtatatac gacgccgagg gaaaataaat gaaagtagct    9600
attataggag caggctcggc aggcttaact gcagctataa ggcttgaatc ttatgggata    9660
aagcctgata tatttgagag aaaatcgaaa gtcggcgatg cttttaacca tgtaggagga    9720
cttttaaatg tcataaatag gccaataaat gatcctttag agtatctaaa aaataacttt    9780
gatgtagcta ttgcaccgct taacaacata gacaagattg tgatgcatgg gccaacagtc    9840
actcgcacaa ttaaaggcag aaggcttgga tactttatgc tgaaagggca aggagaattg    9900
tcagtagaaa gccaactata caagaaatta aagacaaatg tcaattttga tgtccacgca    9960
gactacaaga acctaaagga aatttatgat tatgtcattg tagcaactgg aaatcatcag   10020
ataccaaatg agttaggatg ttggcagacg cttgttgata cgaggcttaa aattgctgag   10080
gtaatcggta aattcgaccc gtctatcagc tgtccctcct gttcagctac tgacggggtg   10140
gtgcgtaacg gcaaaagcac cgccggacat cagcgctagc ggagtgtata ctggcttact   10200
atgttggcac tgatgagggt gtcagtgaag tgcttcatgt ggcaggagaa aaaaggctgc   10260
accggtgcgt cagcagaata tgtgatacag gatatattcc gcttcctcgc tcactgactc   10320
gctacgctcg gtcgttcgac tgcggcgagc ggaaatggct tacgaacggg gcggagattt   10380
cctggaagat gccaggaaga tacttaacag ggaagtgaga gggccgcggc aaagccgttt   10440
ttccataggc tccgccccc tgacaagcat cacgaaatct gacgctcaaa tcagtggtgg   10500
cgaaacccga caggactata agataccag gcgtttcccc ctggcggctc cctcgtgcgc   10560
```

```
tctcctgttc ctgcctttcg gtttaccggt gtcattccgc tgttatggcc gcgtttgtct   10620
cattccacgc ctgacactca gttccgggta ggcagttcgc tccaagctgg actgtatgca   10680
cgaacccccc gttcagtccg accgctgcgc cttatccggt aactatcgtc ttgagtccaa   10740
cccggaaaga catgcaaaag caccactggc agcagccact ggtaattgat ttagaggagt   10800
tagtcttgaa gtcatgcgcc ggttaaggct aaactgaaag gacaagtttt ggtgactgcg   10860
ctcctccaag ccagttacct cggttcaaag agttggtagc tcagagaacc ttcgaaaaac   10920
cgccctgcaa ggcggttttt tcgttttcag agcaagagat tacgcgcaga ccaaaacgat   10980
ctcaagaaga tcatcttatt aatcagataa aatatttcta gatttcagtg caatttatct   11040
cttcaaatgt agcacctgaa gtcagcccca tacgatataa gttgtaattc tcatgtttga   11100
cagcttatca tcgataagct ttaatgcggt agtttatcac agttaaattg ctaacgcagt   11160
caggcaccta tacatgcatt tacttataat acagtttttt agttttgctg ccgcatctt    11220 ctcaaatatg cttcccagcc tgcttttctg taacgttcac cctctacctt agcatccctt   11280 cccttttgcaa atagtcctct tccaacaata ataatgtcag atcctgtaga gaccacatca   11340
tccacggttc tatactgttg acccaatgcg tctcccttgt catctaaacc cacaccgggt   11400
gtcataatca accaatcgta accttcatct cttccaccca tgtctctttg agcaataaag   11460
ccgataacaa aatctttgtc gctcttcgca atgtcaacag taccctttagt atattctcca   11520 gtagataggg agcccttgca tgacaattct gctaacatca aaaggcctct aggttccttt   11580
gttacttctt ctgccgcctg cttcaaaccg ctaacaatac ctgggcccac cacaccgtgt   11640
gcattcgtaa tgtctgccca ttctgctatt ctgtatacac ccgcagagta ctgcaatttg   11700
actgtattac caatgtcagc aaattttctg tcttcgaaga gtaaaaaatt gtacttggcg   11760
gataatgcct ttagcggctt aactgtgccc tccatggaaa aatcagtcaa gatatccaca   11820
tgtgttttta gtaaacaaat tttgggacct aatgcttcaa ctaactccag taattccttg   11880
gtggtacgaa catccaatga agcacacaag tttgtttgct tttcgtgcat gatattaaat   11940
agcttggcag caacaggact aggatgagta gcagcacgtt ccttatatgt agctttcgac   12000
atgatttatc ttcgtttcct gcaggttttt gttctgtgca gttgggttaa gaatactggg   12060
caatttcatg tttcttcaac actacatatg cgtatatata ccaatctaag tctgtgctcc   12120
ttccttcgtt cttccttctg ttcggagatt accgaatcaa aaaatttca aagaaaccga    12180 aatcaaaaaa aagaataaaa aaaaatgat gaattgaatt gaaaagctag cttatcgatg    12240
ggtccttttc atcacgtgct ataaaaataa ttataattta aattttttaa tataaatata   12300
taaattaaaa atagaaagta aaaaagaaa ttaaagaaaa aatagttttt gttttccgaa     12360
gatgtaaaag actctagggg gatcgccaac aaatactacc ttttatcttg ctcttcctgc   12420
tctcaggtat taatgccgaa ttgtttcatc ttgtctgtgt agaagaccac acacgaaaat   12480
cctgtgattt tacattttac ttatcgttaa tcgaatgtat atctatttaa tctgcttttc   12540
ttgtctaata aatatatatg taaagtacgc tttttgttga aattttttaa acctttgttt   12600 atttttttt cttcattccg taactcttct accttcttta tttactttct aaaatccaaa    12660
tacaaaacat aaaaataaat aaaacacagag taaattccca aattattcca tcattaaaag   12720
atacgaggcg cgtgtaagtt acaggcaagc gatctctaag aaaccattat tatcatgaca   12780
ttaacctata aaaaggcct ctcgagctag agtcgatctt cgccagcagg gcgaggatcg     12840
tggcatcacc gaaccgcgcc gtgcgcgggt cgtcggtgag ccagagtttc agcaggccgc   12900
```

```
ccaggcggcc caggtcgcca ttgatgcggg ccagctcgcg gacgtgctca tagtccacga    12960
cgcccgtgat tttgtagccc tggccgacgg ccagcaggta ggccgacagg ctcatgccgg    13020
ccgccgccgc cttttcctca atcgctcttc gttcgtctgg aaggcagtac accttgatag    13080
gtgggctgcc cttcctggtt ggcttggttt catcagccat ccgcttgccc tcatctgtta    13140
cgccggcggt agccggccag cctcgcagag caggattccc gttgagcacc gccaggtgcg    13200
aataagggac agtgaagaag gaacacccgc tcgcgggtgg gcctacttca cctatcctgc    13260
ccggctgacg ccgttggata caccaaggaa agtctacacg aacccttcgg caaaatcctg    13320
tatatcgtgc gaaaaaggat ggatataccg aaaaaatcgc taatgacc   ccgaagcagg    13380 gttatgcagc ggaaaagcgc tgcttccctg ctgttttgtg aatatctac  cgactggaaa    13440 caggcaaatg caggaaatta ctgaactgag gggacaggcg agagacgatg ccaaagagct    13500
acaccgacga gctggccgag tgggttgaat cccgcgcggc caagaagcgc cggcgtgatg    13560
aggctgcggt tgcgttcctg gcggtgaggg cggatgtcga tatgcgtaag gagaaaatac    13620
c                                                                   13621

<210> SEQ ID NO 2
<211> LENGTH: 12206
<212> TYPE: DNA
<213> ORGANISM: Artificial sequence
<220> FEATURE:
<223> OTHER INFORMATION: pMU2741

<400> SEQUENCE: 2
gtccacgacg cccgtgattt tgtagccctg gccgacggcc agcaggtagg ccgacaggct      60
catatgccac tcatcctctc aaagtgtata agataaaga  taaagaaaaa agcgctcata     120
gcgccattta acatcgttaa gcttgtgta  tatctaaaag cagttttaca tccgcttctc     180
tttcaagtat gtgatcattc aaaacatcaa acttcttgtc tattctctta aaattcaatt     240
caaacttgcc aagctggctt gtatgctttg ttacttcttc aaatgtctgt tttaaaatgt     300
aatcaacatc gctttgttgc cttttcaaggt tgtaaagtct attctctaca ctatcaagcc     360
tcttgtccat gccgtcaagt ctattttcaa caccgtcaag ccttctctca acgttatcca     420
gtcttctctc aacgttgtcc agcctttat  ccatattatc cagtcttttg tctacatcgt     480
ccaatctttt gtctacgttg tccaatctct tttcaacact gacaagtctt tcatccatac     540
ttcccagttt cccgtcaatc gagtcaaatc tttgaagcac caaagtcatg aactcttcat     600
ttgtcaaggt ttatccctcc ccttgtacct tgtgtccat tataccatac ccaaaaatca     660
caagcaataa ataatttca  gtaaaatttt ttagttaatc gtttataaaa aattttctat     720
attgacaaaa taatagtgat aatatatcat ataagtgtaa ggtgattgtt aaatgaataa     780
caaaaattat ttacatcaca cagtccaaaa ttcaattcat tcaagcgaat tcctgttga     840 aatgcttgaa aaactgatac aatcacctga aatgtagaga tttattgtta ataaattaac     900
acggaggtgt ttattatggc aacgacaaaa acggaattag acgttcagaa gcagatagat     960
ctacttgtgt caagagcaca agaggctcag aaaaaattca tgtcttacac gcaagagcaa    1020
atcgacgcaa tagttaaggc aatggcttta gcaggcgttg acaaacacgt agagctggca    1080
aagatggcgt acgaagagac aaaaatgggt gtatacgaag ataagataac aaaaaatctc    1140
ttcgcaacag agtacgtgta ccacgacata aaaaatgaaa agactgtagg aatcataaac    1200
gagaacatag aagaaactag catggaagtg cgtgcccatt gtgaagtgga ttgtattcta    1260
caattaaacc taatacgctc ataatatgcg cctttctaaa aaattattaa ttgtacttat    1320
```

```
tattttataa aaaatatgtt aaaatgtaaa atgtgtatac aatatatttc ttcttagtaa    1380
gaggaatgta taaaaataaa tattttaaag aagggacga tctttgctgc accagttgct    1440
ttgtatgcat ttgggaaagg tgcagaaaac tttaatggtt tctacgacaa cactgaaatt    1500
ccaaggatta ttggaagaat agctggatat gagattacat tccctattta cgaacttcca    1560
atttcaggag gacattaaca gtaaaagtgc cttattaatc ttaaactcca ggaattcctg    1620
gagttttttt ttaatgcact ttatatgctt aaaattaaaa aattcacaca tttatcattt    1680
ttgattatcg ttaagaaaaa agttataatt tctttgataa aactttacaa aaaggggtgg    1740
tttatttgaa agttgtagat atatcaaaaa taaacgagtt ggtaaaagaa ggtgcaacgt    1800
taatgatagg tggattttttg ggtgttggaa ctccagaaaa tataattgat gaaatcataa    1860
gacacaacat atcaaacctt acggtaattg caaatgatac agcatttgaa gatagggga    1920
ttggaaaatt agtaaaaaat aaattatgta aaaggtaat tgtttctcac attggaacaa    1980
atccagaaac gcaaaggcaa atgattgaag gaacattgga agttgaattg gttcctcaag    2040
gaacacttgc agaaagaata cgtgccgcag gggttggatt aggtggaatt ttaactccaa    2100
caggtgtagg taccgtggtt gaaaagata aaaagtaat tgaagtggaa ggaaaaaaat    2160
atttacttga acttcccatt cacgctgatg ttgctttaat aaaggcaaaa aaagctgatt    2220
atttaggtaa tttggtctat aacctaactg ctgaaaattt taaccctatt atggcacttg    2280
ccgctaaaac ggtaattgct gaagttgaag aaatagttcc aacaggtacc ttaagtccaa    2340
atgaaattaa aactcccggt ataattgttg attatatagt tacggggtg acaagatgaa    2400
cccaaaagaa aaaatagcca taagagttgc acaggaactt aaaaaaggac aattagtaaa    2460
tcttggcatt ggtcttccta cactagttgc aaattacatt ccaaaagata tacatgtctt    2520
cttttcaaagt gaaaatggaa taattggaat gggccctgct ccaaaagaag ggtatgaaaa    2580
tagcgatcta acaatgccg gagcaagtta taactgct ttacctggtg ctatgacatt    2640
tgatagtgct ttctcatttg gaataattag aggtggccat ttagatgtaa ccgtattagg    2700
aggtttacag gtagatgaag aaggacatct tgcaaattgg atgattccgg gaaaaatgat    2760
tccagggatg ggtggagcaa tggacctcgt aacaggtgca aaaaaggtta tagtagctat    2820
gacacacacc gcaaaggaa caccaaaaat agttaaaaaa tgtactctgc cattaacttc    2880
cattagaaaa gttgatctta tagtaacaga acttgccgta attgaaccta ccgatgaagg    2940
tttattgtta aaagaaatat ctaaagagac tactctagat gaagttctta aacttacaga    3000
agcaaaatta ataatcgctg atgatcttaa aatctttaa catttgtcaa ggtttatccc    3060
tccccttgta cctttgtgtc cattatacca tacccaaaaa tcacaagcaa taaaataatt    3120
tcagtaaaat tttttagtta atcgtttata aaaaatttc tatattgaca aaataatagt    3180
gataatatat catataagtg taaggtgatt gttaaatgaa taacaaaaat tatttacatc    3240
acacagtcca aaattcaatt cattcaagcg aatttcctgt tgaaatgctt gaaaactga    3300
tacaatcacc tgaaatgtag agatttattg ttaataaatt aacacggagg tgtttattat    3360
gaaagaagta gttattgcaa gtggtgtaag gactgctgtc gggaaatttg gtggcacgct    3420
tctaaatgta cctgcagtag atttaggtgc tgtgaataat aaaagaagca taaaaagagc    3480
caatgtgaaa cctgaagatg ttagtgaagt gataatggga aatgtattgc aggcaggtct    3540
tgggcagaac cccgcaagac aagctgaaat aaaagcgggc ataccagtag aagttccggc    3600
tatgactgta aacatggtat gtggatcagg tcttagagct gtgacacttg ctgctcaggc    3660
```

-continued

```
agttatgctt ggtgatgctg acattgttgt agccggtgga atggaaaata tgtcaagagc   3720
accatatata ttaaatgatg ctcgctttgg gtacaggatg aacaatggcc agcttgtaga   3780
tgaaatggta tatgatggtt taacagatgt ttttaaccaa tatcacatgg gaatcactgc   3840
cgaaaatctt gctgaaaaat acggcatatc aagagaagag caggatgaat ttgcatatag   3900
aagccaaaaa ttagcgtcag aagcgatatc atcaggaaga tttgaggatg agatagttcc   3960
tgtgattgtg ccgcagaaaa aaggtgaacc gatagaattt aaagttgatg aacatgtgag   4020
acctaatacg acaattgaag cacttgcaaa attaaaacca gcattccaaa aagatggaac   4080
tgtaactgct ggaaatgcat caggaattaa cgatgcagct gcagcagtag ttgtgatgtc   4140
aaaagaaaag gcatgtgaac ttggaataaa gaccattgca acgattaaat catttggtta   4200
tgcaggtgtt gacccagca tcacgggaat tggtccagta tatgctacga gaaaggcatt   4260
agaaaaagct aatctaactg tagatgattt agatttaatt gaagcaaatg aagcatttgc   4320
agcacaatca ctggctgttg caaaagaatt aaaatttaat atggacagag tgaatgtaaa   4380
tggtggcgca attgcgatag gtcatccaat cggcgccagc ggatgtagaa ttctagtgac   4440
gcttttatat gagatgcaga gaggaattc gcatactgga cttgcaacat tgtgcatcgg   4500
cggaggaatg ggaatagcaa tggttgtcga agatatagcac tgcagcaatt ccatctgtct   4560
gcaccccctc atttatttca ataaatatat ataccttta ttatgtattg gattaaatgt   4620
aaatgcgaat gtaagataat agcatagtta aagaaaagga aagggtgtca ttcaatgaaa   4680
attgatgtga agatatagc aaaaaattta aatacgccac taacagcccc tgcttatcct   4740
atcccaaatt ataaatttgt taaccgtgaa tatttaaata ttatttaccg aacggatgaa   4800
aaagctttac gtgcagcagt gccggaacct cttgaaatta ctgaacctt agtgaaattc   4860 gaagtgatgt ggatgcccga tgtttccgga cttggtgcct atacagaggc aggacaagtc   4920
atccctgtca gctttaatgg tgaagaagga gattatgtac attctatgta tgtagacaat   4980
ttcccggcta ttgcaagcgg acgggaactt actgcatatc caaagaaatt gggtgccct   5040 aagctgtata tagactctga tactcttgtt ggcacattag attatggcag tcttcgtgtg   5100
gcaactgcga ctatggggta taaacatttc gaaatggaca aggaaaaagc gaaaagggaa   5160
atttgccgac ctaattttat ggttaagatt gctactgatt acaatggtga tttaagggtt   5220
tgtgatttgg tgcggacgca aataacaaat atagaagtta aagtgcctg gactggaccg   5280 gcgcggcttc aattatttga acatgctctg gcacctcttg cagatttgcc tgtattagaa   5340
gttgtttcag catctcatat ccttacagat ttaaccttaa atgcagcaca gccggtttat   5400
aactacttag aggaaaaata accctttctg tgatcttgtt ttttgcaaat gctatttat   5460 cacaagagat ttctctagtt cttttttact taaaaaaacc ctacgaaatt ttaaactatg   5520
tcgaataaat tattgataat ttttaactat gtgctattat attattgcaa aaaatttaac   5580
aatcatcgcg taagctagtt ttcacattaa tgacttaccc agtatttag gaggtgttta   5640 atgatgaaag gttttgcaat gctcagtatc ggtaaagttg gctggattga aaggaaaag   5700 cctgctcctg gcccatttga tgctattgta agacctctag ctgtggcccc ttgcacttcg   5760
gacattcata ccgttttga aggagccatt ggcgaaagac ataacatgat actcggtcac   5820
gaagctgtag gtgaagtagt tgaagtaggt agtgaggtaa aagattttaa acctggtgat   5880
cgcgttgttg tgccagctat taccctgat tggtggacct ctgaagtaca aagaggatat   5940
caccagcact ccggtggaat gctggcaggc tggaaatttt cgaatgtaaa agatggtgtt   6000
tttggtgaat tttttcatgt gaatgatgct gatatgaatt tagcacatct gcctaaagaa   6060
```

```
attccattgg aagctgcagt tatgattccc gatatgatga ccactggttt tcacggagct    6120
gaactggcag atatagaatt aggtgcgacg gtagcagttt tgggtattgg cccagtaggt    6180
cttatggcag tcgctggtgc caaattgcgt ggagccggaa gaattattgc cgtaggcagt    6240
agaccagttt gtgtagatgc tgcaaaatac tatggagcta ctgatattgt aaactataaa    6300
gatggtccta tcgaaagtca gattatgaat ctaactgaag gcaaaggtgt cgatgctgcc    6360
atcatcgctg gaggaaatgc tgacattatg gctacagcag ttaagattgt taaacctggt    6420
ggcaccatcg ctaatgtaaa ttattttggc gaaggagagg ttttgcctgt tcctcgtctt    6480
gaatggggtt gcggcatggc tcataaaact ataaaaggcg ggctatgccc cggtggacgt    6540
ctaagaatgg aaagactgat tgaccttgtt ttttataagc ctgtcgatcc ttctaagctc    6600
gtcactcacg ttttccaggg atttgacaat attgaaaaag cctttatgtt gatgaaagac    6660
aaaccaaaag acctaatcaa acctgttgta atattagcat aaaaatgggg acttagtcca    6720
tttttatgct aataaggcta aatacactgg tttttttata tgacacatcg gccagtaaac    6780
tcttggtaaa cccagcgaac catttgaggt gataggtaag attataccga ggtatgaaaa    6840
cgagaattgg acctttacag aattactcta tgaagcgcca tatttaaaaa gctaccaaga    6900
cgaagaggat gaagaggatg aggaggcaga ttgccttgaa tatattgaca atactgataa    6960
gataatatat cttttatata gaagatatcg ccgtatgtaa ggatttcagg gggcaaggca    7020
taggcagcgc gcttatcaat atatctatag aatgggcaaa gcataaaaac ttgcatggac    7080
taatgcttga acccaggac aataaccttc tagcttgtaa attctatcat aattgtggtt     7140
tcaaaatcgg ctccgtcgat actatgttat acgccaactt tcaaacaac tttgaaaaag     7200 ctgttttctg gtatttaagg ttttagaatg caaggaacag tgaattggag ttcgtcttgt    7260
tataattagc ttcttggggt atcttaaat actgtagaaa agaggaagga aataataaat     7320
ggctaaaatg agaatatcac cggaattgaa aaaactgatc gaaaaatacc gctgcgtaaa    7380
agatacggaa ggaatgtctc ctgctaaggt atataagctg gtgggagaaa atgaaaacct    7440
atatttaaaa atgacggaca gccggtataa agggaccacc tatgatgtgg aacgggaaaa    7500
ggacatgatg ctatggctgg aaggaaagct gcctgttcca aaggtcctgc actttgaacg    7560
gcatgatggc tggagcaatc tgctcatgag tgaggccgat ggcgtccttt gctcggaaga    7620
gtatgaagat gaacaaagcc ctgaaaagat tatcgagctg tatgcggagt gcatcaggct    7680 cttttcactcc atcgacatat cggattgtcc ctatacgaat agcttagaca gccgcttagc    7740
cgaattggat tacttactga ataacgatct ggccgatgtg gattgcgaaa actgggaaga    7800
agacactcca tttaaagatc cgcgcgagct gtatgatttt ttaaagacgg aaaagcccga    7860
agaggaactt gtcttttccc acggcgacct gggagacagc aacatctttg tgaaagatgg    7920
caaagtaagt ggctttattg atcttgggag aagcggcagg gcggacaagt ggtatgacat    7980
tgccttctgc gtccggtcga tcagggagga tatcggggaa gaacagtatg tcgagctatt    8040
ttttgactta ctggggatca agcctgattg ggagaaaata aaatattata ttttactgga    8100
tgaattgttt tagtacctag atttagatgt ctaaaaagct ttttagacat ctaatctttt    8160
ctgaagtaca tccgcaactg tccatactct gatgttttat atcttttcta aaagttcgct    8220 agatagggt cccgagcgcc tacgaggaat ttgtatcgaa gttccacata ccacacggaa     8280 gagcaaaatgc aatacttctg ccgtatgtaa taaggtacaa tgcagaaaaa cctacaaagt    8340
ttgtggcatt cccacaatac gaatatccaa aagcagcaga aagatatgcg gaaatcgcca    8400
```

```
aattcttagg actgcctgct tcaactgttg aagaaggcgt agaaagctta atagaagcta    8460
taaagaacct catgaaagag cttaacattc cgcttacact taaagacgcc ggcatcaaca    8520
aagaacagtt tgaaaagaa atagaggaaa tgtcagacat cgccttcaac gatcagtgca     8580
cagggacaaa cccgagaatg cctctcacaa aagaaattgc agagatctac agaaaagcat    8640
acggtgcata gcttaagaaa aagaacggct tacaagttaa ttaaaactta taagccgtct    8700
ttttatcact tttttgatac atacatcaaa atcttataca gcaaatatat tataaaaact    8760
aaagcgccga catttattat taaaaatata gttgaaatta aatacataaa taggactccc    8820
ccttatttac aaattattgc atatttatat aatatcacaa gtcgaaagaa ataaataaac    8880
ggctcattta agagccgcct ttttgtatct atatttaatt ccccataaac atctttatgt    8940
cgtcttccac atttgttatg ccgccgatgc caaagttttc aactaaaact tttgcgacgt    9000
ttggcgacaa gaatgccgga agtgtaggtc ctaagtgaat attctttacc cccaggtaca    9060
gaagtgcaag taatactatt acagcttttt gctcatacca tgcaatgtta aatgatattg    9120
gaagctcatt tatatcttca agtccaaaca cttctttaag tttaagcgca atcactgcca    9180
atgaatacga gtcattgcac tgtcctgcgt caagcactct tggtatgccg tttatatcgc    9240
caagatttaa tttattgtac ctgtactttg cacagcctgc tgtcaatatg accgtatctt    9300
ttggaagttc ttttgcaaat tctgtgtagt attctcttga tttcatcctg ccatctctat    9360
cagctgtccc tcctgttcag ctactgacgg ggtggtgcgt aacggcaaaa gcaccgccgg    9420
acatcagcgc tagcggagtg tatactggct tactatgttg gcactgatga gggtgtcagt    9480
gaagtgcttc atgtggcagg agaaaaaagg ctgcaccggt gcgtcagcag aatatgtgat    9540
acaggatata ttccgcttcc tcgctcactg actcgctacg ctcggtcgtt cgactgcggc    9600
gagcggaaat ggcttacgaa cggggcggag atttcctgga agatgccagg aagatactta    9660
acagggaagt gagagggccg cggcaaagcc gttttccat aggctccgcc cccctgacaa     9720
gcatcacgaa atctgacgct caaatcagtg gtggcgaaac ccgacaggac tataaagata    9780
ccaggcgttt ccccctggcg gctccctcgt gcgctctcct gttcctgcct ttcggtttac    9840
cggtgtcatt ccgctgttat ggccgcgttt gtctcattcc acgcctgaca ctcagttccg    9900
ggtaggcagt tcgctccaag ctggactgta tgcacgaacc ccccgttcag tccgaccgct    9960
gcgccttatc cggtaactat cgtcttgagt ccaacccgga aagacatgca aaagcaccac   10020
tggcagcagc cactggtaat tgatttagag gagttagtct tgaagtcatg cgccggttaa   10080
ggctaaactg aaaggacaag ttttggtgac tgcgctcctc caagccagtt acctcggttc   10140
aaagagttgg tagctcagag aaccttcgaa aaaccgccct gcaaggcggt tttttcgttt   10200
tcagagcaag agattacgcg cagaccaaaa cgatctcaag aagatcatct tattaatcag   10260
ataaaatatt tctagatttc agtgcaattt atctcttcaa atgtagcacc tgaagtcagc   10320
cccatacgat ataagttgta attctcatgt ttgacagctt atcatcgata agctttaatg   10380
cggtagttta tcacagttaa attgctaacg cagtcaggca cctatacatg catttactta   10440
taatacagtt ttttagtttt gctggccgca tcttctcaaa tatgcttccc agcctgcttt   10500
tctgtaacgt tcaccctcta ccttagcatc ccttcccttt gcaaatagtc ctcttccaac   10560
aataataatg tcagatcctg tagagaccac atcatccacg gttctatact gttgacccaa   10620
tgcgtctccc ttgtcatcta aacccacacc gggtgtcata atcaaccaat cgtaaccttc   10680
atctcttcca cccatgtctc tttgagcaat aaagccgata acaaaatctt tgtcgctctt   10740
cgcaatgtca acagtaccct tagtatattc tccagtagat agggagccct tgcatgacaa   10800
```

```
ttctgctaac atcaaaaggc ctctaggttc ctttgttact tcttctgccg cctgcttcaa   10860
accgctaaca ataccctgggc ccaccacacc gtgtgcattc gtaatgtctg cccattctgc   10920
tattctgtat acacccgcag agtactgcaa tttgactgta ttaccaatgt cagcaaattt   10980
tctgtcttcg aagagtaaaa aattgtactt ggcggataat gcctttagcg gcttaactgt   11040
gccctccatg gaaaaatcag tcaagatatc cacatgtgtt tttagtaaac aaattttggg   11100
acctaatgct tcaactaact ccagtaattc cttggtggta cgaacatcca atgaagcaca   11160
caagtttgtt tgcttttcgt gcatgatatt aaatagcttg gcagcaacag gactaggatg   11220
agtagcagca cgttccttat atgtagcttt cgacatgatt tatcttcgtt tcctgcaggt   11280
ttttgttctg tgcagttggg ttaagaatac tgggcaattt catgtttctt caacactaca   11340
tatgcgtata tataccaatc taagtctgtg ctccttcctt cgttcttcct tctgttcgga   11400
gattaccgaa tcaaaaaaat ttcaaagaaa ccgaaatcaa aaaaagaat aaaaaaaaaa   11460 tgatgaattg aattgaaaag ctagcttatc gatgggtcct tttcatcacg tgctataaaa   11520
ataattataa tttaaatttt taatataaa tatataaatt aaaaatagaa agtaaaaaaa   11580
gaaattaaag aaaaaatagt ttttgtttc cgaagatgta aaagactcta gggggatcgc   11640
caacaaatac tacctttat cttgctcttc ctgctctcag gtattaatgc cgaattgttt   11700
catcttgtct gtgtagaaga ccacacacga aaatcctgtg attttacatt ttacttatcg   11760
ttaatcgaat gtatatctat ttaatctgct tttcttgtct aataaatata tatgtaaagt   11820 acgcttttg ttgaaattttt ttaaacctttt gtttattttt tttcttcat tccgtaactc   11880 ttctaccttc tttatttact ttctaaaatc caaatacaaa acataaaaat aaataaacac   11940
agagtaaatt cccaaattat tccatcatta aaagatacga ggcgcgtgta agttacaggc   12000
aagcgatctc taagaaaacca ttattatcat gacattaacc tataaaaag gcctctcgag   12060 ctagagtcga tcttcgccag cagggcgagg atcgtggcat caccgaaccg cgccgtgcgc   12120
gggtcgtcgg tgagccagag tttcagcagg ccgcccaggc ggcccaggtc gccattgatg   12180
cgggccagct cgcggacgtg ctcata                                         12206
```

<210> SEQ ID NO 3
<211> LENGTH: 59
<212> TYPE: DNA
<213> ORGANISM: Artificial sequence
<220> FEATURE:
<223> OTHER INFORMATION: Primer X12406 Amplification target Tme ctfAB

<400> SEQUENCE: 3

```
aagatactga aaagattgta aagagtataa aatagtgctg caccagttgc tttgtatgc     59
```

<210> SEQ ID NO 4
<211> LENGTH: 50
<212> TYPE: DNA
<213> ORGANISM: Artificial sequence
<220> FEATURE:
<223> OTHER INFORMATION: Primer X12407

<400> SEQUENCE: 4

```
gtgcagacag atggaattgc tgcattagat attttcaata acaacagctg               50
```

<210> SEQ ID NO 5
<211> LENGTH: 50
<212> TYPE: DNA
<213> ORGANISM: Artificial sequence
<220> FEATURE:

<223> OTHER INFORMATION: Primer X12408 Amplification target Bam adc

<400> SEQUENCE: 5
cagctgttgt tattgaaaat atctaatgca gcaattccat ctgtctgcac                    50

<210> SEQ ID NO 6
<211> LENGTH: 59
<212> TYPE: DNA
<213> ORGANISM: Artificial sequence
<220> FEATURE:
<223> OTHER INFORMATION: Primer X12409

<400> SEQUENCE: 6
acctatcacc tcaaatggtt cgctgggttt ttatttttcc tctaagtagt tataaaccg          59

<210> SEQ ID NO 7
<211> LENGTH: 59
<212> TYPE: DNA
<213> ORGANISM: Artificial sequence
<220> FEATURE:
<223> OTHER INFORMATION: Primer X13293 Amplification target Tth thl

<400> SEQUENCE: 7
aattaataat cgctgatgat cttaaaatct tttaacattt gtcaaggttt atccctccc          59

<210> SEQ ID NO 8
<211> LENGTH: 59
<212> TYPE: DNA
<213> ORGANISM: Artificial sequence
<220> FEATURE:
<223> OTHER INFORMATION: Primer X13294

<400> SEQUENCE: 8
aaatgagggg gtgcagacag atggaattgc tgcagtgcta tctttcgaca accattgct          59

<210> SEQ ID NO 9
<211> LENGTH: 49
<212> TYPE: DNA
<213> ORGANISM: Artificial sequence
<220> FEATURE:
<223> OTHER INFORMATION: Primer X12411 Amplification target Tet adhB

<400> SEQUENCE: 9
cggtttataa ctacttagag gaaaaataac cctttctgtg atcttgttt                     49

<210> SEQ ID NO 10
<211> LENGTH: 58
<212> TYPE: DNA
<213> ORGANISM: Artificial sequence
<220> FEATURE:
<223> OTHER INFORMATION: Primer X12412

<400> SEQUENCE: 10
tcttacctat cacctcaaat ggttcgctgg gtttaccaag agtttactgg ccgatgtg           58

<210> SEQ ID NO 11
<211> LENGTH: 22
<212> TYPE: DNA
<213> ORGANISM: Artificial sequence
<220> FEATURE:
<223> OTHER INFORMATION: Primer X11276 URA3 deletion 5 prime

<400> SEQUENCE: 11
ggagaatcca tacaagaaat cg                                                  22

```
<210> SEQ ID NO 12
<211> LENGTH: 20
<212> TYPE: DNA
<213> ORGANISM: Artificial sequence
<220> FEATURE:
<223> OTHER INFORMATION: Primer X11279 URA3 deletion 3 prime

<400> SEQUENCE: 12
aggtctgttg agtgcaatcg                                              20

<210> SEQ ID NO 13
<211> LENGTH: 29
<212> TYPE: DNA
<213> ORGANISM: Artificial sequence
<220> FEATURE:
<223> OTHER INFORMATION: Primer X11824 GPD1 5 prime Fwd

<400> SEQUENCE: 13
aagcctacag gcgcaagata acacatcac                                    29

<210> SEQ ID NO 14
<211> LENGTH: 59
<212> TYPE: DNA
<213> ORGANISM: Artificial sequence
<220> FEATURE:
<223> OTHER INFORMATION: Primer X11825 GPD1 5 prime Rev

<400> SEQUENCE: 14
cggcggggac gaggcaagct aaacagatct ctagacctac tatcagcagc agcagacat   59

<210> SEQ ID NO 15
<211> LENGTH: 59
<212> TYPE: DNA
<213> ORGANISM: Artificial sequence
<220> FEATURE:
<223> OTHER INFORMATION: Primer X11828 GPD1 3 prime Fwd

<400> SEQUENCE: 15
tcttcttgtc gcttttctct ctcgatagaa cctctacatg aagattagat ttattggag   59

<210> SEQ ID NO 16
<211> LENGTH: 35
<212> TYPE: DNA
<213> ORGANISM: Artificial sequence
<220> FEATURE:
<223> OTHER INFORMATION: Primer X11829 GPD1 3 prime Rev

<400> SEQUENCE: 16
ctcagcattg atcttagcag attcaggatc taggt                             35

<210> SEQ ID NO 17
<211> LENGTH: 29
<212> TYPE: DNA
<213> ORGANISM: Artificial sequence
<220> FEATURE:
<223> OTHER INFORMATION: Primer X11816 GPD2 5 prime Fwd

<400> SEQUENCE: 17
gcagtcatca ggatcgtagg agataagca                                    29

<210> SEQ ID NO 18
<211> LENGTH: 59
<212> TYPE: DNA
<213> ORGANISM: Artificial sequence
<220> FEATURE:
<223> OTHER INFORMATION: Primer X11817 GPD2 5 prime Rev
```

```
<400> SEQUENCE: 18
ggggacgagg caagctaaac agatctctag acctagacag caagcattga taaggaagg      59

<210> SEQ ID NO 19
<211> LENGTH: 59
<212> TYPE: DNA
<213> ORGANISM: Artificial sequence
<220> FEATURE:
<223> OTHER INFORMATION: Primer X11819 GPD2 3 prime Fwd

<400> SEQUENCE: 19
tatctcttct tgtcgctttt tctcctcgat agaacctctg atctttcctg ttgcctctt      59

<210> SEQ ID NO 20
<211> LENGTH: 30
<212> TYPE: DNA
<213> ORGANISM: Artificial sequence
<220> FEATURE:
<223> OTHER INFORMATION: Primer X11821 GPD2 3 prime Rev

<400> SEQUENCE: 20
tcacaagagt gtgcagaaat aggaggtgga                                      30

<210> SEQ ID NO 21
<211> LENGTH: 59
<212> TYPE: DNA
<213> ORGANISM: Artificial sequence
<220> FEATURE:
<223> OTHER INFORMATION: Primer X11826 Antibiotic Fwd

<400> SEQUENCE: 21
acaaatattg ataatataaa gatgtctgct gctgctgata gtaggtctag agatctgtt      59

<210> SEQ ID NO 22
<211> LENGTH: 59
<212> TYPE: DNA
<213> ORGANISM: Artificial sequence
<220> FEATURE:
<223> OTHER INFORMATION: Primer X11656 Antibiotic Rev

<400> SEQUENCE: 22
aacttcatct tacaaaagat cacgtgatct gttgtattaa gggttctcga gagctcgtt      59

<210> SEQ ID NO 23
<211> LENGTH: 59
<212> TYPE: DNA
<213> ORGANISM: Artificial sequence
<220> FEATURE:
<223> OTHER INFORMATION: Primer X11657 K. Lactis URA3 Fwd

<400> SEQUENCE: 23
ccatccagtg tcgaaaacga gctctcgaga acccttaata caacagatca cgtgatctt      59

<210> SEQ ID NO 24
<211> LENGTH: 59
<212> TYPE: DNA
<213> ORGANISM: Artificial sequence
<220> FEATURE:
<223> OTHER INFORMATION: Primer X11827 K. Lactis URA3 Rev

<400> SEQUENCE: 24
ttatctttct ccaataaatc taatcttcat gtagaggttc tatcgaggag aaaaagcga      59

<210> SEQ ID NO 25
<211> LENGTH: 25
```

```
<212> TYPE: DNA
<213> ORGANISM: Artificial sequence
<220> FEATURE:
<223> OTHER INFORMATION: Primer X10876 URA3 5 prime

<400> SEQUENCE: 25
gcctcacgaa aaggactgtt cgtag                                               25

<210> SEQ ID NO 26
<211> LENGTH: 25
<212> TYPE: DNA
<213> ORGANISM: Artificial sequence
<220> FEATURE:
<223> OTHER INFORMATION: Primer X10877 URA3 3 prime

<400> SEQUENCE: 26
gcgattggca gtggaacagt ggtaa                                               25

<210> SEQ ID NO 27
<211> LENGTH: 60
<212> TYPE: DNA
<213> ORGANISM: Artificial sequence
<220> FEATURE:
<223> OTHER INFORMATION: Primer X14177 GPD1 5 prime Rev2

<400> SEQUENCE: 27
tagattgaac caggcatgcc aaagttagtt agatcagggt atatttgtgt tgtggaggg          60

<210> SEQ ID NO 28
<211> LENGTH: 60
<212> TYPE: DNA
<213> ORGANISM: Artificial sequence
<220> FEATURE:
<223> OTHER INFORMATION: Primer X14170 PFK1p-PiroADH-HXT2t Fwd

<400> SEQUENCE: 28
gtatattgta cacccccccc ctccacaaac acaaatatac cctgatctaa ctaactttgg         60

<210> SEQ ID NO 29
<211> LENGTH: 60
<212> TYPE: DNA
<213> ORGANISM: Artificial sequence
<220> FEATURE:
<223> OTHER INFORMATION: Primer X14176 PFK1p-PiroADH-HXT2t Rev

<400> SEQUENCE: 29
atgtcgctgg ccgggtgacc cggcggggac aaggcaagct ccattattat gttggtcttg        60

<210> SEQ ID NO 30
<211> LENGTH: 59
<212> TYPE: DNA
<213> ORGANISM: Artificial sequence
<220> FEATURE:
<223> OTHER INFORMATION: Primer X14171 Antibiotic Fwd 2

<400> SEQUENCE: 30
acgccgatcg gccatactaa acaagaccaa cataataatg gagcttgcct tgtccccgc         59

<210> SEQ ID NO 31
<211> LENGTH: 59
<212> TYPE: DNA
<213> ORGANISM: Artificial sequence
<220> FEATURE:
<223> OTHER INFORMATION: Primer X13734 Antibiotic Rev 2

<400> SEQUENCE: 31
```
ttcgtccccc cgtttctttt ctttggacta tcatgtagtc tctcgacact ggatggcgg    59

<210> SEQ ID NO 32
<211> LENGTH: 59
<212> TYPE: DNA
<213> ORGANISM: Artificial sequence
<220> FEATURE:
<223> OTHER INFORMATION: Primer X13728 TDK Fwd

<400> SEQUENCE: 32
actgctgtcg attcgatact aacgccgcca tccagtgtcg agagactaca tgatagtcc    59

<210> SEQ ID NO 33
<211> LENGTH: 60
<212> TYPE: DNA
<213> ORGANISM: Artificial sequence
<220> FEATURE:
<223> OTHER INFORMATION: Primer X14175 TDK Rev

<400> SEQUENCE: 33
tttctacgcc acttggtgcg gtccatgtaa aatgattgct ccgatttggt tcccagaaac    60

<210> SEQ ID NO 34
<211> LENGTH: 60
<212> TYPE: DNA
<213> ORGANISM: Artificial sequence
<220> FEATURE:
<223> OTHER INFORMATION: Primer X14172 PDCt-PiroADH-ADH1p Fwd

<400> SEQUENCE: 34
atcttctatg ctcataccct tgtttctgg gaaccaaatc ggagcaatca ttttacatgg    60

<210> SEQ ID NO 35
<211> LENGTH: 60
<212> TYPE: DNA
<213> ORGANISM: Artificial sequence
<220> FEATURE:
<223> OTHER INFORMATION: Primer X14174 PDCt-PiroADH-ADH1p Rev

<400> SEQUENCE: 35
cgaaaaaagt gggggaaagt atgatatgtt atctttctcc cgattttttt ctaaaccgtg    60

<210> SEQ ID NO 36
<211> LENGTH: 60
<212> TYPE: DNA
<213> ORGANISM: Artificial sequence
<220> FEATURE:
<223> OTHER INFORMATION: Primer X14173 GPD1 3 prime Fwd2

<400> SEQUENCE: 36
aggatatccg aaatattcca cggtttagaa aaaaatcggg agaaagataa catatcatac    60

<210> SEQ ID NO 37
<211> LENGTH: 22
<212> TYPE: DNA
<213> ORGANISM: Artificial sequence
<220> FEATURE:
<223> OTHER INFORMATION: Primer X14180 PiroADH Fwd

<400> SEQUENCE: 37
gattgtgcaa agaattggtt ac    22

<210> SEQ ID NO 38
<211> LENGTH: 60
<212> TYPE: DNA
<213> ORGANISM: Artificial sequence

```
<220> FEATURE:
<223> OTHER INFORMATION: Primer X14179 Hxt2 t Rev

<400> SEQUENCE: 38
tctacgccac ttggtgcggt ccatgtaaaa tgattgctcc ccattattat gttggtcttg    60

<210> SEQ ID NO 39
<211> LENGTH: 60
<212> TYPE: DNA
<213> ORGANISM: Artificial sequence
<220> FEATURE:
<223> OTHER INFORMATION: Primer X14178 PDCt Rev

<400> SEQUENCE: 39
cgccgatcgg ccatactaaa caagaccaac ataataatgg ggagcaatca ttttacatgg    60

<210> SEQ ID NO 40
<211> LENGTH: 60
<212> TYPE: DNA
<213> ORGANISM: Artificial sequence
<220> FEATURE:
<223> OTHER INFORMATION: Primer X14186 GPD2 5 prime Rev 2

<400> SEQUENCE: 40
agattgaacc aggcatgcca aagttagtta gatcagggtt gataaggaag gggagcgaag    60

<210> SEQ ID NO 41
<211> LENGTH: 60
<212> TYPE: DNA
<213> ORGANISM: Artificial sequence
<220> FEATURE:
<223> OTHER INFORMATION: Primer X14183 PFK1p-PiroADH-HXT2t Fwd 2

<400> SEQUENCE: 41
ctttcccttt cctttcctt cgctccctt ccttatcaac cctgatctaa ctaactttgg    60

<210> SEQ ID NO 42
<211> LENGTH: 60
<212> TYPE: DNA
<213> ORGANISM: Artificial sequence
<220> FEATURE:
<223> OTHER INFORMATION: Primer X14185 PDCt-PiroADH-ADH1p Rev 2

<400> SEQUENCE: 42
aattggttgg gggaaaaaga ggcaacagga aagatcagac gatttttttc taaaccgtgg    60

<210> SEQ ID NO 43
<211> LENGTH: 60
<212> TYPE: DNA
<213> ORGANISM: Artificial sequence
<220> FEATURE:
<223> OTHER INFORMATION: Primer X14184 GPD2 3 prime Fwd 2

<400> SEQUENCE: 43
aaaaggatat ccgaaatatt ccacggttta gaaaaaaatc gtctgatctt cctgttgcc    60

<210> SEQ ID NO 44
<211> LENGTH: 39
<212> TYPE: DNA
<213> ORGANISM: Artificial sequence
<220> FEATURE:
<223> OTHER INFORMATION: Primer X11631 FCY1 5 prime Fwd

<400> SEQUENCE: 44
ttgccaaagt ggattctcct actcaagctt tgcaaacat                          39
```

<210> SEQ ID NO 45
<211> LENGTH: 59
<212> TYPE: DNA
<213> ORGANISM: Artificial sequence
<220> FEATURE:
<223> OTHER INFORMATION: Primer X12233 FCY1 5 prime Rev

<400> SEQUENCE: 45
gttagttaga tcagggtaaa aattatagat gaggttagct atgaaatttt taactctttt    59

<210> SEQ ID NO 46
<211> LENGTH: 59
<212> TYPE: DNA
<213> ORGANISM: Artificial sequence
<220> FEATURE:
<223> OTHER INFORMATION: Primer X12232 PFK1p-PiroADH-HXT2t Fwd 3

<400> SEQUENCE: 46
gagagccagc ttaaagagtt aaaaatttca tagctaacct catctataat ttttaccct     59

<210> SEQ ID NO 47
<211> LENGTH: 59
<212> TYPE: DNA
<213> ORGANISM: Artificial sequence
<220> FEATURE:
<223> OTHER INFORMATION: Primer X11750 PDCt-PiroADH-ADH1p Rev 3

<400> SEQUENCE: 47
ataaaattaa atacgtaaat acagcgtgct gcgtgctcga ttttttttcta aaccgtgga    59

<210> SEQ ID NO 48
<211> LENGTH: 27
<212> TYPE: DNA
<213> ORGANISM: Artificial sequence
<220> FEATURE:
<223> OTHER INFORMATION: Primer X11633 FCY1 3 prime Fwd

<400> SEQUENCE: 48
agcacgcagc acgctgtatt tacgtat                                       27

<210> SEQ ID NO 49
<211> LENGTH: 33
<212> TYPE: DNA
<213> ORGANISM: Artificial sequence
<220> FEATURE:
<223> OTHER INFORMATION: Primer X11634 FCY1 3 prime Rev

<400> SEQUENCE: 49
tagcccttgg ttgagcttga gcgacgttga ggt                                33

<210> SEQ ID NO 50
<211> LENGTH: 891
<212> TYPE: PRT
<213> ORGANISM: Escherichia coli AADH

<400> SEQUENCE: 50

Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Ala Leu Ala Ala Ala Asp Ala Arg Ile Pro
        35                  40                  45

Leu Ala Lys Met Ala Val Ala Glu Ser Gly Met Gly Ile Val Glu Asp
    50                  55                  60

```
Lys Val Ile Lys Asn His Phe Ala Ser Glu Tyr Ile Tyr Asn Ala Tyr
 65                  70                  75                  80

Lys Asp Glu Lys Thr Cys Gly Val Leu Ser Glu Asp Thr Phe Gly
             85                  90                  95

Thr Ile Thr Ile Ala Glu Pro Ile Gly Ile Ile Cys Gly Ile Val Pro
             100                 105                 110

Thr Thr Asn Pro Thr Ser Thr Ala Ile Phe Lys Ser Leu Ile Ser Leu
             115                 120                 125

Lys Thr Arg Asn Ala Ile Ile Phe Ser Pro His Pro Arg Ala Lys Asp
             130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
             165                 170                 175

Leu Ser Asn Ala Leu Met His His Pro Asp Ile Asn Leu Ile Leu Ala
             180                 185                 190

Thr Gly Gly Pro Gly Met Val Lys Ala Ala Tyr Ser Ser Gly Lys Pro
             195                 200                 205

Ala Ile Gly Val Gly Ala Gly Asn Thr Pro Val Val Ile Asp Glu Thr
             210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Asp
             245                 250                 255

Ser Val Tyr Asp Ala Val Arg Glu Arg Phe Ala Thr His Gly Gly Tyr
             260                 265                 270

Leu Leu Gln Gly Lys Glu Leu Lys Ala Val Gln Asp Val Ile Leu Lys
             275                 280                 285

Asn Gly Ala Leu Asn Ala Ala Ile Val Gly Gln Pro Ala Tyr Lys Ile
290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
             325                 330                 335

Leu Ser Pro Thr Leu Ala Met Tyr Arg Ala Lys Asp Phe Glu Asp Ala
             340                 345                 350

Val Glu Lys Ala Glu Lys Leu Val Ala Met Gly Gly Ile Gly His Thr
             355                 360                 365

Ser Cys Leu Tyr Thr Asp Gln Asp Asn Gln Pro Ala Arg Val Ser Tyr
             370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
             405                 410                 415

Leu Thr Leu Gly Cys Gly Ser Trp Gly Gly Asn Ser Ile Ser Glu Asn
             420                 425                 430

Val Gly Pro Lys His Leu Ile Asn Lys Lys Thr Val Ala Lys Arg Ala
             435                 440                 445

Glu Asn Met Leu Trp His Lys Leu Pro Lys Ser Ile Tyr Phe Arg Arg
             450                 455                 460

Gly Ser Leu Pro Ile Ala Leu Asp Glu Val Ile Thr Asp Gly His Lys
465                 470                 475                 480
```

```
Arg Ala Leu Ile Val Thr Asp Arg Phe Leu Phe Asn Asn Gly Tyr Ala
                485                 490                 495

Asp Gln Ile Thr Ser Val Leu Lys Ala Ala Gly Val Glu Thr Glu Val
            500                 505                 510

Phe Phe Glu Val Glu Ala Asp Pro Thr Leu Ser Ile Val Arg Lys Gly
            515                 520                 525

Ala Glu Leu Ala Asn Ser Phe Lys Pro Asp Val Ile Ala Leu Gly
            530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
                565                 570                 575

Arg Lys Arg Ile Tyr Lys Phe Pro Lys Met Gly Val Lys Ala Lys Met
            580                 585                 590

Ile Ala Val Thr Thr Thr Ser Gly Thr Gly Ser Glu Val Thr Pro Phe
            595                 600                 605

Ala Val Val Thr Asp Asp Ala Thr Gly Gln Lys Tyr Pro Leu Ala Asp
            610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
                660                 665                 670

Gly Gln Ala Leu Gln Ala Leu Lys Leu Leu Lys Glu Tyr Leu Pro Ala
            675                 680                 685

Ser Tyr His Glu Gly Ser Lys Asn Pro Val Ala Arg Glu Arg Val His
            690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
            740                 745                 750

Ala Asn Asp Asn Pro Thr Lys Gln Thr Ala Phe Ser Gln Tyr Asp Arg
            755                 760                 765

Pro Gln Ala Arg Arg Arg Tyr Ala Glu Ile Ala Asp His Leu Gly Leu
            770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
            820                 825                 830

Ser Glu Asp Ala Phe Asp Gln Cys Thr Gly Ala Asn Pro Arg Tyr
            835                 840                 845

Pro Leu Ile Ser Glu Leu Lys Gln Ile Leu Leu Asp Thr Tyr Tyr Gly
            850                 855                 860

Arg Asp Tyr Val Glu Gly Glu Thr Ala Ala Lys Glu Ala Ala Pro
865                 870                 875                 880

Ala Lys Ala Glu Lys Lys Ala Lys Lys Ser Ala
            885                 890
```

```
<210> SEQ ID NO 51
<211> LENGTH: 2676
<212> TYPE: DNA
<213> ORGANISM: Escherichia coli AADH

<400> SEQUENCE: 51
atggctgtta ctaatgtcgc tgaacttaac gcactcgtag agcgtgtaaa aaaagcccag      60
cgtgaatatg ccagtttcac tcaagagcaa gtagacaaaa tcttccgcgc cgccgctctg     120
gctgctgcag atgctcgaat cccactcgcg aaaatggccg ttgccgaatc cggcatgggt     180
atcgtcgaag ataaagtgat caaaaaccac tttgcttctg aatatatcta caacgcctat     240
aaagatgaaa aaacctgtgg tgttctgtct gaagacgaca cttttggtac catcactatc     300
gctgaaccaa tcggtattat ttgcggtatc gttccgacca ctaacccgac ttcaactgct     360
atcttcaaat cgctgatcag tctgaagacc cgtaacgcca ttatcttctc cccgcacccg     420
cgtgcaaaag atgccaccaa caaagcggct gatatcgttc tgcaggctgc tatcgctgcc     480
ggtgctccga agatctgat cggctggatc gatcaacctt ctgttgaact gtctaacgca     540
ctgatgcacc acccagacat caacctgatc ctcgcgactg gtggtccggg catggttaaa     600
gccgcataca gctccggtaa accagctatc ggtgtaggcg cgggcaacac tccagttgtt     660
atcgatgaaa ctgctgatat caaacgtgca gttgcatctg tactgatgtc caaaaccttc     720
gacaacggcg taatctgtgc ttctgaacag tctgttgttg ttgttgactc tgtttatgac     780
gctgtacgtg aacgttttgc aacccacggc ggctatctgt gcagggtaa agagctgaaa     840 gctgttcagg atgttatcct gaaaaacggt gcgctgaacg cggctatcgt tggtcagcca     900
gcctataaaa ttgctgaact ggcaggcttc tctgtaccag aaaacaccaa gattctgatc     960
ggtgaagtga ccgttgttga tgaaagcgaa ccgttcgcac atgaaaaact gtcccccgact    1020 ctggcaatgt accgcgctaa agatttcgaa gacgcggtag aaaaagcaga gaactggtt     1080 gctatgggcg gtatccggtca tacctcttgc ctgtacactg accaggataa ccaaccggct    1140
cgcgtttctt acttcggtca gaaaatgaaa acggcgcgta cctgattaa caccccagcg     1200 tctcagggtg gtatcggtga cctgtataac ttcaaactcg caccttccct gactctgggt    1260
tgtggttctt ggggtggtaa ctccatctct gaaaacgttg gtccgaaaca cctgatcaac    1320
aagaaaaccg ttgctaagcg agctgaaaac atgttgtggc acaaacttcc gaaatctatc    1380
tacttccgcc gtggctcctt gccaatcgcg ctggatgaag tgattactga tggccacaaa    1440
cgtgcgctca tcgtgactga ccgcttcctg ttcaacaatg ttatgctga tcagatcact    1500 tccgtactga aagcagcagg cgttgaaact gaagtcttct tcgaagtaga gcggacccg     1560 accctgagca tcgttcgtaa aggtgcagaa ctggcaaact ccttcaaacc agacgtgatt    1620
atcgcgctgg gtggtggttc cccgatggac gccgcgaaga tcatgtgggt tatgtacgaa    1680
catccggaaa ctcacttcga gagctggcg ctgcgcttta tggatatccg taaacgtatc    1740
tacaagttcc cgaaaatggg cgtgaaagcg aaaatgatcg ctgtcaccac cacttctggt    1800
acaggttctg aagtcactcc gtttgcggtt gtaactgacg acgctactgg tcagaaatat    1860
ccgctggcag actatgcgct gactccggat atggcgattg tcgacgccaa cctggttatg    1920
gacatgccga gtccctgtg tgcttttcggt ggtctgacca gtaactca cgccatggaa    1980 gcttatgttt ctgtactggc atctgagttc tctgatggtc aggctctgca ggcactgaaa    2040
ctgctgaaag aatatctgcc agcgtcctac acgaagggt ctaaaaatcc ggtagcgcgt    2100
gaacgtgttc acagtgcagc gactatcgcg ggtatcgcgt ttgcgaacgc cttcctgggt    2160
```

-continued

```
gtatgtcact caatggcgca caaactgggt tcccagttcc atattccgca cggtctggca      2220
aacgccctgc tgatttgtaa cgttattcgc tacaatgcga acgacaaccc gaccaagcag      2280
actgcattca gccagtatga ccgtccgcag gctcgccgtc gttatgctga aattgccgac      2340
cacttgggtc tgagcgcacc gggcgaccgt actgctgcta agatcgagaa actgctggca      2400
tggctggaaa cgctgaaagc tgaactgggt attccgaaat ctatccgtga agctggcgtt      2460
caggaagcag acttcctggc gaacgtggat aaactgtctg aagatgcatt cgatgaccag      2520
tgcaccggcg ctaacccgcg ttacccgctg atctccgagc tgaaacagat tctgctggat      2580
acctactacg tcgtgatta tgtagaaggt gaaactgcag cgaagaaaga agctgctccg      2640
gctaaagctg agaaaaaagc gaaaaaatcc gcttaa                               2676
```

<210> SEQ ID NO 52
<211> LENGTH: 872
<212> TYPE: PRT
<213> ORGANISM: Clostridium phytofermentans AADH

<400> SEQUENCE: 52

```
Met Thr Lys Lys Val Glu Leu Gln Thr Thr Gly Leu Val Asp Ser Leu
1               5                   10                  15

Glu Ala Leu Thr Ala Lys Phe Arg Glu Leu Lys Glu Ala Gln Glu Leu
            20                  25                  30

Phe Ala Thr Tyr Thr Gln Glu Gln Val Asp Lys Ile Phe Phe Ala Ala
        35                  40                  45

Ala Met Ala Ala Asn Gln Gln Arg Ile Pro Leu Ala Lys Met Ala Val
    50                  55                  60

Glu Glu Thr Gly Met Gly Ile Val Glu Asp Lys Val Ile Lys Asn His
65                  70                  75                  80

Tyr Ala Ala Glu Tyr Ile Tyr Asn Ala Tyr Lys Asp Thr Lys Thr Cys
                85                  90                  95

Gly Val Val Glu Glu Asp Pro Ser Phe Gly Ile Lys Lys Ile Ala Glu
            100                 105                 110

Pro Ile Gly Val Val Ala Ala Val Ile Pro Thr Thr Asn Pro Thr Ser
        115                 120                 125

Thr Ala Ile Phe Lys Thr Leu Leu Cys Leu Lys Thr Arg Asn Ala Ile
    130                 135                 140

Ile Ile Ser Pro His Pro Arg Ala Lys Asn Cys Thr Ile Ala Ala Ala
145                 150                 155                 160

Lys Val Val Leu Asp Ala Ala Val Ala Ala Gly Ala Pro Ala Gly Ile
                165                 170                 175

Ile Gly Trp Ile Asp Val Pro Ser Leu Glu Leu Thr Asn Glu Val Met
            180                 185                 190

Lys Asn Ala Asp Ile Ile Leu Ala Thr Gly Gly Pro Gly Met Val Lys
        195                 200                 205

Ala Ala Tyr Ser Ser Gly Lys Pro Ala Leu Gly Val Gly Ala Gly Asn
    210                 215                 220

Thr Pro Val Ile Met Asp Glu Ser Cys Asp Val Arg Leu Ala Val Ser
225                 230                 235                 240

Ser Ile Ile His Ser Lys Thr Phe Asp Asn Gly Met Ile Cys Ala Ser
                245                 250                 255

Glu Gln Ser Val Ile Ser Asp Lys Ile Tyr Glu Ala Ala Lys Lys
            260                 265                 270

Glu Phe Lys Asp Arg Gly Cys His Ile Cys Ser Pro Glu Glu Thr Gln
        275                 280                 285
```

```
Lys Leu Arg Glu Thr Ile Leu Ile Asn Gly Ala Leu Asn Ala Lys Ile
            290                 295                 300
Val Gly Gln Ser Ala His Thr Ile Ala Lys Leu Ala Gly Phe Asp Val
305                 310                 315                 320
Ala Glu Ala Ala Lys Ile Leu Ile Gly Glu Val Glu Ser Val Glu Leu
                325                 330                 335
Glu Glu Gln Phe Ala His Glu Lys Leu Ser Pro Val Leu Ala Met Tyr
            340                 345                 350
Lys Ser Lys Ser Phe Asp Asp Ala Val Ser Lys Ala Ala Arg Leu Val
            355                 360                 365
Ala Asp Gly Gly Tyr Gly His Thr Ser Ser Ile Tyr Ile Asn Val Gly
370                 375                 380
Thr Gly Gln Glu Lys Ile Ala Lys Phe Ser Asp Ala Met Lys Thr Cys
385                 390                 395                 400
Arg Ile Leu Val Asn Thr Pro Ser Ser His Gly Gly Ile Gly Asp Leu
                405                 410                 415
Tyr Asn Phe Lys Leu Ala Pro Ser Leu Thr Leu Gly Cys Gly Ser Trp
                420                 425                 430
Gly Gly Asn Ser Val Ser Glu Asn Val Gly Val Lys His Leu Ile Asn
            435                 440                 445
Ile Lys Thr Val Ala Glu Arg Arg Glu Asn Met Leu Trp Phe Arg Ala
            450                 455                 460
Pro Glu Lys Val Tyr Phe Lys Lys Gly Cys Leu Pro Val Ala Leu Ala
465                 470                 475                 480
Glu Leu Lys Asp Val Met Asn Lys Lys Val Phe Ile Val Thr Asp
                485                 490                 495
Ala Phe Leu Tyr Lys Asn Gly Tyr Thr Lys Cys Val Thr Asp Gln Leu
                500                 505                 510
Asp Ala Met Gly Ile Gln His Thr Thr Tyr Tyr Asp Val Ala Pro Asp
            515                 520                 525
Pro Ser Leu Ala Ser Ala Thr Glu Gly Ala Glu Ala Met Arg Leu Phe
530                 535                 540
Glu Pro Asp Cys Ile Ile Ala Leu Gly Gly Gly Ser Ala Met Asp Ala
545                 550                 555                 560
Gly Lys Ile Met Trp Val Met Tyr Glu His Pro Glu Val Asn Phe Leu
                565                 570                 575
Asp Leu Ala Met Arg Phe Met Asp Ile Arg Lys Arg Val Tyr Ser Phe
            580                 585                 590
Pro Lys Met Gly Glu Lys Ala Tyr Phe Ile Ala Val Pro Thr Ser Ser
            595                 600                 605
Gly Thr Gly Ser Glu Val Thr Pro Phe Ala Val Ile Thr Asp Glu Arg
610                 615                 620
Thr Gly Val Lys Tyr Pro Leu Ala Asp Tyr Glu Leu Leu Pro Lys Met
625                 630                 635                 640
Ala Ile Ile Asp Ala Asp Met Met Met Asn Gln Pro Lys Gly Leu Thr
                645                 650                 655
Ser Ala Ser Gly Ile Asp Ala Leu Thr His Ala Leu Glu Ala Tyr Ala
            660                 665                 670
Ser Ile Met Ala Thr Asp Tyr Thr Asp Gly Leu Ala Leu Lys Ala Met
            675                 680                 685
Lys Asn Ile Phe Ala Tyr Leu Pro Ser Ala Tyr Glu Asn Gly Ala Ala
            690                 695                 700
```

```
Asp Pro Val Ala Arg Glu Lys Met Ala Asp Ala Ser Thr Leu Ala Gly
705                 710                 715                 720

Met Ala Phe Ala Asn Ala Phe Leu Gly Ile Cys His Ser Met Ala His
                725                 730                 735

Lys Leu Gly Ala Phe His His Leu Pro His Gly Val Ala Asn Ala Leu
            740                 745                 750

Leu Ile Asn Glu Val Met Arg Phe Asn Ser Val Ser Ile Pro Thr Lys
        755                 760                 765

Met Gly Thr Phe Ser Gln Tyr Gln Tyr Pro His Ala Leu Asp Arg Tyr
770                 775                 780

Val Glu Cys Ala Asn Phe Leu Gly Ile Ala Gly Lys Asn Asp Asn Glu
785                 790                 795                 800

Lys Phe Glu Asn Leu Leu Lys Ala Ile Asp Glu Leu Lys Glu Lys Val
                805                 810                 815

Gly Ile Lys Lys Ser Ile Lys Glu Tyr Gly Val Asp Glu Lys Tyr Phe
            820                 825                 830

Leu Asp Thr Leu Asp Ala Met Val Glu Gln Ala Phe Asp Asp Gln Cys
        835                 840                 845

Thr Gly Ala Asn Pro Arg Tyr Pro Leu Met Lys Glu Ile Lys Glu Ile
850                 855                 860

Tyr Leu Lys Val Tyr Tyr Gly Lys
865                 870

<210> SEQ ID NO 53
<211> LENGTH: 2619
<212> TYPE: DNA
<213> ORGANISM: Clostridium phytofermentans AADH

<400> SEQUENCE: 53
atgacgaaaa aagtggaatt acagacaact ggattagtag actctctcga agcattaaca      60
gcaaaattta gagagttaaa agaagcacaa gagctctttg ctacctacac tcaagagcaa     120
gtagataaaa tcttctttgc tgctgccatg gctgccaatc agcaacgtat tccgttagca     180
aagatggctg tagaagaaac gggtatgggt attgtagaag ataaagtaat taagaatcat     240
tatgctgcag agtatattta caatgcatac aaagatacaa aacatgtgg agtggttgaa     300 gaagatccta gcttcggtat caaaaaaatt gcagagccaa tcggcgtagt tgcagctgta     360
atcccaacta ccaatcctac ctccactgct atctttaaaa cattactttg tttaaagact     420
cgtaacgcaa tcatcatcag cccacatcct cgtgctaaga actgtaccat cgcagctgct     480
aaggtagttt tagatgctgc agttgctgca ggtgctcctg ctggtataat tggatggatt     540
gatgttccat cacttgaatt aaccaatgaa gttatgaaaa atgcagacat catccttgca     600
actggtggac ctggtatggt aaaggctgct tattcttctg gtaaaccagc acttggtgtt     660
ggcgcaggta ataccctgt tattatggat gaaagctgcg atgttcgcct gcagtaagc      720 tctattattc actctaagac atttgataac ggtatgattt gtgcttccga gcaatccgta     780
attattagtg ataagattta tgaagctgct aagaaagaat caaggatcg tggttgccac     840 atctgctccc cagaagagac tcagaagctt cgtgaaacaa tcctaattaa tggtgctctt     900
aacgctaaaa ttgttggaca aagcgctcat acgattgcaa agcttgcagg atttgatgta     960
gcagaagctg ctaagatttt aattggtgaa gtagaatccg ttgaactaga agaacaattt    1020
gcacacgaga aactttctcc agttcttgct atgtacaaat caaatccctt tgatgatgca    1080
gtaagcaaag ctgctcgtct tgttgcagat ggcggttatg ccatacttc ttccatctat    1140
```

```
attaatgtag gtaccggaca agaaaagatt gcaaagtttt ctgatgctat gaagacttgc    1200
cgtattcttg taaatacacc atcctcccat ggtggtatcg gtgaccttta taactttaaa    1260
ttagctccat ctcttactct tggttgtggc tcctggggcg gtaactctgt atcagaaaac    1320
gtaggagtaa agcacttaat caacattaag acagttgctg agaggagaga aaacatgctt    1380
tggtttagag cacctgagaa agtatacttt aagaagggtt gtttaccagt agccctcgca    1440
gaattaaaag atgtaatgaa taaaagaaaa gtattcattg taaccgatgc tttcctttat    1500
aaaaatggct atacaaaatg tgttactgat cagttagatg ctatgggaat tcagcatact    1560
acttactatg atgttgctcc agatccatct ttagctagtg ctacagaagg tgcagaagcg    1620
atgagactct tcgagccaga ctgtattatc gcactcggtg gtggttctgc aatggatgcc    1680
ggaaagatta tgtgggttat gtatgaacac cctgaagtaa acttccttga ccttgcaatg    1740
cgtttcatgg atattagaaa gcgtgtttac tccttcccta agatgggcga aaaagcttac    1800
tttatcgcag ttccaacttc ctccggtact ggttctgaag ttacaccatt tgctgttatt    1860
accgatgaga gaactggcgt aaaatatcca cttgcagatt acgaattact tcctaagatg    1920
gctattattg atgccgatat gatgatgaat caacctaagg gattaacttc tgcttccggt    1980
attgatgccc ttacccatgc attagaggca tatgcttcta tcatggctac tgactatacg    2040
gatggtttag cattaaaagc tatgaagaat atcttcgctt accttccaag cgcatatgaa    2100
aatggtgccg ctgatccggt tgcaagagaa aagatggcag atgcttctac cttagctggt    2160
atggcattcg caaatgcatt cttaggaatt gccactcca tggctcataa attaggtgca    2220
ttccaccact taccacacgg tgtagcaaac gcactcttaa tcaacgaagt aatgcgcttt    2280
aactccgtta gcattcctac aaagatgggt actttctctc aataccaata cccacatgcg    2340
ttagatcgtt atgtagaatg tgcgaacttc ttaggtattg ccggaaagaa cgacaatgag    2400
aaattcgaaa accttcttaa ggcaattgat gaattaaaag aaaagttgg tatcaagaaa    2460 tccatcaaag aatatggcgt agacgagaaa tatttcttag atactttaga tgctatggtt    2520
gaacaggctt tcgatgatca gtgtactggt gctaacccaa gatatccatt aatgaaggaa    2580
atcaaggaaa tctatcttaa agtgtactac ggtaaataa                            2619
```

<210> SEQ ID NO 54
<211> LENGTH: 910
<212> TYPE: PRT
<213> ORGANISM: Bifidobacterium adolescentis AADH

<400> SEQUENCE: 54

```
Met Ala Asp Ala Lys Lys Lys Glu Glu Pro Thr Lys Pro Thr Pro Glu
 1               5                  10                  15

Glu Lys Leu Ala Ala Ala Glu Ala Glu Val Asp Ala Leu Val Lys Lys
            20                  25                  30

Gly Leu Lys Ala Leu Asp Glu Phe Glu Lys Leu Asp Gln Lys Gln Val
        35                  40                  45

Asp His Ile Val Ala Lys Ala Ser Val Ala Ala Leu Asn Lys His Leu
    50                  55                  60

Val Leu Ala Lys Met Ala Val Glu Glu Thr His Arg Gly Leu Val Glu
65                  70                  75                  80

Asp Lys Ala Thr Lys Asn Ile Phe Ala Cys Glu His Val Thr Asn Tyr
                85                  90                  95

Leu Ala Gly Gln Lys Thr Val Gly Ile Ile Arg Glu Asp Asp Val Leu
            100                 105                 110
```

-continued

Gly Ile Asp Glu Ile Ala Glu Pro Val Gly Val Val Ala Gly Val Thr
            115                 120                 125

Pro Val Thr Asn Pro Thr Ser Thr Ala Ile Phe Lys Ser Leu Ile Ala
        130                 135                 140

Leu Lys Thr Arg Cys Pro Ile Ile Phe Gly Phe His Pro Gly Ala Gln
145                 150                 155                 160

Asn Cys Ser Val Ala Ala Ala Lys Ile Val Arg Asp Ala Ala Ile Ala
                165                 170                 175

Ala Gly Ala Pro Glu Asn Cys Ile Gln Trp Ile Glu His Pro Ser Ile
            180                 185                 190

Glu Ala Thr Gly Ala Leu Met Lys His Asp Gly Val Ala Thr Ile Leu
        195                 200                 205

Ala Thr Gly Gly Pro Gly Met Val Lys Ala Ala Tyr Ser Ser Gly Lys
    210                 215                 220

Pro Ala Leu Gly Val Gly Ala Gly Asn Ala Pro Ala Tyr Val Asp Lys
225                 230                 235                 240

Asn Val Asp Val Val Arg Ala Ala Asn Asp Leu Ile Leu Ser Lys His
                245                 250                 255

Phe Asp Tyr Gly Met Ile Cys Ala Thr Glu Gln Ala Ile Ile Ala Asp
            260                 265                 270

Lys Asp Ile Tyr Ala Pro Leu Val Lys Glu Leu Lys Arg Arg Lys Ala
        275                 280                 285

Tyr Phe Val Asn Ala Asp Glu Lys Ala Lys Leu Glu Gln Tyr Met Phe
    290                 295                 300

Gly Cys Thr Ala Tyr Ser Gly Gln Thr Pro Lys Leu Asn Ser Val Val
305                 310                 315                 320

Pro Gly Lys Ser Pro Gln Tyr Ile Ala Lys Ala Ala Gly Phe Glu Ile
                325                 330                 335

Pro Glu Asp Ala Thr Ile Leu Ala Ala Glu Cys Lys Glu Val Gly Glu
            340                 345                 350

Asn Glu Pro Leu Thr Met Glu Lys Leu Ala Pro Val Gln Ala Val Leu
        355                 360                 365

Lys Ser Asp Asn Lys Glu Gln Ala Phe Glu Met Cys Glu Ala Met Leu
    370                 375                 380

Lys His Gly Ala Gly His Thr Ala Ala Ile His Thr Asn Asp Arg Asp
385                 390                 395                 400

Leu Val Arg Glu Tyr Gly Gln Arg Met His Ala Cys Arg Ile Ile Trp
                405                 410                 415

Asn Ser Pro Ser Ser Leu Gly Gly Val Gly Asp Ile Tyr Asn Ala Ile
            420                 425                 430

Ala Pro Ser Leu Thr Leu Gly Cys Gly Ser Tyr Gly Gly Asn Ser Val
        435                 440                 445

Ser Gly Asn Val Gln Ala Val Asn Leu Ile Asn Ile Lys Arg Ile Ala
    450                 455                 460

Arg Arg Asn Asn Asn Met Gln Trp Phe Lys Ile Pro Ala Lys Thr Tyr
465                 470                 475                 480

Phe Glu Pro Asn Ala Ile Lys Tyr Leu Arg Asp Met Tyr Gly Ile Glu
                485                 490                 495

Lys Ala Val Ile Val Cys Asp Lys Val Met Glu Gln Leu Gly Ile Val
            500                 505                 510

Asp Lys Ile Ile Asp Gln Leu Arg Ala Arg Ser Asn Arg Val Thr Phe
        515                 520                 525

Arg Ile Ile Asp Tyr Val Glu Pro Glu Pro Ser Val Glu Thr Val Glu

Arg Gly Ala Ala Met Met Arg Glu Glu Phe Glu Pro Asp Thr Ile Ile
545                 550                 555                 560

Ala Val Gly Gly Gly Ser Pro Met Asp Ala Ser Lys Ile Met Trp Leu
                565                 570                 575

Leu Tyr Glu His Pro Glu Ile Ser Phe Ser Asp Val Arg Glu Lys Phe
            580                 585                 590

Phe Asp Ile Arg Lys Arg Ala Phe Lys Ile Pro Pro Leu Gly Lys Lys
        595                 600                 605

Ala Lys Leu Val Cys Ile Pro Thr Ser Ser Gly Thr Gly Ser Glu Val
    610                 615                 620

Thr Pro Phe Ala Val Ile Thr Asp His Lys Thr Gly Tyr Lys Tyr Pro
625                 630                 635                 640

Ile Thr Asp Tyr Ala Leu Thr Pro Ser Val Ala Ile Val Asp Pro Val
                645                 650                 655

Leu Ala Arg Thr Gln Pro Arg Lys Leu Ala Ser Asp Ala Gly Phe Asp
            660                 665                 670

Ala Leu Thr His Ala Phe Glu Ala Tyr Val Ser Val Tyr Ala Asn Asp
        675                 680                 685

Phe Thr Asp Gly Met Ala Leu His Ala Ala Lys Leu Val Trp Asp Asn
690                 695                 700

Leu Ala Glu Ser Val Asn Gly Glu Pro Gly Glu Glu Lys Thr Arg Ala
705                 710                 715                 720

Gln Glu Lys Met His Asn Ala Ala Thr Met Ala Gly Met Ala Phe Gly
                725                 730                 735

Ser Ala Phe Leu Gly Met Cys His Gly Met Ala His Thr Ile Gly Ala
            740                 745                 750

Leu Cys His Val Ala His Gly Arg Thr Asn Ser Ile Leu Leu Pro Tyr
        755                 760                 765

Val Ile Arg Tyr Asn Gly Ser Val Pro Glu Glu Pro Thr Ser Trp Pro
770                 775                 780

Lys Tyr Asn Lys Tyr Ile Ala Pro Glu Arg Tyr Gln Glu Ile Ala Lys
785                 790                 795                 800

Asn Leu Gly Val Asn Pro Gly Lys Thr Pro Glu Glu Gly Val Glu Asn
                805                 810                 815

Leu Ala Lys Ala Val Glu Asp Tyr Arg Asp Asn Lys Leu Gly Met Asn
            820                 825                 830

Lys Ser Phe Gln Glu Cys Gly Val Asp Glu Asp Tyr Tyr Trp Ser Ile
        835                 840                 845

Ile Asp Gln Ile Gly Met Arg Ala Tyr Glu Asp Gln Cys Ala Pro Ala
850                 855                 860

Asn Pro Arg Ile Pro Gln Ile Glu Asp Met Lys Asp Ile Ala Ile Ala
865                 870                 875                 880

Ala Tyr Tyr Gly Val Ser Gln Ala Glu Gly His Lys Leu Arg Val Gln
                885                 890                 895

Arg Gln Gly Glu Ala Ala Thr Glu Glu Ala Ser Glu Arg Ala
            900                 905                 910

<210> SEQ ID NO 55
<211> LENGTH: 2733
<212> TYPE: DNA
<213> ORGANISM: Bifidobacterium adolescentis AADH

<400> SEQUENCE: 55

-continued

```
atggcagacg caaagaagaa ggaagagccg accaagccga ctccggaaga gaagctcgcc      60
gcagccgagg ctgaggtcga cgctctggtc aagaagggcc tgaaggctct tgatgaattc     120
gagaagctcg atcagaagca ggttgaccac atcgtggcca aggcttccgt cgcagccctg     180
aacaagcact ggtgctcgc caagatggcc gtcgaggaga cccaccgtgg tctggtcgaa     240
gacaaggcca ccaagaacat cttcgcctgc gagcatgtca ccaactacct ggctggtcag     300
aagaccgtcg gcatcatccg cgaggacgac gtgctgggca tcgacgaaat cgccgagccg     360
gttggcgtcg tcgctggcgt gaccccggtc accaacccga cctccaccgc catcttcaag     420
tcgctgatcg cactgaagac ccgctgcccg atcatcttcg gcttccaccc gggcgcacag     480
aactgctccg tcgcggccgc caagatcgtt cgcgatgccg ctatcgcagc aggcgctcct     540
gagaactgta ttcagtggat cgagcatccg tccatcgagg ccactggcgc cctgatgaag     600
catgatggtg tcgccaccat cctcgccacc ggtggtccgg gcatggtcaa ggccgcatac     660
tcctccggca gccggccct gggcgtcggc gcgggcaatg ctccggcata cgttgacaag     720
aacgtcgacg tcgtgcgtgc agccaacgat ctgattcttt ccaagcactt cgattacggc     780
atgatctgcg ctaccgagca ggccatcatc gccgacaagg acatctacgc tccgctcgtt     840
aaggaactca agcgtcgcaa ggcctatttc gtgaacgctg acgagaaggc caagctcgag     900
cagtacatgt tcggctgcac cgcttactcc ggacagaccc cgaagctcaa ctccgtggtg     960
ccgggcaagt ccccgcagta catcgccaag gccgccggct cgagattcc ggaagacgcc    1020
accatccttg ccgctgagtg caaggaagtc ggcgagaacg agccgctgac catggagaag    1080
cttgctccgg tccaggccgt gctgaagtcc gacaacaagg aacaggcctt cgagatgtgc    1140
gaagccatgc tgaagcatgg cgccggccac accgccgcca tccacaccaa cgaccgtgac    1200
ctggtccgcg agtacggcca gcgcatgcac gcctgccgta tcatctggaa ctccccgagc    1260
tccctcggcg gcgtgggcga catctacaac gccatcgctc cgtccctgac cctgggctgc    1320
ggctcctacg gcggcaactc cgtgtccggc aacgtccagg cagtcaacct catcaacatc    1380
aagcgcatcg ctcggaggaa caacaacatg cagtggttca agattccggc caagacctac    1440
ttcgagccga cgccatcaa gtacctgcgc gacatgtacg gcatcgaaaa ggccgtcatc    1500
gtgtgcgata aggtcatgga gcagctcggc atcgttgaca agatcatcga tcagctgcgt    1560
gcacgttcca accgcgtgac cttccgtatc atcgattatg tcgagccgga gccgagcgtg    1620
gagaccgtcg aacgtggcgc cgccatgatg gcgcgaggagt tcgagccgga taccatcatc    1680
gccgtcggcg gtggttcccc gatggatgcg tccaagatta tgtggctgct gtacgagcac    1740
ccggaaatct ccttctccga tgtgcgtgag aagttcttcg atatccgtaa gcgcgcgttc    1800
aagattccgc cgctgggcaa gaaggccaag ctggtctgca ttccgacttc ttccggcacc    1860
ggttccgaag tcacgccgtt cgctgtgatt accgaccaca agaccggcta aagtacccg    1920
atcaccgatt acgcgctgac cccgtccgtc gctatcgtcg atccggtgct ggcacgtact    1980
cagccgcgca agctggcttc cgatgctggt ttcgatgctc tgacccacgc ttttgaggct    2040
tatgtgtccg tgtatgccaa cgacttcacc gatggtatgg cattgcacgc tgccaagctg    2100
gtttgggaca acctcgctga gtccgtcaat ggcgagccgg tgaggagaa gacccgtgcc    2160
caggagaaga tgcataatgc cgccaccatg gccggcatgg cttttcggctc cgccttcctc    2220
ggcatgtgcc acggcatggc ccacaccatt ggtgcactgt gccacgttgc ccacggtcgt    2280
accaactcca tcctcctgcc gtacgtgatc cgttacaacg gttccgtccc ggaggagccg    2340
accagctggc cgaagtacaa caagtacatc gctccggaac gctaccagga gatcgccaag    2400
```

```
aaccttggcg tgaacccggg caagactccg gaagagggcg tcgagaacct ggccaaggct    2460
gttgaggatt accgtgacaa caagctcggt atgaacaaga gcttccagga gtgcggtgtg    2520
gatgaggact actattggtc catcatcgac cagatcggca tgcgcgccta cgaagaccag    2580
tgcgcaccgg cgaacccgcg tatcccgcag atcgaggata tgaaggatat cgccattgcc    2640
gcctactacg gcgtcagcca ggcggaaggc cacaagctgc gcgtccagcg tcagggcgaa    2700
gccgctacgg aggaagcttc cgagcgcgcc tga                                2733
```

<210> SEQ ID NO 56
<211> LENGTH: 885
<212> TYPE: PRT
<213> ORGANISM: Piromyces SP E2 AADH

<400> SEQUENCE: 56

```
Met Ser Gly Leu Gln Met Phe Gln Asn Leu Ser Leu Tyr Gly Ser Leu
 1               5                  10                  15

Ala Glu Ile Asp Thr Ser Glu Lys Leu Asn Glu Ala Met Asp Lys Leu
            20                  25                  30

Thr Ala Ala Gln Glu Gln Phe Arg Glu Tyr Asn Gln Glu Gln Val Asp
        35                  40                  45

Lys Ile Phe Lys Ala Val Ala Leu Ala Ala Ser Gln Asn Arg Val Ala
    50                  55                  60

Phe Ala Lys Tyr Ala His Glu Glu Thr Gln Lys Gly Val Phe Glu Asp
65                  70                  75                  80

Lys Val Ile Lys Asn Glu Phe Ala Ala Asp Tyr Ile Tyr His Lys Tyr
                85                  90                  95

Cys Asn Asp Lys Thr Ala Gly Ile Ile Glu Tyr Asp Glu Ala Asn Gly
            100                 105                 110

Leu Met Glu Ile Ala Glu Pro Val Gly Pro Val Val Gly Ile Ala Pro
        115                 120                 125

Val Thr Asn Pro Thr Ser Thr Ile Ile Tyr Lys Ser Leu Ile Ala Leu
    130                 135                 140

Lys Thr Arg Asn Cys Ile Ile Phe Ser Pro His Pro Gly Ala His Lys
145                 150                 155                 160

Ala Ser Val Phe Val Val Lys Val Leu His Gln Ala Ala Val Lys Ala
                165                 170                 175

Gly Ala Pro Glu Asn Cys Ile Gln Ile Ile Phe Pro Lys Met Asp Leu
            180                 185                 190

Thr Thr Glu Leu Leu His His Gln Lys Thr Arg Phe Ile Trp Ala Thr
        195                 200                 205

Gly Gly Pro Gly Leu Val His Ala Ser Tyr Thr Ser Gly Lys Pro Ala
    210                 215                 220

Leu Gly Gly Gly Pro Gly Asn Ala Pro Ala Leu Ile Asp Glu Thr Cys
225                 230                 235                 240

Asp Met Asn Glu Ala Val Gly Ser Ile Val Ser Lys Thr Phe Asp
                245                 250                 255

Cys Gly Met Ile Cys Ala Thr Glu Asn Ala Val Val Val Glu Ser
            260                 265                 270

Val Tyr Glu Asn Phe Val Ala Thr Met Lys Lys Arg Gly Ala Tyr Phe
        275                 280                 285

Met Thr Pro Glu Glu Thr Lys Lys Ala Ser Asn Leu Leu Phe Gly Glu
    290                 295                 300

Gly Met Arg Leu Asn Ala Lys Ala Val Gly Gln Thr Ala Lys Thr Leu
```

-continued

```
            305                 310                 315                 320
        Ala Glu Met Ala Gly Phe Glu Val Pro Glu Asn Thr Val Val Leu Cys
                        325                 330                 335

Gly Glu Ala Ser Glu Val Lys Phe Glu Glu Pro Met Ala His Glu Lys
                        340                 345                 350

Leu Thr Thr Ile Leu Gly Ile Tyr Lys Ala Lys Asp Phe Asp Asp Gly
                        355                 360                 365

Val Arg Leu Cys Lys Glu Leu Val Thr Phe Gly Gly Lys Gly His Thr
                    370                 375                 380

Ala Val Leu Tyr Thr Asn Gln Asn Lys Asp Arg Ile Glu Lys Tyr
        385                 390                 395                 400

Gln Asn Glu Val Pro Ala Phe His Ile Leu Val Asp Met Pro Ser Ser
                        405                 410                 415

Leu Gly Cys Ile Gly Asp Met Tyr Asn Phe Arg Leu Ala Pro Ala Leu
                        420                 425                 430

Thr Ile Thr Cys Gly Thr Met Gly Gly Gly Ser Ser Ser Asp Asn Ile
                        435                 440                 445

Gly Pro Lys His Leu Leu Asn Ile Lys Arg Val Gly Met Arg Arg Glu
                    450                 455                 460

Asn Met Leu Trp Phe Lys Ile Pro Lys Ser Val Tyr Phe Lys Arg Ala
        465                 470                 475                 480

Ile Leu Ser Glu Ala Leu Ser Asp Leu Arg Asp Thr His Lys Arg Ala
                        485                 490                 495

Ile Ile Ile Thr Asp Arg Thr Met Thr Met Leu Gly Gln Thr Asp Lys
                        500                 505                 510

Ile Ile Lys Ala Cys Glu Gly His Gly Met Val Cys Thr Val Tyr Asp
                        515                 520                 525

Lys Val Val Pro Asp Pro Thr Ile Lys Cys Ile Met Glu Gly Val Asn
                    530                 535                 540

Glu Met Asn Val Phe Lys Pro Asp Leu Ala Ile Ala Leu Gly Gly Gly
        545                 550                 555                 560

Ser Ala Met Asp Ala Ala Lys Met Met Arg Leu Phe Tyr Glu Tyr Pro
                        565                 570                 575

Asp Gln Asp Leu Gln Asp Ile Ala Thr Arg Phe Val Asp Ile Arg Lys
                        580                 585                 590

Arg Val Val Gly Cys Pro Lys Leu Gly Arg Leu Ile Lys Thr Leu Val
                    595                 600                 605

Cys Ile Pro Thr Thr Ser Gly Thr Gly Ala Glu Val Thr Pro Phe Ala
                    610                 615                 620

Val Val Thr Ser Glu Glu Gly Arg Lys Tyr Pro Leu Val Asp Tyr Glu
        625                 630                 635                 640

Leu Thr Pro Asp Met Ala Ile Val Asp Pro Glu Phe Ala Val Gly Met
                        645                 650                 655

Pro Lys Arg Leu Thr Ser Trp Thr Gly Ile Asp Ala Leu Thr His Ala
                        660                 665                 670

Ile Glu Ser Tyr Val Ser Ile Met Ala Thr Asp Phe Thr Arg Pro Tyr
                    675                 680                 685

Ser Leu Arg Ala Val Gly Leu Ile Phe Glu Ser Leu Ser Leu Ala Tyr
                    690                 695                 700

Asn Asn Gly Lys Asp Ile Glu Ala Arg Glu Lys Met His Asn Ala Ser
        705                 710                 715                 720

Ala Ile Ala Gly Met Ala Phe Ala Asn Ala Phe Leu Gly Cys Cys His
                        725                 730                 735
```

```
Ser Val Ala His Gln Leu Gly Ser Val Tyr His Ile Pro His Gly Leu
            740                 745                 750

Ala Asn Ala Leu Met Leu Ser His Ile Ile Lys Tyr Asn Ala Thr Asp
        755                 760                 765

Ser Pro Val Lys Met Gly Thr Phe Pro Gln Tyr Lys Tyr Pro Gln Ala
    770                 775                 780

Met Arg His Tyr Ala Glu Ile Ala Glu Leu Leu Leu Pro Pro Thr Gln
785                 790                 795                 800

Val Val Lys Met Thr Asp Val Asp Lys Val Gln Tyr Leu Ile Asp Arg
                805                 810                 815

Val Glu Gln Leu Lys Ala Asp Val Gly Ile Pro Lys Ser Ile Lys Glu
            820                 825                 830

Thr Gly Met Val Thr Glu Glu Asp Phe Phe Asn Lys Val Asp Gln Val
        835                 840                 845

Ala Ile Met Ala Phe Asp Asp Gln Cys Thr Gly Ala Asn Pro Arg Tyr
    850                 855                 860

Pro Leu Val Ser Glu Leu Lys Gln Leu Met Ile Asp Ala Trp Asn Gly
865                 870                 875                 880

Val Val Pro Lys Leu
                885

<210> SEQ ID NO 57
<211> LENGTH: 2658
<212> TYPE: DNA
<213> ORGANISM: Piromyces SP E2 AADH

<400> SEQUENCE: 57
atgtccggat tacaaatgtt ccaaaacctt tctctttacg gtagtctcgc cgaaatcgat      60
actagcgaaa agcttaacga agctatggac aaattaactg ctgcccaaga caattcaga     120 gaatacaacc aagaacaagt tgacaaaatc ttcaaggctg ttgctttagc tgcttctcaa     180
aaccgtgttg ctttcgctaa gtacgcacac gaagaaaccc aaaagggtgt tttcgaagat     240
aaggttatca gaacgaatt cgctgctgat tacatttacc acaagtactg caatgacaag     300
accgccggta tcattgaata tgatgaagcc aatggtctta tggaaattgc tgaaccagtt     360
ggtccagttg ttggtattgc tccagttact aacccaactt ctactatcat ctacaagtct     420
ttaattgcct taaagacccg taactgtatt atcttctcac acatccagg agctcacaag     480 gcctctgttt tcgttgttaa ggtcttacac caagctgctg ttaaggctgg tgccccagaa     540
aactgtattc aaatcatctt cccaaagatg gatttaacta ctgaattatt acaccaccaa     600
aagactcgtt tcatttgggc tactggtggt ccaggtttag ttcacgcctc ttacacttct     660
ggtaagccag ctcttggtgg tggtccaggt aatgctccag ctcttattga tgaaacttgt     720
gatatgaacg aagctgttgg ttctatcgtt gtttctaaga cttttcgattg tggtatgatc     780 tgtgccactg aaaacgctgt tgtcgttgtc gaatctgtct acgaaaactt cgttgctacc     840
atgaagaagc gtggtgccta cttcatgact ccagaagaaa ccaagaaggc ttctaacctt     900
cttttcggag aaggtatgag attaaatgct aaggctgttg gtcaaactgc caagacttta     960
gctgaaatgg ccggtttcga agtcccagaa acaccgttg ttctctgtgg tgaagcttct    1020
gaagttaaat tcgaagaacc aatggctcac gaaaagttaa ctactatcct cggtatctac    1080
aaggctaagg actttgacga tggtgtcaga ttatgtaagg aattagttac tttcggtggt    1140
aagggtcaca ctgctgttct ctacaccaac caaaacaaca aggaccgtat tgaaaagtac    1200
```

```
caaaacgaag ttccagcctt ccacatctta gttgacatgc catcttccct cggttgtatt    1260
ggtgatatgt acaacttccg tcttgctcca gctcttacca ttacttgtgg tactatgggt    1320
ggtggttcct cctctgataa cattggtcca aagcacttac ttaacatcaa gcgtgttggt    1380
atgagacgcg aaaacatgct ttggttcaag attccaaagt ctgtctactt caagcgtgct    1440
atcctttctg aagctttatc tgacttacgt gacacccaca agcgtgctat cattattacc    1500
gatagaacta tgactatgtt aggtcaaact gacaagatca ttaaggcttg tgaaggtcat    1560
ggtatggtct gcactgtcta cgataaggtt gtcccagatc caactatcaa gtgtattatg    1620
gaaggtgtta atgaaatgaa cgtcttcaag ccagatttag ctattgctct tggtggtggt    1680
tctgctatgg atgccgctaa gatgatgcgt ttattctacg aatacccaga ccaagactta    1740
caagatattg ctactcgttt cgtcgatatc cgtaagcgtg ttgttggttg tccaaagctt    1800
ggtagactta ttaagactct tgtctgtatc ccaactacct ctggtactgg tgccgaagtt    1860
actccattcg ctgtcgttac ctctgaagaa ggtcgtaagt acccattagt cgactacgaa    1920
cttactccag atatggctat tgttgatcca gaattcgctg ttggtatgcc aaagcgttta    1980
acttcttgga ctggtattga tgctcttacc cacgccattg aatcttacgt ttctattatg    2040
gctactgact tcactagacc atactctctc cgtgctgttg gtcttatctt cgaatccctt    2100
tcccttgctt acaacaacgg taaggatatt gaagctcgtg aaaagatgca caatgcttct    2160
gctattgctg gtatggcctt tgccaacgct ttccttggtt gttgtcactc tgttgctcac    2220
caacttggtt ccgtctacca cattccacac ggtcttgcca acgctttaat gctttctcac    2280
atcattaagt acaacgctac tgactctcca gttaagatgg gtaccttccc acaatacaag    2340
tacccacaag ctatgcgtca ctacgctgaa attgctgaac tcttattacc accaactcaa    2400
gttgttaaga tgactgatgt tgataaggtt caatacttaa ttgaccgtgt tgaacaatta    2460
aaggctgacg ttggtattcc aaagtctatt aaggaaactg gaatggttac tgaagaagac    2520
ttcttcaaca aggttgacca agttgctatc atggccttcg atgaccaatg tactggtgct    2580
aacccacgtt acccattagt ttctgaatta aaacaattaa tgattgatgc ctggaacggt    2640
gttgtcccaa agctctaa                                                 2658
```

<210> SEQ ID NO 58
<211> LENGTH: 954
<212> TYPE: PRT
<213> ORGANISM: Chlamydomonas reinhardtii AADH

<400> SEQUENCE: 58

Met Met Ser Ser Ser Leu Val Ser Gly Lys Arg Val Ala Val Pro Ser
1               5                   10                  15

Ala Ala Lys Pro Cys Ala Ala Val Pro Leu Pro Arg Val Ala Gly Arg
            20                  25                  30

Arg Thr Ala Ala Arg Val Val Cys Glu Ala Ala Pro Ser Gly Ala Ala
        35                  40                  45

Pro Ala Ser Pro Lys Ala Glu Ala Ala Pro Val Ala Ala Ala Pro
    50                  55                  60

Ala Thr Pro His Ala Glu Val Lys Lys Glu Arg Ala Pro Ala Thr Asp
65                  70                  75                  80

Glu Ala Leu Thr Glu Leu Lys Ala Leu Leu Lys Arg Ala Gln Thr Ala
                85                  90                  95

Gln Ala Gln Tyr Ser Thr Tyr Thr Gln Glu Gln Val Asp Glu Ile Phe
            100                 105                 110

```
Arg Ala Ala Ala Glu Ala Ala Asn Ala Ala Arg Ile Pro Leu Ala Lys
            115                 120                 125
Met Ala Val Glu Glu Thr Arg Met Gly Val Ala Glu Asp Lys Val Val
130                 135                 140
Lys Asn His Phe Ala Ser Glu Phe Ile Tyr Asn Lys Tyr Lys His Thr
145                 150                 155                 160
Lys Thr Cys Gly Val Ile Glu His Asp Pro Ala Gly Ile Gln Lys
            165                 170                 175
Val Ala Glu Pro Val Gly Val Ile Ala Gly Ile Val Pro Thr Thr Asn
            180                 185                 190
Pro Thr Ser Thr Ala Ile Phe Lys Ser Leu Leu Ser Leu Lys Thr Arg
            195                 200                 205
Asn Ala Leu Val Leu Cys Pro His Pro Arg Ala Ala Lys Ser Thr Ile
210                 215                 220
Ala Ala Ala Arg Ile Val Arg Asp Ala Ala Val Ala Ala Gly Ala Pro
225                 230                 235                 240
Pro Asn Ile Ile Ser Trp Val Glu Thr Pro Ser Leu Pro Val Ser Gln
            245                 250                 255
Ala Leu Met Gln Ala Thr Glu Ile Asn Leu Ile Leu Ala Thr Gly Gly
            260                 265                 270
Pro Ala Met Val Arg Ala Ala Tyr Ser Ser Gly Asn Pro Ser Leu Gly
            275                 280                 285
Val Gly Ala Gly Asn Thr Pro Ala Leu Ile Asp Glu Thr Ala Asp Val
            290                 295                 300
Ala Met Ala Val Ser Ser Ile Leu Leu Ser Lys Thr Phe Asp Asn Gly
305                 310                 315                 320
Val Ile Cys Ala Ser Glu Gln Ser Val Val Val Ala Lys Ala Tyr
            325                 330                 335
Asp Ala Val Arg Thr Glu Phe Val Arg Arg Gly Ala Tyr Phe Leu Thr
            340                 345                 350
Glu Asp Asp Lys Val Lys Val Arg Ala Gly Val Val Asp Gly Lys
            355                 360                 365
Leu Asn Pro Asn Ile Val Gly Gln Ser Ile Pro Lys Leu Ala Ala Leu
370                 375                 380
Phe Gly Ile Lys Val Pro Gln Gly Thr Lys Val Leu Ile Gly Glu Val
385                 390                 395                 400
Glu Lys Ile Gly Pro Glu Ala Leu Ser Gln Glu Lys Leu Cys Pro
            405                 410                 415
Ile Leu Ala Met Tyr Arg Ala Pro Asp Tyr Asp His Gly Val Lys Met
            420                 425                 430
Ala Cys Glu Leu Ile Met Tyr Gly Gly Ala Gly His Thr Ser Val Leu
            435                 440                 445
Tyr Thr Asn Pro Leu Asn Asn Ala His Ile Gln Gln Tyr Gln Ser Ala
            450                 455                 460
Val Lys Thr Val Arg Ile Leu Ile Asn Thr Pro Ala Ser Gln Gly Ala
465                 470                 475                 480
Ile Gly Asp Leu Tyr Asn Phe His Leu Asp Pro Ser Leu Thr Leu Gly
            485                 490                 495
Cys Gly Thr Trp Gly Ser Thr Ser Val Ser Thr Asn Val Gly Pro Gln
            500                 505                 510
His Leu Leu Asn Ile Lys Thr Val Thr Ala Arg Arg Glu Asn Met Leu
            515                 520                 525
Trp Phe Arg Val Pro Pro Lys Ile Tyr Phe Lys Gly Gly Cys Leu Glu
```

-continued

```
            530                 535                 540
Val Ala Leu Thr Asp Leu Arg Gly Lys Ser Arg Ala Phe Ile Val Thr
545                 550                 555                 560

Asp Lys Pro Leu Phe Asp Met Gly Tyr Ala Asp Lys Val Thr His Ile
                565                 570                 575

Leu Asp Ser Ile Asn Val His His Gln Val Phe Tyr His Val Thr Pro
            580                 585                 590

Asp Pro Thr Leu Ala Cys Ile Glu Ala Gly Leu Lys Glu Ile Leu Glu
        595                 600                 605

Phe Lys Pro Asp Val Ile Ile Ala Leu Gly Gly Ser Pro Met Asp
        610                 615                 620

Ala Ala Lys Ile Met Trp Leu Met Tyr Glu Cys Pro Asp Thr Arg Phe
625                 630                 635                 640

Asp Gly Leu Ala Met Arg Phe Met Asp Ile Arg Lys Arg Val Tyr Glu
                645                 650                 655

Val Pro Glu Leu Gly Lys Lys Ala Thr Met Val Cys Ile Pro Thr Thr
                660                 665                 670

Ser Gly Thr Gly Ser Glu Val Thr Pro Phe Ser Val Val Thr Asp Glu
            675                 680                 685

Arg Leu Gly Ala Lys Tyr Pro Leu Ala Asp Tyr Ala Leu Thr Pro Ser
        690                 695                 700

Met Ala Ile Val Asp Pro Gln Leu Val Leu Asn Met Pro Lys Lys Leu
705                 710                 715                 720

Thr Ala Trp Gly Gly Ile Asp Ala Leu Thr His Ala Leu Glu Ser Tyr
                725                 730                 735

Val Ser Ile Cys Ala Thr Asp Tyr Thr Lys Gly Leu Ser Arg Glu Ala
                740                 745                 750

Ile Ser Leu Leu Phe Lys Tyr Leu Pro Arg Ala Tyr Ala Asn Gly Ser
            755                 760                 765

Asn Asp Tyr Leu Ala Arg Glu Lys Val His Tyr Ala Ala Thr Ile Ala
        770                 775                 780

Gly Met Ala Phe Ala Asn Ala Phe Leu Gly Ile Cys His Ser Met Ala
785                 790                 795                 800

His Lys Leu Gly Ala Ala Tyr His Val Pro His Gly Leu Ala Asn Ala
                805                 810                 815

Ala Leu Ile Ser His Val Ile Arg Tyr Asn Ala Thr Asp Met Pro Ala
                820                 825                 830

Lys Gln Ala Ala Phe Pro Gln Tyr Glu Tyr Pro Thr Ala Lys Gln Asp
            835                 840                 845

Tyr Ala Asp Leu Ala Asn Met Leu Gly Leu Gly Gly Asn Thr Val Asp
        850                 855                 860

Glu Lys Val Ile Lys Leu Ile Glu Ala Val Glu Leu Lys Ala Lys
865                 870                 875                 880

Val Asp Ile Pro Pro Thr Ile Lys Glu Ile Phe Asn Asp Pro Lys Val
                885                 890                 895

Asp Ala Asp Phe Leu Ala Asn Val Asp Ala Leu Ala Glu Asp Ala Phe
            900                 905                 910

Asp Asp Gln Cys Thr Gly Ala Asn Pro Arg Tyr Pro Leu Met Ala Asp
        915                 920                 925

Leu Lys Gln Leu Tyr Leu Asp Ala His Ala Ala Pro Ile Leu Pro Val
    930                 935                 940

Lys Thr Leu Glu Phe Phe Ser Lys Ile Asn
945                 950
```

<210> SEQ ID NO 59
<211> LENGTH: 2865
<212> TYPE: DNA
<213> ORGANISM: Chlamydomonas reinhardtii AADH

<400> SEQUENCE: 59

```
atgatgtcct ccagcctcgt ctctggcaag agggttgccg tgccctctgc tgccaagccc      60
tgtgctgctg tgccgctgcc ccgcgtggcc ggtcgccgga ctgctgcacg cgttgtctgc     120
gaggctgctc cctctggcgc cgcccctgcc agccccaagg ctgaggctgc tgcgcccgtt     180
gccgctgccc cggccacccc ccatgctgag gtgaagaagg agcgcgcccc agccaccgat     240
gaggcgctga cggagctgaa ggcgctgctg aagcgcgccc agaccgccca ggcgcagtac     300
tccacctaca cccaggagca ggtggacgag atcttccgcg ccgccgccga ggccgccaac     360
gccgcccgta tcccctggc caagatggcc gtggaggaga cccgcatggg cgtggctgag     420
gacaaggtgg tgaagaacca cttcgcctcc gagttcatct acaacaagta caagcacact     480
aagacctgcg gcgtcatcga gcacgacccc gccggcggca tccagaaggt ggctgagccc     540
gtgggcgtca ttgccggtat cgtgcccacc accaaccca cctccaccgc catcttcaag     600
tcgctgctgt cgctcaagac ccgcaacgcg ctggtgctgt gcccgcaccc ccgcgccgcc     660
aagagcacca tcgccgccgc gcgcatcgtg cgtgacgccg ccgtggccgc cggcgcgccg     720
cccaacatca tcagctgggt ggagacgccc tcgctgccgg tgtcccaggc gctgatgcag     780
gcgactgaga tcaacctcat cctggccacc ggtggcccgg ccatggtgcg cgccgcctac     840
tcgtccggca acccgtcgct gggtgtgggc gccggcaaca cccccggccct gattgacgag     900
actgccgacg tggccatggc cgtgtcctcc atcctgctgt ccaagacctt tgacaacggc     960
gtcatctgcg cctcggagca gtcggtggtg gtggtggcca aggcctacga cgccgtgcgc    1020
accgagttcg tgcgccgcgg ggcctacttc ctgaccgagg acgacaaggt caaggtccgc    1080
gccggtgtgg ttgtggacgg caagctgaac cccaacattg gggccagtc catccccaag    1140
ctggcggccc tgttcggcat caaggtgccc cagggcacca aggtgctcat cggcgaggtg    1200
gagaagatcg ccccgagga ggcgctgtcg caggagaagc tgtgccccat cctggccatg    1260
tacccgggcg cccgactacga ccacggcgtc aagatggcct gcgagctcat catgtacggc    1320
ggcgccggcc acacctcggt gctgtacacc aacccgctca caacgcccca catccagcag    1380
taccagagcg cggtcaagac cgtgcgcatc ctcatcaaca ccccgcctc gcagggcgcc    1440
attggtgacc tgtacaactt ccacctggac ccctccctca ccctgggctg cggcacctgg    1500
ggctccacct cggtgtccac caacgtgggc ccgcagcacc tgctgaacat caagaccgtc    1560
accgcgcgcc gcgagaacat gctgtggttc cgcgtgccgc caagatcta cttcaagggc    1620
ggctgcctgg aggtggcgct gaccgatctg cgtggcaaat cgcgcgcttt cattgtcacg    1680
gacaagccgc tttttgacat gggatacgcc gacaaggtca cccacatcct ggacagcatt    1740
aacgtgcacc accaggtgtt ctaccacgtg accccgaccc gaccctggc ctgcattgag    1800
gcgggtctga aggagatcct ggagttcaag cccgatgtca tcatcgcgct gggtggtggc    1860
tcgcccatgg acgccgccaa gatcatgtgg ctgatgtacg agtgccccga cacccgcttc    1920
gacggcctgg ccatgcgctt catggacatc cgcaagcgcg tgtacgaggt gccggagctg    1980
ggcaagaagg ccaccatggt gtgcatcccc accaccagtg gcaccggctc ggaggtgacg    2040
cccttctcgg tggtcaccga cgagcgcctg ggcgccaagt accccctggc cgattacgcc    2100
```

```
ctgaccccca gcatggccat tgtggacccc cagctggtgc tcaacatgcc caagaagctg    2160
accgcctggg gcggcattga cgcgctcacg cacgcgctgg agagctacgt gtccatctgc    2220
gccaccgact acaccaaggg tctgtcgcgc gaggccatca gcctgctgtt caagtacctg    2280
ccccgcgcct acgccaacgg ctccaacgac tacctggcgc gtgagaaggt gcactacgcc    2340
gccacgattg ccggcatggc cttcgccaac gccttcctgg gcatctgcca ctccatggcg    2400
cacaagctgg gcgccgccta ccacgtgcct cacggcctgg ccaacgccgc gctgatcagc    2460
cacgtcatcc gctacaacgc caccgacatg cccgccaagc aggccgcctt ccgcagtac     2520 gagtacccca ccgccaagca ggactacgcc gacctggcca catgctgggc ctgggcggc     2580 aacacggtgg acgagaaggt gatcaagctg attgaggcgg tggaggagct caaggccaag    2640
gtggacatcc cgcccaccat caaggagatc ttcaacgacc ccaaggtgga cgccgacttc    2700
ctggcgaacg tggacgccct ggccgaggac gccttcgacg accagtgcac gggcgccaac    2760
ccgcgctacc cgctcatggc cgacctgaag cagctctacc tggacgccca cgccgcgccc    2820
atcctgcccg tcaagaccct ggagttcttc tccaagatca actaa                    2865
```

<210> SEQ ID NO 60
<211> LENGTH: 316
<212> TYPE: PRT
<213> ORGANISM: Escherichia coli mhpF

<400> SEQUENCE: 60

```
Met Ser Lys Arg Lys Val Ala Ile Ile Gly Ser Gly Asn Ile Gly Thr
1               5                   10                  15

Asp Leu Met Ile Lys Ile Leu Arg His Gly Gln His Leu Glu Met Ala
            20                  25                  30

Val Met Val Gly Ile Asp Pro Gln Ser Asp Gly Leu Ala Arg Ala Arg
        35                  40                  45

Arg Met Gly Val Ala Thr Thr His Glu Gly Val Ile Gly Leu Met Asn
    50                  55                  60

Met Pro Glu Phe Ala Asp Ile Asp Ile Val Phe Asp Ala Thr Ser Ala
65                  70                  75                  80

Gly Ala His Val Lys Asn Asp Ala Ala Leu Arg Glu Ala Lys Pro Asp
                85                  90                  95

Ile Arg Leu Ile Asp Leu Thr Pro Ala Ala Ile Gly Pro Tyr Cys Val
            100                 105                 110

Pro Val Val Asn Leu Glu Ala Asn Val Asp Gln Leu Asn Val Asn Met
        115                 120                 125

Val Thr Cys Gly Gly Gln Ala Thr Ile Pro Met Val Ala Ala Val Ser
    130                 135                 140

Arg Val Ala Arg Val His Tyr Ala Glu Ile Ile Ala Ser Ile Ala Ser
145                 150                 155                 160

Lys Ser Ala Gly Pro Gly Thr Arg Ala Asn Ile Asp Glu Phe Thr Glu
                165                 170                 175

Thr Thr Ser Arg Ala Ile Glu Val Val Gly Gly Ala Ala Lys Gly Lys
            180                 185                 190

Ala Ile Ile Val Leu Asn Pro Ala Glu Pro Pro Leu Met Met Arg Asp
        195                 200                 205

Thr Val Tyr Val Leu Ser Asp Glu Ala Ser Gln Asp Ile Glu Ala
    210                 215                 220

Ser Ile Asn Glu Met Ala Glu Ala Val Gln Ala Tyr Val Pro Gly Tyr
225                 230                 235                 240
```

```
Arg Leu Lys Gln Arg Val Gln Phe Glu Val Ile Pro Gln Asp Lys Pro
                245                 250                 255

Val Asn Leu Pro Gly Val Gly Gln Phe Ser Gly Leu Lys Thr Ala Val
            260                 265                 270

Trp Leu Glu Val Glu Gly Ala Ala His Tyr Leu Pro Ala Tyr Ala Gly
        275                 280                 285

Asn Leu Asp Ile Met Thr Ser Ser Ala Leu Ala Thr Ala Glu Lys Met
    290                 295                 300

Ala Gln Ser Leu Ala Arg Lys Ala Gly Glu Ala Ala
305                 310                 315
```

<210> SEQ ID NO 61
<211> LENGTH: 951
<212> TYPE: DNA
<213> ORGANISM: Escherichia coli mhpF

<400> SEQUENCE: 61

```
atgagtaagc gtaaagtcgc cattatcggt tctggcaaca ttggtaccga tctgatgatt      60
aaaatttgc gtcacggtca gcatctggag atggcggtga tggttggcat tgatcctcag     120
tccgacggtc tggcgcgcgc cagacgtatg ggcgtcgcca ccacccatga aggggtgatc     180
ggactgatga acatgcctga atttgctgat atcgacattg tatttgatgc gaccagcgcc     240
ggtgctcatg tgaaaaacga tgccgcttta cgcgaagcga accggatat cgcttaatt      300
gacctgacgc ctgctgccat cggcccttac tgcgtgccgg tggttaacct cgaggcgaac     360
gtcgatcaac tgaacgtcaa catggtcacc tgcggcggcc aggccaccat tccaatggtg     420
gcggcagttt cacgcgtggc gcgtgttcat tacgccgaaa ttatcgcttc tatcgccagt     480
aaatctgccg gacctggcac gcgtgccaat atcgatgaat ttacgaaaac cacttcccga     540
gccattgaag tggtgggcgg cgcggcaaaa gggaaggcga ttattgtgct aacccagca     600
gagccaccgt tgatgatgcg tgacacggtg tatgtattga gcgacgaagc ttcacaagat     660
gatatcgaag cctcaatcaa tgaaatggct gaggcggtgc aggcttacgt accgggttat     720
cgcctgaaac agcgcgtgca gtttgaagtt atcccgcagg ataaaccggt caatttaccg     780
ggcgtggggc aattctccgg actgaaaaca gcggtctggc tggaagtcga aggcgcagcg     840
cattatctgc ctgcctatgc gggcaacctc gacattatga cttccagtgc gctggcgaca     900
gcggaaaaaa tggcccagtc actggcgcgc aaggcaggag aagcggcatg a             951
```

<210> SEQ ID NO 62
<211> LENGTH: 515
<212> TYPE: PRT
<213> ORGANISM: Clostridium phytofermentans ADH 1428

<400> SEQUENCE: 62

```
Met Glu Asn Phe Asp Phe Asp Leu Arg Ser Ile Gln Glu Ala Arg Asp
1               5                   10                  15

Leu Ala Arg Ser Gly Glu Ala Ala Lys Lys Ile Ala Gln Phe Ser
            20                  25                  30

Glu Glu Gln Ile Asp Arg Ile Leu Lys Ser Met Ala Lys Ala Gly Glu
        35                  40                  45

Glu His Ala Leu Cys Leu Gly Glu Met Ala Ser Glu Thr Gly Phe
    50                  55                  60

Gly Lys Ala Met Asp Lys Ala Tyr Lys Asn His Ala Ala Ser Thr Leu
65                  70                  75                  80

Leu Tyr Glu Glu Ile Lys Asp Met Lys Thr Arg Gly Ile Leu Ala Glu
```

```
                85                  90                  95
Asp Thr Val Asn Lys Thr Ile Asp Val Ala Glu Pro Val Gly Leu Val
                100                 105                 110
Met Gly Ile Val Pro Ser Thr Asn Pro Thr Ser Thr Val Phe Phe Lys
                115                 120                 125
Ser Met Val Ala Val Lys Ser Gly Asn Ala Ile Val Phe Ser Pro His
            130                 135                 140
Pro Ser Ala Ala Lys Cys Thr Leu Lys Ala Ala Glu Ile Met Arg Asp
145                 150                 155                 160
Ala Ala Ile Ala Ala Gly Ala Pro Glu Gly Ile Ile Gly Cys Val Thr
                165                 170                 175
Met Pro Ser Met Gly Ser Thr Asn Glu Leu Met Lys Cys Lys Glu Val
            180                 185                 190
Ser Val Ile Ile Ala Thr Gly Gly Pro Ala Met Val Lys Ala Ala Tyr
            195                 200                 205
Ser Ala Gly Lys Pro Ala Ile Gly Val Gly Ala Gly Asn Ser Pro Ala
        210                 215                 220
Tyr Ile Glu Lys Thr Ala Asp Val Lys Gln Ala Val Lys Thr Ile Ile
225                 230                 235                 240
Ala Ser Lys Thr Phe Asp Tyr Gly Thr Ile Cys Ala Ser Glu Gln Ser
                245                 250                 255
Ile Ile Cys Glu Glu Ser Asn Glu Ala Glu Val Leu Ala Glu Leu Lys
            260                 265                 270
Ser Gln Gly Gly Tyr Phe Met Thr Lys Glu Glu Thr Asp Lys Val Cys
        275                 280                 285
Gly Leu Leu Phe Lys Asn Gly Tyr Thr Met Asn Ala Lys Phe Val Gly
        290                 295                 300
Arg Ser Pro Gln Val Ile Ala Gln Ala Ala Gly Ile Glu Ile Pro Met
305                 310                 315                 320
Asp Thr Lys Val Leu Ile Gly Arg Gln Glu Gly Val Gly Gln Gly Tyr
                325                 330                 335
Pro Leu Ser Phe Glu Lys Leu Thr Thr Val Leu Gly Phe Tyr Thr Val
            340                 345                 350
Lys Asp Cys His Glu Ala Cys Asp Leu Ser Ile Arg Leu Leu Gln Asn
            355                 360                 365
Gly Ile Gly His Thr Met Ser Ile His Thr Gln Asp Arg Asp Met Val
        370                 375                 380
Leu Lys Phe Ala Ala Lys Pro Ala Ser Arg Ile Leu Val Asn Thr Gly
385                 390                 395                 400
Gly Ser Gln Gly Gly Thr Gly Ile Ser Thr Gly Leu Pro Ile Ser Phe
                405                 410                 415
Thr Leu Gly Cys Gly Thr Cys Gly Gly Ser Ser Val Ser Glu Asn Val
            420                 425                 430
Ser Pro Lys His Leu Leu Asn Val Lys Val Ala Phe Gly Leu Lys
            435                 440                 445
Asp Cys Ser Thr Ile Ala Ala Asp Asp Glu Thr Phe Thr Trp Lys Glu
        450                 455                 460
Lys Ala Gly Thr Asn Ser Cys Ser Pro Ala Asp Phe Val Ala Ser Phe
465                 470                 475                 480
Val Lys Lys Glu Gly Thr Thr Ala Asn Ser Cys Gln Gly Ser Cys Asp
                485                 490                 495
Asp Asn Glu Lys Leu Ala Ala Leu Val Lys Glu Ile Val Leu Ala Met
            500                 505                 510
```

<210> SEQ ID NO 63
<211> LENGTH: 1548
<212> TYPE: DNA
<213> ORGANISM: Clostridium phytofermentans ADH 1428

<400> SEQUENCE: 63

```
atggaaaact ttgattttga tttacgttcc atccaagaag caagggattt agcaagaagc      60
ggtgaagctg ctgctaagaa gattgctcag tttagtgaag aacagataga tcgtattctt     120
aagagtatgg ctaaggcagg agaggaacat gccctatgct taggagaaat ggcttctgag     180
gaaactggat tggaaaggc tatggataag gcatataaga accacgctgc ttctacccct     240
ttatatgaag agataaagga tatgaagact agaggaatcc tagctgagga taccgtaaat     300
aagactattg atgtagctga gccggttggt ttggtaatgg aatcgttcc ttctacaaac     360
cctacctcaa ccgtattctt aaatccatg gttgcagtaa atcaggaaa tgctattgta     420
ttttctcctc acccttccgc agcaaaatgt acattaaagg cagctgaaat tatgcgcgac     480
gctgcaatcg ctgcaggcgc accagaagga atcatcggtt gtgtgaccat gccttccatg     540
ggatctacca atgaacttat gaagtgtaag gaagtttccg ttattatcgc aactggaggt     600
ccagctatgg taaggctgc ttatagtgca ggaaagccag ctatcggtgt aggtgcaggt     660
aactctcctg cttacattga aagacagca gatgtaaaac aagcagttaa acaatcatt     720
gccagcaaga catttgacta tggtactatc tgtgcatccg agcagtccat catctgcgag     780
gaaagcaatg aagcagaagt attagctgaa ttaaagagtc agggcggata cttcatgaca     840
aaagaagaaa ccgataaggt ttgtggcttg ttattcaaga acggatacac tatgaacgct     900
aaatttgtag gtcgttcccc tcaggtgatt gctcaggcag ctggaattga aattccgatg     960
gataccaagg ttcttatcgg aagacaggaa ggcgtaggtc aaggctatcc attatccttt    1020
gaaaagctta acacagttct tggcttctat accgtaaagg actgccatga ggcttgcgat    1080
ttaagcattc gtcttttaca gaacggaatc ggacatacca tgagtattca cactcaggat    1140
agagatatgg ttcttaagtt tgctgcaaag ccagcttcca gaattcttgt taacacaggc    1200
ggtagccagg gcggaactgg aatcagcaca ggtcttccaa tttcctttac attaggatgc    1260
ggtacttgcg gcggaagttc tgtttctgaa acgtgagtc caaaacatct ccttaatgtt    1320
aagaaggtag cctttggctt aaaggattgt tctactatcg cagcagatga tgaaactttc    1380
acatggaagg aaaaagcagg aactaattcc tgtagtccag cagattttgt tgcttccttt    1440
gtaaagaaag aaggtactac agctaattcc tgtcagggaa gctgtgatga taacgagaag    1500
ctagcagcac ttgttaagga aattgtgttg gccatgaaag gtcagtag                 1548
```

<210> SEQ ID NO 64
<211> LENGTH: 495
<212> TYPE: PRT
<213> ORGANISM: Clostridium phytofermentans ADH 2642

<400> SEQUENCE: 64

```
Met Glu Leu Gln Glu Lys Asp Leu Met Ser Ile Gln Glu Val Arg Leu
1               5                   10                  15

Leu Leu Lys Thr Ala Lys Glu Ala His Lys Ile Leu Ser Thr Phe Asn
            20                  25                  30

Gln Glu Gln Ile Asp Arg Ile Val Lys Ala Ile Thr Glu Ala Cys Leu
```

```
            35                  40                  45
Lys Asn Ala Glu Arg Leu Ala Lys Met Ala Asn Glu Glu Thr Gly Phe
 50                  55                  60

Gly Ile Trp Gln Asp Lys Val Ile Lys Asn Val Phe Gly Ser Met Gly
 65                  70                  75                  80

Ile Tyr Glu Ala Ile Lys Asp Met Lys Thr Ile Gly Ile Leu Arg Glu
                 85                  90                  95

Asp Lys Lys Asn Gln Thr Met Glu Ile Gly Pro Val Gly Ile Val
                100                 105                 110

Ala Gly Val Ile Pro Ser Thr Asn Pro Thr Ser Thr Val Met Tyr Lys
            115                 120                 125

Thr Leu Ile Ser Ile Lys Ala Gly Asn Cys Ile Val Phe Ser Pro His
        130                 135                 140

Pro Gly Ala Lys Lys Cys Ile Leu Glu Thr Val Lys Val Ile Cys Glu
145                 150                 155                 160

Ala Ala Glu Ala Ala Gly Cys Pro Lys Gly Ala Ile Ser Cys Ile Ser
                165                 170                 175

Ile Pro Thr Leu Glu Ala Thr Asn Glu Leu Met Lys His Pro Asn Thr
            180                 185                 190

Asn Leu Ile Leu Ala Thr Gly Gly Tyr Ala Met Val Lys Ser Ala Tyr
        195                 200                 205

Ser Ser Gly Thr Pro Ala Ile Gly Val Gly Ala Gly Asn Gly Pro Ala
210                 215                 220

Phe Ile Asp Lys Thr Ala Asn Val Lys Leu Ala Val Lys Arg Ile Met
225                 230                 235                 240

Asp Ser Lys Thr Phe Asp Asn Gly Thr Ile Cys Ala Ser Glu Gln Ser
                245                 250                 255

Val Ile Val Glu Arg Cys Met Glu Gln Ala Val Lys Glu Glu Leu Thr
            260                 265                 270

Ala Gln Gly Gly Phe Phe Leu Asn Glu Ala Glu Ser Glu Lys Leu Ala
        275                 280                 285

Arg Phe Ile Leu Arg Ala Asn Gly Thr Met Asn Pro Gln Ile Val Gly
290                 295                 300

Arg Ser Val Ala His Ile Ser Lys Leu Ala Gly Leu Thr Thr Val Pro
305                 310                 315                 320

Ala Asn Ala Arg Val Leu Ile Ala Lys Glu Thr Arg Val Gly Asp Glu
                325                 330                 335

Ala Pro Tyr Ser Arg Glu Lys Leu Ala Pro Ile Leu Ala Phe Phe Val
            340                 345                 350

Glu Glu Thr Val Asp Asp Val Ile Asn Lys Val Val Glu Ile Leu Ser
        355                 360                 365

Phe Glu Gly Met Gly His Thr Phe Thr Met His Ser Thr Asn Glu Glu
370                 375                 380

Leu Ile Lys Arg Phe Ala Leu Arg Val Pro Ala Ser Arg Ile Leu Val
385                 390                 395                 400

Asn Ser Met Gly Ser Leu Gly Gly Val Gly Ala Ser Thr Asn Leu Phe
                405                 410                 415

Pro Ala Leu Thr Leu Gly Cys Gly Ala Val Gly Gly Ser Ser Ser Ser
            420                 425                 430

Asn Asn Ile Gly Pro Met Asp Leu Ile Asn Ile Lys Arg Val Ala Phe
        435                 440                 445

Gly Val Lys Glu Leu Glu Glu Ile Lys Arg Asp Ala Thr Asn Ser Leu
450                 455                 460
```

```
Gly Glu Thr Lys Ser Ser Cys Cys Gly Ala Tyr Gly Asn Val Asn Thr
465                 470                 475                 480

Glu Leu Val Glu Glu Ile Val Lys Arg Ile Met Lys Gln Leu Ile
                485                 490                 495

<210> SEQ ID NO 65
<211> LENGTH: 1488
<212> TYPE: DNA
<213> ORGANISM: Clostridium phytofermentans ADH 2642

<400> SEQUENCE: 65
atggagttac aagagaaaga tttaatgtca atacaagaag tccgtttgct tttaaaaaca      60
gcaaaggaag cccataagat attatcaacc ttcaatcaag aacaaatcga tcgtattgta     120
aaggcaatta cagaagcatg tttaaagaat gcagagcggc ttgctaagat ggcaaatgaa     180
gaaacaggat ttggtatctg caagataaaa gtaataaaaa atgtgtttgg ttctatggga     240
atctacgaag caataaagga tatgaaaaca atcggtattc ttcgcgagga taagaaaaat     300
caaacgatgg agattggtat accggtaggt attgtagcag gtgttatacc ttccactaat     360
ccaacttcta ctgttatgta taaaacttta atttcaatta aagcaggtaa ctgtatcgta     420
ttctcgccac atcctggtgc aaaaaaatgt atcttggaaa cagttaaggt tatttgtgag     480
gctgcagaag cagcaggatg tccaaaagga gccatatcct gtatttccat tccaacccct     540
gaggcaacga atgagttgat gaaacatcca atacaaatc ttatcttagc gaccggtggc     600
tatgcaatgt gaaatctgc atactcatcc ggtacacctg caataggtgt tggtgctggt     660
aatggaccag cattcatcga caaacagca atgtgaaat tagcagtaaa gcgtattatg     720
gattccaaaa catttgacaa tggaaccatt tgtgcatcgg agcaatctgt aattgtggaa     780
cgatgtatgg aacaggcggt aaaagaagaa ctaactgctc aaggcggatt tttcttaaat     840
gaggcagagt cagaaaaatt agcacgtttt atcttacgtg ccaatggaac aatgaatcca     900
caaatcgttg aagatcggt agctcatatt agtaagcttg ccggtttaac aacagtacca     960
gcaaatgcaa gagttttaat tgcaaaggaa acaagagtcg gcgatgaagc tccatattcc    1020
agagagaaat tagctccaat cttagcattc tttgtagaag aaacggttga tgatgtcatt    1080
aataaagtgg tagagatact aagttttgaa ggaatgggac ataccttta catgcactct    1140 accaatgaag aattgatcaa acgattgcc ttacgtgtac cagcttccag aatcttagtt    1200
aattcaatgg ttcactagg tggcgttgga cctctacaa atctattccc tgcattaact    1260
cttggctgtg gagccgtagg aggaagttct tcatctaata atattggtcc tatggactta    1320
attaatataa aacgagtagc atttggagta aaagaattag aagaaattaa aagggatgct    1380
acgaatagcc taggtgaaac caaatcctct tgttgtggtg catacggtaa tgtgaataca    1440
gaattggtag aggaaattgt aaaaagaatt atgaaacaac taatataa                1488

<210> SEQ ID NO 66
<211> LENGTH: 862
<212> TYPE: PRT
<213> ORGANISM: Thermoanaerobacterium saccharolyticum AADH

<400> SEQUENCE: 66

Met Phe Ile Met Ala Thr Thr Lys Thr Glu Leu Asp Val Gln Lys Gln
1               5                   10                  15

Ile Asp Leu Leu Val Ser Arg Ala Gln Glu Ala Gln Lys Lys Phe Met
            20                  25                  30
```

```
Ser Tyr Thr Gln Glu Gln Ile Asp Ala Ile Val Lys Ala Met Ala Leu
         35                  40                  45
Ala Gly Val Asp Lys His Val Glu Leu Ala Lys Met Ala Tyr Glu Glu
 50                  55                  60
Thr Lys Met Gly Val Tyr Glu Asp Lys Ile Thr Lys Asn Leu Phe Ala
 65                  70                  75                  80
Thr Glu Tyr Val Tyr His Asp Ile Lys Asn Glu Lys Thr Val Gly Ile
                 85                  90                  95
Ile Asn Glu Asn Ile Glu Glu Asn Tyr Met Glu Val Ala Glu Pro Ile
            100                 105                 110
Gly Val Ile Ala Gly Val Thr Pro Val Thr Asn Pro Thr Ser Thr Thr
            115                 120                 125
Met Phe Lys Cys Leu Ile Ser Ile Lys Thr Arg Asn Pro Ile Ile Phe
            130                 135                 140
Ser Phe His Pro Lys Ala Ile Lys Cys Ser Ile Ala Ala Ala Lys Val
145                 150                 155                 160
Met Tyr Glu Ala Ala Leu Lys Ala Gly Ala Pro Glu Gly Cys Ile Gly
            165                 170                 175
Trp Ile Glu Thr Pro Ser Ile Glu Ala Thr Gln Leu Leu Met Thr His
            180                 185                 190
Pro Gly Val Ser Leu Ile Leu Ala Thr Gly Gly Ala Gly Met Val Lys
            195                 200                 205
Ala Ala Tyr Ser Ser Gly Lys Pro Ala Leu Gly Val Gly Pro Gly Asn
            210                 215                 220
Val Pro Cys Tyr Ile Glu Lys Ser Ala Asn Ile Lys Arg Ala Val Ser
225                 230                 235                 240
Asp Leu Ile Leu Ser Lys Thr Phe Asp Asn Gly Val Ile Cys Ala Ser
            245                 250                 255
Glu Gln Ala Val Ile Ile Asp Glu Glu Ile Ala Asp Glu Val Lys Lys
            260                 265                 270
Leu Met Lys Glu Tyr Gly Cys Tyr Phe Leu Asn Lys Asp Glu Ile Lys
            275                 280                 285
Lys Leu Glu Lys Phe Ala Ile Asp Glu Gln Ser Cys Ala Met Ser Pro
            290                 295                 300
Ala Val Val Gly Gln Pro Ala Ala Lys Ile Ala Glu Met Ala Gly Phe
305                 310                 315                 320
Lys Val Pro Glu Gly Thr Lys Ile Leu Val Ala Glu Tyr Glu Gly Val
            325                 330                 335
Gly Pro Lys Tyr Pro Leu Ser Arg Glu Lys Leu Ser Pro Ile Leu Ala
            340                 345                 350
Cys Tyr Thr Val Lys Asp Tyr Asn Glu Gly Ile Lys Lys Cys Glu Glu
            355                 360                 365
Met Thr Glu Phe Gly Gly Leu Gly His Ser Ala Val Ile His Ser Glu
            370                 375                 380
Asn Gln Asn Val Ile Asn Glu Phe Ala Arg Arg Val Arg Thr Gly Arg
385                 390                 395                 400
Leu Ile Val Asn Ser Pro Ser Ser Gln Gly Ala Ile Gly Asp Ile Tyr
            405                 410                 415
Asn Thr Asn Thr Pro Ser Leu Thr Leu Gly Cys Gly Ser Met Gly Arg
            420                 425                 430
Asn Ser Thr Thr Asp Asn Val Ser Val Lys Asn Leu Leu Asn Ile Lys
            435                 440                 445
Arg Val Val Ile Arg Asn Asp Arg Met Lys Trp Phe Lys Ile Pro Pro
```

```
                450             455             460
Lys Ile Tyr Phe Glu Ser Gly Ser Leu Gln Tyr Leu Cys Lys Val Lys
465                 470                 475                 480

Arg Lys Lys Ala Phe Ile Val Thr Asp Pro Phe Met Val Lys Leu Gly
                485                 490                 495

Phe Val Asp Lys Val Thr Tyr Gln Leu Asp Lys Ala Asn Ile Glu Tyr
            500                 505                 510

Glu Ile Phe Ser Glu Val Glu Pro Asp Pro Ser Val Asp Thr Val Met
        515                 520                 525

Asn Gly Val Lys Ile Met Asn Ser Tyr Asn Pro Asp Leu Ile Ile Ala
    530                 535                 540

Val Gly Gly Ser Ala Ile Asp Ala Ala Lys Gly Met Trp Leu Phe
545                 550                 555                 560

Tyr Glu Tyr Pro Asp Thr Glu Phe Glu Thr Leu Arg Leu Lys Phe Ala
                565                 570                 575

Asp Ile Arg Lys Arg Ala Phe Lys Phe Pro Glu Leu Gly Lys Lys Ala
            580                 585                 590

Leu Phe Ile Ala Ile Pro Thr Thr Ser Gly Thr Gly Ser Glu Val Thr
        595                 600                 605

Ala Phe Ala Val Ile Thr Asp Lys Lys Arg Asn Ile Lys Tyr Pro Leu
    610                 615                 620

Ala Asp Tyr Glu Leu Thr Pro Asp Ile Ala Ile Asp Pro Asp Leu
625                 630                 635                 640

Thr Lys Thr Val Pro Pro Ser Val Thr Ala Asp Thr Gly Met Asp Val
                645                 650                 655

Leu Thr His Ala Ile Glu Ala Tyr Val Ser Val Met Ala Ser Asp Tyr
            660                 665                 670

Thr Asp Ala Leu Ala Glu Lys Ala Ile Lys Ile Val Phe Glu Tyr Leu
        675                 680                 685

Pro Arg Ala Tyr Lys Asn Gly Asn Asp Glu Glu Ala Arg Glu Lys Met
    690                 695                 700

His Asn Ala Ser Cys Met Ala Gly Met Ala Phe Thr Asn Ala Phe Leu
705                 710                 715                 720

Gly Ile Asn His Ser Met Ala His Ile Leu Gly Gly Lys Phe His Ile
                725                 730                 735

Pro His Gly Arg Ala Asn Ala Ile Leu Leu Pro Tyr Val Ile Arg Tyr
            740                 745                 750

Asn Ala Glu Lys Pro Thr Lys Phe Val Ala Phe Pro Gln Tyr Glu Tyr
        755                 760                 765

Pro Lys Ala Ala Glu Arg Tyr Ala Glu Ile Ala Lys Phe Leu Gly Leu
    770                 775                 780

Pro Ala Ser Thr Val Glu Gly Val Glu Ser Leu Ile Glu Ala Ile
785                 790                 795                 800

Lys Asn Leu Met Lys Glu Leu Asn Ile Pro Leu Thr Leu Lys Asp Ala
                805                 810                 815

Gly Ile Asn Lys Glu Gln Phe Glu Lys Glu Ile Glu Glu Met Ser Asp
            820                 825                 830

Ile Ala Phe Asn Asp Gln Cys Thr Gly Thr Asn Pro Arg Met Pro Leu
        835                 840                 845

Thr Lys Glu Ile Ala Glu Ile Tyr Arg Lys Ala Tyr Gly Ala
    850                 855                 860

<210> SEQ ID NO 67
```

<211> LENGTH: 2586
<212> TYPE: DNA
<213> ORGANISM: Thermoanaerobacterium saccharolyticum AADH

<400> SEQUENCE: 67

| | | | | | |
|---|---|---|---|---|---|
| atgtttatta | tggcaacgac | aaaaacggaa | ttagacgttc | agaagcagat | agatctactt | 60 |
| gtgtcaagag | cacaagaggc | tcagaaaaaa | ttcatgtctt | acacgcaaga | gcaaatcgac | 120 |
| gcaatagtta | aggcaatggc | tttagcaggc | gttgacaaac | acgtagagct | ggcaaagatg | 180 |
| gcgtacgaag | agacaaaaat | gggtgtatac | gaagataaga | taacaaaaaa | tctcttcgca | 240 |
| acagagtacg | tgtaccacga | cataaaaaat | gaaaagactg | taggaatcat | aaacgagaac | 300 |
| atagaagaaa | actacatgga | agtggcagaa | ccgataggcg | taattgccgg | tgtcacacct | 360 |
| gtcacaaacc | caacatctac | cacgatgttt | aaatgcttaa | tatccataaa | gacgcgaaat | 420 |
| cctataatat | tcagcttcca | tccaaaggca | ataaagtgca | gcatcgcagc | agccaaagtg | 480 |
| atgtatgaag | ctgcactaaa | ggcaggcgca | cctgaaggat | gcataggatg | gatagaaacg | 540 |
| ccatcaattg | aggccacaca | gcttctcatg | acacatccag | gcgtatcgct | gatccttgca | 600 |
| acgggcggtg | caggaatggt | aaaagcggca | tacagctcag | gaaaaccggc | attaggcgta | 660 |
| ggtcctggca | atgtgccatg | ctacatcgaa | aaatcagcaa | acataaagag | ggctgtatcg | 720 |
| gatctcatac | taagcaagac | atttgacaat | ggagtaatat | gcgcatcaga | gcaggccgta | 780 |
| ataatagacg | aggaaatagc | agatgaagtc | aaaaagctta | tgaaagaata | cggctgctac | 840 |
| ttcttaaaca | agatgaaat | aaagaagctt | gagaaatttg | caattgatga | gcaaagctgc | 900 |
| gccatgagcc | ctgcagtggt | aggtcagcca | gcggcgaaga | ttgctgaaat | ggcaggcttc | 960 |
| aaagtccccg | aaggcacaaa | gatattagtg | gcagagtacg | aaggagtagg | tccaaaatat | 1020 |
| cctctatcaa | gggagaaact | aagcccgatt | cttgcttgct | acaccgtcaa | agactacaat | 1080 |
| gaaggaatca | aaaagtgcga | ggaaatgact | gaattcggag | gtttaggcca | ctctgctgta | 1140 |
| atacactctg | aaaatcaaaa | cgtcataaat | gaatttgcaa | ggcgagtccg | cacaggaaga | 1200 |
| cttatcgtaa | attcaccatc | atcacaggga | gcaataggag | atatatacaa | tacaaacacg | 1260 |
| ccatcactta | cattaggctg | tggttctatg | ggaagaaact | caacgacaga | caatgtaagc | 1320 |
| gtcaagaacc | ttttgaatat | taagcgtgtc | gtgataagga | atgatagaat | gaaatggttc | 1380 |
| aagattccac | cgaagattta | ctttgaaagc | gggtcactcc | agtacctgtg | caaagtcaaa | 1440 |
| agaaaaaaag | cgtttatcgt | cacagatcca | ttcatggtta | agcttggctt | cgtagacaaa | 1500 |
| gtgacatatc | aattagacaa | agcaaacatc | gaatacgaaa | tattctcaga | agtagagcca | 1560 |
| gatccatctg | ttgacacagt | catgaacggc | gtaaaaataa | tgaattcgta | caatcctgac | 1620 |
| ttaataatcg | ctgtaggcgg | tggctctgca | atagacgcag | caaagggaat | gtggcttttc | 1680 |
| tacgaatatc | ctgatacaga | gtttgaaaca | ttgaggctta | aatttgcaga | catcagaaaa | 1740 |
| agggcattta | agttcccaga | acttggcaaa | aaagcgctat | tcatcgcaat | accgacaaca | 1800 |
| agcggcacag | gctcagaagt | gacagcattt | gccgtaataa | ccgacaaaaa | gagaaacatc | 1860 |
| aagtatccac | tggcagacta | cgaacttaca | cctgacatag | ccataataga | tcctgacctt | 1920 |
| acaaagactg | taccgccatc | tgtaacagca | gacacaggca | tggatgtgct | gacacacgcc | 1980 |
| atagaagcat | acgtatcagt | aatggcatca | gactacacag | atgcactggc | ggaaaaggct | 2040 |
| ataaagatcg | tatttgaata | cctgccaagg | gcttataaaa | acggcaatga | tgaagaagcc | 2100 |
| cgcgaaaaga | tgcacaatgc | ttcctgcatg | gctggtatgg | cattcacaaa | tgcattctta | 2160 |
| ggaataaaacc | acagcatggc | acacatactg | ggcggaaagt | tccacatacc | acacggaaga | 2220 |

| | |
|---|---|
| gcaaatgcaa tacttctgcc gtatgtaata aggtacaatg cagaaaaacc tacaaagttt | 2280 |
| gtggcattcc cacaatacga atatccaaaa gcagcagaaa gatatgcgga aatcgccaaa | 2340 |
| ttcttaggac tgcctgcttc aactgttgaa gaaggcgtag aaagcttaat agaagctata | 2400 |
| aagaacctca tgaaagagct taacattccg cttacactta aagacgccgg catcaacaaa | 2460 |
| gaacagtttg aaaagaaat agaggaaatg tcagacatcg ccttcaacga tcagtgcaca | 2520 |
| gggacaaacc cgagaatgcc tctcacaaaa gaaattgcag agatctacag aaaagcatac | 2580 |
| ggtgca | 2586 |

<210> SEQ ID NO 68
<211> LENGTH: 10605
<212> TYPE: DNA
<213> ORGANISM: Artificial sequence
<220> FEATURE:
<223> OTHER INFORMATION: Plasmid pMU2484

<400> SEQUENCE: 68

| | |
|---|---|
| gagattatac ttaaactagc actgattttt ttaaggctaa tggctactaa tactttaata | 60 |
| gatgatcttc atactttttt atttaacgat ttttaatgat gttttattt gtaccactca | 120 |
| tttatctaga ttttttaat actgatcaaa tcttacggac tcgacgttaa aaagttccta | 180 |
| catacgtctg gtacttgaaa cgctgcttcg aggtattgac actataagaa tacgatccaa | 240 |
| atacttacac cgcatgtaaa aatatgccga caatatgaat acttgttgat gaatgatatt | 300 |
| tgattttaat ccggcaattt acctccttta tataatccaa taattgttga taattagtgg | 360 |
| ttaggttgca gtactaataa gaattaagac aaatattctt ctactatata aaggtgcaa | 420 |
| acaaaacaca cgccgatcgg ccatactaaa caagaccaac ataataatgg tggaaccatt | 480 |
| tactgtattt tcaatgtaac atttaaatcc gcggtaaacc tctttgcggg caagcttggc | 540 |
| actggccgtc gttttacaac gtcgtgactg ggaaacccct ggcgttaccc aacttaatcg | 600 |
| ccttgcagca catcccccctt tcgccagctg gcgtaatagc gaagaggccc gcaccgatcg | 660 |
| cccttcccaa cagttgcgca gcctgaatgg cgaatggcgc ctgatgcggt attttctcct | 720 |
| tacgcatctg tgcggtattt cacaccgcat aggagatcta agctctggcg taatagcgaa | 780 |
| gaggcccgca ccgatcgccc ttcccaacag ttgcgcagcc tgaatggcga atggcgcctg | 840 |
| atgcggtatt ttctccttac gcatctgtgc ggtatttcac accgcatagg gtaataactg | 900 |
| atataattaa attgaagctc taatttgtga gtttagtata catgcattta cttataatac | 960 |
| agttttttag ttttgctggc cgcatcttct caaatatgct tcccagcctg cttttctgta | 1020 |
| acgttcaccc tctaccttag catcccttcc ctttgcaaat agtcctcttc aacaataat | 1080 |
| aatgtcagat cctgtagaga ccacatcatc cacggttcta tactgttgac ccaatgcgtc | 1140 |
| tcccttgtca tctaaaccca caccgggtgt cataatcaac caatcgtaac cttcatctct | 1200 |
| tccacccatg tctctttgag caataaagcc gataacaaaa tctttgtcgc tcttcgcaat | 1260 |
| gtcaacagta cccttagtat attctccagt agatagggag cccttgcatg acaattctgc | 1320 |
| taacatcaaa aggcctctag gttcctttgt tacttcttct gccgcctgct tcaaaccgct | 1380 |
| aacaatacct gggcccacca caccgtgtgc attcgtaatg tctgcccatt ctgctattct | 1440 |
| gtatacaccc gcagagtact gcaatttgac tgtattacca atgtcagcaa attttctgtc | 1500 |
| ttcgaagagt aaaaaattgt acttggcgga taatgccttt agcggcttaa ctgtgccctc | 1560 |
| catggaaaaa tcagtcaaga tatccacatg tgtttttagt aaacaaattt tgggacctaa | 1620 |

| | |
|---|---|
| tgcttcaact aactccagta attccttggt ggtacgaaca tccaatgaag cacacaagtt | 1680 |
| tgtttgcttt tcgtgcatga tattaaatag cttggcagca acaggactag gatgagtagc | 1740 |
| agcacgttcc ttatatgtag ctttcgacat gatttatctt cgtttcggtt tttgttctgt | 1800 |
| gcagttgggt taagaatact gggcaatttc atgtttcttc aacactacat atgcgtatat | 1860 |
| ataccaatct aagtctgtgc tccttccttc gttcttcctt ctgttcggag attaccgaat | 1920 |
| caaaaaaatt tcaaagaaac cgaaatcaaa aaaagaata aaaaaaaat gatgaattga | 1980 |
| aaagctcttg ttacccatca ttgaattttg aacatccgaa cctgggagtt ttccctgaaa | 2040 |
| cagatagtat atttgaacct gtataataat atatagtcta gcgctttacg aagacaatg | 2100 |
| tatgtatttc ggttcctgga gaaactattg catctattgc ataggtaatc ttgcacgtcg | 2160 |
| catccccggt tcattttctg cgtttccatc ttgcacttca atagcatatc tttgttaacg | 2220 |
| aagcatctgt gcttcatttt gtagaacaaa aatgcaacgc gagagcgcta attttttcaaa | 2280 |
| caaagaatct gagctgcatt tttacagaac agaaatgcaa cgcgaaagcg ctattttacc | 2340 |
| aacgaagaat ctgtgcttca ttttgtaaa acaaaaatgc aacgcgagag cgctaatttt | 2400 |
| tcaaacaaag aatctgagct gcattttac agaacagaaa tgcaacgcga gagcgctatt | 2460 |
| ttaccaacaa agaatctata cttctttttt gttctacaaa aatgcatccc gagagcgcta | 2520 |
| tttttctaac aaagcatctt agattacttt ttttctcctt tgtgcgctct ataatgcagt | 2580 |
| ctcttgataa cttttttgcac tgtaggtccg ttaaggttag aagaaggcta ctttggtgtc | 2640 |
| tattttctct tccataaaaa aagcctgact ccacttcccg cgtttactga ttactagcga | 2700 |
| agctgcgggt gcattttttc aagataaagg catccccgat tatattctat accgatgtgg | 2760 |
| attgcgcata ctttgtgaac agaaagtgat agcgttgatg attcttcatt ggtcagaaaa | 2820 |
| ttatgaacgg tttcttctat tttgtctcta tatactacgt ataggaaatg tttacatttt | 2880 |
| cgtattgttt tcgattcact ctatgaatag ttcttactac aatttttttg tctaaagagt | 2940 |
| aatactagag ataaacataa aaaatgtaga ggtcgagttt agatgcaagt tcaaggagcg | 3000 |
| aaaggtggat gggtaggtta tatagggata tagcacagag atatatagca aagagatact | 3060 |
| tttgagcaat gtttgtggaa gcggtattcg caatatttta gtagctcgtt acagtccggt | 3120 |
| gcgtttttgg ttttttgaaa gtgcgtcttc agagcgcttt tggttttcaa aagcgctctg | 3180 |
| aagttcctat actttctagc tagagaatag gaacttcgga ataggaactt caaagcgttt | 3240 |
| ccgaaaacga gcgcttccga aaatgcaacg cgagctgcgc acatacagct cactgttcac | 3300 |
| gtcgcaccta tatctgcgtg ttgcctgtat atatatatac atgagaagaa cggcatagtg | 3360 |
| cgtgtttatg cttaaatgcg ttatggtgca ctctcagtac aatctgctct gatgccgcat | 3420 |
| agttaagcca gccccgacac ccgccaacac ccgctgacgc gccctgacgg gcttgtctgc | 3480 |
| tcccggcatc cgcttacaga caagctgtga ccgtctccgg gagctgcatg tgtcagaggt | 3540 |
| tttcaccgtc atcaccgaaa cgcgcgagac gaaagggcct cgtgatacgc ctatttttat | 3600 |
| aggttaatgt catgataata atggtttctt agacgtcagg tggcactttt cggggaaatg | 3660 |
| tgcgcggaac ccctatttgt ttatttttct aaatacattc aaatatgtat ccgctcatga | 3720 |
| gacaataacc ctgataaatg cttcaataat attgaaaaag gaagagtatg agtattcaac | 3780 |
| atttccgtgt cgcccttatt cccttttttg cggcattttg ccttcctgtt tttgctcacc | 3840 |
| cagaaacgct ggtgaaagta aaagatgctg aagatcagtt gggtgcacga gtgggttaca | 3900 |
| tcgaactgga tctcaacagc ggtaagatcc ttgagagttt cgccccgaa gaacgttttc | 3960 |
| caatgatgag cactttttaaa gttctgctat gtggcgcggt attatcccgt attgacgccg | 4020 |

```
ggcaagagca actcggtcgc cgcatacact attctcagaa tgacttggtt gagtactcac   4080
cagtcacaga aaagcatctt acggatggca tgacagtaag agaattatgc agtgctgcca   4140
taaccatgag tgataacact gcggccaact tacttctgac aacgatcgga ggaccgaagg   4200
agctaaccgc ttttttgcac aacatggggg atcatgtaac tcgccttgat cgttgggaac   4260
cggagctgaa tgaagccata ccaaacgacg agcgtgacac cacgatgcct gtagcaatgg   4320
caacaacgtt gcgcaaacta ttaactggcg aactacttac tctagcttcc cggcaacaat   4380
taatagactg gatggaggcg gataaagttg caggaccact tctgcgctcg gcccttccgg   4440
ctggctggtt tattgctgat aaatctggag ccggtgagcg tgggtctcgc ggtatcattg   4500
cagcactggg gccagatggt aagccctccc gtatcgtagt tatctacacg acggggagtc   4560
aggcaactat ggatgaacga atagacaga tcgctgagat aggtgcctca ctgattaagc   4620
attggtaact gtcagaccaa gttactcat atatacttta gattgattta aaacttcatt   4680
tttaatttaa aaggatctag gtgaagatcc ttttttgataa tctcatgacc aaaatccctt   4740
aacgtgagtt ttcgttccac tgagcgtcag accccgtaga aaagatcaaa ggatcttctt   4800
gagatccttt ttttctgcgc gtaatctgct gcttgcaaac aaaaaaacca ccgctaccag   4860
cggtggtttg tttgccggat caagagctac caactctttt tccgaaggta actggcttca   4920
gcagagcgca gataccaaat actgtccttc tagtgtagcc gtagttaggc caccacttca   4980
agaactctgt agcaccgcct acatacctcg ctctgctaat cctgttacca gtggctgctg   5040
ccagtggcga taagtcgtgt cttaccgggt tggactcaag acgatagtta ccggataagg   5100
cgcagcggtc gggctgaacg gggggttcgt gcacacagcc cagcttggag cgaacgacct   5160
acaccgaact gagatacca cagcgtgagc attgagaaag cgccacgctt cccgaaggga   5220
gaaaggcgga caggtatccg gtaagcggca gggtcggaac aggagagcgc acgagggagc   5280
ttccaggggg aaacgcctgg tatctttata gtcctgtcgg gtttcgccac ctctgacttg   5340
agcgtcgatt tttgtgatgc tcgtcagggg ggcggagcct atggaaaaac gccagcaacg   5400
cggccttttt acggttcctg gccttttgct ggccttttgc tcacatgttc tttcctgcgt   5460
tatcccctga ttctgtggat aaccgtatta ccgcctttga gtgagctgat accgctcgcc   5520
gcagccgaac gaccgagcgc agcgagtcag tgagcgagga agcggaagag cgcccaatac   5580
gcaaaccgcc tctccccgcg cgttggccga ttcattaatc caggatccca attaatgtga   5640
gttacctcac tcattaggca ccccaggctt tacactttat gcttccggct cgtatgttgt   5700
gtggaattgt gagcggataa caatttcaca caggaaacag ctatgaccat gattacgaat   5760
taattcgagc tcggtacccg gggatcgatc cactagagat ctgtttagct tgcctcgtcc   5820
ccgccgggtc acccggccag cgacatggag gcccagaata ccctccttga cagtcttgac   5880
gtgcgcagct caggggcatg atgtgactgt cgcccgtaca tttagcccat acatccccat   5940
gtataatcat ttgcatccat acattttgat ggccgcacgg cgcgaagcaa aaattacggc   6000
tcctcgctgc agacctgcga gcagggaaac gctcccctca cagacgcgtt gaattgtccc   6060
cacgccgcgc ccctgtagag aaatataaaa ggttaggatt tgccactgag gttcttcttt   6120
catatacttc cttttaaaat cttgctagga tacagttctc acatcacatc cgaacataaa   6180
caaccatggc cgaccaagcg acgcccaacc tgccatcacg agatttcgat tccacggccg   6240
ccttctatga aaggttgggc ttcggaatcg ttttccggga cgccggctgg atgatcctcc   6300
agcgcgggga tctcaagctg gagttcttcg cccaccccgg gctcgatccc ctcgcgagtt   6360
```

```
ggttcagctg ctgcctgagg ctggacgacc tcgcggagtt ctaccggcag tgcaaatccg   6420
tcggcatcca ggaaaccagc agcggctatc cgcgcatcca tgcccccgaa ctgcaggagt   6480
ggggaggcac gatggccgct ttggtcgacc cggacgggac gctcctgcgc ctgatacaga   6540
acgaattgct tgcaggcatc tcatgatcag tactgacaat aaaaagattc ttgttttcaa   6600
gaacttgtca tttgtatagt ttttttatat tgtagttgtt ctattttaat caaatgttag   6660
cgtgatttat atttttttc gcctcgacat catctgccca gatgcgaagt taagtgcgca   6720
gaaagtaata tcatgcgtca atcgtatgtg aatgctggtc gctatactgc tgtcgattcg   6780
atactaacgc cgccatccag tgtcgaaaac gagctctcga gaacccttaa tataacttcg   6840
tataatgtat gctatacgaa gttattaggt gatatcagat ccactagtgt ttaaacacct   6900
catctataat ttttaccctg atctaactaa ctttggcatg cctggttcaa tctacgggtt   6960
acagtcatcg ttgaaaacga tggaaaaaca tgtcgagatt cctcaatcca tacaccatta   7020
tagtccgttt tatcagcttc cactaatttt ttaaatctca gtttcttctt gaaatttagc   7080
atcgtgcatg ggatagcggc tagtaaaaaa gaaaattaat atctcattaa caaagttatt   7140
gtacataatc cggtacaata ttcttcaatg tactctctaa tatcgagcac actggcaata   7200
ttcatgcaca cattcgccta atgctgacga atgcttaatc agtgcaatta ctgccaccct   7260
cttgatatgt gggctaaatc ctttaggacc tgtaaaaaat gcaatcacgt tttcacattt   7320
ttttttttct tgcggaattg cggaatttcc cagttggcag cgttatccga tttgagatcg   7380
acttgcatca acctttgaaa aatataagga tgagaaagtg aaatcggttt ttttttttcca   7440 ttgtcgtcat caacatgatt ttttaaataa ataaatacga ttttttatt tttttccctt   7500 ctttgttttt gttttgctta ttcccatctt cattattaaa ttcttccgct cttaataaag   7560
gagttttttt attatcttct tgtgtaatca tcctttttct ttaattttct tccttttctt   7620
tttctcttta ctggtttttt tacttcttta ttctcaacca tctaaagaat attattgctt   7680
tctaccaata aaatctgtta attctatttg gattgtcgtc tactcaagtc tcgcctagta   7740
aataaacgat aaacaaattt gaagtaagaa taacaatata gggagagaaa ttttctatt   7800 tttaatttcg aaacaggtac caaaaaatct aagttcactt tagcactatt tgggaaagct   7860
tttatataaa aaatctgaaa caaaatcata tcaaagttaa ttaagaatta tggctgttac   7920
taatgtcgct gaacttaacg cactcgtaga gcgtgtaaaa aaagcccagc gtgaatatgc   7980
cagtttcact caagagcaag tagacaaaat cttccgcgcc gccgctctgg ctgctgcaga   8040
tgctcgaatc ccactcgcga aaatggccgt tgccgaatcc ggcatgggta tcgtcgaaga   8100
taaagtgatc aaaaaccact ttgcttctga atatatctac aacgcctata agatgaaaaa   8160
aacctgtggt gttctgtctg aagacgacac ttttggtacc atcactatcg ctgaaccaat   8220
cggtattatt tgcggtatcg ttccgaccac taacccgact tcaactgcta tcttcaaatc   8280
gctgatcagt ctgaagaccc gtaacgccat tatcttctcc ccgcacccgc gtgcaaaaga   8340
tgccaccaac aaagcggctg atatcgttct gcaggctgct atcgctgccg gtgctccgaa   8400
agatctgatc ggctggatcg atcaaccttc tgttgaactg tctaacgcac tgatgcacca   8460
cccagacatc aacctgatcc tcgcgactgg tggtccgggc atggttaaag ccgcatacag   8520
ctccggtaaa ccagctatcg gtgtaggcgc gggcaacact ccagttgtta tcgatgaaac   8580
tgctgatatc aaacgtgcag ttgcatctgt actgatgtcc aaaaccttcg acaacggcgt   8640
aatctgtgct tctgaacagt ctgttgttgt tgttgactct gtttatgacg ctgtacgtga   8700
acgttttgca acccacggcg gctatctgtt gcagggtaaa gagctgaaag ctgttcagga   8760
```

```
tgttatcctg aaaaacggtg cgctgaacgc ggctatcgtt ggtcagccag cctataaaat    8820
tgctgaactg gcaggcttct ctgtaccaga aacaccaag attctgatcg gtgaagtgac    8880
cgttgttgat gaaagcgaac cgttcgcaca tgaaaaactg tccccgactc tggcaatgta    8940
ccgcgctaaa gatttcgaag acgcggtaga aaaagcagag aaactggttg ctatgggcgg    9000
tatcggtcat acctcttgcc tgtacactga ccaggataac caaccggctc gcgtttctta    9060
cttcggtcag aaaatgaaaa cggcgcgtat cctgattaac accccagcgt ctcagggtgg    9120
tatcggtgac ctgtataact tcaaactcgc accttccctg actctgggtt gtggttcttg    9180
gggtggtaac tccatctctg aaaacgttgg tccgaaacac ctgatcaaca agaaaaccgt    9240
tgctaagcga gctgaaaaca tgttgtggca caaacttccg aaatctatct acttccgccg    9300
tggctccctg ccaatcgcgc tggatgaagt gattactgat ggccacaaac gtgcgctcat    9360
cgtgactgac cgcttcctgt tcaacaatgg ttatgctgat cagatcactt ccgtactgaa    9420
agcagcaggc gttgaaactg aagtcttctt cgaagtagaa gcggacccga ccctgagcat    9480
cgttcgtaaa ggtgcagaac tggcaaactc cttcaaacca gacgtgatta tcgcgctggg    9540
tggtggttcc ccgatggacg ccgcgaagat catgtgggtt atgtacgaac atccggaaac    9600
tcacttcgaa gagctggcgc tgcgctttat ggatatccgt aaacgtatct acaagttccc    9660
gaaaatgggc gtgaaagcga aaatgatcgc tgtcaccacc acttctggta caggttctga    9720
agtcactccg tttgcggttg taactgacga cgctactggt cagaaatatc cgctggcaga    9780
ctatgcgctg actccggata tggcgattgt cgacgccaac ctggttatgg acatgccgaa    9840
gtccctgtgt gctttcggtg gtctggacgc agtaactcac gccatggaag cttatgtttc    9900
tgtactggca tctgagttct ctgatggtca ggctctgcag gcactgaaac tgctgaaaga    9960
atatctgcca gcgtcctacc acgaagggtc taaaaatccg gtagcgcgtg aacgtgttca   10020
cagtgcagcg actatcgcgg gtatcgcgtt tgcgaacgcc ttcctgggtg tatgtcactc   10080
aatggcgcac aaactggggt cccagttcca tattccgcac ggtctggcaa acgccctgct   10140
gatttgtaac gttattcgct acaatgcgaa cgacaacccg accaagcaga ctgcattcag   10200
ccagtatgac cgtccgcagg ctcgccgtcg ttatgctgaa attgccgacc acttgggtct   10260
gagcgcaccg ggcgaccgta ctgctgctaa gatcgagaaa ctgctggcat ggctggaaac   10320
gctgaaagct gaactgggta ttccgaaatc tatccgtgaa gctggcgttc aggaagcaga   10380
cttcctggcg aacgtggata aactgtctga agatgcattc gatgaccagt gcaccggcgc   10440
taacccgcgt tacccgctga ctctccgagct gaaacagatt ctgctggata cctactacgg   10500
tcgtgattat gtagaaggtg aaactgcagc gaagaaagaa gctgctccgg ctaaagctga   10560
gaaaaagcg aaaaatccg cttaaccgcc tcggccggcg cgccc             10605
```

<210> SEQ ID NO 69
<211> LENGTH: 10539
<212> TYPE: DNA
<213> ORGANISM: Artificial sequence
<220> FEATURE:
<223> OTHER INFORMATION: Plasmid pMU2570

<400> SEQUENCE: 69

```
gagattatac ttaaactagc actgattttt ttaaggctaa tggctactaa tactttaata      60
gatgatcttc atacttttt atttaacgat ttttaatgat gttttattt gtaccactca      120
tttatctaga tttttttaat actgatcaaa tcttacggac tcgacgttaa aaagttccta     180
```

```
catacgtctg gtacttgaaa cgctgcttcg aggtattgac actataagaa tacgatccaa    240
atacttacac cgcatgtaaa aatatgccga caatatgaat acttgttgat gaatgatatt    300
tgattttaat ccggcaattt acctccttta tataatccaa taattgttga taattagtgg    360
ttaggttgca gtactaataa gaattaagac aaatattctt ctactatata aaaggtgcaa    420
acaaaacaca cgccgatcgg ccatactaaa caagaccaac ataataatgg tggaaccatt    480
tactgtattt tcaatgtaac atttaaatcc gcggtaaacc tctttgcggg caagcttggc    540
actggccgtc gttttacaac gtcgtgactg ggaaaaccct ggcgttaccc aacttaatcg    600
ccttgcagca catccccctt tcgccagctg gcgtaatagc gaagaggccc gcaccgatcg    660
cccttcccaa cagttgcgca gcctgaatgg cgaatggcgc ctgatgcggt attttctcct    720
tacgcatctg tgcggtattt cacaccgcat aggagatcta agctctggcg taatagcgaa    780
gaggcccgca ccgatcgccc ttcccaacag ttgcgcagcc tgaatggcga atggcgcctg    840
atgcggtatt ttctccttac gcatctgtgc ggtatttcac accgcatagg gtaataactg    900
atataattaa attgaagctc taatttgtga gtttagtata catgcattta cttataatac    960 agtttttttag ttttgctggc cgcatcttct caaatatgct tcccagcctg cttttctgta   1020
acgttcaccc tctaccttag catcccttcc ctttgcaaat agtcctcttc caacaataat   1080
aatgtcagat cctgtagaga ccacatcatc cacggttcta tactgttgac ccaatgcgtc   1140
tcccttgtca tctaaaccca caccgggtgt cataatcaac caatcgtaac cttcatctct   1200
tccacccatg tctctttgag caataaagcc gataacaaaa tctttgtcgc tcttcgcaat   1260
gtcaacagta cccttagtat attctccagt agatagggag cccttgcatg acaattctgc   1320
taacatcaaa aggcctctag gttcctttgt tacttcttct gccgcctgct tcaaaccgct   1380
aacaatacct gggcccacca caccgtgtgc attcgtaatg tctgcccatt ctgctattct   1440
gtatacaccc gcagagtact gcaatttgac tgtattacca atgtcagcaa attttctgtc   1500
ttcgaagagt aaaaaattgt acttggcgga taatgccttt agcggcttaa ctgtgccctc   1560
catggaaaaa tcagtcaaga tatccacatg tgttttttagt aaacaaattt gggacctaa    1620 tgcttcaact aactccagta attccttggt ggtacgaaca tccaatgaag cacacaagtt   1680
tgtttgcttt tcgtgcatga tattaaatag cttggcagca acaggactag gatgagtagc   1740
agcacgttcc ttatatgtag ctttcgacat gatttatctt cgtttcggtt tttgttctgt   1800
gcagttgggt taagaatact gggcaatttc atgtttcttc aacactacat atgcgtatat   1860
ataccaatct aagtctgtgc tccttccttc gttcttcctt ctgttcggag attaccgaat   1920
caaaaaaatt tcaaagaaac cgaaatcaaa aaaagaata aaaaaaaat gatgaattga    1980 aaagctcttg ttacccatca ttgaattttg aacatccgaa cctgggagtt ttccctgaaa   2040
cagatagtat atttgaacct gtataataat atatagtcta gcgctttacg gaagacaatg   2100
tatgtatttc ggttcctgga gaaactattg catctattgc ataggtaatc ttgcacgtcg   2160
catccccggt tcattttctg cgtttccatc ttgcacttca atagcatatc tttgttaacg   2220
aagcatctgt gcttcatttt gtagaacaaa aatgcaacgc gagagcgcta attttcaaa   2280 caaagaatct gagctgcatt tttacagaac agaaatgcaa cgcgaaagcg ctatttacc    2340 aacgaagaat ctgtgcttca ttttttgtaaa acaaaaatgc aacgcgagag cgctaatttt   2400
tcaaacaaag aatctgagct gcattttttac agaacagaaa tgcaacgcga gagcgctatt   2460
ttaccaacaa agaatctata cttctttttt gttctacaaa aatgcatccc gagagcgcta   2520
tttttctaac aaagcatctt agattacttt ttttctcctt tgtgcgctct ataatgcagt   2580
```

```
ctcttgataa cttttttgcac tgtaggtccg ttaaggttag aagaaggcta ctttggtgtc    2640
tattttctct tccataaaaa aagcctgact ccacttcccg cgtttactga ttactagcga    2700
agctgcgggt gcatttttc aagataaagg catccccgat tatattctat accgatgtgg     2760
attgcgcata ctttgtgaac agaaagtgat agcgttgatg attcttcatt ggtcagaaaa    2820
ttatgaacgg tttcttctat tttgtctcta tatactacgt ataggaaatg tttacatttt    2880
cgtattgttt tcgattcact ctatgaatag ttcttactac aatttttttg tctaaagagt    2940
aatactagag ataaacataa aaaatgtaga ggtcgagttt agatgcaagt tcaaggagcg    3000
aaaggtggat gggtaggtta tagggata tagcacagag atatatagca aagagatact     3060
tttgagcaat gtttgtggaa gcggtattcg caatatttta gtagctcgtt acagtccggt    3120 gcgttttttgg ttttttgaaa gtgcgtcttc agagcgcttt tggttttcaa aagcgctctg   3180
aagttcctat actttctagc tagagaatag gaacttcgga ataggaactt caaagcgttt    3240
ccgaaaacga gcgcttccga aaatgcaacg cgagctgcgc acatacagct cactgttcac    3300
gtcgcaccta tatctgcgtg ttgcctgtat atatatatac atgagaagaa cggcatagtg    3360
cgtgtttatg cttaaatgcg ttatggtgca ctctcagtac aatctgctct gatgccgcat    3420
agttaagcca gccccgacac ccgccaacac ccgctgacgc gccctgacgg gcttgtctgc    3480
tcccggcatc cgcttacaga caagctgtga ccgtctccgg gagctgcatg tgtcagaggt    3540
tttcaccgtc atcaccgaaa cgcgcgagac gaaagggcct cgtgatacgc ctatttttat    3600
aggttaatgt catgataata atggtttctt agacgtcagg tggcactttt cggggaaatg    3660
tgcgcggaac ccctatttgt ttatttttct aaatacattc aaatatgtat ccgctcatga    3720
gacaataacc ctgataaatg cttcaataat attgaaaaag gaagagtatg agtattcaac    3780
atttccgtgt cgcccttatt ccctttttg cggcattttg ccttcctgtt tttgctcacc     3840
cagaaacgct ggtgaaagta aaagatgctg aagatcagtt gggtgcacga gtgggttaca    3900
tcgaactgga tctcaacagc ggtaagatcc ttgagagttt cgccccgaa gaacgttttc     3960 caatgatgag cacttttaaa gttctgctat gtggcgcggt attatcccgt attgacgccg    4020
ggcaagagca actcggtcgc cgcatacact attctcagaa tgacttggtt gagtactcac    4080
cagtcacaga aaagcatctt acggatggca tgacagtaag agaattatgc agtgctgcca    4140
taaccatgag tgataacact gcggccaact tacttctgac aacgatcgga ggaccgaagg    4200
agctaaccgc ttttttgcac aacatggggg atcatgtaac tcgccttgat cgttgggaac    4260
cggagctgaa tgaagccata ccaaacgacg agcgtgacac cacgatgcct gtagcaatgg    4320
caacaacgtt gcgcaaacta ttaactggcg aactacttac tctagcttcc cggcaacaat    4380
taatagactg gatggaggcg gataaagttg caggaccact tctgcgctcg gcccttccgg    4440
ctggctggtt tattgctgat aaatctggag ccggtgagcg tgggtctcgc ggtatcattg    4500
cagcactggg gccagatggt aagccctccc gtatcgtagt tatctacacg acggggagtc    4560
aggcaactat ggatgaacga aatagacaga tcgctgagat aggtgcctca ctgattaagc    4620
attggtaact gtcagaccaa gtttactcat atatacttta gattgattta aaacttcatt    4680
tttaatttaa aaggatctag gtgaagatcc ttttttgataa tctcatgacc aaaatccctt    4740
aacgtgagtt ttcgttccac tgagcgtcag accccgtaga aaagatcaaa ggatcttctt    4800
gagatccttt ttttctgcgc gtaatctgct gcttgcaaac aaaaaaacca ccgctaccag    4860
cggtggtttg tttgccggat caagagctac caactctttt tccgaaggta actggcttca    4920
```

```
gcagagcgca gataccaaat actgtccttc tagtgtagcc gtagttaggc caccacttca    4980
agaactctgt agcaccgcct acatacctcg ctctgctaat cctgttacca gtggctgctg    5040
ccagtggcga taagtcgtgt cttaccgggt tggactcaag acgatagtta ccggataagg    5100
cgcagcggtc gggctgaacg gggggttcgt gcacacagcc cagcttggag cgaacgacct    5160
acaccgaact gagatacccta cagcgtgagc attgagaaag cgccacgctt cccgaaggga    5220
gaaaggcgga caggtatccg gtaagcggca gggtcggaac aggagagcgc acagggagc    5280 ttccaggggg aaacgcctgg tatctttata gtcctgtcgg gtttcgccac ctctgacttg    5340
agcgtcgatt tttgtgatgc tcgtcagggg gcggagcct atggaaaaac gccagcaacg    5400 cggcctttt acggttcctg ccttttgct ggccttttgc tcacatgttc tttcctgcgt      5460
tatcccctga ttctgtggat aaccgtatta ccgcctttga gtgagctgat accgctcgcc   5520
gcagccgaac gaccgagcgc agcgagtcag tgagcgagga agcggaagag cgcccaatac   5580
gcaaaccgcc tctccccgcg cgttggccga ttcattaatc caggatccca attaatgtga   5640
gttacctcac tcattaggca ccccaggctt tacactttat gcttccggct cgtatgttgt   5700
gtggaattgt gagcggataa caatttcaca caggaaacag ctatgaccat gattacgaat   5760
taattcgagc tcggtacccg gggatcgatc cactagagat ctgtttagct tgcctcgtcc   5820
ccgccgggtc acccggccag cgacatggag gcccagaata ccctccttga cagtcttgac   5880
gtgcgcagct caggggcatg atgtgactgt cgcccgtaca tttagcccat acatccccat   5940
gtataatcat ttgcatccat acattttgat ggccgcacgg cgcgaagcaa aaattacggc   6000
tcctcgctgc agacctgcga gcagggaaac gctcccctca cagacgcgtt gaattgtccc   6060
cacgccgcgc ccctgtagag aaatataaaa ggttaggatt tgccactgag gttcttcttt   6120
catatacttc cttttaaaat cttgctagga tacagttctc acatcacatc cgaacataaa   6180
caaccatggc cgaccaagcg acgcccaacc tgccatcacg agatttcgat tccacggccg   6240
ccttctatga aaggttgggc ttcggaatcg tttttccggga cgccggctgg atgatcctcc   6300
agcgcgggga tctcaagctg gagttcttcg cccacccgg gctcgatccc ctcgcgagtt   6360
ggttcagctg ctgcctgagg ctggacgacc tcgcggagtt ctaccggcag tgcaaatccg   6420
tcggcatcca ggaaaccagc agcggctatc cgcgcatcca tgcccccgaa ctgcaggagt   6480
ggggaggcac gatggccgct ttggtcgacc cggacgggac gctcctgcgc ctgatacaga   6540
acgaattgct tgcaggcatc tcatgatcag tactgacaat aaaaagattc ttgttttcaa   6600
gaacttgtca tttgtatagt ttttttatat tgtagttgtt ctattttaat caaatgttag   6660
cgtgatttat attttttttc gcctcgacat catctgccca gatgcgaagt taagtgcgca   6720
gaaagtaata tcatgcgtca atcgtatgtg aatgctggtc gctatactgc tgtcgattcg   6780
atactaacgc cgccatccag tgtcgaaaac gagctctcga gaacccttaa tataacttcg   6840
tataatgtat gctatacgaa gttattaggt gatatcagat ccactagtgt ttaaacacct   6900
catctataat ttttaccctg atctaactaa ctttggcatg cctggttcaa tctacgggtt   6960
acagtcatcg ttgaaaacga tggaaaaaca tgtcgagatt cctcaatcca tacaccatta   7020
tagtccgttt tatcagcttc cactaatttt ttaaatctca gtttcttctt gaaatttagc   7080
atcgtgcatg ggatagcggc tagtaaaaaa gaaaattaat atctcattaa caaagttatt   7140
gtacataatc cggtacaata ttcttcaatg tactctctaa tatcgagcac actggcaata   7200
ttcatgcaca cattcgccta atgctgacga atgcttaatc agtgcaatta ctgccaccct   7260
cttgatatgt gggctaaatc ctttaggacc tgtaaaaaat gcaatcacgt tttcacattt   7320
```

```
tttttttttct tgcggaattg cggaatttcc cagttggcag cgttatccga tttgagatcg    7380
acttgcatca acctttgaaa aatataagga tgagaaagtg aaatcggttt ttttttttcca   7440 ttgtcgtcat caacatgatt ttttaaataa ataaatacga ttttttattt ttttccctt    7500 ctttgttttt gttttgctta ttcccatctt cattattaaa ttcttccgct cttaataaag    7560 gagtttttt attatcttct tgtgtaatca tcctttttct ttaattttct tccttttctt    7620
tttctcttta ctggtttttt tacttcttta ttctcaacca tctaaagaat attattgctt    7680
tctaccaata aaatctgtta attctatttg gattgtcgtc tactcaagtc tcgcctagta    7740
aataaacgat aaacaaattt gaagtaagaa taacaatata gggagagaaa tttttctatt    7800
tttaatttcg aaacaggtac caaaaaatct aagttcactt tagcactatt tgggaaagct    7860
tttatataaa aaatctgaaa caaaatcata tcaaagttaa ttaagaatta tgacgaaaaa    7920
agtggaatta cagacaactg gattagtaga ctctctcgaa gcattaacag caaaatttag    7980
agagttaaaa gaagcacaag agctctttgc tacctacact caagagcaag tagataaaat    8040
cttctttgct gctgccatgg ctgccaatca gcaacgtatt ccgttagcaa agatggctgt    8100
agaagaaacg ggtatgggta ttgtagaaga taaagtaatt aagaatcatt atgctgcaga    8160
gtatatttac aatgcataca aagatacaaa aacatgtgga gtggttgaag aagatcctag    8220
cttcggtatc aaaaaaattg cagagccaat cggcgtagtt gcagctgtaa tcccaactac    8280
caatcctacc tccactgcta tctttaaaac attactttgt ttaaagactc gtaacgcaat    8340
catcatcagc ccacatcctc gtgctaagaa ctgtaccatc gcagctgcta aggtagtttt    8400
agatgctgca gttgctgcag gtgctcctgc tggtataatt ggatggattg atgttccatc    8460
acttgaatta accaatgaag ttatgaaaaa tgcagacatc atccttgcaa ctggtggacc    8520
tggtatggta aaggctgctt attcttctgg taaaccagca cttggtgttg cgcaggtaa    8580 taccctgtt attatggatg aaagctgcga tgttcgcctt gcagtaagct ctattattca    8640
ctctaagaca tttgataacg gtatgatttg tgcttccgag caatccgtaa ttattagtga    8700
taagatttat gaagctgcta agaaagaatt caaggatcgt ggttgccaca tctgctcccc    8760
agaagagact cagaagcttc gtgaaacaat cctaattaat ggtgctctta acgctaaaat    8820
tgttggacaa agcgctcata cgattgcaaa gcttgcagga tttgatgtag cagaagctgc    8880
taagatttta attggtgaag tagaatccgt tgaactagaa gaacaatttg cacacgaaga    8940
actttctcca gttcttgcta tgtacaaatc aaaatccttt gatgatgcag taagcaaagc    9000
tgctcgtctt gttgcagatg gcggttatgg ccatacttct tccatctata ttaatgtagg    9060
taccggacaa gaaaagattg caaagttttc tgatgctatg aagacttgcc gtattcttgt    9120
aaatacacca tcctcccatg gtggtatcgg tgacctttat aactttaaat tagctccatc    9180
tcttactctt ggttgtggct cctggggcgg taactctgta tcagaaaacg taggagtaaa    9240
gcacttaatc aacattaaga cagttgctga gaggagagaa aacatgcttt ggtttagagc    9300
acctgagaaa gtatacttta agaagggttg tttaccagta gccctcgcag aattaaaaga    9360
tgtaatgaat aaaagaaag tattcattgt aaccgatgct ttccttttata aaaatggcta    9420 tacaaaatgt gttactgatc agttagatgc tatgggaatt cagcatacta cttactgaa    9480 tgttgctcca gatccatctt tagctagtgc tacagaaggt gcagaagcga tgagactctt    9540
cgagccagac tgtattatcg cactcggtgg tggttctgca atggatgccg aaagattat    9600 gtgggttatg tatgaacacc ctgaagtaaa cttccttgac cttgcaatgc gtttcatgga    9660
```

| | | |
|---|---|---|
| tattagaaag cgtgtttact ccttccctaa gatgggcgaa aaagcttact ttatcgcagt | 9720 |
| tccaacttcc tccggtactg gttctgaagt tacaccattt gctgttatta ccgatgagag | 9780 |
| aactggcgta aaatatccac ttgcagatta cgaattactt cctaagatgg ctattattga | 9840 |
| tgccgatatg atgatgaatc aacctaaggg attaacttct gcttccggta ttgatgccct | 9900 |
| tacccatgca ttagaggcat atgcttctat catggctact gactatacgg atggtttagc | 9960 |
| attaaaagct atgaagaata tcttcgctta ccttccaagc gcatatgaaa atggtgccgc | 10020 |
| tgatccggtt gcaagagaaa agatggcaga tgcttctacc ttagctggta tggcattcgc | 10080 |
| aaatgcattc ttaggaattt gccactccat ggctcataaa ttaggtgcat tccaccactt | 10140 |
| accacacggt gtagcaaacg cactcttaat caacgaagta atgcgcttta ctccgttag | 10200 |
| cattcctaca aagatgggta ctttctctca ataccaatac ccacatgcgt tagatcgtta | 10260 |
| tgtagaatgt gcgaacttct taggtattgc cggaaagaac gacaatgaga aattcgaaaa | 10320 |
| ccttcttaag gcaattgatg aattaaaaga aaaagttggt atcaagaaat ccatcaaaga | 10380 |
| atatggcgta gacgagaaat atttcttaga tactttagat gctatggttg aacaggcttt | 10440 |
| cgatgatcag tgtactggtg ctaacccaag atatccatta atgaaggaaa tcaaggaaat | 10500 |
| ctatcttaaa gtgtactacg gtaaataacc ggcgcgccc | 10539 |

<210> SEQ ID NO 70
<211> LENGTH: 10629
<212> TYPE: DNA
<213> ORGANISM: Artificial sequence
<220> FEATURE:
<223> OTHER INFORMATION: Plasmid pMU2745

<400> SEQUENCE: 70

| | | |
|---|---|---|
| cgctcgccgc agccgaacga ccgagcgcag cgagtcagtg agcgaggaag cggaagagcg | 60 |
| cccaatacgc aaaccgcctc tccccgcgcg ttggccgatt cattaatcca ggatcccaat | 120 |
| taatgtgagt tacctcactc attaggcacc ccaggcttta cactttatgc ttccggctcg | 180 |
| tatgttgtgt ggaattgtga gcggataaca atttcacaca ggaaacagct atgaccatga | 240 |
| ttacgaatta attcgagctc ggtacccggg gatcgatcca ctagagatct gtttagcttg | 300 |
| cctcgtcccc gccgggtcac ccggccagcg acatggaggc ccagaatacc ctccttgaca | 360 |
| gtcttgacgt gcgcagctca ggggcatgat gtgactgtcg cccgtacatt tagcccatac | 420 |
| atccccatgt ataatcattt gcatccatac attttgatgg ccgcacggcg cgaagcaaaa | 480 |
| attacggctc ctcgctgcag acctgcgagc agggaaacgc tccctcaca gacgcgttga | 540 |
| attgtcccca cgccgcgccc ctgtagagaa atataaaagg ttaggatttg ccactgaggt | 600 |
| tcttctttca tactttcct tttaaaatct tgctaggata cagttctcac atcacatccg | 660 |
| aacataaaca accatggccg accaagcgac gcccaacctg ccatcacgag atttcgattc | 720 |
| cacgccgcc ttctatgaaa ggttgggctt cggaatcgtt ttcgggacg ccggctggat | 780 |
| gatcctccag cgcggggatc tcaagctgga gttcttcgcc caccccgggc tcgatcccct | 840 |
| cgcgagttgg ttcagctgct gcctgaggct ggacgacctc gcggagttct accggcagtg | 900 |
| caaatccgtc ggcatccagg aaaccagcag cggctatccg cgcatccatg cccccgaact | 960 |
| gcaggagtgg ggaggcacga tggccgcttt ggtcgacccg gacgggacgc tcctgcgcct | 1020 |
| gatacagaac gaattgcttg caggcatctc atgatcagta ctgacaataa aaagattctt | 1080 |
| gttttcaaga acttgtcatt tgtatagttt ttttatattg tagttgttct attttaatca | 1140 |
| aatgttagcg tgatttatat tttttttcgc ctcgacatca tctgcccaga tgcgaagtta | 1200 |

```
agtgcgcaga aagtaatatc atgcgtcaat cgtatgtgaa tgctggtcgc tatactgctg    1260
tcgattcgat actaacgccg ccatccagtg tcgaaaacga gctctcgaga acccttaata    1320
taacttcgta taatgtatgc tatacgaagt tattaggtga tatcagatcc actagtgttt    1380
aaacacctca tctataattt ttaccctgat ctaactaact ttggcatgcc tggttcaatc    1440
tacgggttac agtcatcgtt gaaaacgatg gaaaaacatg tcgagattcc tcaatccata    1500
caccattata gtccgtttta tcagcttcca ctaattttt aaatctcagt ttcttcttga     1560
aatttagcat cgtgcatggg atagcggcta gtaaaaaaga aaattaatat ctcattaaca    1620
aagttattgt acataatccg gtacaatatt cttcaatgta ctctctaata tcgagcacac    1680
tggcaatatt catgcacaca ttcgcctaat gctgacgaat gcttaatcag tgcaattact    1740
gccaccctct tgatatgtgg gctaaatcct ttaggacctg taaaaaatgc aatcacgttt    1800
tcacattttt tttttcttg cggaattgcg gaatttccca gttggcagcg ttatccgatt     1860
tgagatcgac ttgcatcaac ctttgaaaaa tataaggatg agaaagtgaa atcggttttt    1920
tttttccatt gtcgtcatca acatgatttt ttaaataaat aaatacgatt ttttatttt     1980 tttcccttct ttgttttttgt tttgcttatt cccatcttca ttattaaatt cttccgctct   2040
taataaagga gttttttat tatcttcttg tgtaatcatc cttttctttt aattttcttc     2100
cttttctttt tctctttact ggttttttta cttcttatt ctcaaccatc taaagaatat     2160
tattgctttc taccaataaa atctgttaat tctatttgga ttgtcgtcta ctcaagtctc    2220
gcctagtaaa taaacgataa acaaatttga agtaagaata acaatatagg gagagaaatt    2280
tttctatttt taatttcgaa acaggtacca aaaaatctaa gttcacttta gcactatttg    2340
ggaaagcttt tatataaaaa atctgaaaca aaatcatatc aaagatggca gacgcaaaga    2400
agaaggaaga gccgaccaag ccgactccgg aagagaagct cgccgcagcc gaggctgagg    2460
tcgacgctct ggtcaagaag ggcctgaagg ctcttgatga attcgagaag ctcgatcaga    2520
agcaggttga ccacatcgtg gccaaggctt ccgtcgcagc cctgaacaag cacttggtgc    2580
tcgccaagat ggccgtcgag gagacccacc gtggtctggt cgaagacaag gccaccaaga    2640
acatcttcgc ctgcgagcat gtcaccaact acctggctgg tcagaagacc gtcggcatca    2700
tccgcgagga cgacgtgctg ggcatcgacg aaatcgccga gccggttggc gtcgtcgctg    2760
gcgtgacccc ggtcaccaac ccgacctcca ccgccatctt caagtcgctg atcgcactga    2820
agacccgctg cccgatcatc ttcggcttcc acccgggcgc acagaactgc tccgtcgcgg    2880
ccgccaagat cgttcgcgat gccgctatcg cagcaggcgc tcctgagaac tgtattcagt    2940
ggatcgagca tccgtccatc gaggccactg gcgccctgat gaagcatgat ggtgtcgcca    3000
ccatcctcgc caccggtggt ccgggcatgg tcaaggccgc atactcctcc ggcaagccgg    3060
ccctgggcgt cggcgcgggc aatgctccgg catacgttga caagaacgtc gacgtcgtgc    3120
gtgcagccaa cgatctgatt cttttccaagc acttcgatta cggcatgatc tgcgctaccg    3180
agcaggccat catcgccgac aaggacatct acgctccgct cgttaaggaa ctcaagcgtc    3240
gcaaggccta tttcgtgaac gctgacgaga aggccaagct cgagcagtac atgttcggct    3300
gcaccgctta ctccggacag accccgaagc tcaactccgt ggtgccgggc aagtccccgc    3360
agtacatcgc caaggccgcc ggcttcgaga ttccggaaga cgccaccatc cttgccgctg    3420
agtgcaagga agtcggcgag aacgagccgc tgaccatgga gaagcttgct ccggtccagg    3480
ccgtgctgaa gtccgacaac aaggaacagg ccttcgagat gtgcgaagcc atgctgaagc    3540
```

```
atggcgccgg ccacaccgcc gccatccaca ccaacgaccg tgacctggtc cgcgagtacg   3600
gccagcgcat gcacgcctgc cgtatcatct ggaactcccc gagctccctc ggcggcgtgg   3660
gcgacatcta caacgccatc gctccgtccc tgaccctggg ctgcggctcc tacggcggca   3720
actccgtgtc cggcaacgtc caggcagtca acctcatcaa catcaagcgc atcgctcgga   3780
ggaacaacaa catgcagtgg ttcaagattc cggccaagac ctacttcgag ccgaacgcca   3840
tcaagtacct gcgcgacatg tacggcatcg aaaaggccgt catcgtgtgc gataaggtca   3900
tggagcagct cggcatcgtt gacaagatca tcgatcagct gcgtgcacgt tccaaccgcg   3960
tgaccttccg tatcatcgat tatgtcgagc cggagccgag cgtggagacc gtcgaacgtg   4020
gcgccgccat gatgcgcgag gagttcgagc cggataccat catcgccgtc ggcggtggtt   4080
ccccgatgga tgcgtccaag attatgtggc tgctgtacga gcacccggaa atctccttct   4140
ccgatgtgcg tgagaagttc ttcgatatcc gtaagcgcgc gttcaagatt ccgccgctgg   4200
gcaagaaggc caagctggtc tgcattccga cttcttccgg caccggttcc gaagtcacgc   4260
cgttcgctgt gattaccgac cacaagaccg gctataagta cccgatcacc gattacgcgc   4320
tgaccccgtc cgtcgctatc gtcgatccgt gctggcacg tactcagccg cgcaagctgg   4380
cttccgatgc tggtttcgat gctctgaccc acgcttttga ggcttatgtg tccgtgtatg   4440
ccaacgactt caccgatggt atggcattgc acgctgccaa gctggtttgg gacaaccgcg   4500
ctgagtccgt caatggcgag ccgggtgagg agaagaccg tgcccaggag aagatgcata   4560
atgccgccac catggccggc atggctttcg gctccgcctt cctcggcatg tgccacggca   4620
tggcccacac cattggtgca ctgtgccacg ttgcccacgg tcgtaccaac tccatcctcc   4680
tgccgtacgt gatccgttac aacggttccg tcccggagga gccgaccagc tggccgaagt   4740
acaacaagta catcgctccg gaacgctacc aggagatcgc caagaacctt ggcgtgaacc   4800
cgggcaagac tccggaagag ggcgtcgaga acctggccaa ggctgttgag gattaccgtg   4860
acaacaagct cggtatgaac aagagcttcc aggagtgcgg tgtggatgag gactactatt   4920
ggtccatcat cgaccagatc ggcatgcgcg cctacgaaga ccagtgcgca ccggcgaacc   4980
cgcgtatccc gcagatcgag gatatgaagg atatcgccat tgccgcctac tacggcgtca   5040
gccaggcgga aggccacaag ctgcgcgtcc agcgtcaggg cgaagccgct acggaggaag   5100
cttccgagcg cgcctgagag attatactta aactagcact gatttttta aggctaatgg   5160 ctactaatac tttaatagat gatcttcata cttttttatt taacgatttt taatgatgtt   5220
tttatttgta ccactcattt atctagattt ttttaatact gatcaaatct tacggactcg   5280
acgttaaaaa gttcctacat acgtctggta cttgaaacgc tgcttcgagg tattgacact   5340
ataagaatac gatccaaata cttacaccgc atgtaaaaat atgccgacaa tatgaatact   5400
tgttgatgaa tgatatttga ttttaatccg gcaatttacc tcctttatat aatccaataa   5460
ttgttgataa ttagtggtta ggttgcagta ctaataagaa ttaagacaaa tattcttcta   5520
ctatataaaa ggtgcaaaca aaacacacgc cgatcggcca tactaaacaa gaccaacata   5580
ataatggtgg aaccatttac tgtattttca atgtaacatt taaatccgcg gtaaacctct   5640
ttgcgggcaa gcttggcact ggccgtcgtt ttacaacgtc gtgactggga aaaccctggc   5700
gttacccaac ttaatcgcct tgcagcacat ccccctttcg ccagctggcg taatagcgaa   5760
gaggcccgca ccgatcgccc ttcccaacag ttgcgcagcc tgaatggcga atggcgcctg   5820
atgcggtatt ttctccttac gcatctgtgc ggtatttcac accgcatagg agatctaagc   5880
tctggcgtaa tagcgaagag gcccgcaccg atcgcccttc ccaacagttg cgcagcctga   5940
```

```
atggcgaatg gcgcctgatg cggtattttc tccttacgca tctgtgcggt atttcacacc    6000
gcatagggta ataactgata taattaaatt gaagctctaa tttgtgagtt tagtatacat    6060
gcatttactt ataatacagt tttttagttt tgctggccgc atcttctcaa atatgcttcc    6120
cagcctgctt ttctgtaacg ttcaccctct accttagcat cccttccctt tgcaaatagt    6180
cctcttccaa caataataat gtcagatcct gtagagacca catcatccac ggttctatac    6240
tgttgaccca atgcgtctcc cttgtcatct aaacccacac cgggtgtcat aatcaaccaa    6300
tcgtaacctt catctcttcc acccatgtct ctttgagcaa taaagccgat aacaaaatct    6360
ttgtcgctct tcgcaatgtc aacagtaccc ttagtatatt ctccagtaga tagggagccc    6420
ttgcatgaca attctgctaa catcaaaagg cctctaggtt cctttgttac ttcttctgcc    6480
gcctgcttca aaccgctaac aatacctggg cccaccacac cgtgtgcatt cgtaatgtct    6540
gcccattctg ctattctgta tacacccgca gagtactgca atttgactgt attaccaatg    6600
tcagcaaatt ttctgtcttc gaagagtaaa aaattgtact tggcggataa tgcctttagc    6660
ggcttaactg tgccctccat ggaaaaatca gtcaagatat ccacatgtgt ttttagtaaa    6720
caaattttgg gacctaatgc ttcaactaac tccagtaatt ccttggtggt acgaacatcc    6780
aatgaagcac acaagtttgt ttgcttttcg tgcatgatat taaatagctt ggcagcaaca    6840
ggactaggat gagtagcagc acgttcctta tatgtagctt tcgacatgat ttatcttcgt    6900
ttcggttttt gttctgtgca gttgggttaa gaatactggg caatttcatg tttcttcaac    6960
actacatatg cgtatatata ccaatctaag tctgtgctcc ttccttcgtt cttccttctg    7020
ttcggagatt accgaatcaa aaaaatttca agaaaccga atcaaaaaa agaataaaa    7080 aaaaaatgat gaattgaaaa gctcttgtta cccatcattg aattttgaac atccgaacct    7140
gggagttttc cctgaaacag atagtatatt tgaacctgta taataatata tagtctagcg    7200
ctttacggaa gacaatgtat gtatttcggt tcctggagaa actattgcat ctattgcata    7260
ggtaatcttg cacgtcgcat ccccggttca ttttctgcgt ttccatcttg cacttcaata    7320
gcatatcttt gttaacgaag catctgtgct tcattttgta gaacaaaaat gcaacgcgag    7380
agcgctaatt tttcaaacaa agaatctgag ctgcattttt acagaacaga aatgcaacgc    7440
gaaagcgcta ttttaccaac gaagaatctg tgcttcattt ttgtaaaaca aaaatgcaac    7500
gcgagagcgc taattttttca aacaaagaat ctgagctgca tttttacaga acagaaatgc    7560
aacgcgagag cgctatttta ccaacaaaga atctatactt cttttttgtt ctacaaaaat    7620
gcatcccgag agcgctattt ttctaacaaa gcatcttaga ttacttttttt tctcctttgt    7680 gcgctctata atgcagtctc ttgataactt tttgcactgt aggtccgtta aggttagaag    7740
aaggctactt tggtgtctat tttctcttcc ataaaaaaag cctgactcca cttcccgcgt    7800
ttactgatta ctagcgaagc tgcgggtgca ttttttcaag ataaaggcat ccccgattat    7860
attctatacc gatgtggatt gcgcatactt tgtgaacaga aagtgatagc gttgatgatt    7920
cttcattggt cagaaaatta tgaacggttt cttctatttt gtctctatat actacgtata    7980
ggaaatgttt acattttcgt attgttttcg attcactcta tgaatagttc ttactacaat    8040 tttttgtct aaagagtaat actagagata aacataaaaa atgtagaggt cgagtttaga    8100
tgcaagttca aggagcgaaa ggtggatggg taggttatat agggatatag cacagagata    8160
tatagcaaag agatactttt gagcaatgtt tgtggaagcg gtattcgcaa tattttagta    8220
gctcgttaca gtccggtgcg ttttggtttt tttgaaagtg cgtcttcaga gcgcttttgg    8280
```

```
ttttcaaaag cgctctgaag ttcctatact ttctagctag agaataggaa cttcggaata    8340
ggaacttcaa agcgtttccg aaaacgagcg cttccgaaaa tgcaacgcga gctgcgcaca    8400
tacagctcac tgttcacgtc gcacctatat ctgcgtgttg cctgtatata tatatacatg    8460
agaagaacgg catagtgcgt gtttatgctt aaatgcgtta tggtgcactc tcagtacaat    8520
ctgctctgat gccgcatagt taagccagcc ccgacacccg ccaacacccg ctgacgcgcc    8580
ctgacgggct tgtctgctcc cggcatccgc ttacagacaa gctgtgaccg tctccgggag    8640
ctgcatgtgt cagaggtttt caccgtcatc accgaaacgc gcgagacgaa agggcctcgt    8700
gatacgccta tttttatagg ttaatgtcat gataataatg gtttcttaga cgtcaggtgg    8760
cacttttcgg ggaaatgtgc gcggaacccc tatttgttta tttttctaaa tacattcaaa    8820
tatgtatccg ctcatgagac aataaccctg ataaatgctt caataatatt gaaaaaggaa    8880
gagtatgagt attcaacatt tccgtgtcgc ccttattccc ttttttgcgg cattttgcct    8940
tcctgttttt gctcacccag aaacgctggt gaaagtaaaa gatgctgaag atcagttggg    9000
tgcacgagtg ggttacatcg aactggatct caacagcggt aagatccttg agagttttcg    9060
ccccgaagaa cgttttccaa tgatgagcac ttttaaagtt ctgctatgtg gcgcggtatt    9120
atcccgtatt gacgccgggc aagagcaact cggtcgccgc atacactatt ctcagaatga    9180
cttggttgag tactcaccag tcacagaaaa gcatcttacg gatggcatga cagtaagaga    9240
attatgcagt gctgccataa ccatgagtga taacactgcg gccaacttac ttctgacaac    9300
gatcggagga ccgaaggagc taaccgcttt tttgcacaac atgggggatc atgtaactcg    9360
ccttgatcgt tgggaaccgg agctgaatga agccatacca aacgacgagc gtgacaccac    9420
gatgcctgta gcaatggcaa caacgttgcg caaactatta actggcgaac tacttactct    9480
agcttcccgg caacaattaa tagactggat ggaggcggat aaagttgcag gaccacttct    9540
gcgctcggcc cttccggctg gctggtttat tgctgataaa tctggagccg gtgagcgtgg    9600
gtctcgcggt atcattgcag cactggggcc agatggtaag ccctcccgta tcgtagttat    9660
ctacacgacg gggagtcagg caactatgga tgaacgaaat agacagatcg ctgagatagg    9720
tgcctcactg attaagcatt ggtaactgtc agaccaagtt tactcatata ctttagat    9780
tgatttaaaa cttcattttt aatttaaaag gatctaggtg aagatccttt tgataatct    9840
catgaccaaa atcccttaac gtgagttttc gttccactga gcgtcagacc ccgtagaaaa    9900
gatcaaagga tcttcttgag atcctttttt tctgcgcgta atctgctgct tgcaaacaaa    9960
aaaaccaccg ctaccagcgg tggtttgttt gccggatcaa gagctaccaa ctctttttcc   10020
gaaggtaact ggcttcagca gagcgcagat accaaatact gtccttctag tgtagccgta   10080
gttaggccac cacttcaaga actctgtagc accgcctaca tacctcgctc tgctaatcct   10140
gttaccagtg gctgctgcca gtggcgataa gtcgtgtctt accgggttgg actcaagacg   10200
atagttaccg gataaggcgc agcggtcggg ctgaacgggg ggttcgtgca cacagcccag   10260
cttggagcga acgacctaca ccgaactgag atacctacag cgtgagcatt gagaaagcgc   10320
cacgcttccc gaagggagaa aggcggacag gtatccggta agcggcaggg tcggaacagg   10380
agagcgcacg agggagcttc caggggggaaa cgcctggtat ctttatagtc ctgtcgggtt   10440
tcgccacctc tgacttgagc gtcgattttt gtgatgctcg tcaggggggc ggagcctatg   10500
gaaaaacgcc agcaacgcgg cctttttacg gttcctggcc ttttgctggc cttttgctca   10560
catgttcttt cctgcgttat cccctgattc tgtggataac cgtattaccg cctttgagtg   10620
agctgatac                                                           10629
```

<210> SEQ ID NO 71
<211> LENGTH: 10277
<212> TYPE: DNA
<213> ORGANISM: Artificial sequence
<220> FEATURE:
<223> OTHER INFORMATION: Plasmid pMU2690

<400> SEQUENCE: 71

```
atgtctggtt tacaaatgtt ccaaaacttg tccttgtacg gttccttggc tgaaattgat     60
acctctgaaa agttgaacga agccatggat aagttgactg ctgctcaaga acaattcaga    120
gagtacaatc aagaacaagt cgacaagatc ttcaaggctg ttgctttggc tgcttctcaa    180
aacagagttg cttttgctaa gtacgctcat gaagaaactc aaaagggtgt tttcgaagat    240
aaggtcatca agaatgaatt cgctgccgat tacatctacc ataagtactg taacgataag    300
accgccggta ttatcgaata cgatgaagct aatggtttga tggaaattgc tgaaccagtt    360
ggtccagttg ttggtattgc tccagttact aatccaacct ctaccattat ctacaagtcc    420
ttgattgcct tgaaaaccag aaactgcatc atctttttcac cacatccagg tgctcataag    480
gcttcagttt tgttgttaa ggtcttgcat caagctgctg ttaaggctgg tgctccagaa    540
aactgcattc aaattatctt cccaaagatg gacttgacca ccgaattatt gcatcatcaa    600
aagaccagat tcatttgggc tactggtggt ccaggtttgg ttcatgcttc ttatacttca    660
ggtaaaccag ctttgggtgg tggtcctggt aatgctccag ctttgattga cgaaacttgc    720
gatatgaatg aagctgttgg ttctatcgtt gtttccaaga ctttcgattg cggtatgatt    780
tgtgctactg aaaacgctgt tgttgttgtt gaatccgtct acgaaaactt cgttgctacc    840
atgaagaaac gtggcgctta ctttatgacc ccagaagaaa ctaagaaggc ttctaatttg    900
ttgttcggtg aaggtatgag attgaatgct aagctgttg gtcaaactgc taagactttg    960
gctgaaatgg ctggttttga agttccagaa acaccgttg ttttgtgtgg tgaagcttct   1020
gaagtcaagt ttgaagaacc tatggctcac gaaaagttga ctactatttt gggtatctac   1080
aaggccaagg atttcgatga tggtgttaga ttgtgcaaag aattggttac tttcggtggt   1140
aaaggtcata ctgctgtctt gtacaccaat caaaacaaca aggacagaat cgaaaagtac   1200
caaaacgaag ttccagcctt ccatatcttg gttgatatgc catcttcctt gggttgtatt   1260
ggtgatatgt acaacttcag attggctcca gccttgacta ttacttgtgg tactatgggt   1320
ggtggatctt cttctgataa cattggtcca agcacttgt tgaacatcaa gcgtgttggt   1380
atgagaagag aaaacatgtt gtggttcaag atcccaaagt ccgtttactt caagagagct   1440
attttgtctg aagccttgtc cgatttgaga gatactcaca aaagagccat catcattacc   1500
gatagaacca tgactatgtt gggtcaaacc gataagatta ttaaggcttg tgaaggtcat   1560
ggtatggtct gtactgtttta cgataaggtt gttccagatc caaccattaa gtgcattatg   1620
gaaggtgtca acgaaatgaa cgtttttcaaa ccagatttgg ctattgcttt aggtggtggt   1680
tcagctatgg atgctgctaa aatgatgaga ttattctacg aatacccaga ccaagacttg   1740
caagatattg ctactagatt cgtcgacatc agaaagagag ttgttggttg tccaaagttg   1800
ggtagattga ttaagacctt ggtctgtatt ccaactactc tggtactgg tgctgaagtt   1860
actccttttg ctgttgttac ttccgaagaa ggtagaaagt acccattggt tgattacgaa   1920
ttgactccag atatggctat cgttgatcca gaatttgctg ttggtatgcc aaagagattg   1980
acttcttgga ctggtattga tgctttgacc catgctattg aatcctacgt ttctattatg   2040
```

```
gctaccgatt ttaccagacc atactctttg agagccgttg gtttgatttt cgaatctttg    2100
tctttggcct acaacaacgg taaggatatt gaagctagag aaaagatgca taacgcttca    2160
gctattgctg gtatggcttt tgctaatgct ttcttgggtt gttgtcattc tgttgctcat    2220
caattgggtt ccgtttacca tattccacat ggtttggcta acgctttgat gttgtcccat    2280
atcattaagt acaacgctac tgattcccca gttaagatgg gtacttttcc acagtacaag    2340
tacccacaag ccatgagaca ttatgctgaa atcgccgaat tattattgcc accaacccaa    2400
gttgttaaga tgactgatgt tgacaaggtc caatacttga tcgatagagt cgaacaattg    2460
aaggccgatg ttggtattcc taagtctatc aaagaaaccg gtatggttac cgaagaagat    2520
ttcttcaaca aggttgatca agttgccatt atggccttcg atgatcaatg tactggtgct    2580
aatccaagat acccctttggt ttctgaattg aagcaattga tgatcgatgc ttggaatggt    2640
gttgttccaa agttgtaagc gatttaatct ctaattatta gttaaagttt tataagcatt    2700
tttatgtaac gaaaaataaa ttggttcata ttattactgc actgtcactt accatggaaa    2760
gaccagacaa gaagttgccg acagtctgtt gaattggcct ggttaggctt aagtctgggt    2820
ccgcttcttt acaaatttgg agaatttctc ttaaacgata tgtatattct tttcgttgga    2880
aaagatgtct tccaaaaaaa aaaccgatga attagtggaa ccaaggaaaa aaaaagaggt    2940
atccttgatt aaggaacact gtttaaacag tgtggtttcc aaaaccctga aactgcatta    3000
gtgtaataga agactagaca cctcgataca aataatggtt actcaattca aaactgccag    3060
cgaattcgac tctgcaattg ctcaagacaa gctagttgtc gtagatttct acgccacttg    3120
gtgcggtcca tgtaaaatga ttgctccaat gattgaaata aacctctttg cgggcaagct    3180
tggcactggc cgtcgtttta caacgtcgtg actgggaaaa ccctggcgtt acccaactta    3240
atcgccttgc agcacatccc cctttcgcca gctggcgtaa tagcgaagag gcccgcaccg    3300 atcgccctc ccaacagttg cgcagcctga atggcgaatg cgcctgatg cggtattttc     3360 tccttacgca tctgtgcggt atttcacacc gcataggaga tctaagctct ggcgtaatag    3420
cgaagaggcc cgcaccgatc gcccttccca acagttgcgc agcctgaatg cgaatggcg    3480 cctgatgcgg tattttctcc ttacgcatct gtgcggtatt tcacaccgca tagggtaata    3540
actgatataa ttaaattgaa gctctaattt gtgagtttag tatacatgca tttacttata    3600
atacagtttt ttagttttgc tggccgcatc ttctcaaata tgcttcccag cctgcttttc    3660
tgtaacgttc accctctacc ttagcatccc ttccctttgc aaatagtcct cttccaacaa    3720
taataatgtc agatcctgta gagaccacat catccacggt tctatactgt tgacccaatg    3780
cgtctccctt gtcatctaaa cccacaccgg gtgtcataat caaccaatcg taaccttcat    3840
ctcttccacc catgtctctt tgagcaataa agccgataac aaaatctttg tcgctcttcg    3900
caatgtcaac agtacccttg gtatattctc agtagatag ggagcccttg catgacaatt    3960
ctgctaacat caaaaggcct ctaggttcct ttgttacttc ttctgccgcc tgcttcaaac    4020
cgctaacaat acctgggccc accacaccgt gtgcattcgt aatgtctgcc cattctgcta    4080
ttctgtatac acccgcagag tactgcaatt tgactgtatt accaatgtca gcaaattttc    4140
tgtcttcgaa gagtaaaaaa ttgtacttgg cggataatgc ctttagcggc ttaactgtgc    4200
cctccatgga aaaatcagtc aagatatcca catgtgtttt tagtaaacaa attttgggac    4260
ctaatgcttc aactaactcc agtaattcct tggtggtacg aacatccaat gaagcacaca    4320
agtttgtttg cttttcgtgc atgatattaa atagcttggc agcaacagga ctaggatgag    4380
tagcagcacg ttccttatat gtagctttcg acatgattta tcttcgtttc ggttttttgtt    4440
```

```
ctgtgcagtt gggttaagaa tactgggcaa tttcatgttt cttcaacact acatatgcgt    4500
atatatacca atctaagtct gtgctccttc cttcgttctt ccttctgttc ggagattacc    4560
gaatcaaaaa aatttcaaag aaaccgaaat caaaaaaaag aataaaaaaa aaatgatgaa    4620
ttgaaaagct cttgttaccc atcattgaat tttgaacatc cgaacctggg agttttccct    4680
gaaacagata gtatatttga acctgtataa taatatatag tctagcgctt acggaagac    4740 aatgtatgta tttcggttcc tgagaaaact attgcatcta ttgcataggt aatcttgcac    4800
gtcgcatccc cggttcattt tctgcgtttc catcttgcac ttcaatagca tatctttgtt    4860
aacgaagcat ctgtgcttca ttttgtagaa caaaaatgca acgcgagagc gctaattttt    4920
caaacaaaga atctgagctg cattttaca gaacagaaat gcaacgcgaa agcgctattt    4980
taccaacgaa gaatcgtgtgc ttcattttg taaaacaaaa atgcaacgcg agagcgctaa    5040
tttttcaaac aaagaatctg agctgcattt ttacagaaca gaaatgcaac gcgagagcgc    5100
tattttacca caaagaatc tatacttctt ttttgttcta caaaatgca tcccgagagc    5160 gctattttc taacaaagca tcttagatta ctttttttct cctttgtgcg ctctataatg    5220
cagtctcttg ataactttt gcactgtagg tccgttaagg ttagaagaag gctactttgg    5280
tgtctatttt ctcttccata aaaaaagcct gactccactt cccgcgttta ctgattacta    5340
gcgaagctgc gggtgcattt tttcaagata aaggcatccc cgattatatt ctataccgat    5400
gtggattgcg catactttgt gaacagaaag tgatagcgtt gatgattctt cattggtcag    5460
aaaattatga acggtttctt ctattttgtc tctatatact acgtatagga atgtttaca    5520 ttttcgtatt gttttcgatt cactctatga atagttctta ctacaatttt tttgtctaaa    5580
gagtaatact agagataaac ataaaaaatg tagaggtcga gtttagatgc aagttcaagg    5640
agcgaaaggt ggatgggtag gttatatagg gatatagcac agagatatat agcaaagaga    5700
tacttttgag caatgtttgt ggaagcggta ttcgcaatat tttagtagct cgttacagtc    5760
cggtgcgttt ttggttttt gaaagtgcgt cttcagagcg cttttggttt tcaaaagcgc    5820
tctgaagttc ctatactttc tagctagaga ataggaactt cggaatagga acttcaaagc    5880
gtttccgaaa acgagcgctt ccgaaaatgc aacgcgagct gcgcacatac agctcactgt    5940
tcacgtcgca cctatatctg cgtgttgcct gtatatatat atacatgaga gaacggcat    6000 agtgcgtgtt tatgcttaaa tgcgttatgg tgcactctca gtacaatctg ctctgatgcc    6060
gcatagttaa gccagccccg acacccgcca acacccgctg acgcgccctg acgggcttgt    6120
ctgctcccgg catccgctta cagacaagct gtgaccgtct ccgggagctg catgtgtcag    6180
aggttttcac cgtcatcacc gaaacgcgcg agacgaaagg cctcgtgat acgcctattt    6240 ttataggtta atgtcatgat aataatggtt tcttagacgt caggtggcac ttttcgggga    6300
aatgtgcgcg gaacccctat ttgtttattt ttctaaatac attcaaatat gtatccgctc    6360
atgagacaat aaccctgata aatgcttcaa taatattgaa aaggaagag tatgagtatt    6420 caacatttcc gtgtcgccct tattcccttt tttgcggcat tttgccttcc tgttttgct    6480 cacccagaaa cgctggtgaa agtaaaagat gctgaagatc agttgggtgc acgagtgggt    6540
tacatcgaac tggatctcaa cagcggtaag atccttgaga gttttcgccc cgaagaacgt    6600
tttccaatga tgagcacttt taaagttctg ctatgtggcg cggtattatc ccgtattgac    6660
gccgggcaag agcaactcgg tcgccgcata cactattctc agaatgactt ggttgagtac    6720
tcaccagtca cagaaaagca tcttacggat ggcatgacag taagagaatt atgcagtgct    6780
```

```
gccataacca tgagtgataa cactgcggcc aacttacttc tgacaacgat cggaggaccg   6840
aaggagctaa ccgcttttt gcacaacatg ggggatcatg taactcgcct tgatcgttgg   6900
gaaccggagc tgaatgaagc cataccaaac gacgagcgtg acaccacgat gcctgtagca   6960
atggcaacaa cgttgcgcaa actattaact ggcgaactac ttactctagc ttcccggcaa   7020
caattaatag actggatgga ggcggataaa gttgcaggac cacttctgcg ctcggccctt   7080
ccggctggct ggtttattgc tgataaatct ggagccggtg agcgtgggtc tcgcggtatc   7140
attgcagcac tggggccaga tggtaagccc tcccgtatcg tagttatcta cacgacgggg   7200
agtcaggcaa ctatggatga acgaaataga cagatcgctg agataggtgc ctcactgatt   7260
aagcattggt aactgtcaga ccaagtttac tcatatatac tttagattga tttaaaactt   7320
catttttaat ttaaaaggat ctaggtgaag atccttttg ataatctcat gaccaaaatc   7380
ccttaacgtg agttttcgtt ccactgagcg tcagaccccg tagaaagat caaaggatct   7440 tcttgagatc ctttttttct gcgcgtaatc tgctgcttgc aaacaaaaaa accaccgcta   7500
ccagcggtgg tttgtttgcc ggatcaagag ctaccaactc ttttccgaa ggtaactggc   7560 ttcagcagag cgcagatacc aaatactgtc cttctagtgt agccgtagtt aggccaccac   7620
ttcaagaact ctgtagcacc gcctacatac ctcgctctgc taatcctgtt accagtggct   7680
gctgccagtg gcgataagtc gtgtcttacc gggttggact caagacgata gttaccggat   7740
aaggcgcagc ggtcgggctg aacggggggt cgtgcacac agcccagctt ggagcgaacg   7800
acctacaccg aactgagata cctacagcgt gagcattgag aaagcgccac gcttcccgaa   7860
gggagaaagg cggacaggta tccggtaagc ggcagggtcg aacaggaga gcgcacgagg   7920 gagcttccag ggggaaacgc ctggtatctt tatagtcctg tcgggtttcg ccacctctga   7980
cttgagcgtc gatttttgtg atgctcgtca ggggggcgga gcctatggaa aaacgccagc   8040
aacgcggcct ttttacggtt cctggccttt tgctggcctt ttgctcacat gttctttcct   8100
gcgttatccc ctgattctgt ggataaccgt attaccgcct ttgagtgagc tgataccgct   8160
cgccgcagcc gaacgaccga gcgcagcgag tcagtgagcg aggaagcgga agagcgccca   8220
atacgcaaac cgcctctccc cgcgcgttgg ccgattcatt aatccaggat cccaattaat   8280
gtgagttacc tcactcatta ggcaccccag gctttacact ttatgcttcc ggctcgtatg   8340
ttgtgtggaa ttgtgagcgg ataacaattt cacacaggaa acagctatga ccatgattac   8400
gaattaattc gagctcggta cccggggatc gatccactag agatctgttt agcttgcctc   8460
gtccccgccg ggtcacccgg ccagcgacat ggaggcccag aatacccctcc ttgacagtct   8520 tgacgtgcgc agctcagggg catgatgtga ctgtcgcccg tacatttagc ccatacatcc   8580
ccatgtataa tcatttgcat ccatacattt tgatggccgc acggcgcgaa gcaaaaatta   8640
cggctcctcg ctgcagacct gcgagcaggg aaacgctccc ctcacagacg cgttgaattg   8700
tccccacgcc gcgcccctgt agagaaatat aaaaggttag gatttgccac tgaggttctt   8760
ctttcatata cttcctttta aaatcttgct aggatacagt tctcacatca catccgaaca   8820
taaacaacca tggccgacca agcgacgccc aacctgccat cacgagattt cgattccacg   8880
gccgccttct atgaaaggtt gggcttcgga atcgttttcc gggacgccgg ctggatgatc   8940
ctccagcgcg gggatctcaa gctggagttc ttcgcccacc ccgggctcga tcccctcgcg   9000
agttggttca gctgctgcct gaggctggac gacctcgcgg agttctaccg gcagtgcaaa   9060
tccgtcggca tccaggaaac cagcagcggc tatccgcgca tccatgcccc gaactgcag   9120 gagtggggag gcacgatggc cgctttggtc gacccggacg ggacgctcct gcgcctgata   9180
```

```
cagaacgaat tgcttgcagg catctcatga tcagtactga caataaaaag attcttgttt      9240
tcaagaactt gtcatttgta tagttttttt atattgtagt tgttctattt taatcaaatg      9300
ttagcgtgat ttatatttt tttcgcctcg acatcatctg cccagatgcg aagttaagtg       9360
cgcagaaagt aatatcatgc gtcaatcgta tgtgaatgct ggtcgctata ctgctgtcga      9420
ttcgatacta acgccgccat ccagtgtcga aaacgagctc tcgagaaccc ttaatataac      9480
ttcgtataat gtatgctata cgaagttatt aggtgatatc agatccacga ttttttctta     9540
aaccgtggaa tatttcggat atccttttgt tgtttccggg tgtacaatat ggacttcctc      9600 tttctggca accaaaccca tacatcggga ttcctataat accttcgttg gtctccctaa       9660
catgtaggtg gcggagggga gatatacaat agaacagata ccagacaaga cataatgggc     9720
taaacaagac tacaccaatt acactgcctc attgatggtg gtacataacg aactaatact     9780
gtagccctag acttgatagc catcatcata tcgaagtttc actacccttt ttccatttgc     9840
catctattga agtaataata ggcgcatgca acttcttttc ttttttttc ttttctctct      9900 cccccgttgt tgtctcacca tatccgcaat gacaaaaaaa tgatggaaga cactaaagga    9960
aaaaattaac gacaaagaca gcaccaacag atgtcgttgt tccagagctg atgagggta     10020 tctcgaagca cacgaaactt tttccttcct tcattcacgc acactactct ctaatgagca    10080
acggtatacg gccttccttc cagttacttg aatttgaaat aaaaaaaagt ttgctgtctt    10140
gctatcaagt ataaatagac ctgcaattat taatcttttg tttcctcgtc attgttctcg    10200 ttcccttct tccttgtttc tttttctgca caatatttca agctatacca agcatacaat     10260
caactatctc atataca                                                   10277

<210> SEQ ID NO 72
<211> LENGTH: 10554
<212> TYPE: DNA
<213> ORGANISM: Artificial sequence
<220> FEATURE:
<223> OTHER INFORMATION: Plasmid pMU2691

<400> SEQUENCE: 72
atgtctggtt tacaaatgtt ccaaaacttg tccttgtacg gttccttggc tgaaattgat       60
acctctgaaa agttgaacga agccatggat aagttgactg ctgctcaaga acaattcaga      120
gagtacaatc aagaacaagt cgacaagatc ttcaaggctg ttgctttggc tgcttctcaa      180
aacagagttg cttttgctaa gtacgctcat gaagaaactc aaaagggtgt tttcgaagat      240
aaggtcatca agaatgaatt cgctgccgat tacatctacc ataagtactg taacgataag      300
accgccggta ttatcgaata cgatgaagct aatggtttga tggaaattgc tgaaccagtt      360
ggtccagttt tggtattgc tccagttact aatccaacct ctaccattat ctacaagtcc       420
ttgattgcct tgaaaaccag aaactgcatc atcttttcac cacatccagg tgctcataag      480
gcttcagttt ttgttgttaa ggtcttgcat caagctgctg ttaaggctgg tgctccagaa      540
aactgcattc aaattatctt cccaaagatg gacttgacca ccgaattatt gcatcatcaa      600
aagaccagat tcatttgggc tactggtggt ccaggtttgg ttcatgcttc ttatacttca      660
ggtaaaccag ctttgggtgg tggtcctggt aatgctccag ctttgattga cgaaacttgc      720
gatatgaatg aagctgttgg ttctatcgtt gttccaagac ttcgattg cggtatgatt         780 tgtgctactg aaaacgctgt tgttgttgtt gaatccgtct acgaaaactt cgttgctacc      840
atgaagaaac gtggcgctta ctttatgacc ccagaagaaa ctaagaaggc ttctaatttg      900
```

```
ttgttcggtg aaggtatgag attgaatgct aaagctgttg gtcaaactgc taagactttg    960
gctgaaatgg ctggttttga agttccagaa acaccgttg ttttgtgtgg tgaagcttct   1020
gaagtcaagt ttgaagaacc tatggctcac gaaaagttga ctactatttt gggtatctac   1080
aaggccaagg atttcgatga tggtgttaga ttgtgcaaag aattggttac tttcggtggt   1140
aaggtcata ctgctgtctt gtacaccaat caaaacaaca aggacagaat cgaaaagtac   1200
caaaacgaag ttccagcctt ccatatcttg gttgatatgc catcttcctt gggttgtatt   1260
ggtgatatgt acaacttcag attggctcca gccttgacta ttacttgtgg tactatgggt   1320
ggtggatctt cttctgataa cattggtcca agcacttgt tgaacatcaa gcgtgttggt   1380
atgagaagag aaaacatgtt gtggttcaag atcccaaagt ccgtttactt caagagagct   1440
attttgtctg aagccttgtc cgatttgaga gatactcaca aaagagccat catcattacc   1500
gatagaacca tgactatgtt gggtcaaacc gataagatta ttaaggcttg tgaaggtcat   1560
ggtatggtct gtactgttta cgataaggtt gttccagatc caaccattaa gtgcattatg   1620
gaaggtgtca acgaaatgaa cgttttcaaa ccagatttgg ctattgcttt aggtggtggt   1680
tcagctatgg atgctgctaa aatgatgaga ttattctacg aatacccaga ccaagacttg   1740
caagatattg ctactagatt cgtcgacatc agaaagagag ttgttggttg tccaaagttg   1800
ggtagattga ttaagacctt ggtctgtatt ccaactactt ctggtactgg tgctgaagtt   1860
actccttttg ctgttgttac ttccgaagaa ggtagaaagt acccattggt tgattacgaa   1920
ttgactccag atatggctat cgttgatcca gaatttgctg ttggtatgcc aaagagattg   1980
acttcttgga ctggtattga tgctttgacc catgctattg aatcctacgt ttctattatg   2040
gctaccgatt ttaccagacc atactctttg agagccgttg gtttgatttt cgaatctttg   2100
tctttggcct acaacaacgg taaggatatt gaagctagag aaaagatgca taacgcttca   2160
gctattgctg gtatggcttt tgctaatgct ttcttgggtt gttgtcattc tgttgctcat   2220
caattgggtt ccgtttacca tattccacat ggttttggcta acgctttgat gttgtcccat   2280
atcattaagt acaacgctac tgattcccca gttaagatgg gtacttttcc acagtacaag   2340
tacccacaag ccatgagaca ttatgctgaa atcgccgaat tattattgcc accaaccccaa   2400
gttgttaaga tgactgatgt tgacaaggtc aatacttga tcgatagagt cgaacaattg   2460
aaggccgatg ttggtattcc taagtctatc aaagaaaccg gtatggttac cgaagaagat   2520
ttcttcaaca aggttgatca agttgccatt atggccttcg atgatcaatg tactggtgct   2580
aatccaagat acccttttggt ttctgaattg aagcaattga tgatcgatgc ttggaatggt   2640
gttgttccaa agttgtaaga gattatactt aaactagcac tgattttttt aaggctaatg   2700
gctactaata ctttaataga tgatcttcat actttttat ttaacgattt ttaatgatgt   2760
ttttatttgt accactcatt tatctagatt ttttaatac tgatcaaatc ttacggactc   2820
gacgttaaaa agttcctaca tacgtctggt acttgaaacg ctgcttcgag gtattgacac   2880
tataagaata cgatccaaat acttacaccg catgtaaaaa tatgccgaca atatgaatac   2940
ttgttgatga atgatatttg attttaatcc ggcaatttac ctcctttata taatccaata   3000
attgttgata ttagtggtt aggttgcagt actaataaga attaagacaa atattcttct   3060
actatataaa aggtgcaaac aaaacacacg ccgatcggcc atactaaaca agaccaacat   3120
aataatggtg gaaccattta ctgtatttc aatgtaacat ttaaatccgc ggtaaacctc   3180
tttgcgggca agcttggcac tggccgtcgt tttacaacgt cgtgactggg aaaaccctgg   3240
cgttacccaa cttaatcgcc ttgcagcaca tccccctttc gccagctggc gtaatagcga   3300
```

```
agaggcccgc accgatcgcc cttcccaaca gttgcgcagc ctgaatggcg aatggcgcct   3360
gatgcggtat tttctcctta cgcatctgtg cggtatttca caccgcatag gagatctaag   3420
ctctggcgta atagcgaaga ggcccgcacc gatcgccctt cccaacagtt gcgcagcctg   3480
aatggcgaat ggcgcctgat gcggtatttt ctccttacgc atctgtgcgg tatttcacac   3540
cgcatagggt aataactgat ataattaaat tgaagctcta atttgtgagt ttagtataca   3600
tgcatttact tataatacag ttttttagtt ttgctggccg catcttctca aatatgcttc   3660
ccagcctgct tttctgtaac gttcaccctc taccttagca tcccttccct ttgcaaatag   3720
tcctcttcca acaataataa tgtcagatcc tgtagagacc acatcatcca cggttctata   3780
ctgttgaccc aatgcgtctc ccttgtcatc taaacccaca ccgggtgtca taatcaacca   3840
atcgtaacct tcatctcttc cacccatgtc tctttgagca ataaagccga taacaaaatc   3900
tttgtcgctc ttcgcaatgt caacagtacc cttagtatat tctccagtag atagggagcc   3960
cttgcatgac aattctgcta acatcaaaag gcctctaggt tcctttgtta cttcttctgc   4020
cgcctgcttc aaaccgctaa caatacctgg gcccaccaca ccgtgtgcat tcgtaatgtc   4080
tgcccattct gctattctgt atacacccgc agagtactgc aatttgactg tattaccaat   4140
gtcagcaaat tttctgtctt cgaagagtaa aaaattgtac ttggcggata atgcctttag   4200
cggcttaact gtgccctcca tggaaaaatc agtcaagata tccacatgtg tttttagtaa   4260
acaaattttg ggacctaatg cttcaactaa ctccagtaat tccttggtgg tacgaacatc   4320
caatgaagca cacaagtttg tttgcttttc gtgcatgata ttaaatagct tggcagcaac   4380
aggactagga tgagtagcag cacgttcctt atatgtagct ttcgacatga tttatcttcg   4440
tttcggtttt tgttctgtgc agttgggtta agaatactgg gcaatttcat gtttcttcaa   4500
cactacatat gcgtatatat accaatctaa gtctgtgctc cttccttcgt tcttccttct   4560
gttcggagat taccgaatca aaaaaatttc aaagaaaccg aaatcaaaaa aaagaataaa   4620
aaaaaaatga tgaattgaaa agctcttgtt acccatcatt gaattttgaa catccgaacc   4680
tgggagtttt ccctgaaaca gatagtatat ttgaacctgt ataataatat atagtctagc   4740
gctttacgga agacaatgta tgtatttcgg ttcctggaga aactattgca tctattgcat   4800
aggtaatctt gcacgtcgca tccccggttc attttctgcg tttccatctt gcacttcaat   4860
agcatatctt tgttaacgaa gcatctgtgc ttcattttgt agaacaaaaa tgcaacgcga   4920
gagcgctaat ttttcaaaca aagaatctga gctgcatttt tacagaacag aaatgcaacg   4980
cgaaagcgct attttaccaa cgaagaatct gtgcttcatt tttgtaaaac aaaaatgcaa   5040
cgcgagagcg ctaatttttc aaacaaagaa tctgagctgc attttacag aacagaaatg   5100 caacgcgaga gcgctatttt accaacaaag aatctatact ctttttttgt tctacaaaaa   5160
tgcatcccga gagcgctatt tttctaacaa agcatcttag attactttt ttctcctttg   5220 tgcgctctat aatgcagtct cttgataact ttttgcactg taggtccgtt aaggttagaa   5280
gaaggctact ttggtgtcta ttttctcttc cataaaaaaa gcctgactcc acttcccgcg   5340
tttactgatt actagcgaag ctgcgggtgc attttttcaa gataaaggca tccccgatta   5400
tattctatac cgatgtggat tgcgcatact tgtgaacag aaagtgatag cgttgatgat   5460
tcttcattgg tcagaaaatt atgaacggtt tcttctattt tgtctctata tactacgtat   5520
aggaaatgtt tacattttcg tattgttttc gattcactct atgaatagtt cttactacaa   5580
tttttttgtc taaagagtaa tactagagat aaacataaaa aatgtagagg tcgagtttag   5640
```

```
atgcaagttc aaggagcgaa aggtggatgg gtaggttata tagggatata gcacagagat    5700
atatagcaaa gagatacttt tgagcaatgt ttgtggaagc ggtattcgca atattttagt    5760
agctcgttac agtccggtgc gttttttggtt ttttgaaagt gcgtcttcag agcgcttttg    5820
gttttcaaaa gcgctctgaa gttcctatac tttctagcta gagaatagga acttcggaat    5880
aggaacttca aagcgtttcc gaaaacgagc gcttccgaaa atgcaacgcg agctgcgcac    5940
atacagctca ctgttcacgt cgcacctata tctgcgtgtt gcctgtatat atatatacat    6000
gagaagaacg gcatagtgcg tgtttatgct taaatgcgtt atggtgcact ctcagtacaa    6060
tctgctctga tgccgcatag ttaagccagc cccgacaccc gccaacaccc gctgacgcgc    6120
cctgacgggc ttgtctgctc ccggcatccg cttacagaca agctgtgacc gtctccggga    6180
gctgcatgtg tcagaggttt tcaccgtcat caccgaaacg cgcgagacga aagggcctcg    6240
tgatacgcct atttttatag gttaatgtca tgataataat ggtttcttag acgtcaggtg    6300
gcacttttcg gggaaatgtg cgcggaaccc ctatttgttt attttttctaa atacattcaa    6360 atatgtatcc gctcatgaga caataaccct gataaatgct tcaataatat tgaaaaagga    6420
agagtatgag tattcaacat ttccgtgtcg cccttattcc cttttttgcg gcattttgcc    6480
ttcctgtttt tgctcaccca gaaacgctgg tgaaagtaaa agatgctgaa gatcagttgg    6540
gtgcacgagt gggttacatc gaactggatc tcaacagcgg taagatcctt gagagttttc    6600
gccccgaaga acgttttcca atgatgagca cttttaaagt tctgctatgt ggcgcggtat    6660
tatcccgtat tgacgccggg caagagcaac tcggtcgccg catacactat tctcagaatg    6720
acttggttga gtactcacca gtcacagaaa agcatcttac ggatggcatg acagtaagag    6780
aattatgcag tgctgccata accatgagtg ataacactgc ggccaactta cttctgacaa    6840
cgatcggagg accgaaggag ctaaccgctt ttttgcacaa catgggggat catgtaactc    6900
gccttgatcg ttgggaaccg gagctgaatg aagccatacc aaacgacgag cgtgacacca    6960
cgatgcctgt agcaatggca acaacgttgc gcaaactatt aactggcgaa ctacttactc    7020
tagcttcccg gcaacaatta atagactgga tggaggcgga taaagttgca ggaccacttc    7080
tgcgctcggc ccttccggct ggctggttta ttgctgataa atctggagcc ggtgagcgtg    7140
ggtctcgcgg tatcattgca gcactggggc cagatggtaa gccctcccgt atcgtagtta    7200
tctacacgac ggggagtcag gcaactatgg atgaacgaaa tagacagatc gctgagatag    7260
gtgcctcact gattaagcat tggtaactgt cagaccaagt ttactcatat atactttaga    7320
ttgatttaaa acttcatttt taatttaaaa ggatctaggt gaagatcctt tttgataatc    7380
tcatgaccaa aatcccttaa cgtgagtttt cgttccactg agcgtcagac cccgtagaaa    7440
agatcaaagg atcttcttga gatcctttt ttctgcgcgt aatctgctgc ttgcaaacaa    7500
aaaaaccacc gctaccagcg gtggtttgtt tgccggatca gagctacca actctttttc    7560 cgaaggtaac tggcttcagc agagcgcaga taccaaatac tgtccttcta gtgtagccgt    7620
agttaggcca ccacttcaag aactctgtag caccgcctac atacctcgct ctgctaatcc    7680
tgttaccagt ggctgctgcc agtggcgata agtcgtgtct taccgggttg gactcaagac    7740
gatagttacc ggataaggcg cagcggtcgg gctgaacggg gggttcgtgc acacagccca    7800
gcttggagcg aacgacctac accgaactga gatacctaca gcgtgagcat tgagaaagcg    7860
ccacgcttcc cgaagggaga aaggcggaca ggtatccggt aagcggcagg gtcggaacag    7920
gagagcgcac gagggagctt ccagggggaa acgcctggta tctttatagt cctgtcgggt    7980
ttcgccacct ctgacttgag cgtcgatttt tgtgatgctc gtcagggggg cggagcctat    8040
```

-continued

```
ggaaaaacgc cagcaacgcg gccttttac ggttcctggc cttttgctgg ccttttgctc    8100
acatgttctt tcctgcgtta tcccctgatt ctgtggataa ccgtattacc gcctttgagt    8160
gagctgatac cgctcgccgc agccgaacga ccgagcgcag cgagtcagtg agcgaggaag    8220
cggaagagcg cccaatacgc aaaccgcctc tccccgcgcg ttggccgatt cattaatcca    8280
ggatcccaat taatgtgagt tacctcactc attaggcacc ccaggcttta cactttatgc    8340
ttccggctcg tatgttgtgt ggaattgtga gcggataaca atttcacaca ggaaacagct    8400
atgaccatga ttacgaatta attcgagctc ggtacccggg gatcgatcca ctagagatct    8460
gtttagcttg cctcgtcccc gccgggtcac ccggccagcg catggaggcc cagaatacc    8520
ctccttgaca gtcttgacgt gcgcagctca ggggcatgat gtgactgtcg cccgtacatt    8580
tagcccatac atccccatgt ataatcattt gcatccatac attttgatgg ccgcacggcg    8640
cgaagcaaaa attacggctc ctcgctgcag acctgcgagc agggaaacgc tcccctcaca    8700
gacgcgttga attgtcccca cgccgcgccc ctgtagagaa atataaaagg ttaggatttg    8760
ccactgaggt tcttctttca tatacttcct tttaaaatct tgctaggata cagttctcac    8820
atcacatccg aacataaaca accatggccg accaagcgac gcccaacctg ccatcacgag    8880
atttcgattc cacggccgcc ttctatgaaa ggttgggctt cggaatcgtt ttccgggacg    8940
ccggctggat gatcctccag cgcggggatc tcaagctgga gttcttcgcc caccccgggc    9000
tcgatcccct cgcgagttgg ttcagctgct gcctgaggct ggacgacctc gcggagttct    9060
accggcagtg caaatccgtc ggcatccagg aaaccagcag cggctatccg cgcatccatg    9120
cccccgaact gcaggagtgg ggaggcacga tggccgcttt ggtcgacccg gacgggacgc    9180
tcctgcgcct gatacagaac gaattgcttg caggcatctc atgatcagta ctgacaataa    9240
aaagattctt gttttcaaga acttgtcatt tgtatagttt ttttatattg tagttgttct    9300
atttttaatca aatgttagcg tgatttatat ttttttcgc ctcgacatca tctgcccaga    9360
tgcgaagtta agtgcgcaga aagtaatatc atgcgtcaat cgtatgtgaa tgctggtcgc    9420
tatactgctg tcgattcgat actaacgccg ccatccagtg tcgaaaacga gctctcgaga    9480
acccttaata taacttcgta taatgtatgc tatacgaagt tattaggtga tatcagatcc    9540
actagtgttt aaacacctca tctataattt ttaccctgat ctaactaact ttggcatgcc    9600
tggttcaatc tacgggttac agtcatcgtt gaaaacgatg gaaaacatg tcgagattcc    9660
tcaatccata caccattata gtccgtttta tcagcttcca ctaattttt aaatctcagt    9720
ttcttcttga aatttagcat cgtgcatggg atagcggcta gtaaaaaga aaattaatat    9780
ctcattaaca aagttattgt acataatccg gtacaatatt cttcaatgta ctctctaata    9840
tcgagcacac tggcaatatt catgcacaca ttcgcctaat gctgacgaat gcttaatcag    9900
tgcaattact gccaccctct tgatatgtgg gctaaatcct ttaggacctg taaaaaatgc    9960
aatcacgttt tcacattttt ttttttcttg cggaattgcg gaatttccca gttggcagcg   10020
ttatccgatt tgagatcgac ttgcatcaac ctttgaaaaa tataaggatg agaaagtgaa   10080
atcggttttt ttttccatt gtcgtcatca acatgatttt ttaaataaat aaatacgatt   10140
ttttattttt tttcccttct ttgttttgt ttgcttatt cccatcttca ttattaaatt   10200
cttccgctct taataaagga gttttttat tatcttcttg tgtaatcatc cttttctttt   10260
aattttcttc cttttctttt tctctttact ggttttttta cttctttatt ctcaaccatc   10320
taaagaatat tattgctttc taccaataaa atctgttaat tctatttgga ttgtcgtcta   10380
```

```
ctcaagtctc gcctagtaaa taaacgataa acaaatttga agtaagaata acaatatagg   10440
gagagaaatt tttctatttt taatttcgaa acaggtacca aaaaatctaa gttcacttta   10500
gcactatttg ggaaagcttt tatataaaaa atctgaaaca aaatcatatc aaag         10554
```

<210> SEQ ID NO 73
<211> LENGTH: 10761
<212> TYPE: DNA
<213> ORGANISM: Artificial sequence
<220> FEATURE:
<223> OTHER INFORMATION: Plasmid pMU2687

<400> SEQUENCE: 73

```
atgatgtcat cttcattggt ttctggtaag agagttgctg ttccttcagc tgccaagcca     60
tgtgctgctg ttccattgcc aagagttgct ggtagaagaa ctgctgctag agttgtttgt    120
gaagctgctc catctggtgc tgctccagct tctccaaaag ctgaagctgc tgctccagtt    180
gctgctgccc ctgccactcc acatgctgaa gttaagaaag aaagagcacc agctactgac    240
gaagctttga ctgaattgaa agccttgttg aaaagagccc aaactgctca agctcaatac    300
tctacttaca cccaagaaca agtcgacgaa attttagag ctgctgctga agctgcaaat    360
gctgctagaa ttccattggc taaaatggct gttgaagaaa ctagaatggg tgttgctgaa    420
gataaggttg ttaagaatca tttcgcctcc gaattcatct acaacaagta caaacatacc    480
aagacctgcg tgttattga acatgatcca gctggtggta ttcaaaaagt tgctgaacca    540
gttggtgtta ttgctggtat agttccaact actaatccaa cttccaccgc tattttcaag    600
tctttgttgt ccttgaaaac cagaaacgct ttggttttgt gtccacatcc aagagctgct    660
aaatctacta ttgctgctgc aagaatcgta agagatgcag ctgttgctgc tggtgctcca    720
ccaaatatta tttcttgggt tgaaaccccca tccttgccag tttctcaagc tttgatgcaa    780
gctactgaaa tcaacttgat tttggctact ggtggtccag ctatggttag agctgcttat    840
tcttctggta atccatcttt gggtgttggt gctggtaata ctccagcttt gattgacgaa    900
actgctgatg ttgctatggc tgtttcttct attttgttgt ccaagacctt cgataacggt    960
gttatttgtg cttctgaaca atccgttgtt gttgttgcta agcttacga tgctgttaga   1020 accgaattcg ttagaagagg tgcttacttc ttgaccgaag atgataaggt caaagttaga   1080
gctggtgttg ttgttgacgg taaattgaat ccaaacatcg ttggtcaatc cattccaaaa   1140
ttggctgctt tgttcggtat caaagttcca caaggtacta aggttttgat cggtgaagtt   1200
gaaaagatcg gtccagaaga agctttgtct caagaaaagt tgcccaat tttggctatg   1260 tatagagcac cagattacga tcatggtgtt aagatggctt gcgaattgat tatgtatggt   1320
ggtgcaggtc atacttctgt cttgtataca aacccattga caacgccca catccaacaa   1380 tatcaatctg ctgttaagac cgtcagaatc ttgattaaca caccagcttc tcaaggtgct   1440
attggtgact tgtacaactt tcatttggat ccatctttga ccttgggttg tggtacttgg   1500
ggttctactt ctgtttctac taatgttggt ccacaacact tgttgaacat taagactgtt   1560
accgctagaa gagaaaacat gttgtggttt agagtcccac caaagatcta cttttaaggt   1620
ggttgtttgg aagttgcttt gacagatttg agagtaagt ctagagcttt catcgttact   1680
gataagcctt tgttcgatat gggttacgct gataaggtta cccatatttt ggattccatc   1740
aacgttcacc accaagtttt ctatcatgtt actccagatc caaccttggc ttgtattgaa   1800
gctgtttgaa aagaaatctt ggaattcaag ccagacgtca ttattgctt gggtggtggt   1860 tctccaatgg atgctgctaa aattatgtgg ttgatgtacg aatgcccaga tacaagattt   1920
```

```
gatggtttgg ctatgagatt catggacatc agaaagagag tttacgaagt tccagaattg    1980
ggtaaaaagg ctaccatggt atgtattcca actacttctg gtactggttc tgaagttact    2040
ccattctctg ttgttaccga cgaaagattg ggtgctaaat atccattagc tgattacgct    2100
ttgaccccat ctatggctat agttgatcca caattggtct tgaacatgcc aaaaaaattg    2160
actgcttggg gtggtattga tgctttgact catgctttgg aatcctacgt ttctatttgt    2220
gctaccgatt acaccaaggg tttgtctaga gaagctattt ccttgttgtt caagtacttg    2280
ccaagagctt acgctaatgg ttctaatgat tacttggcca gagaaaaggt tcattacgct    2340
gctacaattg ctggtatggc ttttgctaat gccttcttgg gtatttgtca ttctatggct    2400
cataagttgg gtgctgctta tcatgttcca catggtttag ctaacgctgc tttgatttcc    2460
catgtcatta gatacaacgc tactgatatg ccagctaaac aagctgcttt tccacaatat    2520
gaatacccaa ctgccaagca agattatgct gatttggcta atatgttggg tttgggtggt    2580
aacactgttg acgaaaaggt tatcaagttg atcgaagccg tcgaagaatt gaaagctaag    2640
gttgatattc caccaaccat caaagaaatc ttcaacgatc caaaggttga tgctgatttc    2700
ttggctaatg ttgatgcttt ggctgaagat gctttcgatg atcaatgtac tggtgctaat    2760
ccaagatatc cattgatggc tgacttgaag caattatact tggatgctca tgctgctcca    2820
attttgccag ttaagacttt ggaattcttc tccaaaatca actaagagat tatacttaaa    2880
ctagcactga ttttttttaag gctaatggct actaatactt taatagatga tcttcatact    2940
tttttattta acgattttta atgatgtttt tattgtacc actcatttat ctagatttt     3000
ttaatactga tcaaatctta cggactcgac gttaaaaagt tcctacatac gtctggtact    3060
tgaaacgctg cttcgaggta ttgacactat aagaatacga tccaaatact tacaccgcat    3120
gtaaaaatat gccgacaata tgaatacttg ttgatgaatg atatttgatt ttaatccggc    3180
aatttacctc ctttatataa tccataatt gttgataatt agtggttagg ttgcagtact    3240
aataagaatt aagacaaata ttcttctact atataaaagg tgcaaacaaa acacacgccg    3300
atcggccata ctaaacaaga ccaacataat aatggtggaa ccatttactg tattttcaat    3360
gtaacattta aatccgcggt aaacctcttt gcgggcaagc ttggcactgg ccgtcgtttt    3420
acaacgtcgt gactgggaaa accctggcgt tacccaactt aatcgccttg cagcacatcc    3480
ccctttcgcc agctggcgta atagcgaaga ggcccgcacc gatcgccctt cccaacagtt    3540
gcgcagcctg aatggcgaat ggcgcctgat gcggtatttt ctccttacgc atctgtgcgg    3600
tatttcacac cgcataggag atctaagctc tggcgtaata gcgaagaggc ccgcaccgat    3660
cgcccttccc aacagttgcg cagcctgaat ggcgaatggc gcctgatgcg gtattttctc    3720
cttacgcatc tgtgcggtat ttcacaccgc ataggtaat aactgatata attaaattga    3780
agctctaatt tgtgagttta gtatacatgc atttacttat aatacagttt tttagttttg    3840
ctggccgcat cttctcaaat atgcttccca gcctgctttt ctgtaacgtt caccctctac    3900
cttagcatcc cttcccttttg caaatagtcc tcttccaaca ataataatgt cagatcctgt    3960
agagaccaca tcatccacgg ttctatactg ttgacccaat gcgtctccct tgtcatctaa    4020
acccacaccg ggtgtcataa tcaaccaatc gtaaccttca tctcttccac ccatgtctct    4080
ttgagcaata aagccgataa caaaatcttt gtcgctcttc gcaatgtcaa cagtacccttt   4140
agtatattct ccagtagata gggagcccctt gcatgcaact tctgctaaca tcaaaaggcc   4200
tctaggttcc tttgttactt cttctgccgc ctgcttcaaa ccgctaacaa tacctgggcc   4260
```

```
caccacaccg tgtgcattcg taatgtctgc ccattctgct attctgtata cacccgcaga    4320
gtactgcaat ttgactgtat taccaatgtc agcaaatttt ctgtcttcga agagtaaaaa    4380
attgtacttg gcggataatg cctttagcgg cttaactgtg ccctccatgg aaaaatcagt    4440
caagatatcc acatgtgttt ttagtaaaca aattttggga cctaatgctt caactaactc    4500
cagtaattcc ttggtggtac gaacatccaa tgaagcacac aagtttgttt gcttttcgtg    4560
catgatatta aatagcttgg cagcaacagg actaggatga gtagcagcac gttccttata    4620
tgtagctttc gacatgattt atcttcgttt cggttttgt tctgtgcagt tgggttaaga     4680
atactgggca atttcatgtt tcttcaacac tacatatgcg tatatatacc aatctaagtc    4740
tgtgctcctt ccttcgttct tccttctgtt cggagattac cgaatcaaaa aaatttcaaa    4800
gaaaccgaaa tcaaaaaaaa gaataaaaaa aaaatgatga attgaaaagc tcttgttacc    4860
catcattgaa ttttgaacat ccgaacctgg gagttttccc tgaaacagat agtatatttg    4920
aacctgtata ataatatata gtctagcgct ttacggaaga caatgtatgt atttcggttc    4980
ctggagaaac tattgcatct attgcatagg taatcttgca cgtcgcatcc ccggttcatt    5040
ttctgcgttt ccatcttgca cttcaatagc atatctttgt taacgaagca tctgtgcttc    5100
attttgtaga acaaaaatgc aacgcgagag cgctaatttt tcaaacaaag aatctgagct    5160 gcattttttac agaacagaaa tgcaacgcga aagcgctatt ttaccaacga agaatctgtg    5220
cttcattttt gtaaaacaaa aatgcaacgc gagagcgcta attttcaaa caaagaatct    5280 gagctgcatt tttacagaac agaaatgcaa cgcgagagcg ctattttacc aacaaagaat    5340
ctatacttct tttttgttct acaaaaatgc atcccgagag cgctattttt ctaacaaagc    5400
atcttagatt acttttttc cctttgtgc gctctataat gcagtctctt gataactttt    5460
tgcactgtag gtccgttaag gttagaagaa ggctactttg gtgtctattt tctcttccat    5520
aaaaaaagcc tgactccact tcccgcgttt actgattact agcgaagctg cgggtgcatt    5580
ttttcaagat aaaggcatcc ccgattatat tctataccga tgtggattgc gcatactttg    5640
tgaacagaaa gtgatagcgt tgatgattct tcattggtca gaaaattatg aacggtttct    5700
tctattttgt ctctatatac tacgtatagg aaatgtttac attttcgtat tgttttcgat    5760
tcactctatg aatagttctt actacaattt ttttgtctaa agagtaatac tagagataaa    5820
cataaaaaat gtagaggtcg agtttagatg caagttcaag gagcgaaagg tggatgggta    5880
ggttatatag ggatatagca cagagatata tagcaaagag atactttga gcaatgtttg    5940 tggaagcggt attcgcaata ttttagtagc tcgttacagt ccggtgcgtt tttggttttt    6000
tgaaagtgcg tcttcagagc gcttttggtt ttcaaaagcg ctctgaagtt cctatacttt    6060
ctagctagag aataggaact tcggaatagg aacttcaaag cgtttccgaa aacgagcgct    6120
tccgaaaatg caacgcgagc tgcgcacata cagctcactg ttcacgtcgc acctatatct    6180
gcgtgttgcc tgtatatata tatacatgag aagaacggca tagtgcgtgt ttatgcttaa    6240
atgcgttatg gtgcactctc agtacaatct gctctgatgc cgcatagtta agccagcccc    6300
gacacccgcc aacacccgct gacgcgccct gacgggcttg tctgctcccg gcatccgctt    6360
acagacaagc tgtgaccgtc tccgggagct gcatgtgtca gaggttttca ccgtcatcac    6420
cgaaacgcgc gagacgaaag ggcctcgtga tacgcctatt tttataggtt aatgtcatga    6480
taataatggt ttcttagacg tcaggtggca cttttcgggg aaatgtgcgc ggaacccta     6540 tttgtttatt tttctaaata cattcaaata tgtatccgct catgagacaa taaccctgat    6600
aaatgcttca ataatattga aaaaggaaga gtatgagtat tcaacatttc cgtgtcgccc    6660
```

```
ttattcccct ttttgcggca ttttgccttc ctgttttgc tcacccagaa acgctggtga    6720
aagtaaaaga tgctgaagat cagttgggtg cacgagtggg ttacatcgaa ctggatctca    6780
acagcggtaa gatccttgag agttttcgcc ccgaagaacg ttttccaatg atgagcactt    6840
ttaaagttct gctatgtggc gcggtattat cccgtattga cgccgggcaa gagcaactcg    6900
gtcgccgcat acactattct cagaatgact tggttgagta ctcaccagtc acagaaaagc    6960
atcttacgga tggcatgaca gtaagagaat tatgcagtgc tgccataacc atgagtgata    7020
acactgcggc caacttactt ctgacaacga tcggaggacc gaaggagcta accgcttttt    7080
tgcacaacat gggggatcat gtaactcgcc ttgatcgttg ggaaccggag ctgaatgaag    7140
ccataccaaa cgacgagcgt gacaccacga tgcctgtagc aatggcaaca acgttgcgca    7200
aactattaac tggcgaacta cttactctag cttcccggca acaattaata gactggatgg    7260
aggcggataa agttgcagga ccacttctgc gctcggccct tccggctggc tggtttattg    7320
ctgataaatc tggagccggt gagcgtgggt ctcgcggtat cattgcagca ctggggccag    7380
atggtaagcc ctcccgtatc gtagttatct acacgacggg gagtcaggca actatggatg    7440
aacgaaatag acagatcgct gagataggtg cctcactgat taagcattgg taactgtcag    7500
accaagttta ctcatatata ctttagattg atttaaaact tcatttttaa tttaaaagga    7560
tctaggtgaa gatccttttt gataatctca tgaccaaaat cccttaacgt gagttttcgt    7620
tccactgagc gtcagacccc gtagaaaaga tcaaaggatc ttcttgagat cctttttttc    7680
tgcgcgtaat ctgctgcttg caaacaaaaa aaccaccgct accagcggtg gtttgtttgc    7740
cggatcaaga gctaccaact ctttttccga aggtaactgg cttcagcaga gcgcagatac    7800
caaatactgt ccttctagtg tagccgtagt taggccacca cttcaagaac tctgtagcac    7860
cgcctacata cctcgctctg ctaatcctgt taccagtggc tgctgccagt ggcgataagt    7920
cgtgtcttac cgggttggac tcaagacgat agttaccgga taaggcgcag cggtcgggct    7980 gaacggggggg ttcgtgcaca cagcccagct tggagcgaac gacctacacc gaactgagat    8040
acctacagcg tgagcattga aaagcgccac cgcttcccga agggagaaag gcggacaggt    8100
atccggtaag cggcagggtc ggaacaggag agcgcacgag ggagcttcca gggggaaacg    8160
cctggtatct ttatagtcct gtcgggtttc gccacctctg acttgagcgt cgatttttgt    8220
gatgctcgtc aggggggcgg agcctatgga aaaacgccag caacgcggcc tttttacggt    8280
tcctggcctt ttgctggcct tttgctcaca tgttctttcc tgcgttatcc cctgattctg    8340
tggataaccg tattaccgcc tttgagtgag ctgataccgc tcgccgcagc cgaacgaccg    8400
agcgcagcga gtcagtgagc gaggaagcgg aagagcgccc aatacgcaaa ccgcctctcc    8460
ccgcgcgttg gccgattcat taatccagga tcccaattaa tgtgagttac tcactcatt    8520 aggcacccca ggctttacac tttatgcttc cggctcgtat gttgtgtgga attgtgagcg    8580
gataacaatt tcacacagga aacagctatg accatgatta cgaattaatt cgagctcggt    8640
acccggggat cgatccacta gagatctgtt tagcttgcct cgtcccgccg ggtcacccg    8700 gccagcgaca tggaggccca gaatacctct cttgacagtc ttgacgtgcg cagctcaggg    8760
gcatgatgtg actgtcgccc gtacatttag cccatacatc cccatgtata atcatttgca    8820
tccatacatt ttgatggccg cacggcgcga agcaaaaatt acggctcctc gctgcagacc    8880
tgcgagcagg gaaacgctcc cctcacagac gcgttgaatt gtcccacgc cgcgcccctg    8940 tagagaaata taaaaggtta ggatttgcca ctgaggttct tctttcatat acttcctttt    9000
```

| | | | | | |
|---|---|---|---|---|---|
| aaaatcttgc | taggatacag | ttctcacatc | acatccgaac | ataaacaacc | atggccgacc | 9060 |
| aagcgacgcc | caacctgcca | tcacgagatt | tcgattccac | ggccgccttc | tatgaaaggt | 9120 |
| tgggcttcgg | aatcgttttc | cgggacgccg | gctggatgat | cctccagcgc | ggggatctca | 9180 |
| agctggagtt | cttcgcccac | cccgggctcg | atccctcgc | gagttggttc | agctgctgcc | 9240 |
| tgaggctgga | cgacctcgcg | gagttctacc | ggcagtgcaa | atccgtcggc | atccaggaaa | 9300 |
| ccagcagcgg | ctatccgcgc | atccatgccc | ccgaactgca | ggagtgggga | ggcacgatgg | 9360 |
| ccgctttggt | cgacccggac | gggacgctcc | tgcgcctgat | acagaacgaa | ttgcttgcag | 9420 |
| gcatctcatg | atcagtactg | acaataaaaa | gattcttgtt | ttcaagaact | tgtcatttgt | 9480 |
| atagtttttt | tatattgtag | ttgttctatt | ttaatcaaat | gttagcgtga | tttatatttt | 9540 |
| ttttcgcctc | gacatcatct | gcccagatgc | gaagttaagt | gcgcagaaag | taatatcatg | 9600 |
| cgtcaatcgt | atgtgaatgc | tggtcgctat | actgctgtcg | attcgatact | aacgccgcca | 9660 |
| tccagtgtcg | aaaacgagct | ctcgagaacc | cttaatataa | cttcgtataa | tgtatgctat | 9720 |
| acgaagttat | taggtgatat | cagatccact | agtgtttaaa | cacctcatct | ataattttta | 9780 |
| ccctgatcta | actaactttg | gcatgcctgg | ttcaatctac | gggttacagt | catcgttgaa | 9840 |
| aacgatggaa | aaacatgtcg | agattcctca | atccatacac | cattatagtc | cgttttatca | 9900 |
| gcttccacta | attttttaaa | tctcagtttc | ttcttgaaat | ttagcatcgt | gcatgggata | 9960 |
| gcggctagta | aaaagaaaa | ttaatatctc | attaacaaag | ttattgtaca | taatccgta | 10020 |
| caatattctt | caatgtactc | tctaatatcg | agcacactgg | caatattcat | gcacacattc | 10080 |
| gcctaatgct | gacgaatgct | taatcagtgc | aattactgcc | accctcttga | tatgtgggct | 10140 |
| aaatccttta | ggacctgtaa | aaaatgcaat | cacgttttca | catttttttt | tttcttgcgg | 10200 |
| aattgcggaa | tttcccagtt | ggcagcgtta | tccgatttga | gatcgacttg | catcaacctt | 10260 |
| tgaaaaatat | aaggatgaga | aagtgaaatc | ggttttttt | ttccattgtc | gtcatcaaca | 10320 |
| tgattttta | aataaataaa | tacgatttt | tattttttt | cccttctttg | ttttgtttt | 10380 |
| gcttattccc | atcttcatta | ttaaattctt | ccgctcttaa | taaggagtt | tttttattat | 10440 |
| cttcttgtgt | aatcatcctt | tttctttaat | tttcttcctt | ttctttttct | ctttactggt | 10500 |
| ttttttactt | ctttattctc | aaccatctaa | agaatattat | tgctttctac | caataaaatc | 10560 |
| tgttaattct | atttggattg | tcgtctactc | aagtctcgcc | tagtaaataa | acgataaaca | 10620 |
| aatttgaagt | aagaataaca | atatagggag | agaaattttt | ctatttttaa | tttcgaaaca | 10680 |
| ggtaccaaaa | aatctaagtt | cactttagca | ctatttggga | aagcttttat | ataaaaaatc | 10740 |
| tgaaacaaaa | tcatatcaaa | g | | | | 10761 |

<210> SEQ ID NO 74
<211> LENGTH: 8847
<212> TYPE: DNA
<213> ORGANISM: Artificial sequence
<220> FEATURE:
<223> OTHER INFORMATION: Plasmid pAU31

<400> SEQUENCE: 74

| | | | | | |
|---|---|---|---|---|---|
| gagattatac | ttaaactagc | actgattttt | ttaaggctaa | tggctactaa | tactttaata | 60 |
| gatgatcttc | atacttttt | atttaacgat | ttttaatgat | gttttatttt | gtaccactca | 120 |
| tttatctaga | ttttttaat | actgatcaaa | tcttacggac | tcgacgttaa | aaagttccta | 180 |
| catacgtctg | gtacttgaaa | cgctgcttcg | aggtattgac | actataagaa | tacgatccaa | 240 |
| atacttacac | cgcatgtaaa | aatatgccga | caatatgaat | acttgttgat | gaatgatatt | 300 |

```
tgattttaat ccggcaattt acctccttta tataatccaa taattgttga taattagtgg    360
ttaggttgca gtactaataa gaattaagac aaatattctt ctactatata aaaggtgcaa    420
acaaaacaca cgccgatcgg ccatactaaa caagaccaac ataataatgg tggaaccatt    480
tactgtattt tcaatgtaac atttaaatcc gcggtaaacc tctttgcggg caagcttggc    540
actggccgtc gttttacaac gtcgtgactg ggaaaaccct ggcgttaccc aacttaatcg    600
ccttgcagca catccccctt tcgccagctg gcgtaatagc gaagaggccc gcaccgatcg    660
cccttcccaa cagttgcgca gcctgaatgg cgaatggcgc ctgatgcggt attttctcct    720
tacgcatctg tgcggtattt cacaccgcat aggagatcta agctctggcg taatagcgaa    780
gaggcccgca ccgatcgccc ttcccaacag ttgcgcagcc tgaatggcga atggcgcctg    840
atgcggtatt ttctccttac gcatctgtgc ggtatttcac accgcatagg gtaataactg    900
atataattaa attgaagctc taatttgtga gtttagtata catgcattta cttataatac    960
agttttttag ttttgctggc cgcatcttct caaatatgct tcccagcctg cttttctgta   1020
acgttcaccc tctaccttag catcccttcc ctttgcaaat agtcctcttc aacaataat   1080 aatgtcagat cctgtagaga ccacatcatc cacggttcta tactgttgac ccaatgcgtc   1140
tcccttgtca tctaaaccca caccgggtgt cataatcaac caatcgtaac cttcatctct   1200
tccacccatg tctctttgag caataaagcc gataacaaaa tctttgtcgc tcttcgcaat   1260
gtcaacagta cccttagtat attctccagt agatagggag cccttgcatg acaattctgc   1320
taacatcaaa aggcctctag gttcctttgt tacttcttct gccgcctgct tcaaaccgct   1380
aacaatacct gggcccacca caccgtgtgc attcgtaatg tctgcccatt ctgctattct   1440
gtatacaccc gcagagtact gcaatttgac tgtattacca atgtcagcaa attttctgtc   1500
ttcgaagagt aaaaaattgt acttggcgga taatgccttt agcggcttaa ctgtgccctc   1560
catgaaaaaa tcagtcaaga tatccacatg tgttttagt aaacaaattt tgggacctaa   1620
tgcttcaact aactccagta attccttggt ggtacgaaca tccaatgaag cacacaagtt   1680
tgtttgcttt tcgtgcatga tattaaatag cttggcagca acaggactag gatgagtagc   1740
agcacgttcc ttatatgtag ctttcgacat gatttatctt cgtttcggtt tttgttctgt   1800
gcagttgggt taagaatact gggcaatttc atgtttcttc aacactacat atgcgtatat   1860
ataccaatct aagtctgtgc tccttccttc gttcttcctt ctgttcggag attaccgaat   1920
caaaaaaatt tcaaagaaac cgaaatcaaa aaaagaata aaaaaaaat gatgaattga   1980 aaagctcttg ttacccatca ttgaattttg aacatccgaa cctgggagtt ttccctgaaa   2040
cagatagtat atttgaacct gtataataat atatagtcta gcgctttacg aagacaatg   2100 tatgtatttc ggttcctgga gaaactattg catctattgc ataggtaatc ttgcacgtcg   2160
catccccggt tcattttctg cgtttccatc ttgcacttca atagcatatc tttgttaacg   2220
aagcatctgt gcttcatttt gtagaacaaa atgcaacgc gagagcgcta attttttcaaa   2280 caaagaatct gagctgcatt tttacagaac agaaatgcaa cgcgaaagcg ctattttacc   2340
aacgaagaat ctgtgcttca ttttttgtaaa acaaaaatgc aacgcgagag cgctaatttt   2400
tcaaacaaag aatctgagct gcatttttac agaacagaaa tgcaacgcga gagcgctatt   2460
ttaccaacaa agaatctata cttctttttt gttctacaaa aatgcatccc gagagcgcta   2520
tttttctaac aaagcatctt agattacttt ttttctcctt tgtgcgctct ataatgcagt   2580
ctcttgataa cttttttgcac tgtaggtccg ttaaggttag aagaaggcta ctttggtgtc   2640
```

```
tattttctct tccataaaaa aagcctgact ccacttcccg cgtttactga ttactagcga    2700
agctgcgggt gcatttttc aagataaagg catccccgat tatattctat accgatgtgg    2760
attgcgcata ctttgtgaac agaaagtgat agcgttgatg attcttcatt ggtcagaaaa    2820
ttatgaacgg tttcttctat tttgtctcta tatactacgt ataggaaatg tttacatttt    2880
cgtattgttt tcgattcact ctatgaatag ttcttactac aattttttg tctaaagagt     2940
aatactagag ataaacataa aaaatgtaga ggtcgagttt agatgcaagt tcaaggagcg    3000
aaaggtggat gggtaggtta tatagggata tagcacagag atatatagca aagagatact    3060
tttgagcaat gtttgtggaa gcggtattcg caatatttta gtagctcgtt acagtccggt    3120
gcgttttgg ttttttgaaa gtgcgtcttc agagcgcttt tggttttcaa aagcgctctg     3180
aagttcctat actttctagc tagagaatag gaacttcgga ataggaactt caaagcgttt    3240
ccgaaaacga gcgcttccga aaatgcaacg cgagctgcgc atacagct cactgttcac     3300
gtcgcaccta tatctgcgtg ttgcctgtat atatatatac atgagaagaa cggcatagtg    3360
cgtgtttatg cttaaatgcg ttatggtgca ctctcagtac aatctgctct gatgccgcat    3420
agttaagcca gccccgacac ccgccaacac ccgctgacgc gccctgacgg gcttgtctgc    3480
tcccggcatc cgcttacaga caagctgtga ccgtctccgg gagctgcatg tgtcagaggt    3540
tttcaccgtc atcaccgaaa cgcgcgagac gaaagggcct cgtgatacgc ctatttttat    3600
aggttaatgt catgataata atggtttctt agacgtcagg tggcactttt cggggaaatg    3660
tgcgcggaac ccctatttgt ttatttttct aaatacattc aaatatgtat ccgctcatga    3720
gacaataacc ctgataaatg cttcaataat attgaaaaag gaagagtatg agtattcaac    3780
atttccgtgt cgcccttatt ccctttttg cggcattttg ccttcctgtt tttgctcacc     3840
cagaaacgct ggtgaaagta aaagatgctg aagatcagtt gggtgcacga gtgggttaca    3900
tcgaactgga tctcaacagc ggtaagatcc ttgagagttt tcgccccgaa gaacgttttc    3960
caatgatgag cacttttaaa gttctgctat gtggcgcggt attatcccgt attgacgccg    4020
ggcaagagca actcggtcgc cgcatacact attctcagaa tgacttggtt gagtactcac    4080
cagtcacaga aaagcatctt acggatggca tgacagtaag agaattatgc agtgctgcca    4140
taaccatgag tgataacact gcggccaact tacttctgac aacgatcgga ggaccgaagg    4200
agctaaccgc ttttttgcac aacatggggg atcatgtaac tcgccttgat cgttgggaac    4260
cggagctgaa tgaagccata ccaaacgacg agcgtgacac cacgatgcct gtagcaatgg    4320
caacaacgtt gcgcaaacta ttaactggcg aactacttac tctagcttcc cggcaacaat    4380
taatagactg gatggaggcg gataaagttg caggaccact tctgcgctcg gcccttccgg    4440
ctggctggtt tattgctgat aaatctggag ccggtgagcg tgggtctcgc ggtatcattg    4500
cagcactggg gccagatggt aagccctccc gtatcgtagt tatctacacg acggggagtc    4560
aggcaactat ggatgaacga aatagacaga tcgctgagat aggtgcctca ctgattaagc    4620
attggtaact gtcagaccaa gtttactcat atatacttta gattgattta aaacttcatt    4680
tttaatttaa aaggatctag gtgaagatcc ttttgataa tctcatgacc aaaatccctt     4740
aacgtgagtt ttcgttccac tgagcgtcag accccgtaga aaagatcaaa ggatcttctt    4800
gagatccttt ttttctgcgc gtaatctgct gcttgcaaac aaaaaaacca ccgctaccag    4860
cggtggtttg tttgccggat caagagctac caactctttt tccgaaggta actggcttca    4920
gcagagcgca gataccaaat actgtccttc tagtgtagcc gtagttaggc caccacttca    4980
agaactctgt agcaccgcct acatacctcg ctctgctaat cctgttacca gtggctgctg    5040
```

```
ccagtggcga taagtcgtgt cttaccgggt tggactcaag acgatagtta ccggataagg    5100
cgcagcggtc gggctgaacg gggggttcgt gcacacagcc cagcttggag cgaacgacct    5160
acaccgaact gagataccta cagcgtgagc attgagaaag cgccacgctt cccgaaggga    5220
gaaaggcgga caggtatccg gtaagcggca gggtcggaac aggagagcgc acgagggagc    5280
ttccaggggg aaacgcctgg tatctttata gtcctgtcgg gtttcgccac ctctgacttg    5340
agcgtcgatt tttgtgatgc tcgtcagggg gcgggagcct atggaaaaac gccagcaacg    5400 cggcctttt  acggttcctg gccttttgct ggccttttgc tcacatgttc tttcctgcgt    5460
tatcccctga ttctgtggat aaccgtatta ccgcctttga gtgagctgat accgctcgcc    5520
gcagccgaac gaccgagcgc agcgagtcag tgagcgagga agcggaagag cgcccaatac    5580
gcaaaccgcc tctccccgcg cgttggccga ttcattaatc caggatccca attaatgtga    5640
gttacctcac tcattaggca ccccaggctt tacactttat gcttccggct cgtatgttgt    5700
gtggaattgt gagcggataa caatttcaca caggaaacag ctatgaccat gattacgaat    5760
taattcgagc tcggtacccg gggatcgatc cactagagat ctgtttagct tgcctcgtcc    5820
ccgccgggtc acccggccag cgacatggag gcccagaata ccctccttga cagtcttgac    5880
gtgcgcagct caggggcatg atgtgactgt cgcccgtaca tttagcccat acatccccat    5940
gtataatcat ttgcatccat acattttgat ggccgcacgg cgcgaagcaa aaattacggc    6000
tcctcgctgc agacctgcga gcagggaaac gctcccctca cagacgcgtt gaattgtccc    6060
cacgccgcgc ccctgtagag aaatataaaa ggttaggatt tgccactgag gttcttcttt    6120
catatacttc cttttaaaat cttgctagga tacagttctc acatcacatc cgaacataaa    6180
caaccatggc cgaccaagcg acgcccaacc tgccatcacg agatttcgat tccacggccg    6240
ccttctatga aaggttgggc ttcggaatcg ttttccggga cgccggctgg atgatcctcc    6300
agcgcgggga tctcaagctg gagttcttcg cccaccccgg gctcgatccc ctcgcgagtt    6360
ggttcagctg ctgcctgagg ctggacgacc tcgcggagtt ctaccggcag tgcaaatccg    6420
tcggcatcca ggaaaccagc agcggctatc cgcgcatcca tgcccccgaa ctgcaggagt    6480
ggggaggcac gatggccgct ttggtcgacc cggacgggac gctcctgcgc ctgatacaga    6540
acgaattgct tgcaggcatc tcatgatcag tactgacaat aaaaagattc ttgttttcaa    6600
gaacttgtca tttgtatagt ttttttatat tgtagttgtt ctattttaat caaatgttag    6660
cgtgatttat atttttttc gcctcgacat catctgccca gatgcgaagt taagtgcgca    6720
gaaagtaata tcatgcgtca atcgtatgtg aatgctggtc gctatactgc tgtcgattcg    6780
atactaacgc cgccatccag tgtcgaaaac gagctctcga gaacccttaa tataacttcg    6840
tataatgtat gctatacgaa gttattaggt gatatcagat ccactagtgt ttaaacacct    6900
catctataat ttttaccctg atctaactaa cttttggcatg cctggttcaa tctacgggtt    6960
acagtcatcg ttgaaaacga tggaaaaaca tgtcagatt  cctcaatcca tacaccatta    7020
tagtccgttt tatcagcttc cactaatttt ttaaatctca gtttcttctt gaaatttagc    7080
atcgtgcatg ggatagcggc tagtaaaaaa gaaaattaat atctcattaa caaagttatt    7140
gtacataatc cggtacaata ttcttcaatg tactctctaa tatcgagcac actggcaata    7200
ttcatgcaca cattcgccta atgctgacga atgcttaatc agtgcaatta ctgccaccct    7260
cttgatatgt gggctaaatc ctttaggacc tgtaaaaaat gcaatcacgt ttcacatttt    7320 tttttttct tgcggaattg cggaatttcc cagttggcag cgttatccga tttgagatcg    7380
```

```
acttgcatca accttttgaaa aatataagga tgagaaagtg aaatcggttt tttttttcca      7440
ttgtcgtcat caacatgatt ttttaaataa ataaatacga ttttttattt tttttccctt      7500
ctttgttttt gttttgctta ttcccatctt cattattaaa ttcttccgct cttaataaag      7560
gagttttttt attatcttct tgtgtaatca tcctttttct ttaattttct tcctttttctt     7620 tttctcttta ctggtttttt tacttcttta ttctcaacca tctaaagaat attattgctt      7680
tctaccaata aaatctgtta attctatttg gattgtcgtc tactcaagtc tcgcctagta      7740
aataaacgat aaacaaattt gaagtaagaa taacaatata gggagagaaa tttttctatt      7800
tttaatttcg aaacaggtac caaaaaatct aagttcactt tagcactatt tgggaaagct      7860
tttatataaa aaatctgaaa caaaatcata tcaaagatga gtaagcgtaa agtcgccatt      7920
atcggttctg caacattgg taccgatctg atgattaaaa ttttgcgtca cggtcagcat       7980
ctggagatgg cggtgatggt tggcattgat cctcagtccg acggtctggc gcgcgccaga     8040
cgtatgggcg tcgccaccac ccatgaaggg gtgatcggac tgatgaacat gcctgaattt    8100
gctgatatcg acattgtatt tgatgcgacc agcgccggtg ctcatgtgaa aaacgatgcc    8160
gctttacgcg aagcgaaacc ggatattcgc ttaattgacc tgacgcctgc tgccatcggc    8220
ccttactgcg tgccggtggt taacctcgag gcgaacgtcg atcaactgaa cgtcaacatg    8280
gtcacctgcg gcggccaggc caccattcca atggtggcgg cagtttcacg cgtggcgcgt     8340
gttcattacg ccgaaattat cgcttctatc gccagtaaat ctgccggacc tggcacgcgt    8400
gccaatatcg atgaatttac ggaaaccact tcccgagcca ttgaagtggt gggcggcgcg    8460
gcaaagggga aggcgattat tgtgcttaac ccagcagagc caccgttgat gatgcgtgac    8520
acggtgtatg tattgagcga cgaagcttca caagatgata tcgaagcctc aatcaatgaa     8580
atggctgagg cggtgcaggc ttacgtaccg ggttatcgcc tgaaacagcg cgtgcagttt    8640
gaagttatcc cgcaggataa accggtcaat ttaccgggcg tggggcaatt ctccggactg    8700
aaaacagcgg tctggctgga agtcgaaggc gcagcgcatt atctgcctgc ctatgcgggc    8760
aacctcgaca ttatgacttc cagtgcgctg gcgacagcgg aaaaaatggc ccagtcactg    8820
gcgcgcaagg caggagaagc ggcatga                                         8847

<210> SEQ ID NO 75
<211> LENGTH: 9444
<212> TYPE: DNA
<213> ORGANISM: Artificial sequence
<220> FEATURE:
<223> OTHER INFORMATION: Plasmid pAU34

<400> SEQUENCE: 75
gagattatac ttaaactagc actgattttt ttaaggctaa tggctactaa tactttaata       60
gatgatcttc atactttttt atttaacgat ttttaatgat gttttttattt gtaccactca    120 tttatctaga ttttttttaat actgatcaaa tcttacggac tcgacgttaa aaagttccta    180
catacgtctg gtacttgaaa cgctgcttcg aggtattgac actataagaa tacgatccaa     240
atacttacac cgcatgtaaa aatatgccga caatatgaat acttgttgat gaatgatatt     300
tgattttaat ccggcaattt acctcccttta tataatccaa taattgttga taattagtgg    360
ttaggttgca gtactaataa gaattaagac aaatattctt ctactatata aaaggtgcaa     420
acaaaacaca cgccgatcgg ccatactaaa caagaccaac ataataatgg tggaaccatt     480
tactgtattt tcaatgtaac atttaaatcc gcggtaaacc tctttgcggg caagcttggc      540
actggccgtc gttttacaac gtcgtgactg ggaaaaccct ggcgttaccc aacttaatcg    600
```

```
ccttgcagca catccccctt tcgccagctg gcgtaatagc gaagaggccc gcaccgatcg    660
cccttcccaa cagttgcgca gcctgaatgg cgaatggcgc ctgatgcggt attttctcct    720
tacgcatctg tgcggtattt cacaccgcat aggagatcta agctctggcg taatagcgaa    780
gaggcccgca ccgatcgccc ttcccaacag ttgcgcagcc tgaatggcga atggcgcctg    840
atgcggtatt ttctccttac gcatctgtgc ggtatttcac accgcatagg gtaataactg    900
atataattaa attgaagctc taatttgtga gtttagtata catgcattta cttataatac    960
agttttttag ttttgctggc cgcatcttct caaatatgct tcccagcctg cttttctgta   1020
acgttcaccc tctaccttag catcccttcc ctttgcaaat agtcctcttc caacaataat   1080
aatgtcagat cctgtagaga ccacatcatc cacggttcta tactgttgac ccaatgcgtc   1140
tcccttgtca tctaaaccca caccgggtgt cataatcaac caatcgtaac cttcatctct   1200
tccacccatg tctctttgag caataaagcc gataacaaaa tctttgtcgc tcttcgcaat   1260
gtcaacagta cccttagtat attctccagt agatagggag cccttgcatg acaattctgc   1320
taacatcaaa aggcctctag gttcctttgt tacttcttct gccgcctgct tcaaaccgct   1380
aacaatacct gggcccacca caccgtgtgc attcgtaatg tctgcccatt ctgctattct   1440
gtatacaccc gcagagtact gcaatttgac tgtattacca atgtcagcaa attttctgtc   1500
ttcgaagagt aaaaaattgt acttggcgga taatgccttt agcggcttaa ctgtgccctc   1560
catggaaaaa tcagtcaaga tatccacatg tgttttagt aaacaaattt tgggacctaa   1620
tgcttcaact aactccagta attccttggt ggtacgaaca tccaatgaag cacacaagtt   1680
tgtttgcttt tcgtgcatga tattaaatag cttggcagca acaggactag gatgagtagc   1740
agcacgttcc ttatatgtag ctttcgacat gatttatctt cgtttcggtt tttgttctgt   1800
gcagttgggt taagaatact gggcaatttc atgtttcttc aacactacat atgcgtatat   1860
ataccaatct aagtctgtgc tccttccttc gttcttcctt ctgttcggag attaccgaat   1920
caaaaaaatt tcaaagaaac cgaaatcaaa aaaagaata aaaaaaaat gatgaattga   1980 aaagctcttg ttacccatca ttgaattttg aacatccgaa cctgggagtt ttccctgaaa   2040
cagatagtat atttgaacct gtataataat atatagtcta gcgctttacg gaagacaatg   2100
tatgtatttc ggttcctgga gaaactattg catctattgc ataggtaatc ttgcacgtcg   2160
catccccggt tcattttctg cgtttccatc ttgcacttca atagcatatc tttgttaacg   2220
aagcatctgt gcttcatttt gtagaacaaa aatgcaacgc gagagcgcta attttcaaa    2280 caaagaatct gagctgcatt tttacagaac agaaatgcaa cgcgaaagcg ctattttacc   2340
aacgaagaat ctgtgcttca tttttgtaaa acaaaaatgc aacgcgagag cgctaatttt   2400
tcaaacaaag aatctgagct gcatttttac agaacagaaa tgcaacgcga gagcgctatt   2460
ttaccaacaa agaatctata cttctttttt gttctacaaa aatgcatccc gagagcgcta   2520
tttttctaac aaagcatctt agattacttt ttttctcctt tgtgcgctct ataatgcagt   2580
ctcttgataa cttttttgcac tgtaggtccg ttaaggttag aagaaggcta ctttggtgtc   2640
tattttctct tccataaaaa aagcctgact ccacttcccg cgtttactga ttactagcga   2700
agctgcgggt gcatttttc aagataaagg catccccgat tatattctat accgatgtgg   2760
attgcgcata ctttgtgaac agaaagtgat agcgttgatg attcttcatt ggtcagaaaa   2820
ttatgaacgg tttcttctat tttgtctcta tatactacgt ataggaaatg tttcattttt   2880
cgtattgttt tcgattcact ctatgaatag ttcttactac aattttttg tctaaagagt   2940
```

```
aatactagag ataaacataa aaaatgtaga ggtcgagttt agatgcaagt tcaaggagcg    3000
aaaggtggat gggtaggtta tatagggata tagcacagag atatatagca aagagatact    3060
tttgagcaat gtttgtggaa gcggtattcg caatatttta gtagctcgtt acagtccggt    3120 gcgttttttgg ttttttgaaa gtgcgtcttc agagcgcttt tggttttcaa aagcgctctg   3180
aagttcctat actttctagc tagagaatag gaacttcgga ataggaactt caaagcgttt    3240
ccgaaaacga gcgcttccga aaatgcaacg cgagctgcgc acatacagct cactgttcac    3300
gtcgcaccta tatctgcgtg ttgcctgtat atatatatac atgagaagaa cggcatagtg    3360
cgtgtttatg cttaaatgcg ttatggtgca ctctcagtac aatctgctct gatgccgcat    3420
agttaagcca gccccgacac ccgccaacac ccgctgacgc gccctgacgg gcttgtctgc    3480
tcccggcatc cgcttacaga caagctgtga ccgtctccgg gagctgcatg tgtcagaggt    3540
tttcaccgtc atcaccgaaa cgcgcgagac gaaagggcct cgtgatacgc ctatttttat    3600
aggttaatgt catgataata atggtttctt agacgtcagg tggcactttt cggggaaatg    3660
tgcgcggaac ccctatttgt ttattttct aaatacattc aaatatgtat ccgctcatga    3720
gacaataacc ctgataaatg cttcaataat attgaaaaag gaagagtatg agtattcaac    3780
atttccgtgt cgcccttatt ccctttttg cggcattttg ccttcctgtt tttgctcacc    3840
cagaaacgct ggtgaaagta aaagatgctg aagatcagtt gggtgcacga gtgggttaca    3900
tcgaactgga tctcaacagc ggtaagatcc ttgagagttt cgccccgaa gaacgttttc     3960 caatgatgag cacttttaaa gttctgctat gtggcgcggt attatcccgt attgacgccg    4020
ggcaagagca actcggtcgc cgcatacact attctcagaa tgacttggtt gagtactcac    4080
cagtcacaga aaagcatctt acggatggca tgacagtaag agaattatgc agtgctgcca    4140
taaccatgag tgataacact gcggccaact tacttctgac aacgatcgga ggaccgaagg    4200
agctaaccgc ttttttgcac aacatggggg atcatgtaac tcgccttgat cgttgggaac    4260
cggagctgaa tgaagccata ccaaacgacg agcgtgacac cacgatgcct gtagcaatgg    4320
caacaacgtt gcgcaaacta ttaactggcg aactacttac tctagcttcc cggcaacaat    4380
taatagactg gatggaggcg gataaagttg caggaccact tctgcgctcg gcccttccgg    4440
ctggctggtt tattgctgat aaatctggag ccggtgagcg tgggtctcgc ggtatcattg    4500
cagcactggg gccagatggt aagccctccc gtatcgtagt tatctacacg acggggagtc    4560
aggcaactat ggatgaacga aatagacaga tcgctgagat aggtgcctca ctgattaagc    4620
attggtaact gtcagaccaa gtttactcat atatacttta gattgattta aaacttcatt    4680
tttaatttaa aaggatctag gtgaagatcc ttttgataa tctcatgacc aaaatccctt    4740
aacgtgagtt ttcgttccac tgagcgtcag accccgtaga aaagatcaaa ggatcttctt    4800
gagatccttt ttttctgcgc gtaatctgct gcttgcaaac aaaaaaacca ccgctaccag    4860
cggtggtttg tttgccggat caagagctac caactctttt tccgaaggta actggcttca    4920
gcagagcgca gataccaaat actgtccttc tagtgtagcc gtagttaggc caccacttca    4980
agaactctgt agcaccgcct acatacctcg ctctgctaat cctgttacca gtggctgctg    5040
ccagtggcga taagtcgtgt cttaccgggt tggactcaag acgatagtta ccggataagg    5100
cgcagcggtc gggctgaacg gggggttcgt gcacacagcc cagcttggag cgaacgacct    5160
acaccgaact gagatacctta cagcgtgagc attgagaaag cgccacgctt cccgaaggga    5220
gaaaggcgga caggtatccg gtaagcgca gggtcggaac aggagagcgc acgagggagc    5280
ttccaggggg aaacgcctgg tatctttata gtcctgtcgg gtttcgccac ctctgacttg    5340
```

```
agcgtcgatt tttgtgatgc tcgtcagggg ggcggagcct atggaaaaac gccagcaacg   5400
cggccttttt acggttcctg gccttttgct ggccttttgc tcacatgttc tttcctgcgt   5460
tatcccctga ttctgtggat aaccgtatta ccgcctttga gtgagctgat accgctcgcc   5520
gcagccgaac gaccgagcgc agcgagtcag tgagcgagga gcggaagag cgcccaatac    5580 gcaaaccgcc tctccccgcg cgttggccga ttcattaatc caggatccca attaatgtga   5640
gttacctcac tcattaggca ccccaggctt tacactttat gcttccggct cgtatgttgt   5700
gtggaattgt gagcggataa caatttcaca caggaaacag ctatgaccat gattacgaat   5760
taattcgagc tcggtacccg ggatcgatc cactagagat ctgtttagct tgcctcgtcc    5820
ccgccgggtc acccggccag cgacatggag gcccagaata ccctccttga cagtcttgac   5880
gtgcgcagct caggggcatg atgtgactgt cgcccgtaca tttagcccat acatccccat   5940
gtataatcat ttgcatccat acattttgat ggccgcacgg cgcgaagcaa aaattacggc   6000
tcctcgctgc agacctgcga gcagggaaac gctcccctca cagacgcgtt gaattgtccc   6060
cacgccgcgc ccctgtagag aaatataaaa ggttaggatt tgccactgag gttcttcttt   6120
catatacttc cttttaaaat cttgctagga tacagttctc acatcacatc cgaacataaa   6180
caaccatggc cgaccaagcg acgcccaacc tgccatcacg agatttcgat tccacggccg   6240
ccttctatga aaggttgggc ttcggaatcg ttttccggga cgccggctgg atgatcctcc   6300
agcgcgggga tctcaagctg gagttcttcg cccaccccgg gctcgatccc ctcgcgagtt   6360
ggttcagctg ctgcctgagg ctggacgacc tcgcggagtt ctaccggcag tgcaaatccg   6420
tcggcatcca ggaaaccagc agcggctatc cgcgcatcca tgcccccgaa ctgcaggagt   6480
ggggaggcac gatggccgct ttggtcgacc cggacgggac gctcctgcgc ctgatacaga   6540
acgaattgct tgcaggcatc tcatgatcag tactgacaat aaaaagattc ttgttttcaa   6600
gaacttgtca tttgtatagt ttttttatat tgtagttgtt ctattttaat caaatgttag   6660
cgtgatttat atttttttc gcctcgacat catctgccca gatgcgaagt taagtgcgca   6720
gaaagtaata tcatgcgtca atcgtatgtg aatgctggtc gctatactgc tgtcgattcg   6780
atactaacgc cgccatccag tgtcgaaaac gagctctcga gaacccttaa tataacttcg   6840
tataatgtat gctatacgaa gttattaggt gatatcagat ccactagtgt ttaaacacct   6900
catctataat ttttaccctg atctaactaa ctttggcatg cctggttcaa tctacgggtt   6960
acagtcatcg ttgaaaacga tggaaaaaca tgtcgagatt cctcaatcca tacaccatta   7020
tagtccgttt tatcagcttc cactaatttt ttaaatctca gtttcttctt gaaatttagc   7080
atcgtgcatg ggatagcggc tagtaaaaaa gaaaattaat atctcattaa caaagttatt   7140
gtacataatc cggtacaata ttcttcaatg tactctctaa tatcgagcac actggcaata   7200
ttcatgcaca cattcgccta atgctgacga atgcttaatc agtgcaatta ctgccaccct   7260
cttgatatgt gggctaaatc ctttaggacc tgtaaaaaat gcaatcacgt tttcacattt   7320
ttttttttct tgcggaattg cggaatttcc cagttggcag cgttatccga tttgagatcg   7380
acttgcatca acctttgaaa aatataagga tgagaaagtg aaatcggttt tttttttcca   7440
ttgtcgtcat caacatgatt ttttaaataa ataaatacga ttttttattt tttttccctt   7500
ctttgttttt gttttgctta ttcccatctt cattattaaa ttcttccgct cttaataaag   7560
gagttttttt attatcttct tgtgtaatca tccttttct ttaattttct tccttttctt    7620
tttctcttta ctggtttttt tacttcttta ttctcaacca tctaaagaat attattgctt   7680
```

| | |
|---|---:|
| tctaccaata aaatctgtta attctatttg gattgtcgtc tactcaagtc tcgcctagta | 7740 |
| aataaacgat aaacaaattt gaagtaagaa taacaatata gggagagaaa tttttctatt | 7800 |
| tttaatttcg aaacaggtac caaaaaatct aagttcactt tagcactatt tgggaaagct | 7860 |
| tttatataaa aaatctgaaa caaaatcata tcaaagatgg aaaactttga ttttgattta | 7920 |
| cgttccatcc aagaagcaag ggatttagca agaagcggtg aagctgctgc taagaagatt | 7980 |
| gctcagttta gtgaagaaca gatagatcgt attcttaaga gtatggctaa ggcaggagag | 8040 |
| gaacatgccc tatgcttagg agaaatggct tctgaggaaa ctggatttgg aaaggctatg | 8100 |
| gataaggcat ataagaacca cgctgcttct accctttat atgaagagat aaaggatatg | 8160 |
| aagactagag gaatcctagc tgaggatacc gtaaataaga ctattgatgt agctgagccg | 8220 |
| gttggtttgg taatgggaat cgttccttct acaaacccta cctcaaccgt attctttaaa | 8280 |
| tccatggttg cagtaaaatc aggaaatgct attgtatttt ctcctcaccc ttccgcagca | 8340 |
| aaatgtacat taaaggcagc tgaaattatg cgcgacgctg caatcgctgc aggcgcacca | 8400 |
| gaaggaatca tcggttgtgt gaccatgcct tccatgggat ctaccaatga acttatgaag | 8460 |
| tgtaaggaag tttccgttat tatcgcaact ggaggtccag ctatggtaaa ggctgcttat | 8520 |
| agtgcaggaa agccagctat cggtgtaggt gcaggtaact ctcctgctta cattgagaag | 8580 |
| acagcagatg taaaacaagc agttaaaaca atcattgcca gcaagacatt tgactatggt | 8640 |
| actatctgtg catccgagca gtccatcatc tgcgaggaaa gcaatgaagc agaagtatta | 8700 |
| gctgaattaa agagtcaggg cggatacttc atgacaaaag aagaaaccga taaggtttgt | 8760 |
| ggcttgttat tcaagaacgg atacactatg aacgctaaat ttgtaggtcg ttcccctcag | 8820 |
| gtgattgctc aggcagctgg aattgaaatt ccgatggata ccaaggttct tatcggaaga | 8880 |
| caggaaggcg taggtcaagg ctatccatta tcctttgaaa agcttacaac agttcttggc | 8940 |
| ttctataccg taaaggactg ccatgaggct tgcgatttaa gcattcgtct tttacagaac | 9000 |
| ggaatcggac ataccatgag tattcacact caggatagag atatggttct taagtttgct | 9060 |
| gcaaagccag cttccagaat tcttgttaac acaggcggta gccagggcgg aactggaatc | 9120 |
| agcacaggtc ttccaatttc ctttacatta ggatgcggta cttgcggcgg aagttctgtt | 9180 |
| tctgaaaacg tgagtccaaa acatctcctt aatgttaaga aggtagcctt tggcttaaag | 9240 |
| gattgttcta ctatcgcagc agatgatgaa actttcacat ggaaggaaaa agcaggaact | 9300 |
| aattcctgta gtccagcaga ttttgttgct tccttgtaa agaaagaagg tactacagct | 9360 |
| aattcctgtc agggaagctg tgatgataac gagaagctag cagcacttgt taaggaaatt | 9420 |
| gtgttggcca tgaaaggtca gtag | 9444 |

<210> SEQ ID NO 76
<211> LENGTH: 9384
<212> TYPE: DNA
<213> ORGANISM: Artificial sequence
<220> FEATURE:
<223> OTHER INFORMATION: Plasmid pAU37

<400> SEQUENCE: 76

| | |
|---|---:|
| gagattatac ttaaactagc actgattttt ttaaggctaa tggctactaa tactttaata | 60 |
| gatgatcttc atacttttt atttaacgat ttttaatgat gttttatttt gtaccactca | 120 |
| tttatctaga ttttttaat actgatcaaa tcttacggac tcgacgttaa aaagttccta | 180 |
| catacgtctg gtacttgaaa cgctgcttcg aggtattgac actataagaa tacgatccaa | 240 |
| atacttacac cgcatgtaaa aatatgccga caatatgaat acttgttgat gaatgatatt | 300 |

```
tgattttaat ccggcaattt acctccttta tataatccaa taattgttga taattagtgg    360
ttaggttgca gtactaataa gaattaagac aaatattctt ctactatata aaaggtgcaa    420
acaaaacaca cgccgatcgg ccatactaaa caagaccaac ataataatgg tggaaccatt    480
tactgtattt tcaatgtaac atttaaatcc gcggtaaacc tctttgcggg caagcttggc    540
actggccgtc gttttacaac gtcgtgactg ggaaaaccct ggcgttaccc aacttaatcg    600
ccttgcagca catcccccttt tcgccagctg gcgtaatagc gaagaggccc gcaccgatcg    660
cccttcccaa cagttgcgca gcctgaatgg cgaatggcgc ctgatgcggt attttctcct    720
tacgcatctg tgcggtattt cacaccgcat aggagatcta agctctggcg taatagcgaa    780
gaggcccgca ccgatcgccc ttcccaacag ttgcgcagcc tgaatggcga atggcgcctg    840
atgcggtatt ttctccttac gcatctgtgc ggtatttcac accgcatagg gtaataactg    900
atataattaa attgaagctc taatttgtga gtttagtata catgcattta cttataatac    960
agttttttag ttttgctggc cgcatcttct caaatatgct tcccagcctg cttttctgta   1020
acgttcaccc tctaccttag catcccttcc ctttgcaaat agtcctcttc aacaataat   1080 aatgtcagat cctgtagaga ccacatcatc cacggttcta tactgttgac ccaatgcgtc   1140
tcccttgtca tctaaaccca caccgggtgt cataatcaac caatcgtaac cttcatctct   1200
tccacccatg tctctttgag caataaagcc gataacaaaa tctttgtcgc tcttcgcaat   1260
gtcaacagta cccttagtat attctccagt agatagggag cccttgcatg acaattctgc   1320
taacatcaaa aggcctctag gttcctttgt tacttcttct gccgcctgct tcaaaccgct   1380
aacaatacct gggcccacca caccgtgtgc attcgtaatg tctgcccatt ctgctattct   1440
gtatacaccc gcagagtact gcaatttgac tgtattacca atgtcagcaa attttctgtc   1500
ttcgaagagt aaaaaattgt acttggcgga taatgccttt agcggcttaa ctgtgccctc   1560
catgaaaaaa tcagtcaaga tatccacatg tgttttagt aaacaaattt tgggacctaa   1620
tgcttcaact aactccagta attccttggt ggtacgaaca tccaatgaag cacacaagtt   1680
tgtttgcttt tcgtgcatga tattaaatag cttggcagca acaggactag gatgagtagc   1740
agcacgttcc ttatatgtag ctttcgacat gatttatctt cgtttcggtt tttgttctgt   1800
gcagttgggt taagaatact gggcaatttc atgtttcttc aacactacat atgcgtatat   1860
ataccaatct aagtctgtgc tccttccttc gttcttcctt ctgttcggag attaccgaat   1920
caaaaaaatt tcaaagaaac cgaaatcaaa aaaagaata aaaaaaaaat gatgaattga   1980
aaagctcttg ttacccatca ttgaattttg aacatccgaa cctgggagtt tccctgaaa   2040 cagatagtat atttgaacct gtataataat atatagtcta gcgctttacg gaagacaatg   2100
tatgtatttc ggttcctgga gaaactattg catctattgc ataggtaatc ttgcacgtcg   2160
catccccggt tcattttctg cgtttccatc ttgcacttca atagcatatc tttgttaacg   2220
aagcatctgt gcttcatttt gtagaacaaa atgcaacgc gagagcgcta attttttcaaa   2280 caaagaatct gagctgcatt tttacagaac agaaatgcaa cgcgaaagcg ctattttacc   2340
aacgaagaat ctgtgcttca tttttgtaaa acaaaaatgc aacgcgagag cgctaatttt   2400
tcaaacaaag aatctgagct gcattttac agaacagaaa tgcaacgcga gagcgctatt   2460
ttaccaacaa agaatctata cttcttttttt gttctacaaa aatgcatccc gagagcgcta   2520
tttttctaac aaagcatctt agattacttt ttttctcctt tgtgcgctct ataatgcagt   2580
ctcttgataa ctttttgcac tgtaggtccg ttaaggttag aagaaggcta ctttggtgtc   2640
```

```
tatttctct tccataaaaa aagcctgact ccacttcccg cgtttactga ttactagcga    2700
agctgcgggt gcattttttc aagataaagg catccccgat tatattctat accgatgtgg    2760
attgcgcata ctttgtgaac agaaagtgat agcgttgatg attcttcatt ggtcagaaaa    2820
ttatgaacgg tttcttctat tttgtctcta tatactacgt ataggaaatg tttacatttt    2880
cgtattgttt tcgattcact ctatgaatag ttcttactac aattttttg tctaaagagt    2940 aatactagag ataaacataa aaatgtaga ggtcgagttt agatgcaagt tcaaggagcg    3000
aaaggtggat gggtaggtta tatagggata tagcacagag atatatagca aagagatact    3060
tttgagcaat gtttgtggaa gcggtattcg caatattta gtagctcgtt acagtccggt    3120 gcgttttgg ttttttgaaa gtgcgtcttc agagcgcttt tggttttcaa aagcgctctg    3180
aagttcctat actttctagc tagagaatag gaacttcgga ataggaactt caaagcgttt    3240
ccgaaaacga gcgcttccga aaatgcaacg cgagctgcgc atacagct cactgttcac    3300 gtcgcaccta tatctgcgtg ttgcctgtat atatatatac atgagaagaa cggcatagtg    3360
cgtgtttatg cttaaatgcg ttatggtgca ctctcagtac aatctgctct gatgccgcat    3420
agttaagcca gccccgacac ccgccaacac ccgctgacgc gccctgacgg gcttgtctgc    3480
tcccggcatc cgcttacaga caagctgtga ccgtctccgg gagctgcatg tgtcagaggt    3540
tttcaccgtc atcaccgaaa cgcgcgagac gaaagggcct cgtgatacgc ctatttttat    3600
aggttaatgt catgataata atggtttctt agacgtcagg tggcactttt cggggaaatg    3660
tgcgcggaac ccctatttgt ttatttttct aaatacattc aaatatgtat ccgctcatga    3720
gacaataacc ctgataaatg cttcaataat attgaaaaag gaagagtatg agtattcaac    3780
atttccgtgt cgcccttatt ccctttttg cggcattttg ccttcctgtt tttgctcacc    3840
cagaaacgct ggtgaaagta aaagatgctg aagatcagtt gggtgcacga gtgggttaca    3900
tcgaactgga tctcaacagc ggtaagatcc ttgagagttt tcgccccgaa gaacgttttc    3960
caatgatgag cacttttaaa gttctgctat gtggcgcggt attatcccgt attgacgccg    4020
ggcaagagca actcggtcgc cgcatacact attctcagaa tgacttggtt gagtactcac    4080
cagtcacaga aaagcatctt acggatggca tgacagtaag agaattatgc agtgctgcca    4140
taaccatgag tgataacact gcggccaact tacttctgac aacgatcgga ggaccgaagg    4200
agctaaccgc ttttttgcac aacatggggg atcatgtaac tcgccttgat cgttgggaac    4260
cggagctgaa tgaagccata ccaaacgacg agcgtgacac cacgatgcct gtagcaatgg    4320
caacaacgtt gcgcaaacta ttaactggcg aactacttac tctagcttcc cggcaacaat    4380
taatagactg gatggaggcg gataaagttg caggaccact tctgcgctcg gcccttccgg    4440
ctggctggtt tattgctgat aaatctggag ccggtgagcg tgggtctcgc ggtatcattg    4500
cagcactggg gccagatggt aagccctccc gtatcgtagt tatctacacg acggggagtc    4560
aggcaactat ggatgaacga aatagacaga tcgctgagat aggtgcctca ctgattaagc    4620
attggtaact gtcagaccaa gtttactcat atatacttta gattgattta aaacttcatt    4680
tttaatttaa aaggatctag gtgaagatcc tttttgataa tctcatgacc aaaatccctt    4740
aacgtgagtt ttcgttccac tgagcgtcag accccgtaga aaagatcaaa ggatcttctt    4800
gagatccttt ttttctgcgc gtaatctgct gcttgcaaac aaaaaaacca ccgctaccag    4860
cggtggtttg tttgccggat caagagctac caactctttt tccgaaggta actggcttca    4920
gcagagcgca gataccaaat actgtccttc tagtgtagcc gtagttaggc caccacttca    4980
agaactctgt agcaccgcct acatacctcg ctctgctaat cctgttacca gtggctgctg    5040
```

```
ccagtggcga taagtcgtgt cttaccgggt tggactcaag acgatagtta ccggataagg    5100
cgcagcggtc gggctgaacg gggggttcgt gcacacagcc cagcttggag cgaacgacct    5160
acaccgaact gagataccta cagcgtgagc attgagaaag cgccacgctt cccgaaggga    5220
gaaaggcgga caggtatccg gtaagcggca gggtcggaac aggagagcgc acgagggagc    5280
ttccaggggg aaacgcctgg tatctttata gtcctgtcgg gtttcgccac ctctgacttg    5340
agcgtcgatt tttgtgatgc tcgtcagggg ggcggagcct atggaaaaac gccagcaacg    5400
cggccttttt acggttcctg gccttttgct ggccttttgc tcacatgttc tttcctgcgt    5460
tatcccctga ttctgtggat aaccgtatta ccgcctttga gtgagctgat accgctcgcc    5520
gcagccgaac gaccgagcgc agcgagtcag tgagcgagga agcggaagag cgcccaatac    5580
gcaaaccgcc tctccccgcg cgttggccga ttcattaatc caggatccca attaatgtga    5640
gttacctcac tcattaggca ccccaggctt tacactttat gcttccggct cgtatgttgt    5700
gtggaattgt gagcggataa caatttcaca caggaaacag ctatgaccat gattacgaat    5760
taattcgagc tcggtacccg gggatcgatc cactagagat ctgtttagct tgcctcgtcc    5820
ccgccgggtc acccggccag cgacatggag gcccagaata ccctccttga cagtcttgac    5880
gtgcgcagct caggggcatg atgtgactgt cgcccgtaca tttagcccat acatccccat    5940
gtataatcat ttgcatccat acattttgat ggccgcacgg cgcgaagcaa aaattacggc    6000
tcctcgctgc agacctgcga gcagggaaac gctcccctca cagacgcgtt gaattgtccc    6060
cacgccgcgc ccctgtagag aaatataaaa ggttaggatt tgccactgag gttcttcttt    6120
catatacttc cttttaaaat cttgctagga tacagttctc acatcacatc cgaacataaa    6180
caaccatggc cgaccaagcg acgcccaacc tgccatcacg agatttcgat tccacggccg    6240
ccttctatga aaggttgggc ttcggaatcg ttttccggga cgccggctgg atgatcctcc    6300
agcgcgggga tctcaagctg gagttcttcg cccacccccgg gctcgatccc ctcgcgagtt    6360
ggttcagctg ctgcctgagg ctggacgacc tcgcggagtt ctaccggcag tgcaaatccg    6420
tcggcatcca ggaaaccagc agcggctatc cgcgcatcca tgcccccgaa ctgcaggagt    6480
ggggaggcac gatggccgct ttggtcgacc cggacgggac gctcctgcgc ctgatacaga    6540
acgaattgct tgcaggcatc tcatgatcag tactgacaat aaaaagattc ttgttttcaa    6600
gaacttgtca tttgtatagt ttttttatat tgtagttgtt ctattttaat caaatgttag    6660
cgtgatttat attttttttc gcctcgacat catctgccca gatgcgaagt taagtgcgca    6720
gaaagtaata tcatgcgtca atcgtatgtg aatgctggtc gctatactgc tgtcgattcg    6780
atactaacgc cgccatccag tgtcgaaaac gagctctcga gaacccttaa tataacttcg    6840
tataatgtat gctatacgaa gttattaggt gatatcagat ccactagtgt ttaaaccct    6900
catctataat ttttaccctg atctaactaa cttttggcatg cctggttcaa tctacgggtt    6960
acagtcatcg ttgaaaacga tggaaaaaca tgtcagatt cctcaatcca tacaccatta    7020
tagtccgttt tatcagcttc cactaatttt ttaaatctca gtttcttctt gaaatttagc    7080
atcgtgcatg ggatagcggc tagtaaaaaa gaaaattaat atctcattaa caaagttatt    7140
gtacataatc cggtacaata ttcttcaatg tactctctaa tatcgagcac actggcaata    7200
ttcatgcaca cattcgccta atgctgacga atgcttaatc agtgcaatta ctgccaccct    7260
cttgatatgt gggctaaatc ctttaggacc tgtaaaaaat gcaatcacgt tttcacattt    7320
tttttttttct tgcggaattg cggaatttcc cagttggcag cgttatccga tttgagatcg    7380
```

```
acttgcatca acctttgaaa aatataagga tgagaaagtg aaatcggttt tttttttcca    7440
ttgtcgtcat caacatgatt ttttaaataa ataaatacga ttttttattt tttttccctt    7500
ctttgttttt gttttgctta ttcccatctt cattattaaa ttcttccgct cttaataaag    7560
gagttttttt attatcttct tgtgtaatca tccttttcct ttaattttct tccttttctt    7620
tttctcttta ctggttttt tacttcttta ttctcaacca tctaaagaat attattgctt    7680
tctaccaata aaatctgtta attctatttg gattgtcgtc tactcaagtc tcgcctagta    7740
aataaacgat aaacaaattt gaagtaagaa taacaatata gggagagaaa tttttctatt    7800
tttaatttcg aaacaggtac caaaaaatct aagttcactt tagcactatt tgggaaagct    7860
tttatataaa aaatctgaaa caaaatcata tcaaagatgg agttacaaga gaaagattta    7920
atgtcaatac aagaagtccg tttgctttta aaaacagcaa aggaagccca taagatatta    7980
tcaaccttca atcaagaaca aatcgatcgt attgtaaagg caattacaga agcatgttta    8040
aagaatgcag agcggcttgc taagatggca aatgaagaaa caggatttgg tatctggcaa    8100
gataaagtaa taaaaaatgt gtttggttct atgggaatct acgaagcaat aaaggatatg    8160
aaaacaatcg gtattcttcg cgaggataag aaaaatcaaa cgatggagat tggtataccg    8220
gtaggtattg tagcaggtgt tataccttcc actaatccaa cttctactgt tatgtataaa    8280 actttaatttt caattaaagc aggtaactgt atcgtattct cgccacatcc tggtgcaaaa    8340
aaatgtatct tggaaacagt taaggttatt tgtgaggctg cagaagcagc aggatgtcca    8400
aaaggagcca tatcctgtat ttccattcca acccttgagg caacgaatga gttgatgaaa    8460
catccaaata caaatcttat cttagcgacc ggtggctatg caatggtgaa atctgcatac    8520
tcatccggta cacctgcaat aggtgttggt gctggtaatg accagcatt catcgacaaa    8580 acagcaaatg tgaaattagc agtaaagcgt attatggatt ccaaaacatt tgacaatgga    8640
accatttgtg catcggagca atctgtaatt gtggaacgat gtatggaaca ggcggtaaaa    8700
gaagaactaa ctgctcaagg cggatttttc ttaaatgagg cagagtcaga aaaattagca    8760
cgttttatct tacgtgccaa tggaacaatg aatccacaaa tcgttggaag atcggtagct    8820
catattagta agcttgccgg tttaacaaca gtaccagcaa atgcaagagt tttaattgca    8880
aaggaaacaa gagtcggcga tgaagctcca tattccagag agaaattagc tccaatctta    8940
gcattctttg tagaagaaac ggttgatgat gtcattaata aagtggtaga gatactaagt    9000
tttgaaggaa tgggacatac ctttaccatg cactctacca atgaagaatt gatcaaacga    9060
tttgccttac gtgtaccagc ttccagaatc ttagttaatt caatgggttc actaggtggc    9120
gttggagcct ctacaaatct attccctgca ttaactcttg gctgtggagc cgtaggagga    9180
agttcttcat ctaataatat tggtcctatg gacttaatta atataaaacg agtagcattt    9240
ggagtaaaag aattagaaga aattaaaagg gatgctacga atagcctagg tgaaaccaaa    9300
tcctcttgtt gtggtgcata cggtaatgtg aatacagaat tggtagagga aattgtaaaa    9360
agaattatga aacaactaat ataa                                          9384
```

<210> SEQ ID NO 77
<211> LENGTH: 10205
<212> TYPE: DNA
<213> ORGANISM: Artificial sequence
<220> FEATURE:
<223> OTHER INFORMATION: Plasmid pAU67

<400> SEQUENCE: 77

```
cgattttttt ctaaaccgtg gaatatttcg gatatccttt tgttgttcc gggtgtacaa     60
```

```
tatggacttc ctcttttctg gcaaccaaac ccatacatcg ggattcctat aataccttcg    120
ttggtctccc taacatgtag gtggcggagg ggagatatac aatagaacag ataccagaca    180
agacataatg ggctaaacaa gactacacca attacactgc ctcattgatg gtggtacata    240
acgaactaat actgtagccc tagacttgat agccatcatc atatcgaagt ttcactaccc    300
tttttccatt tgccatctat tgaagtaata ataggcgcat gcaacttctt ttcttttttt    360
ttcttttctc tctccccgt  tgttgtctca ccatatccgc aatgacaaaa aaatgatgga    420
agacactaaa ggaaaaaatt aacgacaaag acagcaccaa cagatgtcgt tgttccagag    480
ctgatgaggg gtatctcgaa gcacacgaaa cttttccttt ccttcattca cgcacactac    540
tctctaatga gcaacggtat acggccttcc ttccagttac ttgaatttga aataaaaaaa    600
agtttgctgt cttgctatca agtataaata gacctgcaat tattaatctt ttgtttcctc    660
gtcattgttc tcgttccctt tcttccttgt ttcttttttct gcacaatatt tcaagctata    720
ccaagcatac aatcaactat ctcatataca gtgtttatta tggcaacgac aaaaacggaa    780
ttagacgttc agaagcagat agatctactt gtgtcaagag cacaagaggc tcagaaaaaa    840
ttcatgtctt acacgcaaga gcaaatcgac gcaatagtta aggcaatggc tttagcaggc    900
gttgacaaac acgtagagct ggcaaagatg gcgtacgaag agacaaaaat gggtgtatac    960
gaagataaga taacaaaaaa tctcttcgca acagagtacg tgtaccacga cataaaaaat   1020
gaaaagactg taggaatcat aaacgagaac atagaagaaa actacatgga agtggcagaa   1080
ccgataggcg taattgccgg tgtcacacct gtcacaaacc caacatctac cacgatgttt   1140
aaatgcttaa tatccataaa gacgcgaaat cctataatat tcagcttcca tccaaaggca   1200 ataagtgca  gcatcgcagc agccaaagtg atgtatgaag ctgcactaaa ggcaggcgca   1260
cctgaaggat gcataggatg gatagaaacg ccatcaattg aggccacaca gcttctcatg   1320
acacatccag gcgtatcgct gatccttgca acgggcggtg caggaatggt aaaagcggca   1380
tacagctcag gaaaaccggc attaggcgta ggtcctggca atgtgccatg ctacatcgaa   1440
aaatcagcaa acataaagag ggctgtatcg gatctcatac taagcaagac atttgacaat   1500
ggagtaatat gcgcatcaga gcaggccgta ataagacg  aggaaatagc agatgaagtc   1560
aaaaagctta tgaaagaata cggctgctac ttcttaaaca aagatgaaat aaagaagctt   1620
gagaaatttg caattgatga gcaaagctgc gccatgagcc ctgcagtggt aggtcagcca   1680
gcggcgaaga ttgctgaaat ggcaggcttc aaagtccccg aaggcacaaa gatattagtg   1740
gcagagtacg aaggagtagg tccaaaatat cctctatcaa gggagaaact aagcccgatt   1800
cttgcttgct acaccgtcaa agactacaat gaaggaatca aaaagtgcga ggaaatgact   1860
gaattcggag gtttaggcca ctctgctgta atacactctg aaaatcaaaa cgtcataaat   1920
gaatttgcaa ggcgagtccg cacaggaaga cttatcgtaa attcaccatc atcacaggga   1980
gcaataggag atatatacaa tacaaacacg ccatcactta cattaggctg tggttctatg   2040
ggaagaaact caacgacaga caatgtaagc gtcaagaacc ttttgaatat taagcgtgtc   2100
gtgataagga atgatagaat gaaatggttc aagattccac cgaagattta ctttgaaagc   2160
gggtcactcc agtacctgtg caaagtcaaa agaaaaaaag cgtttatcgt cacagatcca   2220
ttcatggtta agcttggctt cgtagacaaa gtgacatatc aattagacaa agcaaacatc   2280
gaatacgaaa tattctcaga agtagagcca gatccatctg ttgacacagt catgaacggc   2340
gtaaaaataa tgaattcgta caatcctgac ttaataatcg ctgtaggcgg tggctctgca   2400
```

```
atagacgcag caaagggaat gtggcttttc tacgaatatc ctgatacaga gtttgaaaca    2460
ttgaggctta aatttgcaga catcagaaaa agggcattta agttcccaga acttggcaaa    2520
aaagcgctat tcatcgcaat accgacaaca agcggcacag gctcagaagt gacagcattt    2580
gccgtaataa ccgacaaaaa gagaaacatc aagtatccac tggcagacta cgaacttaca    2640
cctgacatag ccataataga tcctgacctt acaaagactg taccgccatc tgtaacagca    2700
gacacaggca tggatgtgct gacacacgcc atagaagcat acgtatcagt aatggcatca    2760
gactacacag atgcactggc ggaaaaggct ataaagatcg tatttgaata cctgccaagg    2820
gcttataaaa acggcaatga tgaagaagcc cgcgaaaaga tgcacaatgc ttcctgcatg    2880
gctggtatgg cattcacaaa tgcattctta ggaataaacc acagcatggc acacatactg    2940
ggcggaaagt tccacatacc acacggaaga gcaaatgcaa tacttctgcc gtatgtaata    3000
aggtacaatg cagaaaaacc tacaaagttt gtggcattcc cacaatacga atatccaaaa    3060
gcagcagaaa gatatgcgga atcgccaaa ttcttaggac tgcctgcttc aactgttgaa     3120
gaaggcgtag aaagcttaat agaagctata aagaacctca tgaaagagct taacattccg    3180
cttacactta aagacgccgg catcaacaaa gaacagtttg aaaaagaaat agaggaaatg    3240
tcagacatcg ccttcaacga tcagtgcaca gggacaaacc cgagaatgcc tctcacaaaa    3300
gaaattgcag agatctacag aaaagcatac ggtgcagcga tttaatctct aattattagt    3360
taaagtttta taagcatttt tatgtaacga aaaataaatt ggttcatatt attactgcac    3420
tgtcacttac catggaaaga ccagacaaga agttgccgac agtctgttga attggcctgg    3480
ttaggcttaa gtctgggtcc gcttctttac aaatttggag aatttctctt aaacgatatg    3540
tatattcttt tcgttggaaa agatgtcttc caaaaaaaaa accgatgaat tagtggaacc    3600
aaggaaaaaa aaagaggtat ccttgattaa ggaacactgt ttaaacagtg tggtttccaa    3660
aaccctgaaa ctgcattagt gtaatagaag actagacacc tcgatacaaa taatggttac    3720
tcaattcaaa actgccagcg aattcgactc tgcaattgct caagacaagc tagttgtcgt    3780
agatttctac gccacttggt gcggtccatg taaaatgatt gctccaatga ttgaaataaa    3840 cctcttgcg ggcaagcttg gcactggccg tcgttttaca acgtcgtgac tgggaaaacc     3900
ctggcgttac ccaacttaat cgccttgcag cacatccccc tttcgccagc tggcgtaata    3960
gcgaagaggc ccgcaccgat cgcccttccc aacagttgcg cagcctgaat ggcgaatggc    4020
gcctgatgcg gtattttctc cttacgcatc tgtgcggtat ttcacaccgc ataggagatc    4080
taagctctgg cgtaatagcg aagaggcccg caccgatcgc ccttcccaac agttgcgcag    4140
cctgaatggc gaatggcgcc tgatgcggta ttttctcctt acgcatctgt gcggtatttc    4200
acaccgcata gggtaataac tgatataatt aaattgaagc tctaatttgt gagtttagta    4260
tacatgcatt tacttataat acagtttttt agttttgctg gccgcatctt ctcaaatatg    4320
cttcccagcc tgcttttctg taacgttcac cctctacctt agcatccctt cccttttgcaa   4380 atagtcctct tccaacaata taatgtcag atcctgtaga gaccacatca tccacggttc     4440
tatactgttg acccaatgcg tctcccttgt catctaaacc cacaccgggt gtcataatca    4500
accaatcgta accttcatct cttccaccca tgtctctttg agcaataaag ccgataacaa    4560
aatctttgtc gctcttcgca atgtcaacag tacccttagt atattctcca gtagataggg    4620
agcccttgca tgacaattct gctaacatca aaaggcctct aggttccttt gttacttctt    4680
ctgccgcctg cttcaaaccg ctaacaatac ctgggcccac cacaccgtgt gcattcgtaa    4740
tgtctgccca ttctgctatt ctgtatacac ccgcagagta ctgcaatttg actgtattac    4800
```

```
caatgtcagc aaattttctg tcttcgaaga gtaaaaaatt gtacttggcg ataatgcct    4860 ttagcggctt aactgtgccc tccatggaaa aatcagtcaa gatatccaca tgtgttttta   4920
gtaaacaaat tttgggacct aatgcttcaa ctaactccag taattccttg gtggtacgaa   4980
catccaatga agcacacaag tttgtttgct tttcgtgcat gatattaaat agcttggcag   5040
caacaggact aggatgagta gcagcacgtt ccttatatgt agctttcgac atgatttatc   5100
ttcgtttcgg ttttgttct gtgcagttgg gttaagaata ctgggcaatt tcatgtttct    5160
tcaacactac atatgcgtat ataccaat ctaagtctgt gctccttcct tcgttcttcc     5220
ttctgttcgg agattaccga atcaaaaaaa tttcaaagaa accgaaatca aaaaaagaa    5280 taaaaaaaaa atgatgaatt gaaaagctct tgttacccat cattgaattt tgaacatccg   5340
aacctgggag ttttccctga acagatagt atatttgaac ctgtataata atatatagtc    5400
tagcgcttta cggaagacaa tgtatgtatt tcggttcctg gagaaactat tgcatctatt   5460
gcataggtaa tcttgcacgt cgcatcccccg gttcattttc tgcgtttcca tcttgcactt  5520
caatagcata tctttgttaa cgaagcatct gtgcttcatt ttgtagaaca aaaatgcaac   5580
gcgagagcgc taattttttca aacaaagaat ctgagctgca tttttacaga acagaaatgc  5640
aacgcgaaag cgctatttta ccaacgaaga atctgtgctt cattttgta aaacaaaaat    5700 gcaacgcgag agcgctaatt tttcaaacaa agaatctgag ctgcattttt acagaacaga   5760
aatgcaacgc gagagcgcta ttttaccaac aaagaatcta tacttctttt tgttctaca    5820 aaaatgcatc ccgagagcgc tattttttcta caaagcatc ttagattact ttttttctcc   5880
tttgtgcgct ctataatgca gtctcttgat aacttttgc actgtaggtc cgttaaggtt    5940
agaagaaggc tactttggtg tctattttct cttccataaa aaaagcctga ctccacttcc   6000
cgcgtttact gattactagc gaagctgcgg gtgcattttt tcaagataaa ggcatccccg   6060
attatattct ataccgatgt ggattgcgca tactttgtga acagaaagtg atagcgttga   6120
tgattcttca ttggtcagaa aattatgaac ggtttcttct attttgtctc tatatactac   6180
gtataggaaa tgtttacatt ttcgtattgt tttcgattca ctctatgaat agttcttact   6240 acaattttt tgtctaaaga gtaatactag agataaacat aaaaaatgta gaggtcgagt    6300
ttagatgcaa gttcaaggag cgaaaggtgg atgggtaggt tatataggga tatagcacag   6360
agatatatag caaagagata cttttgagca atgtttgtgg aagcggtatt cgcaatattt   6420
tagtagctcg ttacagtccg gtgcgttttt ggttttttga agtgcgtct tcagagcgct    6480 tttggttttc aaaagcgctc tgaagttcct atactttcta gctagagaat aggaacttcg   6540
gaataggaac ttcaaagcgt ttccgaaaac gagcgcttcc gaaaatgcaa cgcgagctgc   6600
gcacatacag ctcactgttc acgtcgcacc tatatctgcg tgttgcctgt atatatatat   6660
acatgagaag aacggcatag tgcgtgttta tgcttaaatg cgttatggtg cactctcagt   6720
acaatctgct ctgatgccgc atagttaagc cagccccgac acccgccaac acccgctgac   6780
gcgccctgac gggcttgtct gctcccggca tccgcttaca gacaagctgt gaccgtctcc   6840
gggagctgca tgtgtcagag gttttcaccg tcatcaccga aacgcgcgag acgaaagggc   6900
ctcgtgatac gcctattttt ataggttaat gtcatgataa taatggtttc ttagacgtca   6960
ggtggcactt ttcggggaaa tgtgcgcgga acccctattt gtttattttt ctaaatacat   7020
tcaaatatgt atccgctcat gagacaataa ccctgataaa tgcttcaata atattgaaaa   7080
aggaagagta tgagtattca acatttccgt gtcgccctta ttcccttttt tgcggcattt   7140
```

```
tgccttcctg tttttgctca cccagaaacg ctggtgaaag taaaagatgc tgaagatcag    7200
ttgggtgcac gagtgggtta catcgaactg gatctcaaca gcggtaagat ccttgagagt    7260
tttcgccccg aagaacgttt tccaatgatg agcacttta aagttctgct atgtggcgcg     7320
gtattatccc gtattgacgc cgggcaagag caactcggtc gccgcataca ctattctcag    7380
aatgacttgg ttgagtactc accagtcaca gaaaagcatc ttacggatgg catgacagta    7440
agagaattat gcagtgctgc cataaccatg agtgataaca ctgcggccaa cttacttctg    7500
acaacgatcg gaggaccgaa ggagctaacc gcttttttgc acaacatggg ggatcatgta    7560
actcgccttg atcgttggga accggagctg aatgaagcca taccaaacga cgagcgtgac    7620
accacgatgc ctgtagcaat ggcaacaacg ttgcgcaaac tattaactgg cgaactactt    7680
actctagctt cccggcaaca attaatagac tggatggagg cggataaagt tgcaggacca    7740
cttctgcgct cggcccttcc ggctggctgg tttattgctg ataaatctgg agccggtgag    7800
cgtgggtctc gcggtatcat tgcagcactg gggccagatg gtaagccctc ccgtatcgta    7860
gttatctaca cgacggggag tcaggcaact atggatgaac gaaatagaca gatcgctgag    7920
ataggtgcct cactgattaa gcattggtaa ctgtcagacc aagtttactc atatatactt    7980
tagattgatt taaaacttca ttttaattt aaaaggatct aggtgaagat cctttttgat     8040
aatctcatga ccaaaatccc ttaacgtgag ttttcgttcc actgagcgtc agaccccgta    8100
gaaaagatca aggatcttc ttgagatcct ttttttctgc gcgtaatctg ctgcttgcaa     8160
acaaaaaaac caccgctacc agcggtggtt tgtttgccgg atcaagagct accaactctt    8220
tttccgaagg taactggctt cagcagagcg cagataccaa atactgtcct tctagtgtag    8280
ccgtagttag gccaccactt caagaactct gtagcaccgc ctacatacct cgctctgcta    8340
atcctgttac cagtggctgc tgccagtggc gataagtcgt gtcttaccgg gttggactca    8400
agacgatagt taccggataa ggcgcagcgg tcgggctgaa cggggggttc gtgcacacag    8460
cccagcttgg agcgaacgac ctacaccgaa ctgagatacc tacagcgtga gcattgagaa    8520
agcgccacgc ttcccgaagg gagaaaggcg gacaggtatc cggtaagcgg cagggtcgga    8580
acaggagagc gcacgaggga gcttccaggg ggaaacgcct ggtatcttta tagtcctgtc    8640
gggtttcgcc acctctgact tgagcgtcga ttttttgtgat gctcgtcagg gggcggagc    8700 ctatggaaaa acgccagcaa cgcggccttt ttacggttcc tggccttttg ctggcctttt    8760
gctcacatgt tctttcctgc gttatcccct gattctgtgg ataaccgtat taccgccttt    8820
gagtgagctg ataccgctcg ccgcagccga acgaccgagc gcagcgagtc agtgagcgag    8880
gaagcggaag agcgcccaat acgcaaaccg cctctccccg cgcgttggcc gattcattaa    8940
tccaggatcc caattaatgt gagttaccrc actcattagg caccccaggc tttacacttt    9000
atgcttccgg ctcgtatgtt gtgtggaatt gtgagcggat aacaatttca cacaggaaac    9060
agctatgacc atgattacga attaattcga gctcggtacc cggggatcga tccactagag    9120
atctgtttag cttgcctcgt ccccgccggg tcacccggcc agcgacatgg aggcccagaa    9180
taccctcctt gacagtcttg acgtgcgcag ctcaggggca tgatgtgact gtcgcccgta    9240
catttagccc atacatcccc atgtataatc atttgcatcc atacattttg atggccgcac    9300
ggcgcgaagc aaaaattacg gctcctcgct gcagacctgc gagcagggaa acgctcccct    9360
cacagacgcg ttgaattgtc cccacgccgc gcccctgtag agaaatataa aaggttagga    9420
tttgccactg aggttcttct ttcatatact tcctttaaa atcttgctag gatacagttc      9480
tcacatcaca tccgaacata aacaaccatg gccgaccaag cgacgcccaa cctgccatca    9540
```

```
cgagatttcg attccacggc cgccttctat gaaaggttgg gcttcggaat cgttttccgg    9600
gacgccggct ggatgatcct ccagcgcggg gatctcaagc tggagttctt cgcccacccc    9660
gggctcgatc ccctcgcgag ttggttcagc tgctgcctga ggctggacga cctcgcggag    9720
ttctaccgga agtgcaaatc cgtcggcatc caggaaacca gcagcggcta tccgcgcatc    9780
catgcccccg aactgcagga gtggggaggc acgatggccg ctttggtcga cccggacggg    9840
acgctcctgc gcctgataca gaacgaattg cttgcaggca tctcatgatc agtactgaca    9900
ataaaaagat tcttgttttc aagaacttgt catttgtata gttttttat attgtagttg     9960 ttctatttta atcaaatgtt agcgtgattt atatttttt tcgcctcgac atcatctgcc    10020
cagatgcgaa gttaagtgcg cagaaagtaa tatcatgcgt caatcgtatg tgaatgctgg   10080
tcgctatact gctgtcgatt cgatactaac gccgccatcc agtgtcgaaa acgagctctc   10140 gagaacccgtt aatataactt cgtataatgt atgctatacg aagttattag gtgatatcag   10200
atcca                                                              10205

<210> SEQ ID NO 78
<211> LENGTH: 8677
<212> TYPE: DNA
<213> ORGANISM: Artificial sequence
<220> FEATURE:
<223> OTHER INFORMATION: Plasmid pMU2623

<400> SEQUENCE: 78
atggcttcat atcctggtca ccaacatgca tccgcttttg atcaagccgc gagatctaga      60
ggacattcta ataggagaac agctttgcgt cctcgtagac aacaggaagc aactgaagta     120
agaccagaac aaaagatgcc aacactactt agagtctaca tcgacggtcc acacggtatg    180
ggtaaaacaa caactacaca attactagtc gctttgggat ctagagatga tattgtctat    240
gttccagagc ctatgaccta ctggagagtt ctaggtgcct cagaaacgat cgcaaacatc     300
tacaccaccc aacatagatt agatcaaggt gaaatctccg ctggtgatgc ggctgttgtt    360
atgacttctg cacagataac catgggcatg ccttacgccg taactgatgc tgttttggcc    420
ccacatattg gcggagaagc tggttcaagt catgccccac caccagcact cacattgata    480
ttcgatagac acccaatcgc ggcattgctt tgttatcctg ctgccagata cctaatgggt    540
tcaatgactc ctcaggctgt gcttgctttt gttgcactta taccacctac attgccaggg    600
accaacatcg tgttaggagc tctgcctgaa gatagacata ttgatagact ggctaagaga    660
caaagacctg gcgagcgatt ggacttagct atgctcgcgg caataagacg tgtctatgga    720
ctattggcaa atacggttag gtacttacaa tgtggtggaa gctggagaga agattggggt    780
caactttctg gcactgcagt tcctccacaa ggcgcagagc cacagagtaa tgcagggcca    840
agaccacaca ttggggacac cctctttact ctcttcagag ctccagagct gttggctcca    900
aacggcgacc tctataacgt gttcgcatgg gcccttgatg tcctagcgaa gcgattgaga    960
tccatgcatg tttttcatctt agattacgat caatctcctg ctggatgcag agatgcactg   1020
ttacaattga catcaggcat ggtacaaact catgtaacaa caccagggtc tattccaacg    1080
atctgcgatc tggccaggac tttcgctagg gaaatgggtg aagccaacta atctctgctt    1140
ttgtgcgcgt atgtttatgt atgtaccctct ctctctattt ctatttttaa accaccctct   1200
caataaaata aaaataataa agtatttta aggaaaagac gtgtttaagc actgactta     1260 tctactttt gtacgttttc attgatataa tgtgtttgt ctctcccttt tctacgaaaa     1320
```

```
tttcaaaaat tgaccaaaaa aaggaatata tatacgaaaa actattatat ttatatatca   1380
tagtgttgat aaaaaatgtt tatccattgg accgtgtatc atatgatcat ctcttcatcg   1440
cttttcagtt ttataggttt atgcaattgc ccttcttggg aggatcttgt agaaccgcca   1500
ttagaatttg agtccggcgt tttgataccc ttttccccat gtaaattggt gccctcttta   1560
ctctcaaatt cgaagaattt atcaatatct tctatgctca tacccttgt ttctgggaac    1620
caaatcaaaa catttaaatc cgcggtaaac ctctttgcgg gcaagcttgg cactggccgt   1680
cgttttacaa cgtcgtgact gggaaaaccc tggcgttacc caacttaatc gccttgcagc   1740
acatccccct ttcgccagct ggcgtaatag cgaagaggcc cgcaccgatc gcccttccca   1800
acagttgcgc agcctgaatg gcgaatggcg cctgatgcgg tattttctcc ttacgcatct   1860
gtgcggtatt tcacaccgca taggagatct aagctctggc gtaatagcga agaggcccgc   1920
accgatcgcc cttcccaaca gttgcgcagc ctgaatggcg aatggcgcct gatgcggtat   1980
tttctcctta cgcatctgtg cggtattca caccgcatag gtaataact gatataatta    2040
aattgaagct ctaatttgtg agtttagtat acatgcattt acttataata cagttttta    2100
gttttgctgg ccgcatcttc tcaaatatgc ttcccagcct gcttttctgt aacgttcacc   2160
ctctacctta gcatcccttc cctttgcaaa tagtcctctt ccaacaataa taatgtcaga   2220
tcctgtagag accacatcat ccacggttct atactgttga cccaatgcgt ctcccttgtc   2280
atctaaaccc acaccgggtg tcataatcaa ccaatcgtaa ccttcatctc ttccacccat   2340
gtctctttga gcaataaagc cgataacaaa atctttgtcg ctcttcgcaa tgtcaacagt   2400
acccttagta tattctccag tagatagga gcccttgcat gacaattctg ctaacatcaa   2460
aaggcctcta ggttcctttg ttacttcttc tgccgcctgc ttcaaaccgc taacaatacc   2520
tgggcccacc acaccgtgtg cattcgtaat gtctgcccat tctgctattc tgtatacacc   2580
cgcagagtac tgcaatttga ctgtattacc aatgtcagca aattttctgt cttcgaagag   2640
taaaaaattg tacttggcgg ataatgcctt tagcggctta actgtgccct ccatggaaaa   2700
atcagtcaag atatccacat gtgtttttag taaacaaatt ttgggaccta atgcttcaac   2760
taactccagt aattccttgg tggtacgaac atccaatgaa gcacacaagt ttgtttgctt   2820
ttcgtgcatg atattaaata gcttggcagc aacaggacta ggatgagtag cagcacgttc   2880
cttatatgta gctttcgaca tgatttatct tcgtttcggt ttttgttctg tgcagttggg   2940
ttaagaatac tgggcaattt catgtttctt caacactaca tatgcgtata tataccaatc   3000
taagtctgtg ctccttcctt cgttcttcct tctgttcgga gattaccgaa tcaaaaaaat   3060
ttcaaagaaa ccgaaatcaa aaaaagaat aaaaaaaaaa tgatgaattg aaaagctctt    3120
gttacccatc attgaatttt gaacatccga acctgggagt tttccctgaa acagatagta   3180
tatttgaacc tgtataataa tatatagtct agcgctttac ggaagacaat gtatgtattt   3240
cggttcctgg agaaactatt gcatctattg cataggtaat cttgcacgtc gcatcccgg    3300
ttcattttct gcgtttccat cttgcacttc aatagcatat ctttgttaac gaagcatctg   3360
tgcttcattt tgtagaacaa aaatgcaacg cgagagcgct aattttttcaa acaaagaatc   3420
tgagctgcat tttacagaa cagaaatgca acgcgaaagc gctattttac caacgaagaa   3480
tctgtgcttc attttttgtaa aacaaaaatg caacgcgaga gcgctaattt tcaaacaaa   3540
gaatctgagc tgcatttta cagaacagaa atgcaacgcg agagcgctat tttaccaaca   3600
aagaatctat acttcttttt tgttctacaa aaatgcatcc cgagagcgct attttttctaa   3660
caaagcatct tagattactt ttttctcct tgtgcgctc tataatgcag tctcttgata   3720
```

```
acttttttgca ctgtaggtcc gttaaggtta gaagaaggct actttggtgt ctattttctc    3780
ttccataaaa aaagcctgac tccacttccc gcgtttactg attactagcg aagctgcggg    3840 tgcattttt   caagataaag gcatccccga ttatattcta taccgatgtg gattgcgcat    3900
actttgtgaa cagaaagtga tagcgttgat gattcttcat tggtcagaaa attatgaacg    3960
gtttcttcta ttttgtctct atatactacg tataggaaat gtttacattt tcgtattgtt    4020
ttcgattcac tctatgaata gttcttacta caattttttt gtctaaagag taatactaga    4080
gataaacata aaaatgtag  aggtcgagtt tagatgcaag ttcaaggagc gaaaggtgga    4140
tgggtaggtt atatagggat atagcacaga gatatatagc aaagagatac ttttgagcaa    4200
tgtttgtgga agcggtattc gcaatatttt agtagctcgt tacagtccgg tgcgttttg     4260 gttttttgaa agtgcgtctt cagagcgctt ttggttttca aaagcgctct gaagttccta    4320
tactttctag ctagagaata ggaacttcgg aataggaact tcaaagcgtt tccgaaaacg    4380
agcgcttccg aaaatgcaac gcgagctgcg cacatacagc tcactgttca cgtcgcacct    4440
atatctgcgt gttgcctgta tatatatata catgagaaga acggcatagt gcgtgtttat    4500
gcttaaatgc gttatggtgc actctcagta caatctgctc tgatgccgca tagttaagcc    4560
agccccgaca cccgccaaca cccgctgacg cgccctgacg ggcttgtctg ctcccggcat    4620
ccgcttacag acaagctgtg accgtctccg ggagctgcat gtgtcagagg ttttcaccgt    4680
catcaccgaa acgcgcgaga cgaaagggcc tcgtgatacg cctattttta taggttaatg    4740
tcatgataat aatggtttct tagacgtcag gtggcacttt tcggggaaat gtgcgcggaa    4800
cccctatttg tttatttttc taaatacatt caaatatgta tccgctcatg agacaataac    4860
cctgataaat gcttcaataa tattgaaaaa ggaagagtat gagtattcaa catttccgtg    4920
tcgcccttat tcccttttt  gcggcatttt gccttcctgt ttttgctcac ccagaaacgc    4980
tggtgaaagt aaaagatgct gaagatcagt tgggtgcacg agtgggttac atcgaactgg    5040
atctcaacag cggtaagatc cttgagagtt ttcgccccga agaacgtttt ccaatgatga    5100
gcacttttaa agttctgcta tgtggcgcgg tattatcccg tattgacgcc gggcaagagc    5160
aactcggtcg ccgcatacac tattctcaga atgacttggt tgagtactca ccagtcacag    5220
aaaagcatct tacgatggc  atgacagtaa gagaattatg cagtgctgcc ataaccatga    5280
gtgataacac tgcggccaac ttacttctga caacgatcgg aggaccgaag gagctaaccg    5340
cttttttgca caacatgggg gatcatgtaa ctcgccttga tcgttgggaa ccggagctga    5400
atgaagccat accaaacgac gagcgtgaca ccacgatgcc tgtagcaatg gcaacaacgt    5460
tgcgcaaact attaactggc gaactactta ctctagcttc ccggcaacaa ttaatagact    5520
ggatggaggc ggataaagtt gcaggaccac ttctgcgctc ggcccttccg gctggctggt    5580
ttattgctga taaatctgga gccggtgagc gtgggtctcg cggtatcatt gcagcactgg    5640
ggccagatgg taagccctcc cgtatcgtag ttatctacac gacggggagt caggcaacta    5700
tggatgaacg aaatagacag atcgctgaga taggtgcctc actgattaag cattggtaac    5760
tgtcagacca agtttactca tatatacttt agattgattt aaaacttcat ttttaattta    5820
aaaggatcta ggtgaagatc ctttttgata atctcatgac caaaatccct taacgtgagt    5880
tttcgttcca ctgagcgtca gaccccgtag aaaagatcaa aggatcttct tgagatcctt    5940 ttttttctgcg cgtaatctgc tgcttgcaaa caaaaaaacc accgctacca gcggtggttt    6000
gtttgccgga tcaagagcta ccaactcttt ttccgaaggt aactggcttc agcagagcgc    6060
```

```
agataccaaa tactgtcctt ctagtgtagc cgtagttagg ccaccacttc aagaactctg    6120
tagcaccgcc tacatacctc gctctgctaa tcctgttacc agtggctgct gccagtggcg    6180
ataagtcgtg tcttaccggg ttggactcaa gacgatagtt accggataag gcgcagcggt    6240
cgggctgaac gggggggttcg tgcacacagc ccagcttgga gcgaacgacc tacaccgaac    6300
tgagatacct acagcgtgag cattgagaaa gcgccacgct tcccgaaggg agaaaggcgg    6360
acaggtatcc ggtaagcggc agggtcggaa caggagagcg cacgagggag cttccagggg    6420
gaaacgcctg gtatctttat agtcctgtcg ggtttcgcca cctctgactt gagcgtcgat    6480
ttttgtgatg ctcgtcaggg gggcggagcc tatggaaaaa cgccagcaac gcggcctttt    6540
tacggttcct ggccttttgc tggccttttg ctcacatgtt ctttcctgcg ttatcccctg    6600
attctgtgga taaccgtatt accgcctttg agtgagctga taccgctcgc cgcagccgaa    6660
cgaccgagcg cagcgagtca gtgagcgagg aagcggaaga gcgcccaata cgcaaaccgc    6720
ctctccccgc gcgttggccg attcattaat ccaggatccc aattaatgtg agttacctca    6780
ctcattaggc accccaggct ttacacttta tgcttccggc tcgtatgttg tgtggaattg    6840
tgagcggata caatttcac acaggaaaca gctatgacca tgattacgaa ttaattcgag    6900
ctcggtaccc ggggatcgat ccactagaga tctgtttagc ttgcctcgtc cccgccgggt    6960
caccccggcca gcgacatgga ggcccagaat accctccttg acagtcttga cgtgcgcagc    7020
tcagggcat gatgtgactg tcgcccgtac atttagccca tacatcccca tgtataatca    7080
tttgcatcca tacattttga tggccgcacg gcgcgaagca aaaattacgg ctcctcgctg    7140
cagacctgcg agcagggaaa cgctcccctc acagacgcgt tgaattgtcc ccacgccgcg    7200
cccctgtaga gaaatataaa aggttaggat ttgccactga ggttcttctt tcatatactt    7260
ccttttaaaa tcttgctagg atacagttct cacatcacat ccgaacataa acaaccatgg    7320
ccgaccaagc gacgcccaac ctgccatcac gagatttcga ttccacggcc gccttctatg    7380
aaaggttggg cttcggaatc gttttccggg acgccggctg gatgatcctc cagcgcgggg    7440
atctcaagct ggagttcttc gcccacccg ggctcgatcc cctcgcgagt tggttcagct    7500
gctgcctgag gctggacgac ctcgcggagt tctaccggca gtgcaaatcc gtcggcatcc    7560
aggaaaccag cagcggctat ccgcgcatcc atgcccccga actgcaggag tggggaggca    7620
cgatggccgc tttggtcgac ccggacggga cgctcctgcg cctgatacag aacgaattgc    7680
ttgcaggcat ctcatgatca gtactgacaa taaaaagatt cttgttttca agaacttgtc    7740
atttgtatag tttttttata ttgtagttgt tctattttaa tcaaatgtta gcgtgattta    7800
tatttttttt cgcctcgaca tcatctgccc agatgcgaag ttaagtgcgc agaaagtaat    7860
atcatgcgtc aatcgtatgt gaatgctggt cgctatactg ctgtcgattc gatactaacg    7920
ccgccatcca gtgtcgaaaa cgagctctcg agaacccctta atataacttc gtataatgta    7980
tgctatacga agttattagg tgatatcaga tccactagtg tttaaacgag actacatgat    8040
agtccaaaga aaagaaacgg ggggacgaag aagaggagag gaaaaaccaa aatataattt    8100
tccgtgaaat agattctttt tctccactgc acgacttctt ctcctcccac aaaaaatgac    8160
gcctcataga cagccccgca gcttcacttt taagtttctt tttctcctca cggcgcaacc    8220
gctaacttaa gctaatcctt atgaatccgg agaaaagcgg ggtctttaa ctcaataaaa    8280
ttttccgaaa tccttttttcc tacgcgtttt cttcgggaac tagataggtg gctcttccac    8340
ctgttttttcc atcattttag ttttttcgcaa gccatgcgtg ccttttcgtt tttgcgatgg    8400
cgaagcaggg ctggaaaaat taacggtacg ccgcctaacg atagtaatag gccacgcaac    8460
```

| | | |
|---|---|---|
| tggcgtggac gacaacaata agtcgcccat tttttatgtt ttcaaaacct agcaaccccc | 8520 |
| accaaacttg tcatcgttcc cggattcaca aatgatataa aaagcgatta caattctaca | 8580 |
| ttctaaccag atttgagatt tcctctttct caattcctct tatattagat tataagaaca | 8640 |
| acaaattaaa ttacaaaaag acttataaag caacata | 8677 |

<210> SEQ ID NO 79
<211> LENGTH: 6123
<212> TYPE: DNA
<213> ORGANISM: Artificial sequence
<220> FEATURE:
<223> OTHER INFORMATION: Plasmid pMU2660

<400> SEQUENCE: 79

| | |
|---|---|
| gacgaaaggg cctcgtgata cgcctatttt tataggttaa tgtcatgata ataatggttt | 60 |
| cttaggacgg atcgcttgcc tgtaacttac acgcgcctcg tatcttttaa tgatggaata | 120 |
| atttgggaat ttactctgtg tttatttatt tttatgtttt gtatttggat tttagaaagt | 180 |
| aaataaagaa ggtagaagag ttacggaatg aagaaaaaaa aataaacaaa ggtttaaaaa | 240 |
| atttcaacaa aaagcgtact ttacatatat atttattaga caagaaaagc agattaaata | 300 |
| gatatacatt cgattaacga taagtaaaat gtaaaatcac aggattttcg tgtgtggtct | 360 |
| tctacacaga caagatgaaa caattcggca ttaatacctg agagcaggaa gagcaagata | 420 |
| aaaggtagta tttgttggcg atcccccctag agtcttttac atcttcggaa aacaaaaact | 480 |
| attttttctt taatttcttt ttttactttc tatttttaat ttatatattt atattaaaaa | 540 |
| atttaaatta taattatttt tatagcacgt gatgaaaagg acccaggtgg cacttttcgg | 600 |
| ggaaatgtgc gcggaacccc tatttgttta tttttctaaa tacattcaaa tatgtatccg | 660 |
| ctcatgagac aataaccctg ataaatgctt caataatatt gaaaaggaa gagtatgagt | 720 |
| attcaacatt tccgtgtcgc ccttattccc ttttttgcgg catttgcct tcctgttttt | 780 |
| gctcacccag aaacgctggt gaaagtaaaa gatgctgaag atcagttggg tgcacgagtg | 840 |
| ggttacatcg aactggatct caacagcggt aagatccttg agagttttcg ccccgaagaa | 900 |
| cgttttccaa tgatgagcac ttttaaagtt ctgctatgtg gcgcggtatt atcccgtatt | 960 |
| gacgccgggc aagagcaact cggtcgccgc atacactatt ctcagaatga cttggttgag | 1020 |
| tactcaccag tcacagaaaa gcatcttacg gatggcatga cagtaagaga attatgcagt | 1080 |
| gctgccataa ccatgagtga taacactgcg gccaacttac ttctgacaac gatcggagga | 1140 |
| ccgaaggagc taaccgcttt ttttcacaac atggggatc atgtaactcg ccttgatcgt | 1200 |
| tgggaaccgg agctgaatga agccatacca aacgacgagc gtgacaccac gatgcctgta | 1260 |
| gcaatggcaa caacgttgcg caaactatta actggcgaac tacttactct agcttcccgg | 1320 |
| caacaattaa tagactggat ggaggcggat aaagttgcag gaccacttct gcgctcggcc | 1380 |
| cttccggctg gctggtttat tgctgataaa tctggagccg gtgagcgtgg gtctcgcggt | 1440 |
| atcattgcag cactggggcc agatggtaag ccctcccgta tcgtagttat ctacacgacg | 1500 |
| ggcagtcagg caactatgga tgaacgaaat agacagatcg ctgagatagg tgcctcactg | 1560 |
| attaagcatt ggtaactgtc agaccaagtt tactcatata tactttagat tgatttaaaa | 1620 |
| cttcattttt aatttaaaag gatctaggtg aagatccttt ttgataatct catgaccaaa | 1680 |
| atcccttaac gtgagttttc gttccactga gcgtcagacc ccgtagaaaa gatcaaagga | 1740 |
| tcttcttgag atcctttttt tctgcgcgta atctgctgct tgcaaacaaa aaaaccaccg | 1800 |

```
ctaccagcgg tggtttgttt gccggatcaa gagctaccaa ctcttttcc gaaggtaact      1860
ggcttcagca gagcgcagat accaaatact gtccttctag tgtagccgta gttaggccac      1920
cacttcaaga actctgtagc accgcctaca tacctcgctc tgctaatcct gttaccagtg      1980
gctgctgcca gtggcgataa gtcgtgtctt accgggttgg actcaagacg atagttaccg      2040
gataaggcgc agcggtcggg ctgaacgggg ggttcgtgca cacagcccag cttggagcga      2100
acgacctaca ccgaactgag atacctacag cgtgagcatt gagaaagcgc cacgcttccc      2160
gaagggagaa aggcggacag gtatccggta agcggcaggg tcggaacagg agagcgcacg      2220
agggagcttc caggggggaa cgcctggtat ctttatagtc ctgtcgggtt tcgccacctc      2280
tgacttgagc gtcgattttt gtgatgctcg tcagggggc cgagcctatg gaaaaacgcc       2340
agcaacgcgg cctttttacg gttcctggcc ttttgctggc cttttgctca catgttcttt       2400
cctgcgttat cccctgattc tgtggataac cgtattaccg cctttgagtg agctgatacc       2460
gctcgccgca gccgaacgac cgagcgcagc gagtcagtga gcgaggaagc ggaagagcgc       2520
ccaatacgca aaccgcctct ccccgcgcgt tggccgattc attaatgcag ctggcacgac       2580
aggtttcccg actggaaagc gggcagtgag cgcaacgcaa ttaatgtgag ttacctcact       2640
cattaggcac cccaggcttt acactttatg cttccggctc ctatgttgtg tggaattgtg       2700
agcggataac aatttcacac aggaaacagc tatgaccatg attacgccaa gctcggaatt       2760
aaccctcact aaagggaaca aaagctggct agagcggccg ccagctgaag cttcgtacgc       2820
tgcaggtcga cggatccccg ggttaattaa ggcgcgccag atctgtttag cttgccttgt       2880
ccccgccggg tcaccggcc agcgacatgg aggcccagaa taccctcctt gacagtcttg       2940
acgtgcgcag ctcaggggca tgatgtgact gtcgcccgta catttagccc atacatcccc       3000
atgtataatc atttgcatcc atacattttg atggccgcac ggcgcgaagc aaaaattacg       3060
gctcctcgct gcagacctgc gagcagggaa acgctcccct cacagacgcg ttgaattgtc       3120
cccacgccgc gcccctgtag agaaatataa aaggttagga tttgccactg aggttcttct       3180
ttcatatact tcctttaaa atcttgctag gatacagttc tcacatcaca tccgaacata       3240
aacaaccatg ggtactactt tggatgatac tgcttacaga tacagaactt ctgttccagg       3300
tgatgctgaa gctattgaag ctttggatgg ttctttcact accgatactg ttttcagagt       3360
tactgctact ggtgatggtt tcactttgag agaagttcca gttgatccac cattgactaa       3420
ggttttcca gatgatgaat ccgatgatga atctgacgat ggtgaagatg gtgatccaga       3480
ttctagaact tttgttgctt acggtgatga tggtgatttg gctggttttg ttgttgtttc       3540
ttactctggt tggaacagaa gattgaccgt tgaagatatt gaagttgccc cagaacatag       3600
aggtcatggt gttggtagag ctttgatggg ttttggctact gaatttgcta gagaagagg       3660
tgctggtcat ttgtggttgg aagttactaa tgttaacgct ccagctattc atgcctatag       3720
aagaatgggt tttaccttgt gtgggtttgga tactgcatta tatgatggta ctgcttccga       3780
tggtgaacaa gccttgtata tgtctatgcc atgtccataa tcagtactga caataaaaag       3840
attcttgttt tcaagaactt gtcatttgta tagtttttt atattgtagt tgttctattt       3900
taatcaaatg ttagcgtgat ttatatttt tttcgcctcg acatcatctg cccagatgcg       3960
aagttaagtg cgcagaaagt aatatcatgc gtcaatcgta tgtgaatgct ggtcgctata       4020
ctgctgtcga ttcgatacta acgccgccat ccagtgtcga aaacgagctc gaattcatcg       4080
atgatatcag atccactagt ggcctatgcg gccgccaccg cggtggagct ccaattcgcc       4140
ctatagtgag tcgtattaca attcactggc cgtcgtttta caacgtcgtg actgggaaaa       4200
```

```
cectggcgtt acccaactta atcgccttgc agcacatccc cccttcgcca gctggcgtaa     4260
tagcgaagag gcccgcaccg atcgcccttc ccaacagttg cgcagcctga atggcgaatg     4320
gcgcgacgcg ccctgtagcg gcgcattaag cgcggcgggt gtggtggtta cgcgcagcgt     4380
gaccgctaca cttgccagcg ccctagcgcc cgctcctttc gctttcttcc cttcctttct     4440
cgccacgttc gccggctttc cccgtcaagc tctaaatcgg gggctcccTt tagggttccg     4500
atttagtgct ttacggcacc tcgacCccaa aaaacttgat tagggtgatg gttcacgtag     4560
tgggccatcg ccctgataga cggttttttcg cccttTgacg ttggagtcca cgttctttaa     4620
tagtggactc ttgttccaaa ctggaacaac actcaaccct atctcggtct attcttttga     4680
tttataaggg attttgccga tttcggccta ttggttaaaa aatgagctga tttaacaaaa     4740
atttaacgcg aattttaaca aaatattaac gtttacaatt tcctgatgcg gtattttctc     4800
cttacgcatc tgtgcggtat ttcacaccgc agggtaataa ctgatataat taaattgaag     4860
ctctaatttg tgagtttagt atacatgcat ttacttataa tacagttttt tagttttgct     4920
ggccgcatct tctcaaatat gcttcccagc ctgcttttct gtaacgttca ccctctacct     4980
tagcatccct tccttttgca atagtcctc ttccaacaat aataatgtca gatcctgtag     5040
agaccacatc atccacggtt ctatactgtt gacccaatgc gtctcccttg tcatctaaac     5100
ccacaccggg tgtcataatc aaccaatcgt aaccttcatc tcttccaccc atgtctcttt     5160
gagcaataaa gccgataaca aaatctttgt cgctcttcgc aatgtcaaca gtacccttag     5220
tatattctcc agtagatagg gagccctgc atgacaattc tgctaacatc aaaaggcctc     5280
taggttcctt tgttacttct tctgccgcct gcttcaaacc gctaacaata cctgggccca     5340
ccacaccgtg tgcattcgta atgtctgccc attctgctat tctgtataca cccgcagagt     5400
actgcaattt gactgtatta ccaatgtcag caaattttct gtcttcgaag agtaaaaaat     5460
tgtacttggc ggataatgcc tttagcggct taactgtgcc ctccatggaa aaatcagtca     5520
agatatccac atgtgttttt agtaaacaaa ttttgggacc taatgcttca actaactcca     5580
gtaattcctt ggtggtacga acatccaatg aagcacacaa gtttgtttgc ttttcgtgca     5640
tgatattaaa tagcttggca gcaacaggac taggatgagt agcagcacgt tccttatatg     5700
tagcttTcga catgatttat cttcgtttcc tgcaggtttt tgttctgtgc agttgggtta     5760
agaatactgg gcaatttcat gtttcttcaa cactacatat gcgtatatat accaatctaa     5820
gtctgtgctc cttccttcgt tcttccttct gttcggagat taccgaatca aaaaatttc     5880 aaagaaaccg aaatcaaaaa aaagaataaa aaaaaaatga tgaattgaat tgaaaagcgt     5940
ggtgcactct cagtacaatc tgctctgatg ccgcatagtt aagccagccc cgacacccgc     6000 caacaccgc tgacgcgccc tgacgggctt gtctgctccc ggcatccgct tacagacaag     6060
ctgtgaccgt ctccgggagc tgcatgtgtc agaggttttc accgtcatca ccgaaacgcg     6120
cga                                                                  6123
```

<210> SEQ ID NO 80
<211> LENGTH: 4009
<212> TYPE: DNA
<213> ORGANISM: Artificial sequence
<220> FEATURE:
<223> OTHER INFORMATION: Plasmid pMU187

<400> SEQUENCE: 80

```
gaacgcggcc gccagctgaa gcttcgtacg ctgcaggtcg acaacccTta atataacttc       60
```

```
gtataatgta tgctatacga agttattagg tctagagatc tgtttagctt gcctcgtccc    120
cgccgggtca cccggccagc gacatggagg cccagaatac cctccttgac agtcttgacg    180
tgcgcagctc aggggcatga tgtgactgtc gcccgtacat ttagcccata catccccatg    240
tataatcatt tgcatccata cattttgatg gccgcacggc gcgaagcaaa aattacggct    300
cctcgctgca gacctgcgag cagggaaacg ctcccctcac agacgcgttg aattgtcccc    360
acgccgcgcc cctgtagaga aatataaaag gttaggattt gccactgagg ttcttctttc    420
atatacttcc ttttaaaatc ttgctaggat acagttctca catcacatcc gaacataaac    480
aaccatgggt aaggaaaaga ctcacgtttc gaggccgcga ttaaattcca acatggatgc    540
tgatttatat gggtataaat gggctcgcga taatgtcggg caatcaggtg cgacaatcta    600
tcgattgtat gggaagcccg atgcgccaga gttgtttctg aaacatggca aaggtagcgt    660
tgccaatgat gttacagatg agatggtcag actaaactgg ctgacggaat ttatgcctct    720
tccgaccatc aagcatttta tccgtactcc tgatgatgca tggttactca ccactgcgat    780
ccccggcaaa acagcattcc aggtattaga agaatatcct gattcaggtg aaaatattgt    840
tgatgcgctg gcagtgttcc tgcgccggtt gcattcgatt cctgttttgta attgtccttt    900 taacagcgat cgcgtatttc gtctcgctca ggcgcaatca cgaatgaata cggtttggt     960 tgatgcgagt gattttgatg acgagcgtaa tggctggcct gttgaacaag tctggaaaga   1020
aatgcataag cttttgccat tctcaccgga ttcagtcgtc actcatggtg atttctcact   1080
tgataacctt attttttgacg aggggaaatt aataggttgt attgatgttg acgagtcgg   1140 aatcgcagac cgataccagg atcttgccat cctatggaac tgcctcggtg agttttctcc   1200
ttcattacag aaacggcttt ttcaaaaata tggtattgat aatcctgata tgaataaatt   1260
gcagtttcat ttgatgctcg atgagttttt ctaatcagta ctgacaataa aaagattctt   1320
gttttcaaga acttgtcatt tgtatagttt ttttatattg tagttgttct attttaatca   1380
aatgttagcg tgatttatat ttttttttcgc ctcgacatca tctgcccaga tgcgaagtta   1440
agtgcgcaga aagtaatatc atgcgtcaat cgtatgtgaa tgctggtcgc tatactgctg   1500
tcgattcgat actaacgccg ccatccagtg tcgaaaacga gctctcgaga acccttaata   1560
taacttcgta taatgtatgc tatacgaagt tattaggtga tatcagatcc actagtggcc   1620
tatgcggccg cggatctgcc ggtctcccta gtgagtcg tattaatttc gataagccag   1680
gttaacctgc attaatgaat cggccaacgc gcggggagag gcggtttgcg tattgggcgc   1740
tcttccgctt cctcgctcac tgactcgctg cgctcggtcg ttcggctgcg gcgagcggta   1800
tcagctcact caaaggcggt aatacggtta tccacagaat caggggataa cgcaggaaag   1860
aacatgtgag caaaaggcca gcaaaaggcc aggaaccgta aaaaggccgc gttgctggcg   1920 ttttttccata ggctccgccc ccctgacgag catcacaaaa atcgacgctc aagtcagagg   1980
tggcgaaacc cgacaggact ataaagatac caggcgtttc ccctggaag ctccctcgtg   2040 cgctctcctg ttccgaccct gccgcttacc ggatacctgt ccgcctttct cccttcggga   2100
agcgtggcgc tttctcaatg ctcacgctgt aggtatctca gttcggtgta ggtcgttcgc   2160
tccaagctgg gctgtgtgca cgaaccccccc gttcagcccg accgctgcgc cttatccggt   2220
aactatcgtc ttgagtccaa cccggtaaga cacgacttat cgccactggc agcagccact   2280
ggtaacagga ttagcagagc gaggtatgta ggcggtgcta cagagttctt gaagtggtgg   2340
cctaactacg gctacactag aaggacagta tttggtatct gcgctctgct gaagccagtt   2400
accttcggaa aaagagttgg tagctcttga tccggcaaac aaaccaccgc tggtagcggt   2460
```

```
ggtttttttg tttgcaagca gcagattacg cgcagaaaaa aaggatctca agaagatcct    2520
ttgatctttt ctacggggtc tgacgctcag tggaacgaaa actcacgtta agggattttg    2580
gtcatgagat tatcaaaaag gatcttcacc tagatccttt taaattaaaa atgaagtttt    2640
aaatcaatct aaagtatata tgagtaaact tggtctgaca gttaccaatg cttaatcagt    2700
gaggcaccta tctcagcgat ctgtctattt cgttcatcca tagttgcctg actccccgtc    2760
gtgtagataa ctacgatacg ggagggctta ccatctggcc ccagtgctgc aatgataccg    2820
cgagacccac gctcaccggc tccagattta tcagcaataa accagccagc cggaagggcc    2880
gagcgcagaa gtggtcctgc aactttatcc gcctccatcc agtctattaa ttgttgccgg    2940
gaagctagag taagtagttc gccagttaat agtttgcgca acgttgttgc cattgctaca    3000
ggcatcgtgg tgtcacgctc gtcgtttggt atggcttcat tcagctccgg ttcccaacga    3060
tcaaggcgag ttacatgatc ccccatgttg tgcaaaaaag cggttagctc cttcggtcct    3120
ccgatcgttg tcagaagtaa gttggccgca gtgttatcac tcatggttat ggcagcactg    3180
cataattctc ttactgtcat gccatccgta agatgctttt ctgtgactgg tgagtactca    3240
accaagtcat tctgagaata gtgtatgcgg cgaccgagtt gctcttgccc ggcgtcaata    3300
cgggataata ccgcgccaca tagcagaact ttaaaagtgc tcatcattgg aaaacgttct    3360
tcggggcgaa aactctcaag gatcttaccg ctgttgagat ccagttcgat gtaacccact    3420
cgtgcaccca actgatcttc agcatctttt actttcacca gcgtttctgg gtgagcaaaa    3480
acaggaaggc aaaatgccgc aaaaaaggga ataagggcga cacggaaatg ttgaatactc    3540
atactcttcc ttttttcaata ttattgaagc atttatcagg gttattgtct catgagcgga    3600
tacatatttg aatgtattta gaaaaataaa caaatagggg ttccgcgcac atttccccga    3660
aaagtgccac ctgacgtcta agaaaccatt attatcatga cattaaccta taaaaatagg    3720
cgtatcacga ggccctttcg tctcgcgcgt ttcggtgatg acggtgaaaa cctctgacac    3780
atgcagctcc cggagacggt cacagcttgt ctgtaagcgg atgccgggag cagacaagcc    3840
cgtcagggcg cgtcagcggg tgttggcggg tgtcggggct ggcttaacta tgcggcatca    3900
gagcagattg tactgagagt gcaccatatg gacatattgt cgttagaacg cggctacaat    3960
taatacataa ccttatgtat catacacata cgatttaggt gacactata              4009
```

<210> SEQ ID NO 81
<211> LENGTH: 1426
<212> TYPE: DNA
<213> ORGANISM: Artificial sequence
<220> FEATURE:
<223> OTHER INFORMATION: URA3 deletion sequence

<400> SEQUENCE: 81

```
aggagaatcc atacaagaaa tcgatcgaat tatcattgaa atccattcaa ctaacatcac      60
acttgctgga agataataac gatctgcgta aaaacgagat attcgctatt attcaagctt     120
tggcacatca atgcatcaat ccgtgtaagc agataagtga atttgcagtg gtaacgctag     180
agcagacgct catcaataaa atcgaaattc caactaatga gatggaatcg gtagaagaat     240
taattgaggg cggattacta ccgttgctaa attcgagtga aacacaggaa gaccagaaaa     300
tcctcatttc atccatatta acaataattt caaatgttta tttgcattat ttgaaactag     360
ggaagacaag caacgaaacg ttttttgaaaa ttttgatgat tttcaataaa tttgtagagg     420
actcagatat tgaaaaaaag ctacagcaat taatacttga taagaagagt attgagaagg     480
```

```
gcaacggttc atcatctcat ggatctgcac atgaacaaac accagagtca aacgacgttg    540
aaattgaggc tactgcgcca attgatgaca atacagacga tgataacaaa ccgaagttat    600
ctgatgtaga aaaggattaa agatgctaag agatagtgat gatatttcat aaataatgta    660
attctatata tgttaattac ctttttttgcg aggcatattt atggtgaagg ataagttttg    720
accatcaaag aaggttaatg tggctcggtc gtaatgattt ctataatgac gaaaaaaaaa    780
aaattggaaa gaaaaagctt catggccttt ataaaaagga actatccaat acctcgccag    840
aaccaagtaa cagtatttta cggggcacaa atcaagaaca ataagacagg actgtaaaga    900
tggacgcatt gaactccaaa gaacaacaag agttccaaaa agtagtggaa caaaagcaaa    960
tgaaggattt catgcgtttg tactctaatc tggtagaaag atgtttcaca gactgtgtca   1020
atgacttcac aacatcaaag ctaaccaata aggaacaaac atgcatcatg aagtgctcag   1080
aaaagttctt gaagcatagc gaacgtgtag ggcagcgttt ccaagaacaa aacgctgcct   1140
tgggacaagg cttgggccga taaggtgtac tggcgtatat atatctaatt atgtatctct   1200
ggtgtagccc atttttagca tgtaaatata aagagaaacc atatctaatc taaccaaatc   1260
caaacaaaat tcaatagtta ctatcgcttt tttctttctg tatcgcaaat aagtgaaaat   1320
taaaaaagaa agattaaatt ggaagttgga tatgggctgg aacagcagca gtaatcggta   1380
tcgggttcgc cactaatgac gtcctacgat tgcactcaac agacct                  1426
```

<210> SEQ ID NO 82
<211> LENGTH: 1060
<212> TYPE: DNA
<213> ORGANISM: Artificial sequence
<220> FEATURE:
<223> OTHER INFORMATION: GPD1 deletion sequence
<220> FEATURE:
<221> NAME/KEY: misc_feature
<222> LOCATION: (523)..(558)
<223> OTHER INFORMATION: A small part of the coding sequence was not
      deleted

<400> SEQUENCE: 82

```
tacaaacgca acacgaaaga acaaaaaaag aagaaaacag aaggccaaga cagggtcaat     60
gagactgttg tcctcctact gtccctatgt ctctggccga tcacgcgcca ttgtccctca    120
gaaacaaatc aaacacccac accccgggca cccaaagtcc ccaccccacac caccaatacg    180 taaacggggc gccccctgca ggccctcctg cgcgcggcct cccgccttgc ttctctcccc    240
ttccttttct tttccagtt ttccctattt tgtccctttt tccgcacaac aagtatcaga    300
atgggttcat caaatctatc caacctaatt cgcacgtaga ctggcttggt attggcagtt    360
tcgtagttat atatatacta ccatgagtga aactgttacg ttaccttaaa ttctttctcc    420 ctttaattt cttttatctt actctcctac ataagacatc aagaaacaat tgtatattgt    480 acacccccccc cctccacaaa cacaaatatt gataatataa agatgtctgc tgctgctgat    540
agtctacatg aagattagat ttattggaga aagataacat atcatacttt cccccacttt    600
tttcgaggct cttctatatc atattcataa attagcatta tgtcatttct cataactact    660
ttatcacgtt agaaattact tattattatt aaattaatac aaaatttagt aaccaaataa    720
atataaataa atatgtatat ttaaatttta aaaaaaaaat cctatagagc aaaaggattt    780
tccattataa tattagctgt acacctcttc cgcattttttt gagggtggtt acaacaccac    840
tcattcagag gctgtcggca cagttgcttc tagcatctgg cgtccgtatg tatgggtgta    900
ttttaaataa taaacaaagt gccacacctt caccaattat gtctttaaga aatggacaag    960
```

| | | |
|---|---|---|
| ttccaaagag cttgcccaag gctcgacaag gatgtacttt ggaatatcta tattcaagta | 1020 |
| cgtggcgcgc atatgtttga gtgtgcacac aataaaggtt | 1060 |

<210> SEQ ID NO 83
<211> LENGTH: 1024
<212> TYPE: DNA
<213> ORGANISM: Artificial sequence
<220> FEATURE:
<223> OTHER INFORMATION: GPD2 deletion sequence

<400> SEQUENCE: 83

| | |
|---|---|
| atagccatca tgcaagcgtg tatcttctaa gattcagtca tcatcattac cgagtttgtt | 60 |
| ttccttcaca tgatgaagaa ggtttgagta tgctcgaaac aataagacga cgatggctct | 120 |
| gccattgtta tattacgctt ttgcggcgag gtgccgatgg gttgctgagg ggaagagtgt | 180 |
| ttagcttacg gacctattgc cattgttatt ccgattaatc tattgttcag cagctcttct | 240 |
| ctaccctgtc attctagtat tttttttttt tttttttggt tttactttttt tttcttcttg | 300 |
| cctttttttc ttgttacttt ttttctagtt tttttttcctt ccactaagct ttttccttga | 360 |
| tttatccttg ggttcttctt tctactcctt tagattttttt tttatatat taattttttaa | 420 |
| gtttatgtat tttggtagat tcaattctct ttcccttttcc tttttccttcg ctcccctttcc | 480 |
| ttatcctctg atctttcctg ttgcctcttt ttcccccaac caatttatca ttatacacaa | 540 |
| gttctacaac tactactagt aacattacta cagttattat aattttctat tctcttttttc | 600 |
| tttaagaatc tatcattaac gttaattttct atatatacat aactaccatt atacacgcta | 660 |
| ttatcgttta catatcacat caccgttaat gaaagatacg acaccctgta cactaacaca | 720 |
| attaaataat cgccataacc ttttctgtta tctatagccc ttaaagctgt ttcttcgagc | 780 |
| tttttcactg cagtaattct ccacatgggc ccagccactg agataagagc gctatgttag | 840 |
| tcactactga cggctctcca gtcatttatg tgattttttta gtgactcatg tcgcatttgg | 900 |
| cccgtttttt tccgctgtcg caacctattt ccattaacgg tgccgtatgg aagagtcatt | 960 |
| taaaggcagg agagagagat tactcatctt cattggatca gattgatgac tgcgtacggc | 1020 |
| agat | 1024 |

<210> SEQ ID NO 84
<211> LENGTH: 376
<212> TYPE: PRT
<213> ORGANISM: Herpes simplex virus 1
<300> PUBLICATION INFORMATION:
<308> DATABASE ACCESSION NUMBER: GenBank AAA45811
<309> DATABASE ENTRY DATE: 1993-08-02
<313> RELEVANT RESIDUES IN SEQ ID NO: (1)..(376)

<400> SEQUENCE: 84

Met Ala Ser Tyr Pro Gly His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Pro Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Arg Val Leu Gly Ala Ser Glu Thr
                85                  90                  95

-continued

```
Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
            115                 120                 125

Gly Met Pro Tyr Ala Val Thr Asp Ala Val Leu Ala Pro His Ile Gly
        130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
            195                 200                 205

Pro Glu Asp Arg His Ile Asp Arg Leu Ala Lys Arg Gln Arg Pro Gly
        210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Cys Gly Gly Ser Trp Arg
                245                 250                 255

Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Ser Met His Val Phe Ile Leu Asp Tyr Asp Gln Ser Pro Ala Gly Cys
                325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
        355                 360                 365

Ala Arg Glu Met Gly Glu Ala Asn
370                 375
```